(12) United States Patent
Uber, III et al.

(10) Patent No.: US 8,182,444 B2
(45) Date of Patent: May 22, 2012

(54) DELIVERY OF AGENTS SUCH AS CELLS TO TISSUE

(75) Inventors: Arthur E. Uber, III, Pittsburgh, PA (US); Alan D. Hirschman, Glenshaw, PA (US); David M. Griffiths, Pittsburgh, PA (US); David M. Reilly, Pittsburgh, PA (US); Kevin P. Cowan, Allison Park, PA (US); Barry L. Tucker, Verona, PA (US); David Mishler, Slippery Rock, PA (US)

(73) Assignee: Medrad, Inc., Indianola, PA (US)

( * ) Notice: Subject to any disclaimer, the term of this patent is extended or adjusted under 35 U.S.C. 154(b) by 993 days.

(21) Appl. No.: 12/092,448

(22) PCT Filed: Nov. 6, 2006

(86) PCT No.: PCT/US2006/043133
§ 371 (c)(1),
(2), (4) Date: May 2, 2008

(87) PCT Pub. No.: WO2007/056247
PCT Pub. Date: May 18, 2007

(65) Prior Publication Data
US 2008/0294096 A1    Nov. 27, 2008

Related U.S. Application Data

(60) Provisional application No. 60/771,206, filed on Feb. 7, 2006, provisional application No. 60/742,224, filed on Dec. 5, 2005, provisional application No. 60/734,035, filed on Nov. 4, 2005.

(51) Int. Cl.
*A61M 5/168* (2006.01)

(52) U.S. Cl. .......................................... 604/66; 604/67
(58) Field of Classification Search .............. 604/65–67
See application file for complete search history.

(56) References Cited

U.S. PATENT DOCUMENTS

| 4,677,980 | A | 7/1987 | Reilly et al. |
|---|---|---|---|
| 5,383,858 | A | 1/1995 | Reilly et al. |
| 5,494,035 | A | 2/1996 | Leuthold et al. |
| 5,526,812 | A | 6/1996 | Dumoulin et al. |
| 5,618,531 | A | 4/1997 | Cherksey |

(Continued)

FOREIGN PATENT DOCUMENTS

EP    1444003    2/2002

(Continued)

OTHER PUBLICATIONS

Hydromer Coating, Hydromer, Inc. Website (www.hydromer.com/MedicalCoatings.html), As early 1985.

(Continued)

*Primary Examiner* — Terry Cecil
(74) *Attorney, Agent, or Firm* — David Schramm

(57) ABSTRACT

A system for delivering a fluid comprising cells to tissue of a patient includes a container holding an injection fluid and a powered drive. A sensor system provides a measurement indicative of at least shear forces on the cells to a control system. Based at least in part on this measurement, the control system is adapted to transmit a control signal to the powered drive for pressurizing the contents of the container to deposit cells within the tissue of a patient via a fluid path and a patient interface. As an example, the cells can be progenitor or stem cells.

23 Claims, 86 Drawing Sheets

U.S. PATENT DOCUMENTS

| | | | |
|---|---|---|---|
| 5,720,720 A | | 2/1998 | Laske et al. |
| 5,750,103 A | | 5/1998 | Cherksey |
| 5,797,870 A | | 8/1998 | March et al. |
| 5,808,203 A | | 9/1998 | Nolan, Jr. et al. |
| 5,823,993 A | * | 10/1998 | Lemelson ............... 604/503 |
| 5,827,216 A | | 10/1998 | Igo et al. |
| 5,840,059 A | | 11/1998 | March et al. |
| 5,846,225 A | | 12/1998 | Rosengart et al. |
| 5,882,343 A | | 3/1999 | Wilson et al. |
| 5,997,509 A | | 12/1999 | Rosengart et al. |
| 6,060,048 A | | 5/2000 | Cherksey |
| 6,122,536 A | | 9/2000 | Sun et al. |
| 6,199,554 B1 | | 3/2001 | Mann et al. |
| 6,224,566 B1 | | 5/2001 | Loeb |
| 6,231,568 B1 | | 5/2001 | Loeb et al. |
| 6,319,230 B1 | | 11/2001 | Palasis et al. |
| 6,322,536 B1 | | 11/2001 | Rosengart et al. |
| 6,344,027 B1 | | 2/2002 | Goll |
| 6,387,367 B1 | | 5/2002 | Davis-Sproul et al. |
| 6,387,369 B1 | | 5/2002 | Pittenger et al. |
| 6,416,510 B1 | | 7/2002 | Altman et al. |
| 6,464,662 B1 | | 10/2002 | Raghavan et al. |
| 6,488,661 B1 | | 12/2002 | Spohn et al. |
| 6,520,930 B2 | | 2/2003 | Critchlow et al. |
| 6,549,803 B1 | | 4/2003 | Raghavan et al. |
| 6,572,579 B1 | | 6/2003 | Raghavan et al. |
| 6,585,700 B1 | | 7/2003 | Trocki et al. |
| 6,591,129 B1 | | 7/2003 | Ben-Haim et al. |
| 6,595,979 B1 | | 7/2003 | Epstein et al. |
| 6,599,274 B1 | | 7/2003 | Kucharczyk et al. |
| 6,602,241 B2 | | 8/2003 | Makower et al. |
| 6,605,061 B2 | | 8/2003 | VanTassel et al. |
| 6,613,026 B1 | | 9/2003 | Palasis et al. |
| 6,652,489 B2 | | 11/2003 | Trocki et al. |
| 6,673,033 B1 | | 1/2004 | Sciulli et al. |
| 6,749,026 B2 | | 6/2004 | Smith et al. |
| 6,749,833 B2 | | 6/2004 | Raghavan et al. |
| 6,758,828 B2 | | 7/2004 | Hammer et al. |
| 6,796,957 B2 | | 9/2004 | Carpenter et al. |
| 6,835,193 B2 | | 12/2004 | Epstein et al. |
| 6,855,132 B2 | | 2/2005 | VanTassel et al. |
| 6,892,091 B1 | | 5/2005 | Ben-Haim et al. |
| 6,958,053 B1 | | 10/2005 | Reilly |
| 7,217,356 B2 | * | 5/2007 | Cork et al. .................. 210/96.1 |
| 7,315,109 B1 | | 1/2008 | Griffiths et al. |
| 2002/0010428 A1 | | 1/2002 | Vedrine et al. |
| 2002/0082546 A1 | | 6/2002 | Crank et al. |
| 2002/0095124 A1 | | 7/2002 | Palasis et al. |
| 2003/0028172 A1 | | 2/2003 | Epstein et al. |
| 2003/0109849 A1 | | 6/2003 | Hammer et al. |
| 2003/0109899 A1 | | 6/2003 | Fisher et al. |
| 2003/0219385 A1 | | 11/2003 | Ahrens |
| 2003/0225370 A1 | | 12/2003 | Mueller |
| 2004/0122366 A1 | | 6/2004 | Kazemzadeh |
| 2004/0191225 A1 | | 9/2004 | Dinsmore et al. |
| 2004/0210188 A1 | | 10/2004 | Glines et al. |
| 2004/0213756 A1 | | 10/2004 | Michal et al. |
| 2004/0228764 A1 | | 11/2004 | Stephens et al. |
| 2004/0254525 A1 | | 12/2004 | Uber, III et al. |
| 2005/0075624 A1 | * | 4/2005 | Miesel ........................ 604/505 |
| 2005/0113744 A1 | * | 5/2005 | Donoghue et al. ............. 604/66 |
| 2005/0124975 A1 | | 6/2005 | Law |
| 2007/0106208 A1 | | 5/2007 | Uber, III et al. |

FOREIGN PATENT DOCUMENTS

| | | |
|---|---|---|
| WO | 9965548 | 12/1999 |
| WO | 0006233 | 2/2000 |
| WO | 0053096 | 9/2000 |
| WO | 0053242 | 9/2000 |
| WO | 0064353 | 11/2000 |
| WO | 0067647 | 11/2000 |
| WO | 0204049 | 1/2002 |
| WO | 02056934 | 7/2002 |
| WO | 02081011 | 10/2002 |
| WO | 02082113 | 10/2002 |
| WO | 03006101 | 1/2003 |
| WO | 03053494 | 7/2003 |
| WO | 03053554 | 7/2003 |
| WO | 03095000 | 11/2003 |
| WO | 2004091688 | 10/2004 |
| WO | 2005072780 | 8/2005 |
| WO | 2006058280 | 6/2006 |

OTHER PUBLICATIONS

Visipaque, Amersham Health, a division of GE Healthcare, Website (www.amershamhealth-us.com/visipaque/), As early as 1997.

Aqualon, Hercules, Inc. Website, (http://www.herc.com/aqualon/), As early as 2001.

Sculptra, Aventis Pharmaceuticals Website (http://www.sculptra.com/US/Index.jsp), As early as 2002.

PuraMatrix, 3DM Inc. Website, (www.puramatrix.com), As early as 2001.

Burton, Alan C., Physiology and Biophysics of the Circulation, 2nd Edition 1972, LC#70-182003, Chapter 5.

Ensite 3000, Endocardial Solutions Website (www.endocardialsolutions.com/patient/index.html), As early as 2000.

Carto XP System, Biosense Webster/Johnson & Johnson Website (www.jnjgateway.com), As early as 2000.

Navi-Star Catheter, Biosense Webster/Johnson & Johnson Website (www.jnjgateway.com), As early as 2000.

LocaLisa Intracardiac Navigation System, Medtronic Website (www.medtronic.com/epsystems/disclaimer.html), As early as 2000.

Realtime Position Management (RPM) System, Boston Scientific Website (www.bostonscientific.com), As early as 2001.

U.S. Appl. No. 10/921,083, Callen et al., filed Aug. 18, 2004.

* cited by examiner

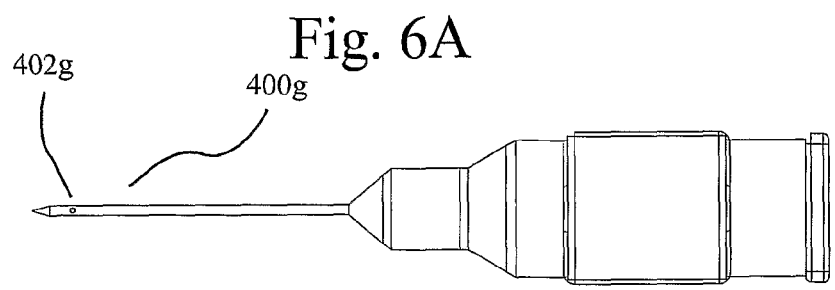
Fig. 6A
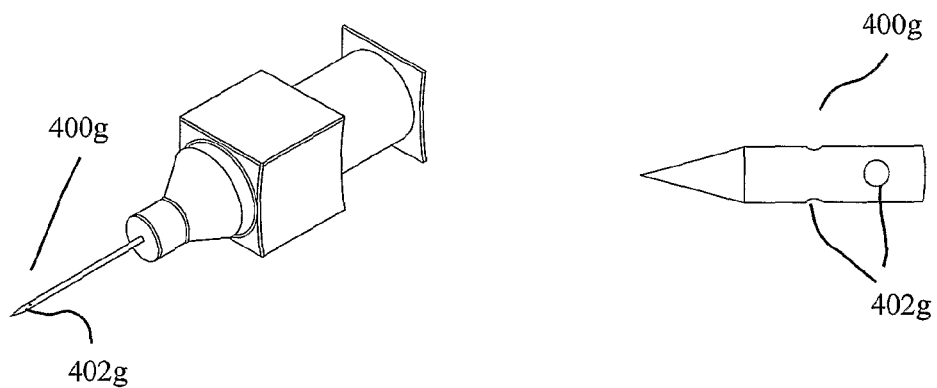
Fig. 6B
Fig. 6C

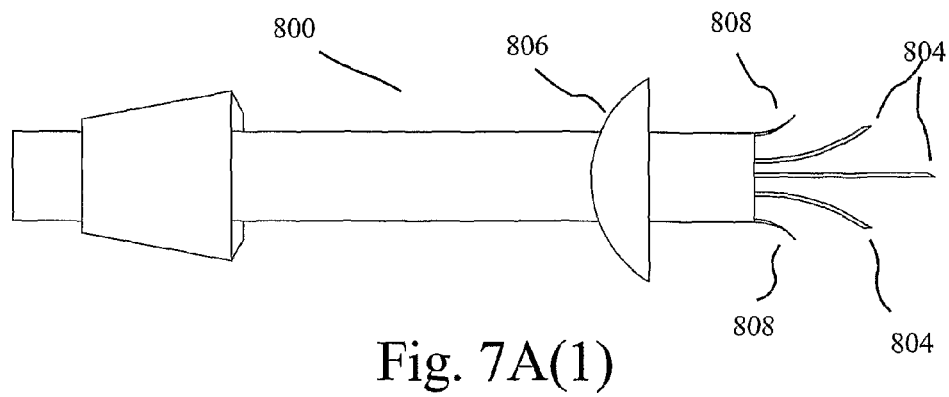
Fig. 7A(1)
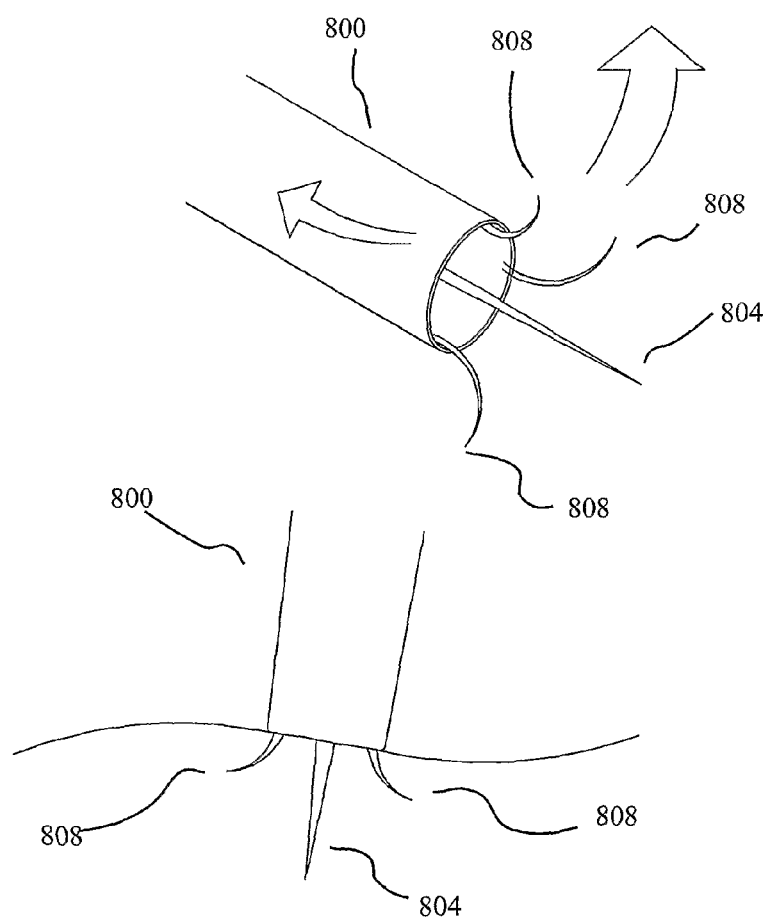
Fig. 7A(2)

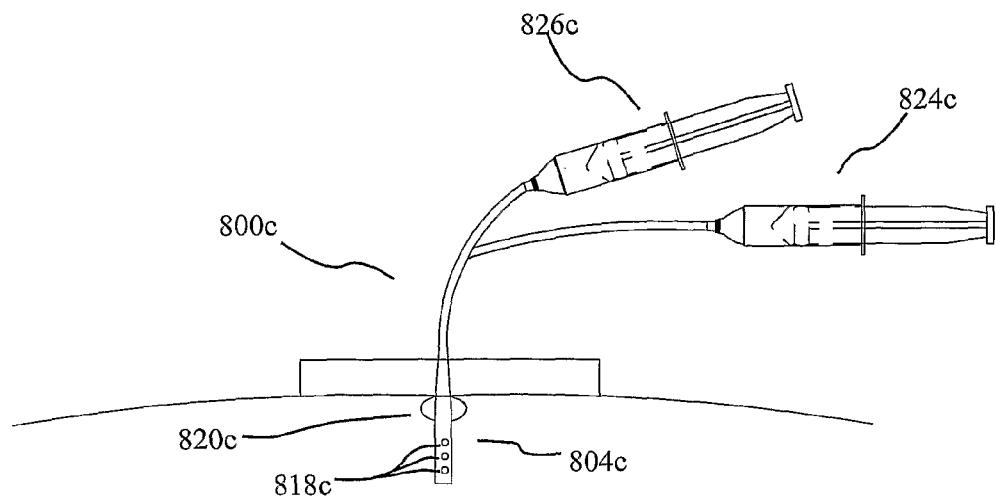
Fig. 7D(1)
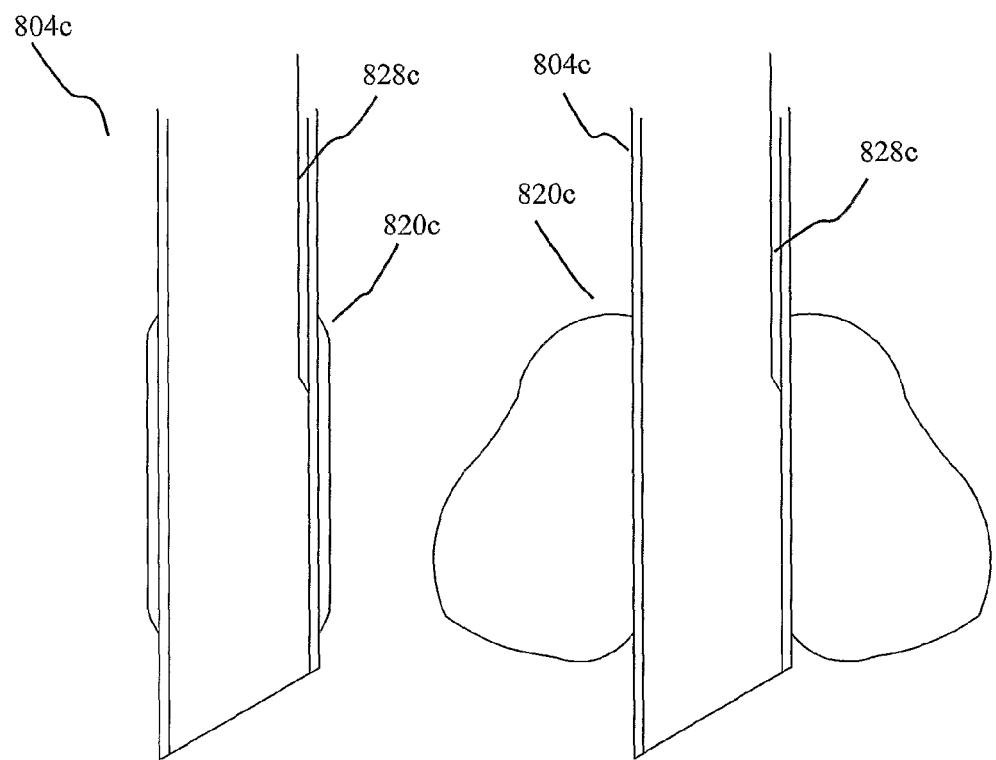
Fig. 7D(2)

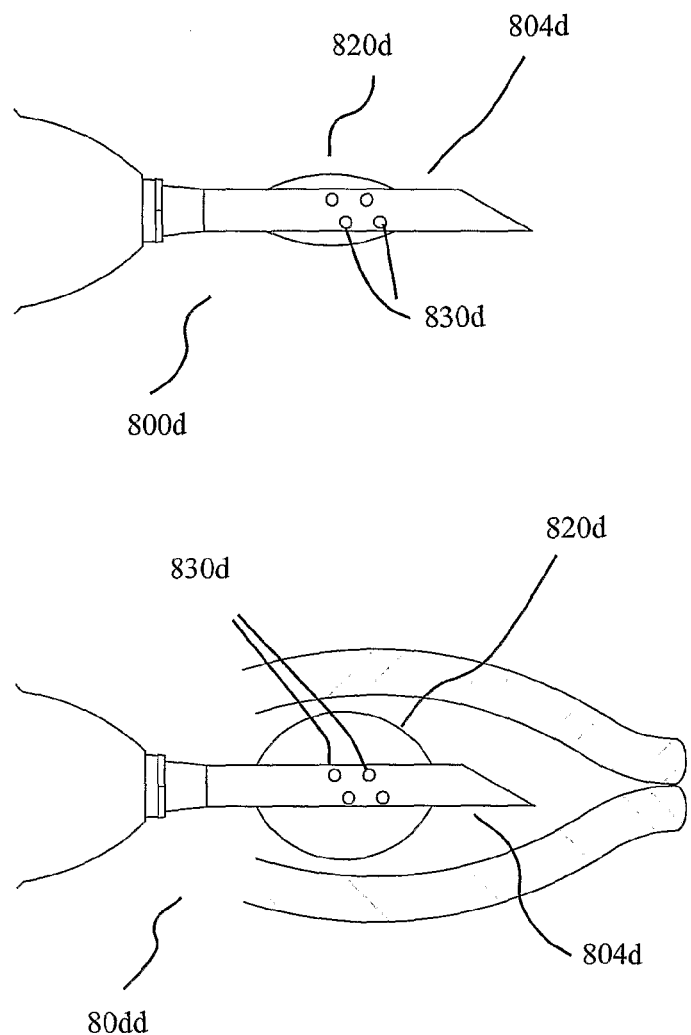
Fig. 7D(3)

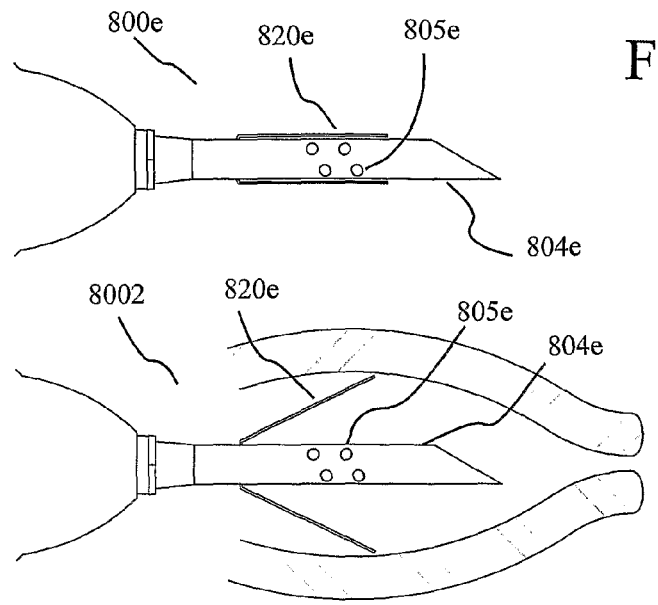
Fig. 7D(4)
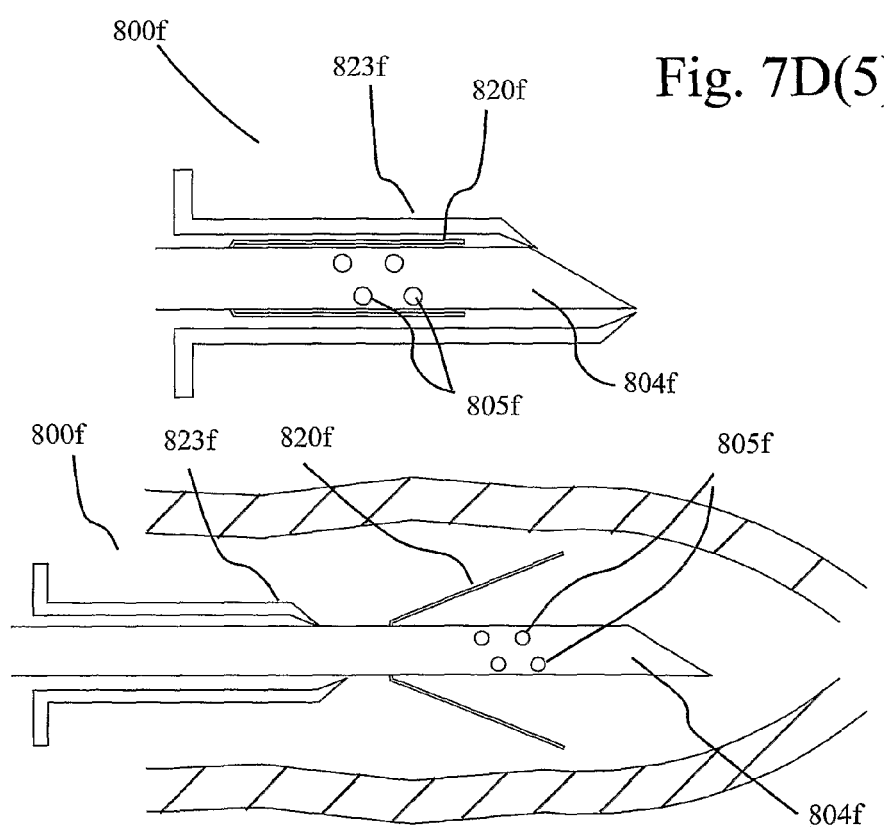
Fig. 7D(5)

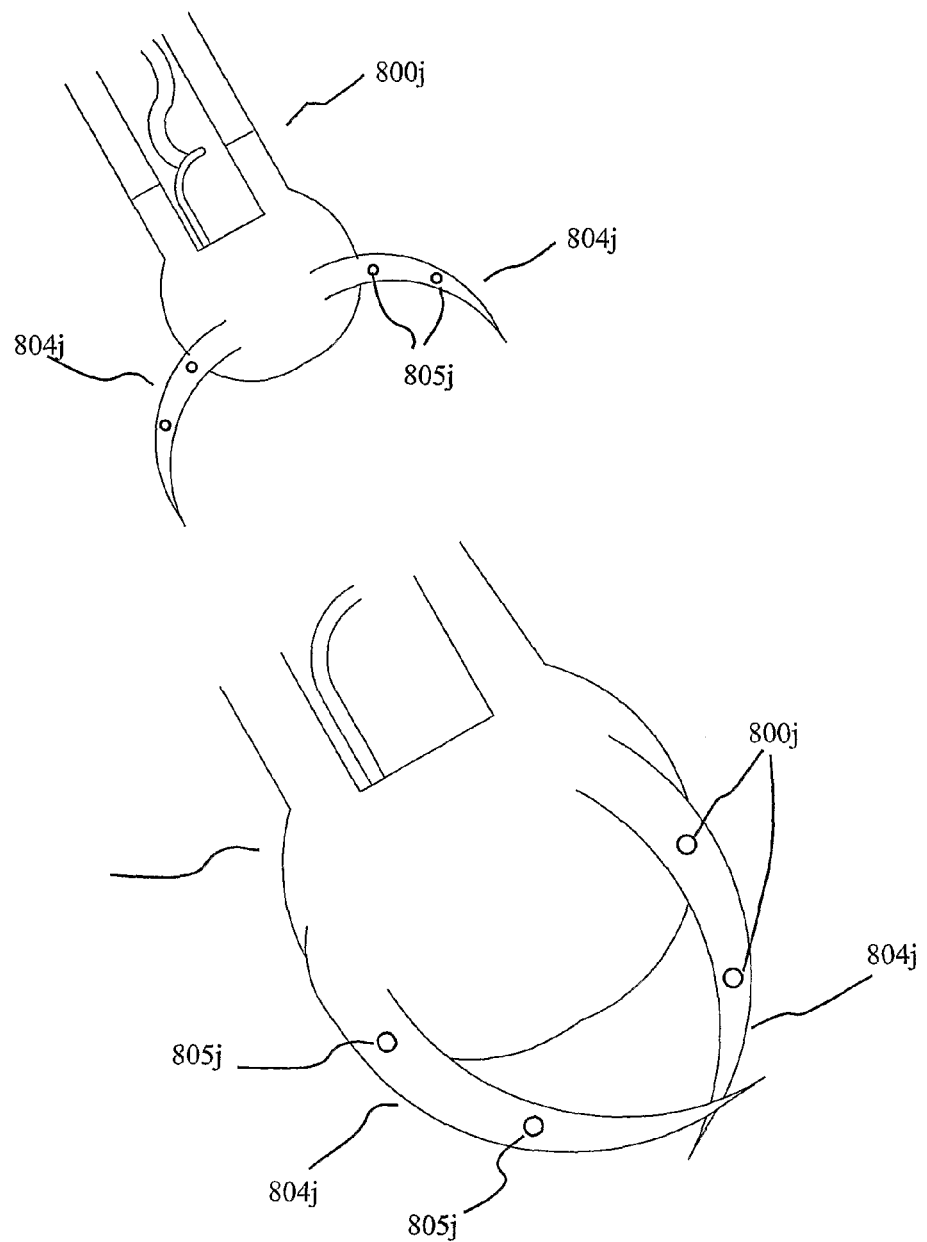
Fig. 7H(1)

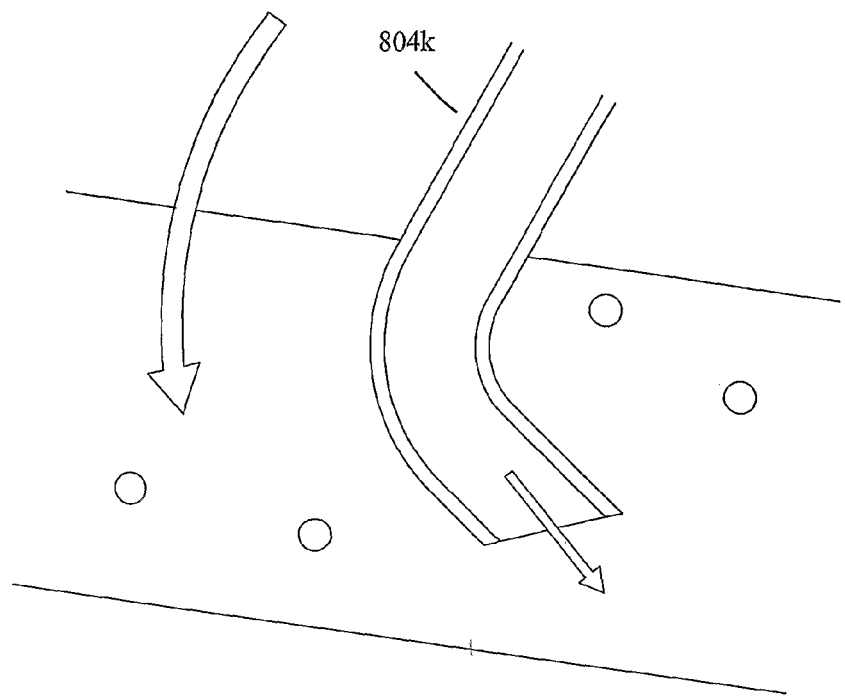
Fig. 7H(2)
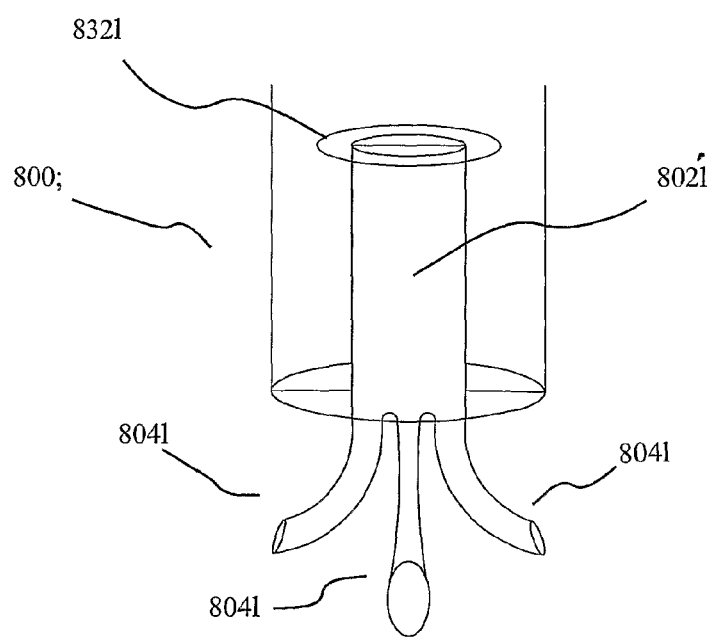
Fig. 7H(3)

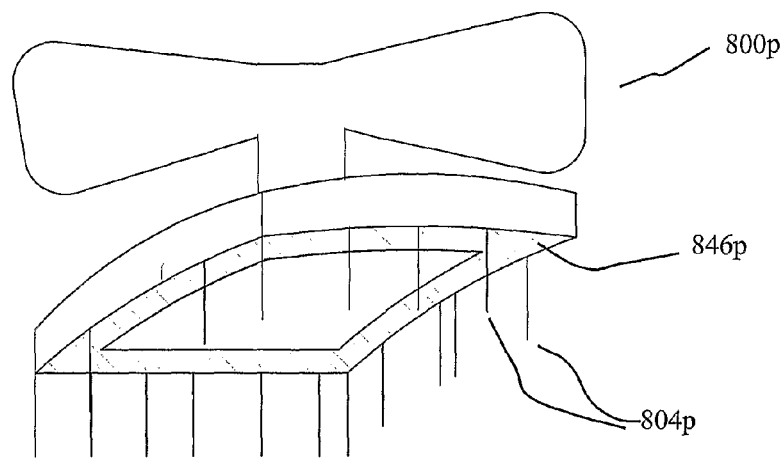
Fig. 7L
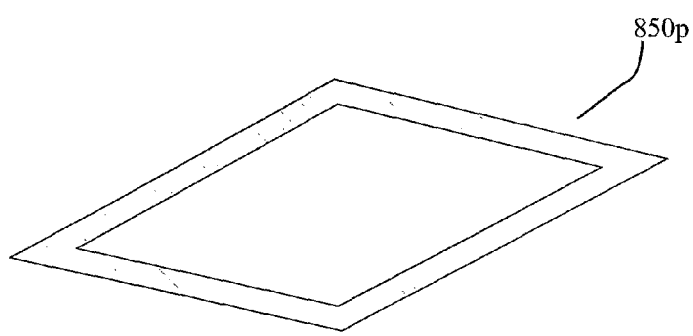
Fig. 7L(1)
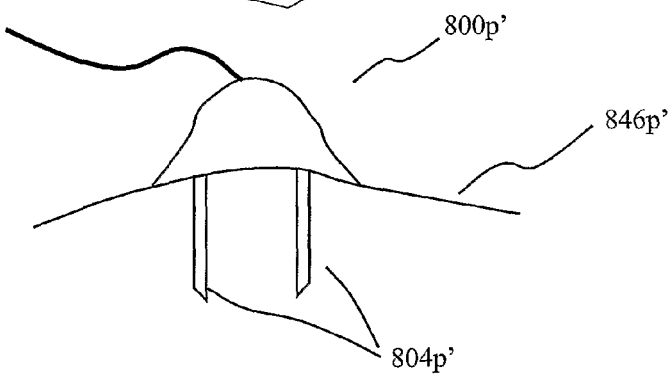
Fig. 7M
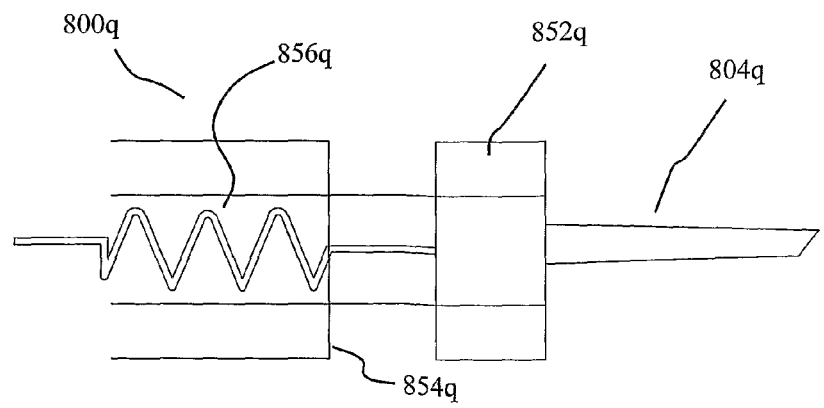

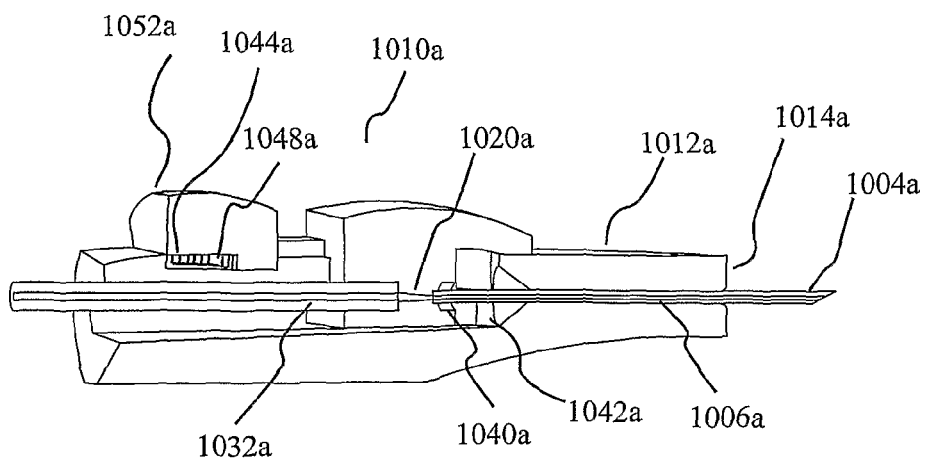
Fig. 9A(1)
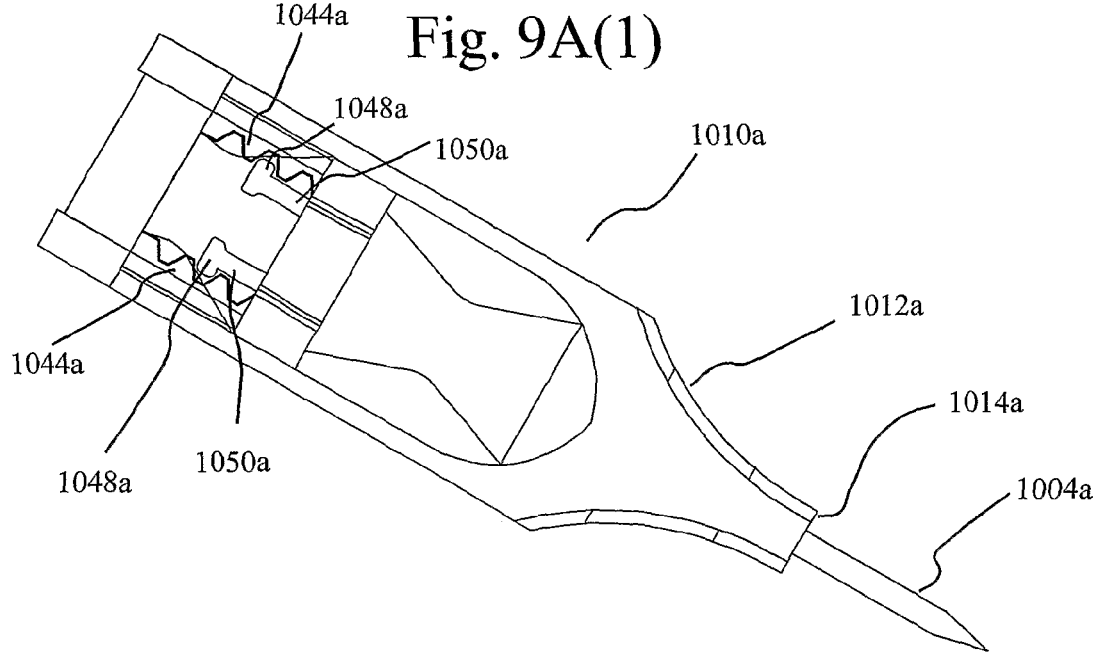
Fig. 9A(2)

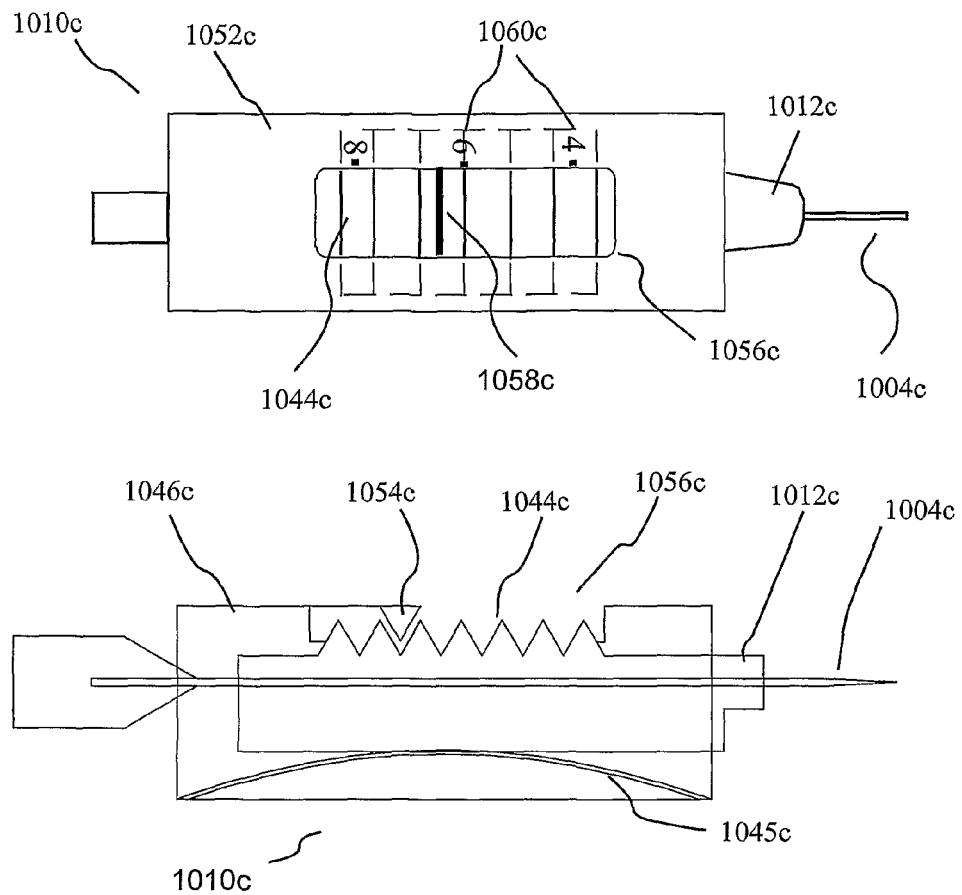
Fig. 9A(4)
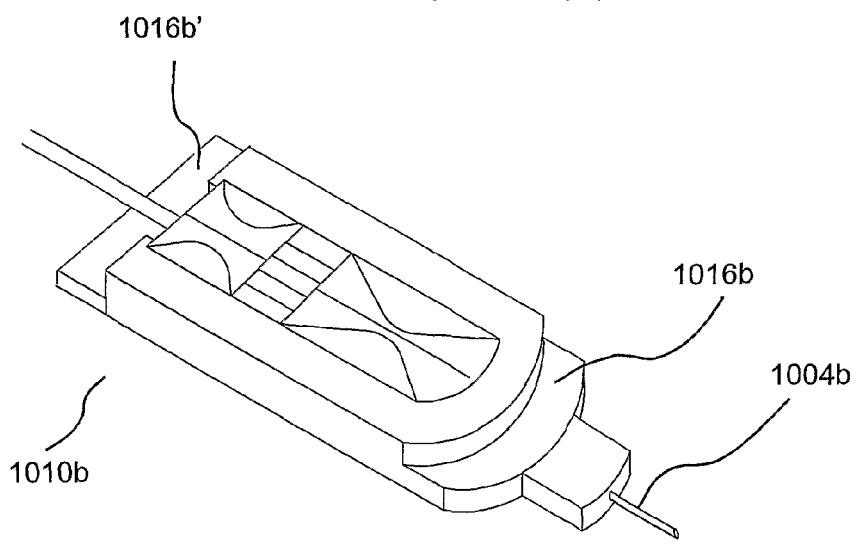
Fig. 9A(3)

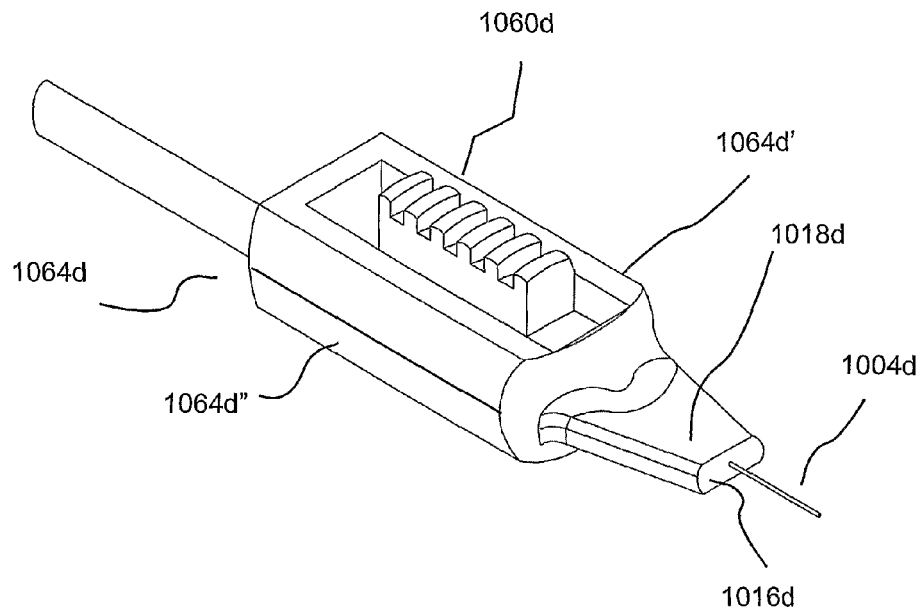
Fig. 9A(5a)
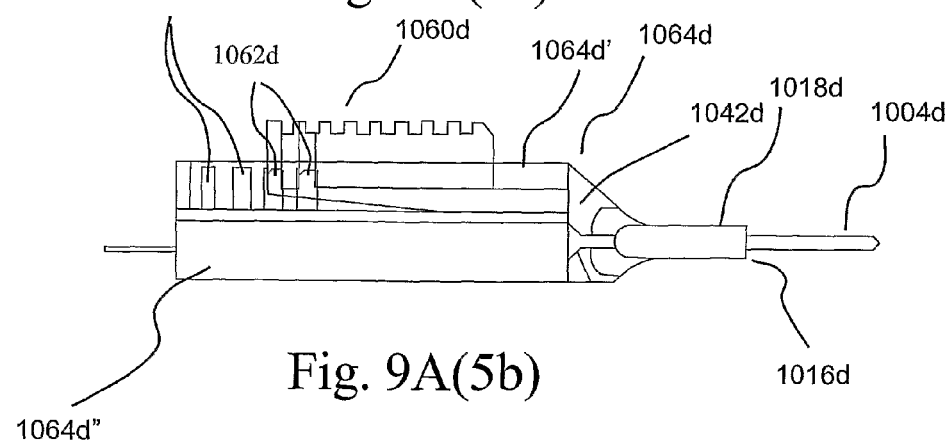
Fig. 9A(5b)
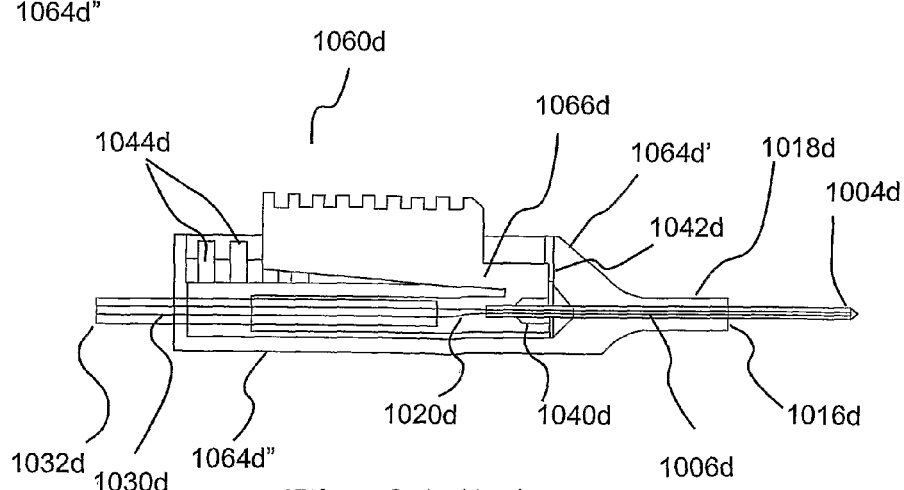
Fig. 9A(5c)

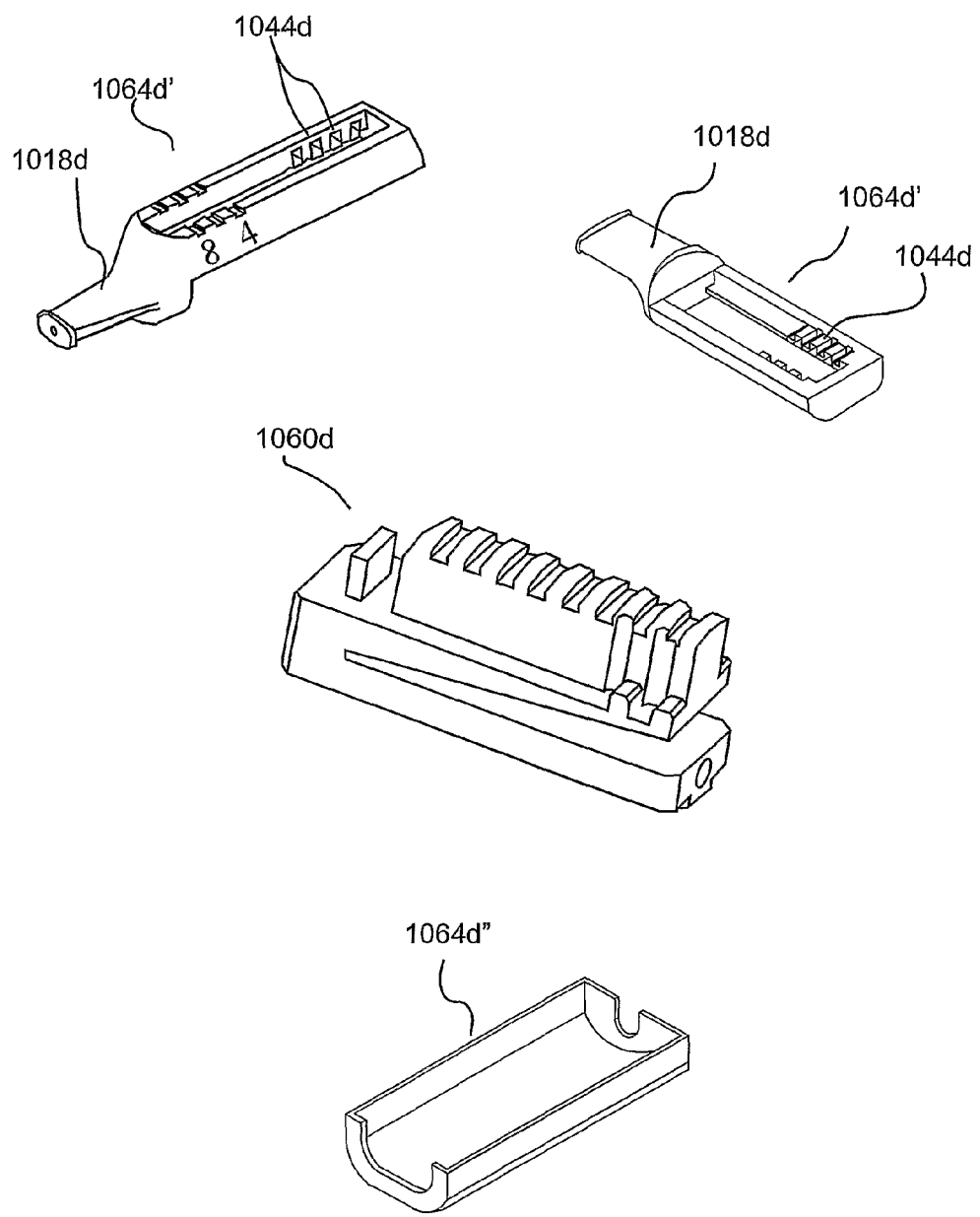
Fig. 9A(5d)

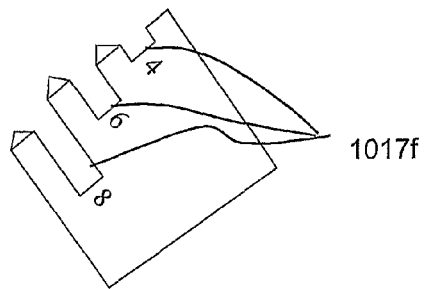
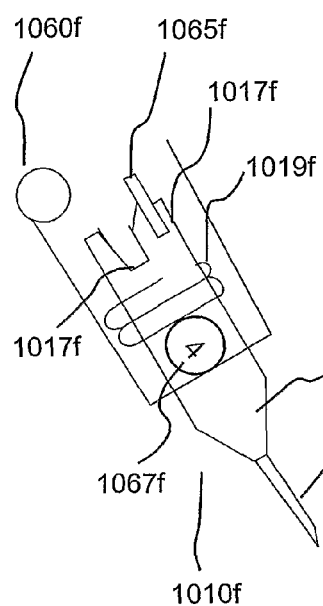
Fig. 9B(1)
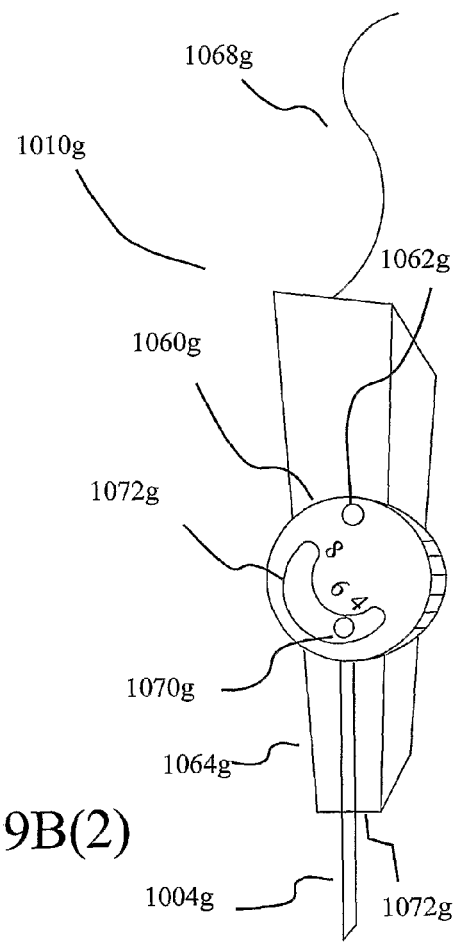
Fig. 9B(2)

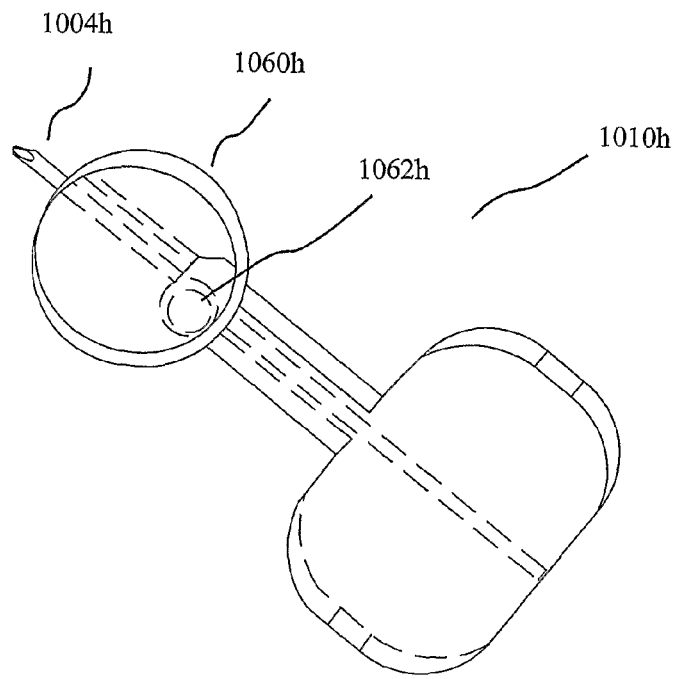
Fig. 9B(3)
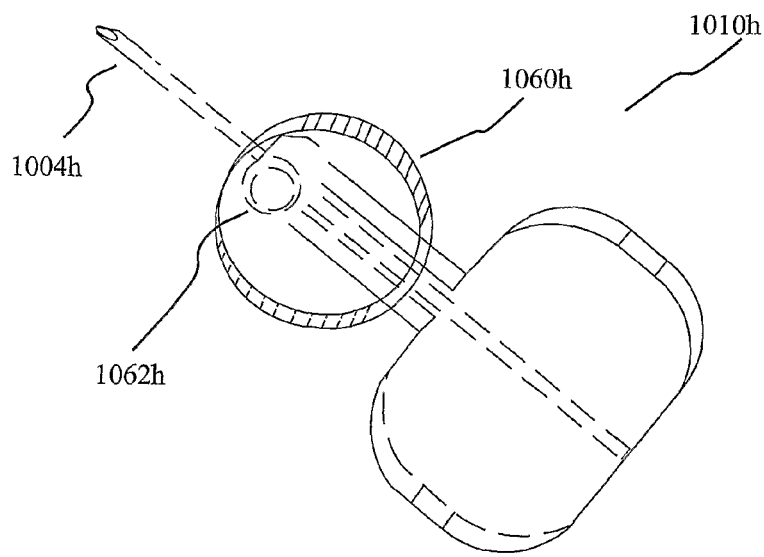
Fig. 9B(4)

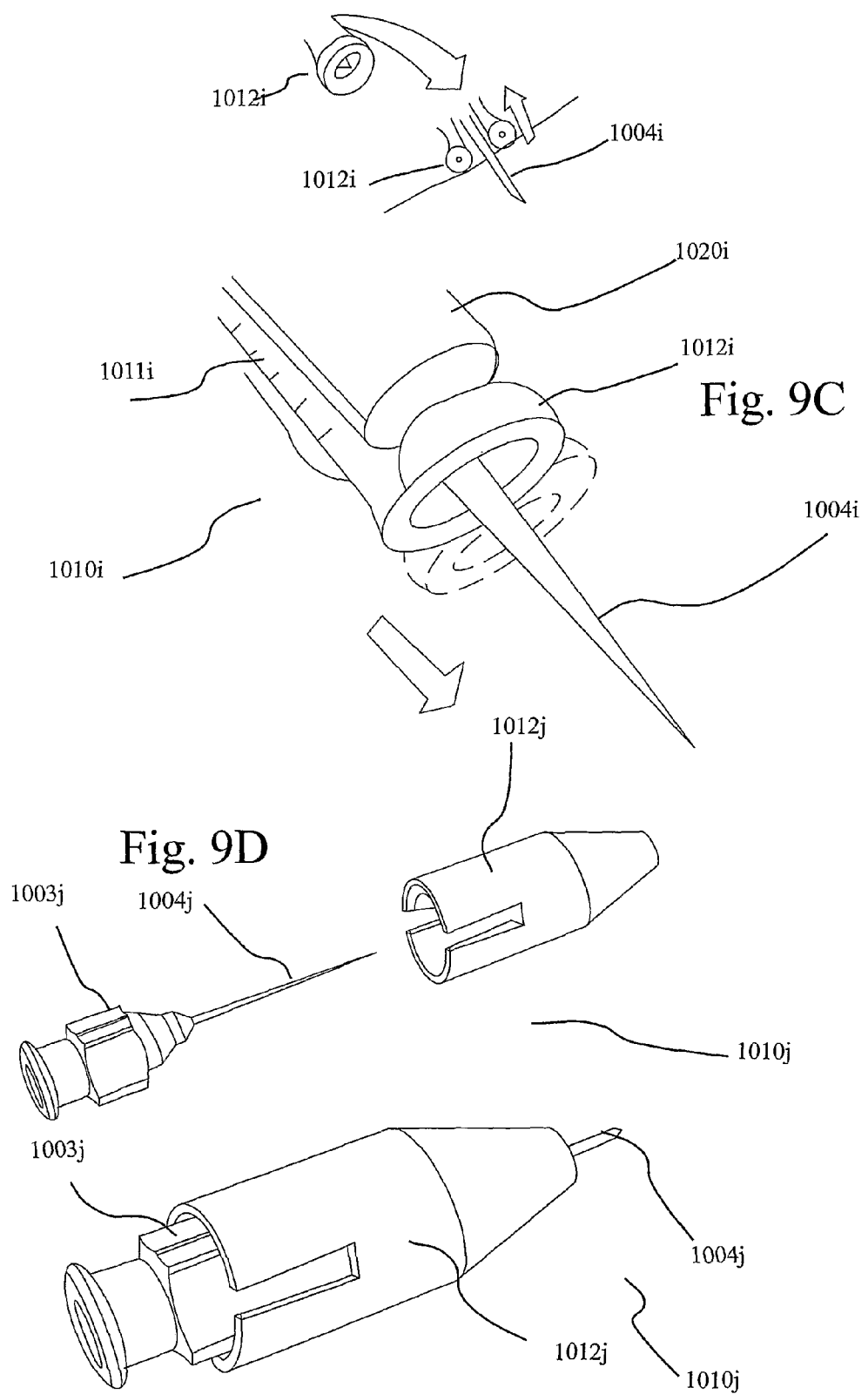

Fig. 9G(1)
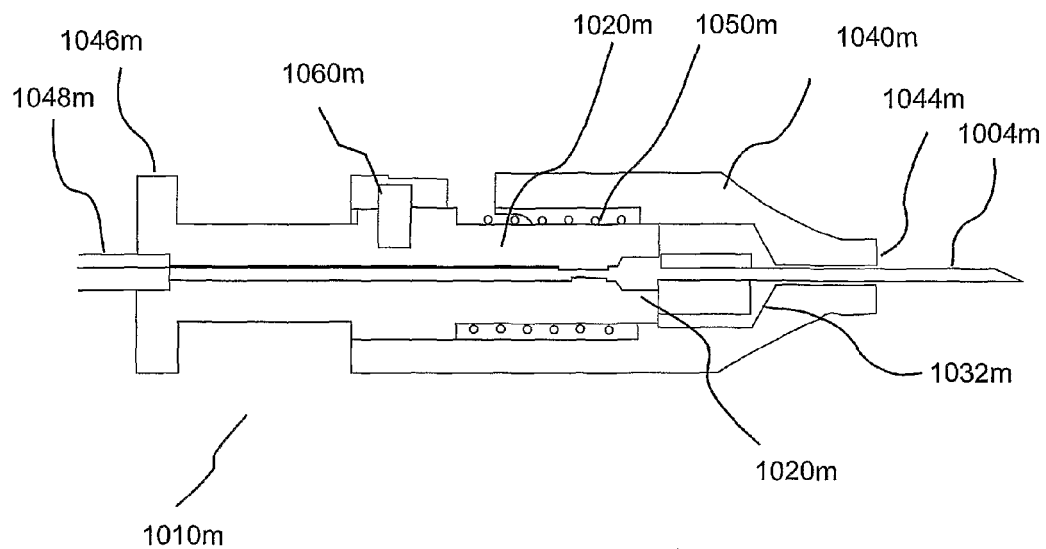
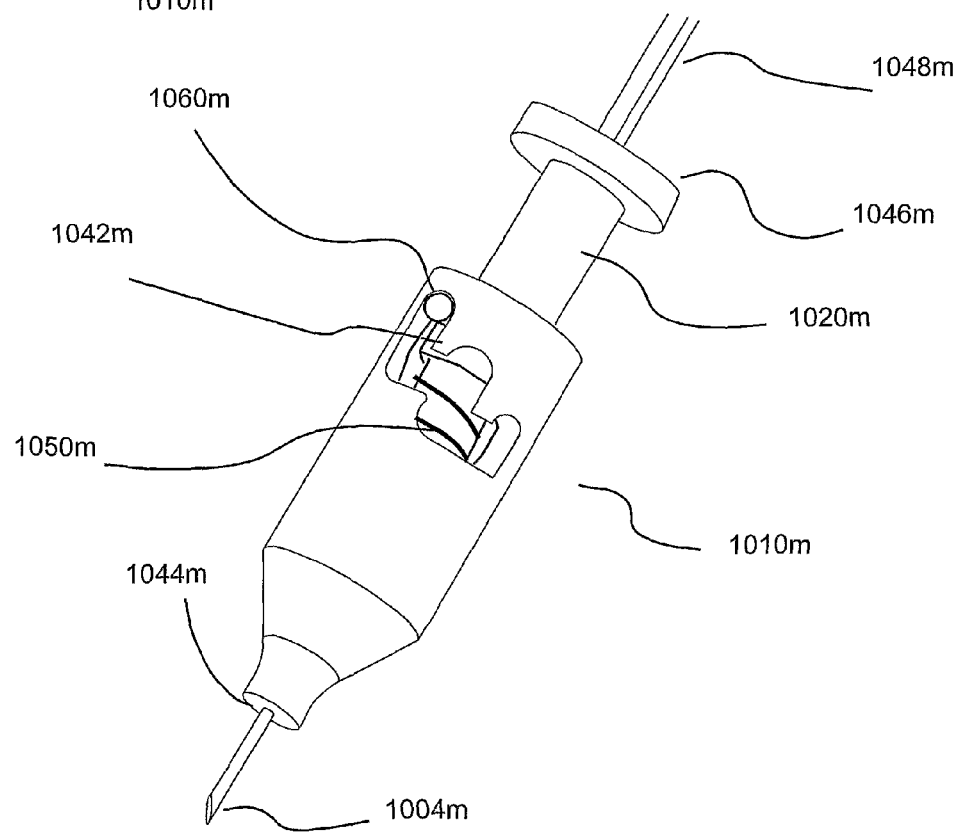
Fig. 9G(2)

Fig. 10D(1)

Fig. 12I
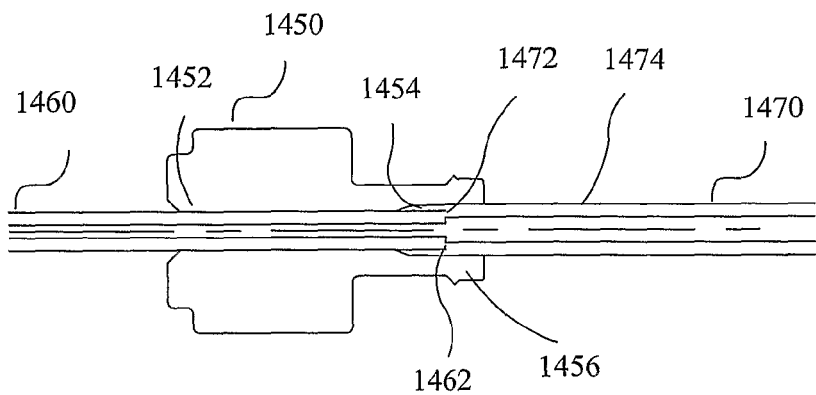
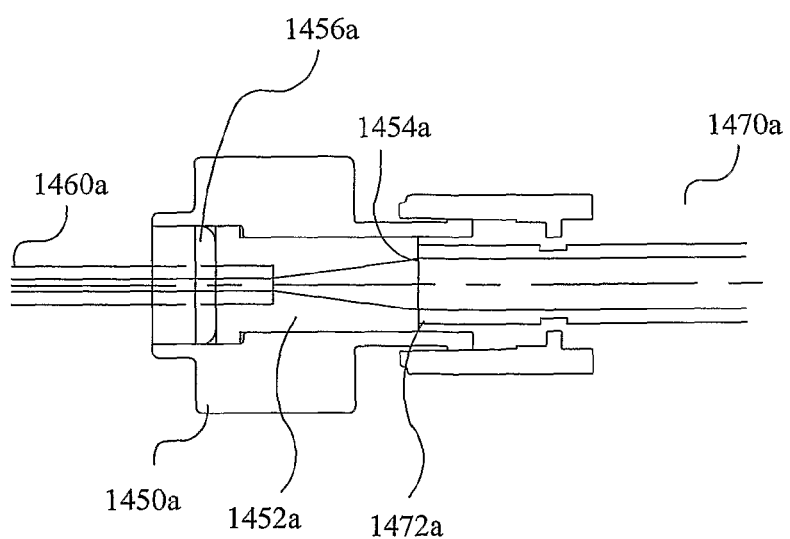
Fig. 12J

Fig. 12K
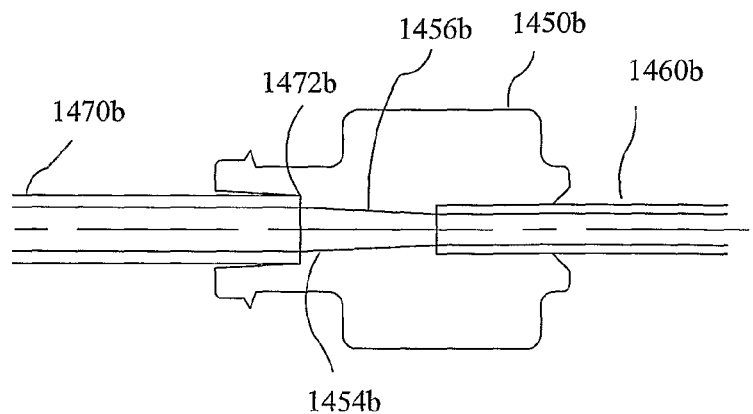
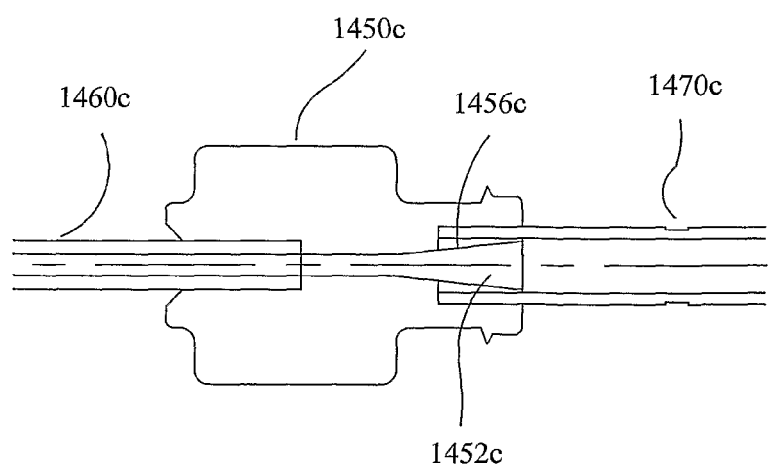
Fig. 12L

Fig. 12L(1)
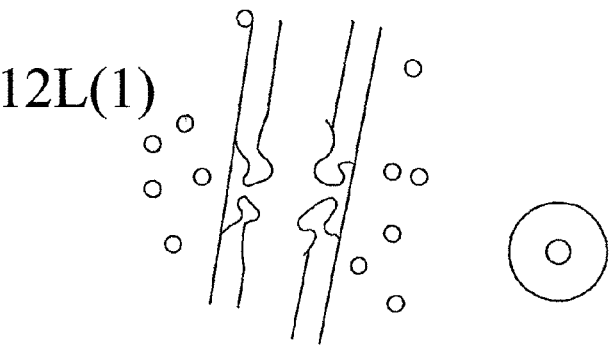
Fig. 12N
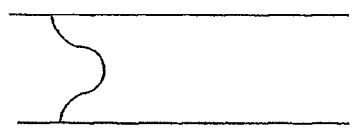
Fig. 12M
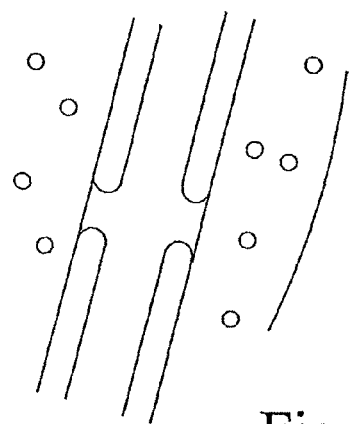
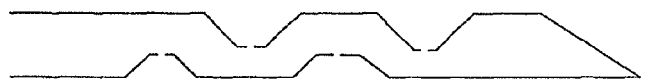

Fig. 13B
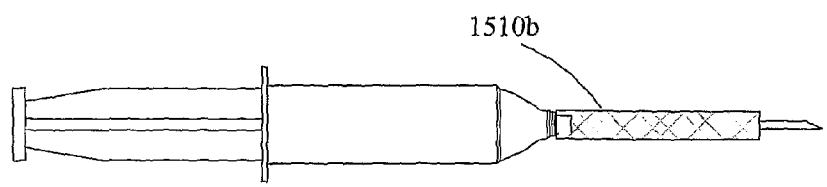
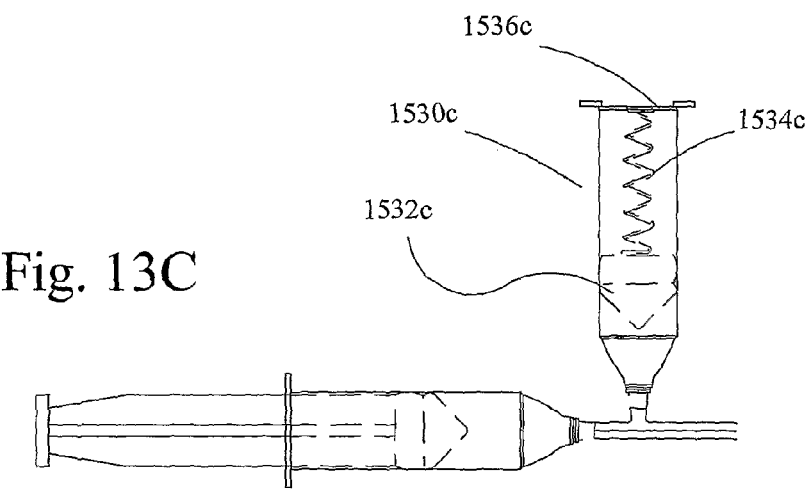
Fig. 13C
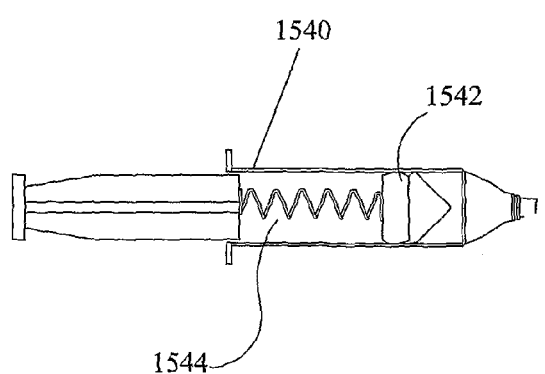
Fig. 13D

Fig. 13E
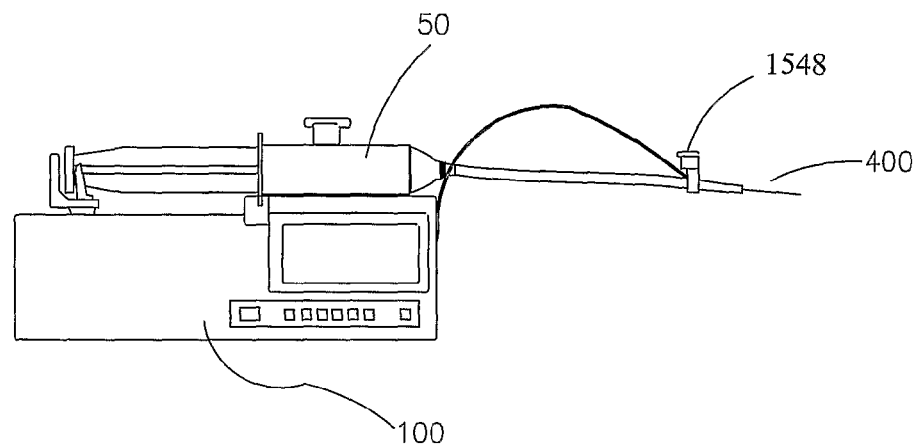
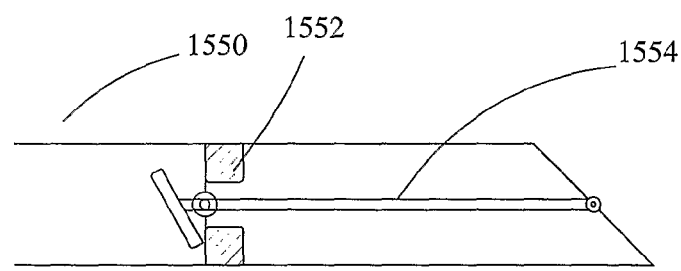
Fig. 13F
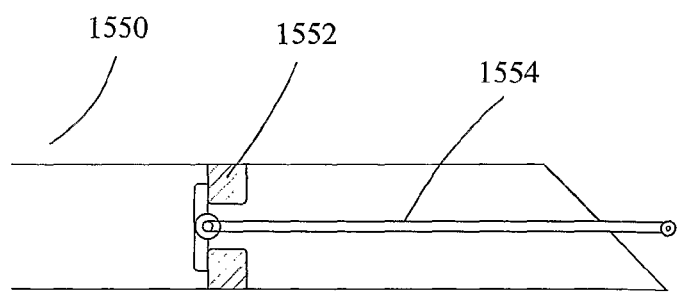
Fig. 13G

Fig. 13H
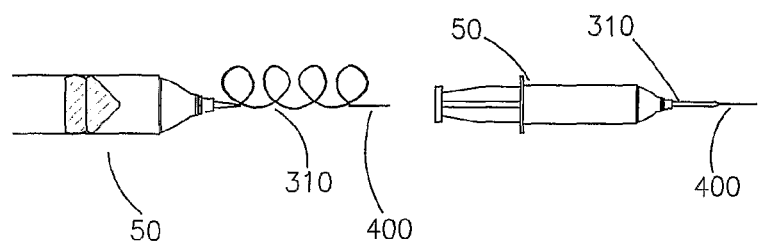
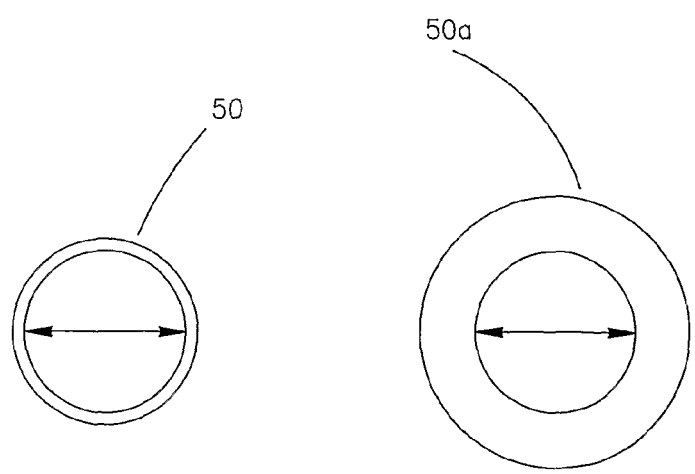
Fig. 13I

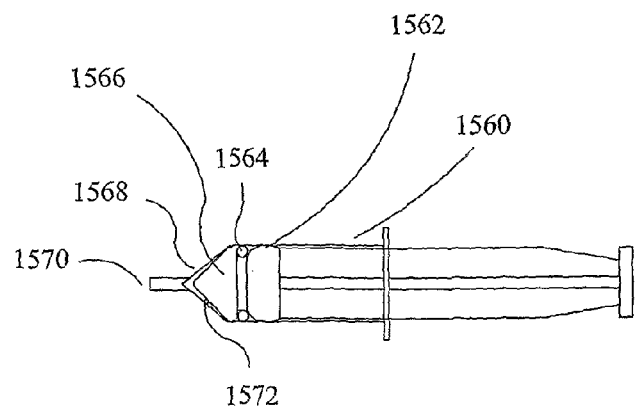
Fig. 13J
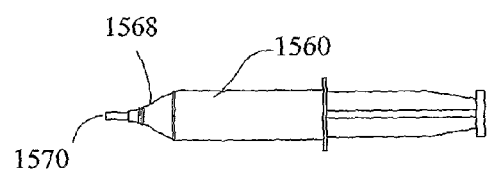
Fig. 13K
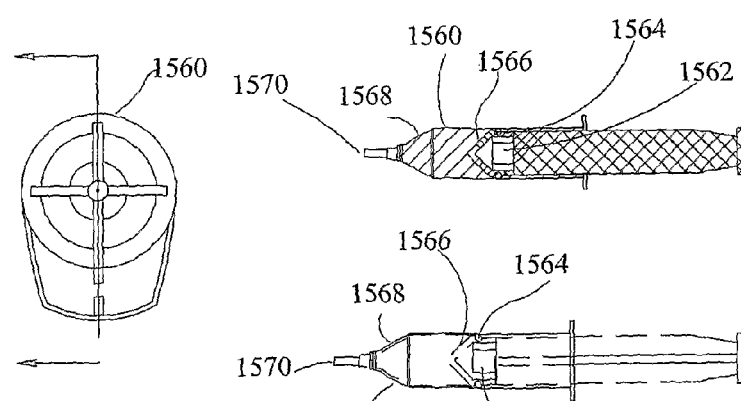
Fig. 13L
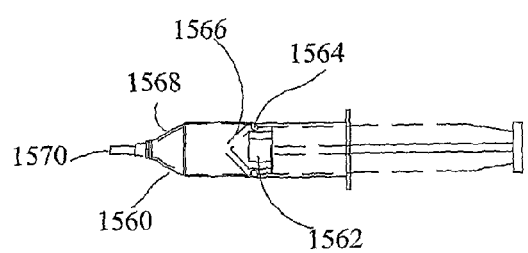
Fig. 13M
Fig. 13N

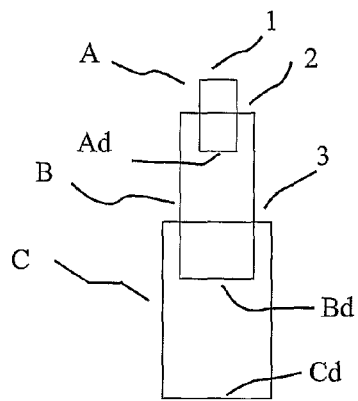
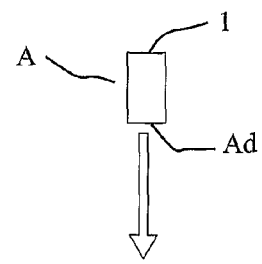
Fig. 14A
Fig. 14B
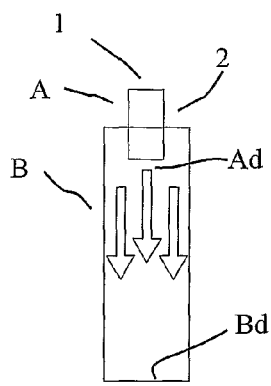
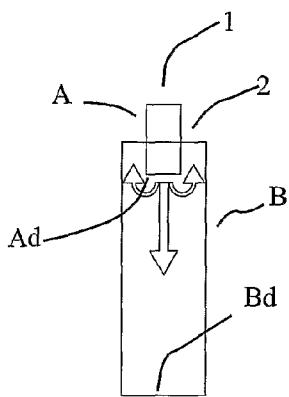
Fig. 14C
Fig. 14D
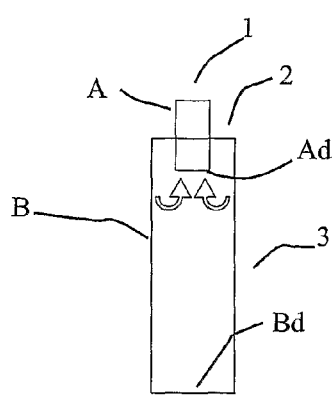
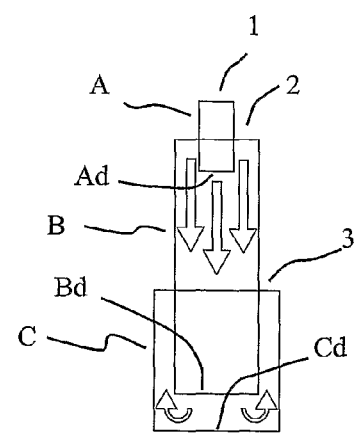
Fig. 14E
Fig. 14F Fig. 16A
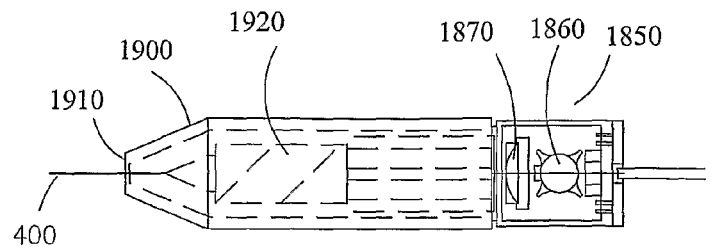
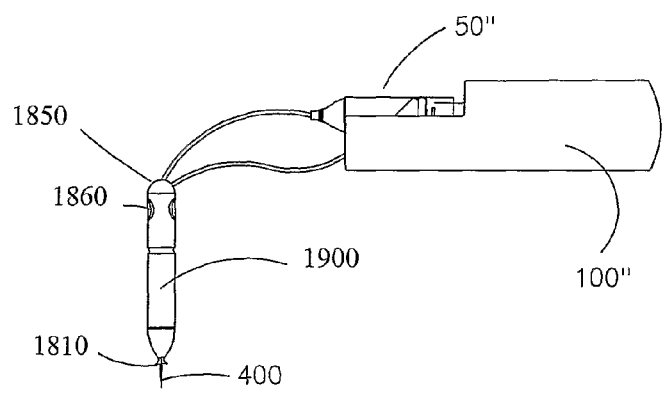
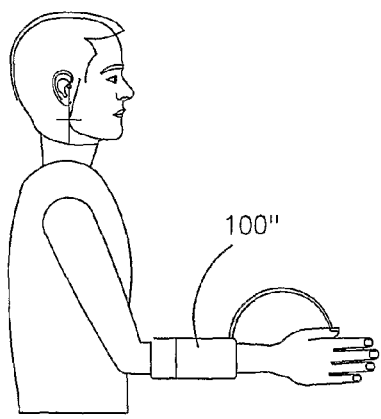
Fig. 16B

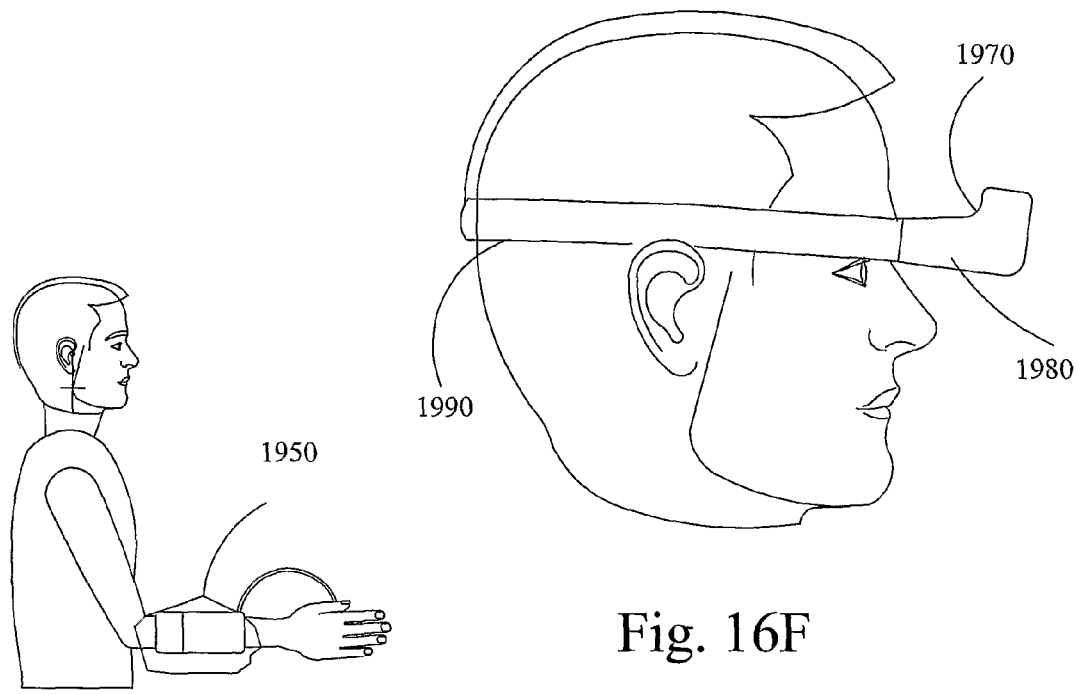
Fig. 16F
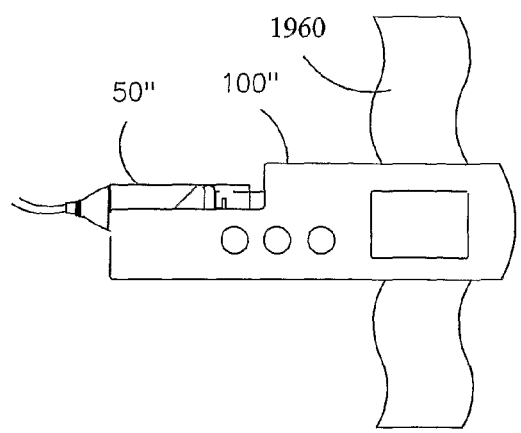
Fig. 16C
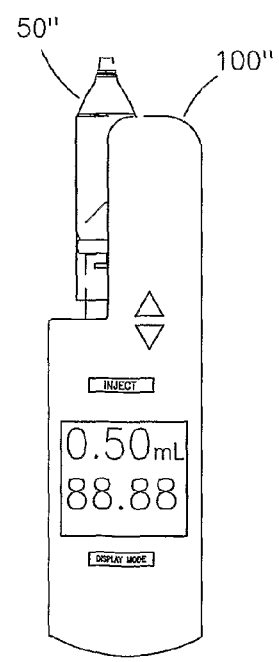
Fig. 16E
Fig. 16D

DELIVERY OF AGENTS SUCH AS CELLS TO TISSUE

CROSS REFERENCE TO RELATED APPLICATION(S)

This application is a 371 of PCT/US2006/043133 filed Nov. 6, 2006 which claims the benefit of U.S. Provisional Patent Application Ser. No. 60/771,206, filed Feb. 7, 2006; U.S. Provisional Patent Application Ser. No. 60/742,224, filed Dec. 5, 2005; U.S. provisional Patent Application Ser. No. 60/734,035, filed Nov. 4, 2005; and U.S. patent application Ser. No. 11/460,635, now U.S. Pat. No. 7,713,232, filed Jul. 28, 2006. The disclosures of which are incorporated herein by reference.

BACKGROUND OF THE INVENTION

The present invention relates to the delivery of agents such as therapeutic agents to tissue and, particularly, to the delivery of cells or cell components to tissue. Hereafter term cells is used to refer to live cells, dead cells, and/or cell components.

The following information is provided to assist the reader to understand the invention disclosed below and the environment in which it will typically be used. The terms used herein are not intended to be limited to any particular narrow interpretation unless clearly stated otherwise in this document. References set forth herein may facilitate understanding of the present invention or the background of the present invention. The disclosure of all references cited herein are incorporated by reference.

The treatment of disease by the injection of living cells into a body is expanding rapidly. There are many types of cells being used to treat an equally diverse set of diseases, and both types of cells and disease conditions are expanding rapidly. Xenogeneic cell therapies involve implantation of cells from one species into another. Allogeneic cell therapies involve implantation from one individual of a species into another individual of the same species. Autologous cell therapies involve implantation of cells from one individual into the same individual. Cell components can also have a beneficial effect on the body in selected instances. Any of the above therapies are examples of approaches that can be delivered with the systems and methods of this invention.

In an example of an allogeneic cell therapy, current phase II clinical trials of SPHERAMINE® by Titan Pharmaceutical of San Francisco, Calif. and Schering AG of Berlin, Germany, retinal pigment epithelial cells are harvested from eyes in eye banks, multiplied many fold in culture medium and placed on 100 micrometer diameter gelatin spheres. A substrate, in this instance spherical microscopic carriers or microcarriers, greatly enhance the cells' survival when injected in the brain. The carriers are injected through needles into the putamen in the brain. The animal precursor work is described in several patents, including U.S. Pat. Nos. 6,060,048, 5,750,103, and 5,618,531, the disclosures of which are incorporated herein by reference. These patents describe many types of cells, carriers, and diseases that can be treated via the disclosed methods. In a rat, about 20 microliters (ul) of injected cells on carriers is sufficient to restore dopamine production to a damaged rat brain. The therapy was injected at the rate of 4 ul/min. This dosage scales to a total injected volume of 0.5 ml in the human brain, although it will have to be distributed over a larger region, probably via multiple individual injections on the order of the 20 ul mentioned above. Cell therapies for the brain and nervous system are discuss further below.

An example of an autologous cell therapy involves the harvesting of mesenchymal stem cell from a patient's bone marrow, concentration of the stem cells, and injection of the cells and other blood components into the heart muscle during open-heart surgery. Further examples include catheter delivered cell therapies, especially to the heart, laparoscopic delivered therapies, and transcutaneous therapies In external cell therapy for the heart, volumes of about 0.5 to 1.0 ml are injected into a beating heart. A multi-milliliter syringe is used to hold and deliver the injectate under manual activation. A challenge is presented in that when the heart is contracting, during systole, the tissue becomes relatively hard and tense. In diastole, the tissue relaxes. It is very difficult for a human to time and control a hand injection so that the proper volume is injected all in one period of diastole. In practice, an indeterminate amount of the injectate can squirt or leak out the needle track and is presumably wasted. In addition, it is desirable to uniformly and thoroughly treat the target areas of the heart, and to avoid puncturing the major blood vessels traversing the outside of the heart. These results can also be difficult to achieve with current manual injection practices. With the current state of practice, scar tissue is not injected or treated because it does not respond well, and the growth that does occur can sometimes create dangerous electrical conduction abnormalities.

Cell therapies are generally delivered by hand injection through a needle or catheter. The benefits of hand or manual injection are conceptual simplicity and familiarity for the doctor. However the simplicity is misleading. Many of the parameters of the injection are not and cannot be controlled or even repeated by that doctor, let alone by other doctors. Flow rate is, for example, very difficult to control manually, especially at low flow rates. The stick slip friction of normal syringes exacerbates this problem. Volume accuracy depends upon manual reading of gradations, which is physically difficult while squeezing the syringe and susceptible to human perceptual or mathematical errors. The use of common infusion pumps limits delivery to generally slow and very simple fluid deliveries. Infusion pumps have no ability to provide automatic response or action to the injection based upon any physiological or other measurement or feedback.

Tremendous variations in manually controlled injectate delivery can produce proportionally wide variations in patient outcomes. In clinical trials, this variation is undesirable because it increases the number of patients and thus cost and time needed to establish efficacy. In long term therapeutic use, such variation remains undesirable as some people can receive suboptimal treatment.

FIG. 1A illustrates the current manual state of the art. Cells are taken from a bag or other storage or intermediate container and loaded into a syringe. This procedure involves making and breaking fluid connections in the room air which can compromise sterility, or requires a special biological enclosure to provide class 100 air for handling. The syringe is then connected to a patient interface or applicator, which is commonly a needle, catheter, or tubing that is then connected to a needle or catheter. For many procedures, there is some type of imaging equipment involved in guiding the applicator or effector to the correct part of the body. For example, the imaging equipment can include X-ray fluoroscopy, CT, MR, ultrasound, or an endoscope. The physician views the image and places the applicator by hand. In some neurological procedures, a stereotaxic (or stereotactic) positioner or head frame is used to guide the applicator to the target tissue, deep in the brain, based on coordinates provided by the imaging system. The patient physiological condition is often monitored for safety, especially when the patient is under general anesthesia.

As discussed briefly above, medical research has demonstrated utility of implantation of cells into the brain and central nervous system as treatment for neurodegenerative disorders such as Parkinson's, Alzheimer's, stroke, motor neuron dysfunction experienced, for example, by victims of spinal cord injury. As with other cell therapies, the mechanisms of repair are not well understood, but the injection of cells into damaged parenchymal tissue has been shown to recruit the body's natural repair processes and to regenerate new functional tissue as well as the cells themselves living and integrating into the tissue.

As with other cell delivery techniques described above, a long recognized, but unmet need in this field is a set of methods and devices that can provide precise, repeatable and reliable control of dosage of these therapeutic agents in actual clinical settings. Current manual approaches (as summarized above and in connection with FIG. 1A) do not address all of the needs required by new procedures. For example, there are no good methods for ensuring the parameters of cell viability, including spatial distribution, cell quantity, metabolic and electrical activity, in real time during the entire implantation procedure. These variables are affected by cell storage conditions, by the fluid dynamics of an injection (for example, flow, shear stresses or forces, fluid density, viscosity, osmolarity, gas concentration), by the biocompatibility of materials, and by the characteristics of surrounding tissues and fluids.

Deleterious effects of flow of cells through fluid paths are also not well addressed in current techniques. For example, Luer standard connectors are used almost universally in the current medical practice, including in fluid paths for cell delivery. An example of a lure standard connector 1 is show in FIG. 1B. FIG. 1B is taken from the standard ISO 594-1-1986, figure number 2. As the tapered sections of the male 1a and female 1b connectors mate, a dead space is created as indicated by 1c. In addition, the sharp transition in the fluid path at the end of the male luer, as indicated at 1d, can create turbulence and increase shear stress in the fluid and on the cells, resulting in cell damage or even death. Moreover, similar problems exist in commonly used fluid path elements other than connectors.

There are current methods for delivery of chemotherapeutic agents directly to the brain and other central nervous system structures (CNS) including, for example, convection enhanced delivery (CED) and other direct injection by needles, catheters, and syringes into CNS structures. These direct injections are an alternative to less effective intravenous drug delivery methods. Other approaches to drug delivery in the CNS include the placement of drug-impregnated hydrogel wafers (GLIADEL®) directly into brain tissue for extended periods of time after tumor excision. In the case of Parkinson's disease treatment, dopamine-producing cells are assembled onto gelatin beads (SPHERAMINE®, Titan Pharmaceuticals), which are hand-injected through precision syringes into the brain. The effectiveness of these methods is typically monitored long after initial treatment with non-invasive imaging (CT, MR).

Examples of systems and methods for convection enhanced delivery to the brain and other solid tissue structures is described in U.S. Pat. No. 5,720,720, the disclosure of which is incorporated herein by reference. Although the '720 patent discloses methods of injecting liquid medications based on a biomechanical model of tissue, it does not address problems unique to the delivery of complex slurries of fragile neural cells. U.S. Pat. No. 6,599,274, the disclosure of which is incorporate herein by reference, discloses methods of cell delivery to the brain using catheter injection systems. The distribution and function of therapeutic cells, growth factors, or other proteins are monitored by various techniques of imaging, physical, chemical, and electrical measurement. The '274 patent mentions closed loop, real-time control based on imaging and measured properties. However, the '274 patent does not describe how the elements of a controlled cell storage system work together with an injection system to guarantee delivery of viable cells of correct dosage and associated growth factors into tissues of the CNS. U.S. Pat. No. 6,758,828 describes a cell storage system for maintaining the viability of cells injected into tissue, but does not describe an integrated control system for monitoring the viability of cells as they enter the patient and take up residence in the parenchyma, nor does it describe how cell viability can be monitored in vivo.

U.S. Pat. No. 6,749,833 discloses methods to sustain the viability of cells by limiting damage resulting from shear stresses during fluid flow. An apparatus is described which allows for continuous bolus flow or peristaltic flow by reducing these shear forces. It is not clear from the '833 patent how the viability of cells is to be measured after delivery of the cells into living tissue. U.S. Pat. Nos. 6,572,579, 6,549,803 and 6,464,662 attempt to address the problem of distributing a dose of biologically active material into tissue by means of direct catheter injection.

In addition to application of cell therapies to internal tissues such a heart tissue, brain tissue and central nervous system tissue, cell therapies have also recently been applied to skin. Dermatologists have been injecting drugs into the skin for years. Recently injections of collagen, which can be thought of as a cell-less tissue, have become popular. Moreover, Intercytex of Cambridge UK has developed the ability to inject autologous dermal papilla cells for the growth of hair to treat baldness. The cells are harvested from a person, multiplied in culture, and then reimplanted into the same person. The implantation requires about 1000 injections of 1 microliter each.

Various aspect of delivery of agent to tissue and related aspects are also discussed in U.S. patent and U.S. Pat. Nos. 5,720,720, 5,797,870, 5,827,216, 5,846,225, 5,997,509, 6,224,566, 6,231,568, 6,319,230, 6,322,536, 6,387,369, 6,416,510, 6,464,662, 6,549,803, 6,572,579, 6,599,274, 6,591,129, 6,595,979, 6,602,241, 6,605,061, 6,613,026, 6,749,833, 6,758,828, 6,796,957, 6,835,193, 6,855,132, 2002/0010428, 2002/0082546, 2002/0095124, 2003/0028172, 2003/0109849, 2003/0109899, 2003/0225370, 2004/0191225, 2004/0210188, 2004/0213756, and 2005/0124975, as well as in, PCT Published International Patent Application WO2000/067647, EP1444003, the disclosures of which are incorporated herein by reference.

The present invention, along with the attributes and attendant advantages thereof, will best be appreciated and understood in view of the following detailed description taken in conjunction with the accompanying drawings.

SUMMARY OF THE INVENTION

In one aspect, the present invention provides a system for delivering a fluid comprising cells to tissue of a patient, including: at least a first container for holding an injection fluid in which the agent is carried; a first powered drive in operative connection with the container, the first powered drive being operable to pressurize contents of the container; a control system in operative connection with the first powered drive and operative to control the first powered drive; a fluid path in fluid connection with the container, the fluid path including a patient interface adapted to deposit the cells within tissue of the patient; a sensor system; and a communication system in connection with at least the control system and the sensor system. The communication system is adapted to provide information to the control system. The control system is adapted to transmit a control signal to at least the first powered drive based at least in part on information provided to the control system. The cells can for example be progenitor cells or stem cells.

The sensor system can include at least one tissue sensor system to measure a property of the tissue and at least one fluid sensor system to measure a property of the fluid to be delivered. The sensor system can includes at least one cell health sensor system to measure the health of the cells. The cell health sensor system can, for example, measure at least one of presence of at least one nutrients, atmosphere, temperature, pressure, cell integrity, cell death, cell count, chemical labeling, conductivity, optical fluorescence, optical scattering, at least one cell biomarkers, DNA content, optical density, UV spectroscopy, IR spectroscopy, at least one metabolic variable, at least one cell culture biomarker, at least one genetic identification, cell apoptosis, or cell senescence. The control system can be adapted to transmit a control signal to the first powered drive based at least in part on the measure of health of the cells from the cell health sensor system.

The system can further include a cell maintenance system adapted to affect at least one property of at least one of the injection fluid or the cells. The sensor system can at least one sensor in operative connection with the maintenance system to measure the value of the at least one property of the fluid or the cells. The controller system can be adapted to transmit a control signal based at least in part on the measured value of the measured property. The cell maintenance system can be in operative connection with the container. The cell maintenance system can additionally or alternatively be in operative connection with the patient interface.

The system can further includes a cell processing system.

In several embodiments, the sensor system includes at least one patient sensor system adapted to measure at least one physiological property of the patient. The communication system is in connection with the patient sensor system to provide information of the measured physiological property of the patient to the controller system. The controller system is adapted to transmit a control signal based at least in part on the measured physiological property of the patient. The value of the physiological property of the patient can, for example, be processed by the control system to transmit a signal to the first powered drive to time an injection. The physiological property of the patient can also be processed by the controller to transmit a signal to the first powered drive to alter an injection protocol. In certain embodiments, the physiological property of the patient is the position of a beating heart of the patient or a phase of a beating heart.

The at least one property of the patient can, for example, be related to mapping of a heart, characterization of tissue of a heart, characterization of a systolic or diastolic phase of a heart, a dynamic position of any portion of a beating heart, brain function, presence or absence of a neurotransmitter (for example, dopamine), EEG characterization, characterization of brain tissue (for example, determination of the presence of ischemic tissue associated with stroke), pancreatic function, presence or absence of hormone (for example, insulin) or islet cell function.

The system can further include an imaging system adapted to image a region of the patient to which the cells are delivered. The communication system can be in connection with the imaging system to provide information of a measured property from the imaging system to the control system. The control system can be adapted to transmit a control signal based at least in part on the measured property from the imaging system.

The sensor system can include one or more sensors to measure at least one property of the injection fluid that provides a measurement of shear forces on the cells. The sensor can, for example, measure fluid pressure or flow rate. The fluid path can be characterized to relate fluid pressure or flow rate to cell shear. The fluid path can include at least one indicator to provide information regarding the characterization of the fluid path to relate fluid pressure or flow rate to cell shear. The sensor system can include a sensor to read information from the fluid path indicator.

The system can also include a depth control mechanism in operative connection with the patient interface. The depth control mechanism can be adjustable to change a depth of penetration into the tissue of a penetrating member of the patient interface. The depth control mechanism can, for example, include an actuator in communication with the depth control mechanism. The actuator can adjust the depth control mechanism and thereby the depth of penetration into the tissue of the penetrating member at least in part on the basis of a control signal from the control system transmitted to the actuator. The sensor system can include a tissue thickness sensor and the control signal from the control system transmitted to the actuator is generated at least in part on the basis of a measurement of the thickness of the tissue. The tissue thickness sensor can, for example, include an ultrasound sensor.

The sensor system can include a sensor adapted to measure fluid diffusion characteristics or fluid bulk flow characteristics in an area of the tissue. The system can further comprising a memory in operative connection with the control system. The memory can, for example, have stored therein data of fluid diffusion characteristics or fluid bulk flow characteristics in an area of the tissue.

The system can include a sterile containment system encompassing at least the container and the first powered drive during an injection procedure. The first powered drive can be part of an injector adapted to be worn by a user. The injector can, for example, include an attachment system adapted to attach the powered injector to a user. The attachment system in several embodiments is adapted to attach the injector to the user's arm.

In several embodiment, the cell maintenance system includes an agitation system to create or maintain a degree of homogeneity of cell concentration within the carrier fluid. The cell maintenance system can, for example, include a system to control at least one of pH, temperature, light energy, pressure, nutrients or gases within the injection fluid. The cell maintenance system can be in operative connection with a fluid path between the pressurizable container and the patient. Likewise, the cell maintenance system can be in operative connection with a cell delivery system that delivers cells to the pressurizable container.

The container can, for example, include a moveable plunger therein. The container can encompass a flexible containment such that the containment can be at least partially collapsed to pressurize contents of the containment. In several embodiments, the container is adapted to be stored under reduced temperature to freeze the cells prior to being placed in operative connection with the first powered drive. The container can likewise be adapted to contain the cells during thawing and rinsing of the cell subsequent to freezing. The system can further include a valve system in fluid communication with an outlet of the container. The container can include a cell growth medium within the chamber.

The container can include at least one indicator providing information regarding the nature of the agent. The indicator can, for example, provide information on container contents, cell media requirements, cell maintenance requirements, cell growth requirements, cell type, cell volume, donor associated unique identifier, patient associated unique identifier, expiration information or cell count. The indicator can be adapted to communicate data to a controller system. The indicator can, for example, a barcode, a digital code, or an RFID.

The system can further include at least a second container for holding a second injection fluid. The system can also include a second powered drive to pressurize contents of the first container and the second container; the control system being in operative connection with the second powered drive. The second fluid can include a contrast medium adapted to enhance an image of a region of interest within the patient produced by an imaging system, a viscosity adjusting agent, a cell sustaining substance, a pushing fluid or a fluid adapted to create a cavity in tissue.

The system can further include a patient interface positioning system in operative connection with the patient interface, wherein the positioning system is adapted to position the patient interface for injection into the patient in response to a signal from the control system.

The patient interface can, for example, include a penetrating member adapted to penetrate tissue and at least one port in fluid communication with at least one lumen. The port is adapted to transport cells therethrough and into the tissue, the port having edges shaped to reduce shear. The port edges can, for example, be formed to have a radius of curvature. The port edges can extend inward within the lumen.

The patient interface can include at least one extending section having at least one lumen passing therethrough and at least one penetrating section having at least one passage therethrough in fluid connection with the lumen of the extending section and being adapted to penetrate tissue. The penetrating section can include at least one port in fluid communication with passage of the penetrating section. The penetrating section can be movable with respect to the extending section over a range of angles, wherein the passage remains in fluid connection with the lumen over the range of angles. The patient interface can include a connector in fluid connection between the extending section and the penetrating section, wherein the connector enables rotation of the penetrating member relative to the extending member about at least one axis.

The patient interface can include at least one penetrating section having at least one passage therethrough and at least one port on the penetrating section in fluid communication with passage. The patient interface can further include a backflow limiting mechanism to at least partially prevent backflow from the tissue upon injection of fluid into the tissue through the port. The backflow limiting mechanism can, for example, be an expandable frame member within the tissue, the backflow limiting mechanism in several embodiments limits backflow of cells but does not substantially limit backflow of a carrier fluid in which cells are carried. For example, the backflow limiting mechanism can include a porous filter in operative connection with a source of vacuum, the pores of the filter being sized to exclude passage of cells therethrough but to all passage of carrier fluid therethrough.

In several embodiments, a blocking mechanism exerts force on the tissue to close the tissue around an injection opening formed by the penetrating member. The backflow limiting mechanism can, for example, include a colet member that can be opened and closed to exert a radially inward force on the tissue around the injection opening.

The backflow mechanism can include at least one penetrating member spaced from the at least one port via which a vacuum is applied. For example, to draw fluid injected via a penetrating member or need through the tissue to distribute the fluid throughout the tissue.

The patient interface can include at least one penetrating section having at least one passage therethrough and at least one port on the penetrating section in fluid communication with passage. The patient interface further includes a cavity creation mechanism in operative connection with penetrating section. The cavity creation mechanism includes an effector adapted to open at least one volume within tissue into which fluid can be injected through the port, wherein the effector comprises a pressurizing mechanism adapted to open the volume by injection of pressurized fluid. The system can further include a source of vacuum to remove at least a portion of the fluid used in cavity creation.

In several embodiments, a depth control mechanism of the present invention includes a sensor to measure depth of penetration and a limiter adapted to stop penetration based at least in part upon the measure depth of penetration.

A depth control mechanism can, for example, include an abutment surface axially movable relative to the penetrating member and a position adjustment mechanism adapted to adjust the position of the abutment surface relative to a forward end of the penetrating member. The adjustment can include a first position setting member biased in connection with a second position setting member, wherein a force can be applied to the first positioning member to remove the first positioning member from connection with the second positioning member to allow adjustment of the position of the abutment surface. The adjustment mechanism can, for example, be a rack mechanism.

Another depth control mechanism includes an abutment surface axially movable relative to the penetrating member and a position adjustment mechanism adapted to adjust the position of the abutment surface relative to a forward end of the penetrating member. The adjustment mechanism includes at least one actuator adapted to effect rotation a stop mechanism in operative connection with the abutment surface. The stop mechanism havs stop indices about its circumference corresponding to different positions of the abutment surface. Each activation of the actuator can cause the stop to rotate to the next stop index corresponding to a different position of the abutment surface than the previous stop index.

In another embodiment of a depth control mechanism of the present invention, an abutment surface is movable relative to the penetrating member and a position adjustment mechanism is adapted to adjust the position of the abutment surface relative to a forward end of the penetrating member. The adjustment mechanism includes a wheel having an eccentric axis of rotation. The penetration member can, for example, be in operative connection with the wheel and be axially movable relative to the abutment surface upon rotation of the wheel. A portion of the wheel can form the abutment surface.

The patient interface of the system of the present invention can include at least one penetrating section encompassing the agent and a force applicator in connection with the penetrating section. The penetrating section is disconnectable from the force applicator such that the penetrating section remains within the tissue upon disconnection from the force applicator.

The patient interface can include at least one penetrating section having at least one passage therethrough and at least one port on a side of the penetrating section in fluid communication with passage. The port can be an elongated opening dimensioned to provide a forward element to radially outward flow emanating therefrom. The elongated opening can have an length in the axial direction of the penetrating member greater than a width of the elongated opening. The penetrating section can include a plurality of ports, wherein each of the plurality of ports includes an elongated opening dimensioned to provide a forward element to radially outward flow emanating therefrom. In one embodiment, the penetrating section includes at least two ports positioned on the side of the penetrating section. The two ports are positioned at a first axial position on the penetrating member and are positioned at different positions about the circumference of the penetrating section. The two ports can differ in position about the circumference of the penetrating section by approximately 180°. The penetrating section can also include at least two other ports. The two other ports can be at a second axial position, different from the first axial position, on the penetrating member. The two other ports can also be at different positions about the circumference of the penetrating section. The two other ports can, for example, differ in position about the circumference of the penetrating section by approximately 180°.

The two ports can differ in position about the circumference of the penetrating section by approximately 180° and be offset from the positions about the circumference of the penetrating section of the other two ports.

The sensor system of the present invention can include at least one pressure sensor to measure pressure in the fluid path, and the controller can be adapted to determine if the measure pressure is above a threshold pressure, wherein the threshold pressure is related to shear damage of the cells in the fluid path. The system can further include an indicator providing an indication that the pressure threshold has been reached. The controller can be adapted control at least one aspect of the injection procedure based upon a signal corresponding to the measured pressure provided to the controller.

The fluid path of the system can, for example, include a connector including a first port to connect to a first fluid path element and a second port to connect to a second fluid path element. The connector can provide for a gradual transition between a first inner diameter of the first fluid path element and a second inner diameter of the second fluid path element. The first fluid path element can, for example, be a connective tubing having a outlet with the first inner diameter that is approximately equal to the second inner diameter. A compression seal can be formed between the outlet and second fluid path element. An intermediate element can have a first port having a first opening of approximately the same size as the first inner diameter, a second opening of approximately the same size as the second inner diameter, and a region of transition between the first opening and the second opening. The intermediate member can be movable within the connector and be biased in connection with at least one of the first fluid path element or the second fluid path element upon connection.

In another embodiment, the second opening of the intermediate member can also positioned upon a projecting member that is adapted to be placed within the second inner diameter of the second fluid path element.

The control system of the present invention can, for example, be adapted to time an injection based upon information from the contact sensor.

In several embodiments of the present invention, a predetermined amount of capacitance is built into the fluid path.

In another aspect, the present invention provides a syringe for injection of a fluid including an abutment element adapted to prevent substantial mating of a forward surface of a syringe plunger slidably positioned with in the syringe with a transition region of the syringe wherein the radius of the syringe is reduced. For example, the plunger can have a different angle of taper than an angle of taper of the transition region and the abutment element can be a portion of the forward surface of the plunger.

In another aspect, the present invention-provides system for delivering cells to a patient, including: a container for holding a pressurizing fluid; a drive member in operative connection with the container to pressurize the pressurizing fluid; and a delivery vessel in fluid connection with the container via a length of conduit such that pressurization of the pressurizing fluid causes delivery of the cells from the delivery vessel. The delivery vessel (for example, a needle or a syringe) can be in operative connection with a stereotactic positioning frame.

In a further aspect, the present invention provides an agent for injection into a patient including a detectible encoded element that provides information regarding the agent. The encoded element can, for example, be a detectible physiochemical entity. The physiochemical entity can be bound to a component of the agent. The physiochemical entity can alternatively or additionally bound to a carrier fluid molecule or to a cell within the carrier fluid. The encoded element can also be a bulk physiochemical characteristic of the agent. For example, the encoded element can be color. More than one encoded element can be included within the agent. An injector or other component of an injection system can include at least one sensor to detect the encoded element as described above.

In another aspect, the present invention provides an injection system for delivery of an injection fluid comprising cells including a fluid path through which the injection fluid flows, wherein the fluid path is adapted to reduce shear forces upon cells. Transitions between connected fluid path elements can, for example, be made without substantially sudden changes in inner diameter. The injection system can further include at least one fitting connectible between a first fluid path element having a first inner diameter and a second fluid path element having a second inner diameter, wherein the fitting is adapted to effect a transition of inner diameter between the first inner diameter and the second inner diameter. The fitting can include an elastomeric element adapted to assist in effecting the transition.

In a further aspect, the present invention provides an injection system for delivery of fluid to a patient including: an injector, the injector comprising; a container; a drive member in operative connection with the container and being adapted to pressurize the contents of the container; and an attachment system adapted to attach the injector to the user. The injector system can further include a patient interface in fluid connection with the container. The patient interface is adapted to be held in the hand of the user during an injection procedure.

In a further aspect, the present invention provides an injection system including a container in operative connection with a drive member. The drive member is adapted to pressurize fluid within the container. The injector system further includes a fluid path in fluid connection with an outlet of the container and an expandable volume in fluid connection with the fluid path. The expandable volume is adapted to expand upon the fluid reaching a predetermine pressure. The injector system further includes a patient interface in fluid connection with the expandable volume. The expandable volume can, for example, be formed by a container having a port in fluid connection with the fluid path, the container having a moveable sealing element disposed therein. The sealing element can be biased such that the sealing element does not substantially move until the predetermined pressure had been reached. The sealing element can include a plunger. The plunger can be biased by a spring.

In still a further aspect, the present invention provides a system for delivering a fluid including an cells to tissue of a patient, including: at least a first container for holding an injection fluid in which the cells are carried; a first powered drive in operative connection with the container, the first powered drive being operable to pressurize contents of the container; a control system in operative connection with the first powered drive and operative to control the first powered drive; a fluid path in fluid connection with the container, the fluid path including a patient interface adapted to deposit the cells within tissue of the patient; a sensor system comprising at least one cell sensor system to measure a property indicative of the health of the cells; and a communication system in connection with at least the control system, the tissue sensor system and the agent sensor system being adapted to provide information to the control system, the control system being adapted to transmit a control signal to the first powered drive based at least in part on information provided to the control system. In several embodiments, the cell sensor system can, for example, be adapted to measure cell viability. The cell sensor system can also be adapted to measure at least one of cell count, cell viability, temperature, pH, concentration, pressure or flow rate.

The present invention also provides methods of use of the systems and devices of the present invention as well as methods of manufacture of the systems and devices of the present invention.

Although various devices, systems and methods have been developed for delivery of agents, including therapeutic agent, to various types of tissue, it remains desirable to develop improved devices, systems and methods for delivering agents to tissue and, particularly, for delivering therapeutic cells to tissue.

BRIEF DESCRIPTION OF THE DRAWINGS

FIG. 6A illustrates a side view of and embodiment of a needle hub and needle of the present invention.

FIG. 6B illustrates a perspective view of the needle hub and needle of FIG. 6A.

FIG. 6C illustrates an enlarged side view of the tip of the needle of FIG. 6A.

FIG. 7A(1) illustrates an embodiment of a patient interface of the present invention including anchor or stabilization members.

FIG. 7A(2) illustrates another embodiment of a patient interface of the present invention including anchor or stabilization members both disconnected from and connected to tissue.

FIG. 7D(1) illustrates an embodiment of a system of the present invention including a patient interface of the present invention including an expanding anchor or stabilization member.

FIG. 7D(2) illustrates the patient interface of FIG. 7D(1) in which the expanding stabilization member is in an expanded and a contracted state.

FIG. 7D(3) illustrates another embodiment of a patient interface of the present invention in which an expanding stabilization member is in an expanded and a contracted state.

FIG. 7D(4) illustrates another embodiment of a patient interface of the present invention in which an expanding stabilization member is in an expanded and a contracted state.

FIG. 7D(5) illustrates another embodiment of a patient interface of the present invention in which an expanding stabilization member is in an expanded and a contracted state.

FIG. 7H(1) illustrates another embodiment of a patient interface of the present invention including movable penetrating members or needles which grasp tissue in a pincer like fashion.

FIG. 7H(2) illustrates another embodiment of a patient interface of the present invention in which a curved penetrating members or needles is used to stabilized the penetrating member in tissue.

FIG. 7H(3) illustrates another embodiment of a patient interface of the present invention in which a plurality of curved penetrating member of needle is used to stabilized the penetrating member in tissue.

FIG. 7L illustrates another embodiment of a patient interface of the present invention in which an adhesive surface is used to anchor or stabilize the patient interface and in which the patient interface marks a tissue area where an injection has (for example, via an array of needles) occurred.

FIG. 7L(1) illustrates an embodiment of a device of the present invention including a flexible cover including a hydrophilic layer that is adapted to adhere (without an adhesive or glue thereon) to a moist surface of tissue.

FIG. 7M illustrates an embodiment of a patient interface of the present invention in which contact with tissue causes initiation of an injection process.

FIG. 9A(1) illustrates a side cutaway view of another embodiment of a patient interface of the present invention including a movable depth control mechanism.

FIG. 9A(2) illustrates a top view of the patient interface of FIG. 9A(1).

FIG. 9A(3) illustrates a perspective view of a patient interface device of the present invention including a movable or adjustable depth control mechanism and flattened areas suitable for grasping the patient interface.

FIG. 9A(4) illustrates a top view and a side cutaway view (bottom of FIG. 9A(4)) of another embodiment of a patient interface of the present invention in which a depth control mechanism is movable or adjustable.

FIG. 9A(5a) illustrates a perspective view of another patient interface device of the present invention including a movable or adjustable depth control mechanism.

FIG. 9A(5b) illustrates a side partially cutaway view of the patient interface device of FIG. 9A(5a).

FIG. 9A(5c) illustrates a side cutaway view of the patient interface device of FIG. 9A(5a).

FIG. 9A(5d) illustrates a perspective exploded view of the patient interface device of FIG. 9A(5a) wherein the top housing portion is shown in both a bottom and a top perspective view.

FIG. 9B(1) illustrates a transparent view of another embodiment of a patient interface of the present invention in which depression of an actuating button causes incremental changes in the position of a depth control mechanism as well as an embodiment of an incrementally adjustable depth stop element for use therewith in a flattened view.

FIG. 9B(2) illustrates an embodiment of a patient interface device of the present invention including an adjustable depth control device comprising a rotating member mounted on an eccentric axle.

FIG. 9B(3) illustrates an embodiment of a patient interface device of the present invention including an adjustable depth control device including a rotating member mounted on an eccentric axle wherein the rotating member is in a fully forward state, minimizing penetration depth.

FIG. 9B(4) illustrates the patient interface device of FIG. 9B(3) wherein the rotating member is in a fully rearward state, maximizing penetration depth.

FIG. 9C illustrates an embodiment of a patient interface including an adjustable annular member surrounding the penetrating member or needle.

FIG. 9D illustrates an embodiment of a patient interface including a removable depth control mechanism.

FIG. 9G(1) illustrates a side cutaway view of an embodiment of a patient interface including an adjustable depth control mechanism.

FIG. 9G(2) illustrates a perspective view of another embodiment of a patient interface including an adjustable depth control mechanism including a sheath surrounding the penetrating member or needle that is rotatable on a needle hub to adjust the position of the sheath relative to the needle.

FIG. 10D(1) illustrates an embodiment of a device of the present invention in which a film is used to limit back flow.

FIG. 12I illustrates a luer-type fitting or connector of the present invention that provides for relatively smooth transitions and low fluid loss.

FIG. 12J illustrates another luer-type fitting or connector of the present invention that provides for relatively smooth transitions and low fluid loss.

FIG. 12K illustrates another luer-type fitting or connector of the present invention that provides for relatively smooth transitions and low fluid loss.

FIG. 12L illustrates another luer-type fitting or connector of the present invention that provides for relatively smooth transitions and low fluid loss.

FIGS. 12L (1), 12M and 12N illustrate embodiments of a needle in various configurations.

FIG. 12M illustrates an embodiment of a needle wherein the interior circumference of the needle hole is rounded.

FIG. 12N illustrates a needle with dimpled injection side holes or ports.

FIG. 13N illustrates a rear view of the syringe of FIG. 13J.

FIG. 13O illustrates an embodiment of an injector or delivery system of the present invention.

FIG. 13P illustrates a pressure profile of the system of FIG. 13O with system capacitance wherein the patient interface is positioned within tissue.

FIG. 13Q illustrates a pressure profile of the system of FIG. 13O with system capacitance wherein the patient interface is removed from tissue.

FIG. 13R illustrates an embodiment of a delivery system or applicator of the present invention in which a generally solid component, element or plug is placed within tissue.

FIG. 14A illustrates a schematic diagram of three fluid path in operative connection as concentric cylinders.

FIG. 14B illustrates a simple fluid path including one fluid path element and one fluid path.

FIG. 14C illustrates a fluid path including two fluid path elements.

FIG. 14D illustrates another fluid path including two fluid path elements.

FIG. 14E illustrates a fluid path in which injectate is pulled back a first fluid path while a purging or physiological solution is injected at the same flow rate down a second fluid path.

FIG. 14F illustrates the fluid path elements of FIG. 14A, with an exemplary fluid flow indicated.

FIG. 15A illustrates an embodiment of an injection system of the present invention in which a disposable container or syringe can be snapped securely and reliably into place with an injector in a simple, two-step operation.

Figure 15A:
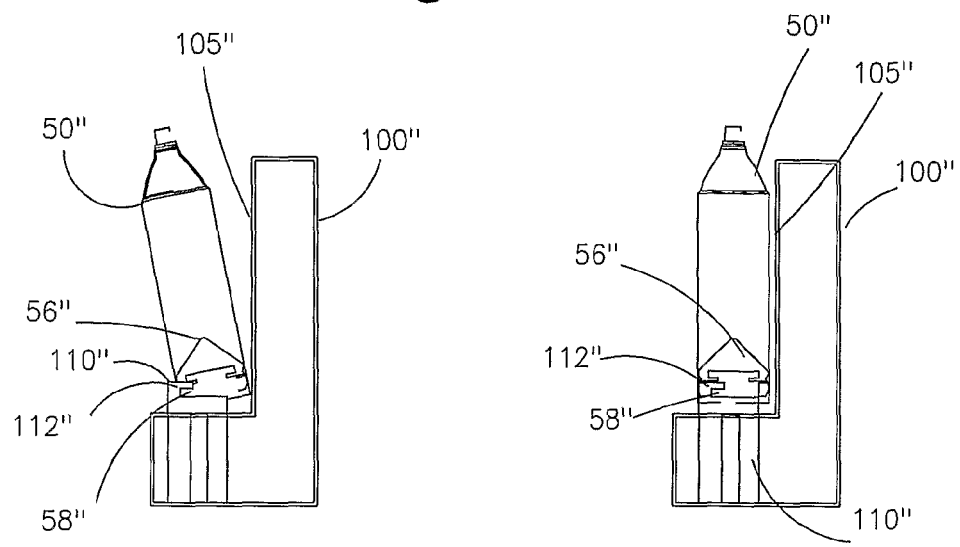
Figure 15B:
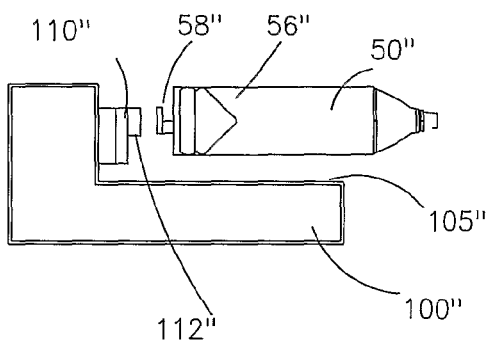
Figure 15B:
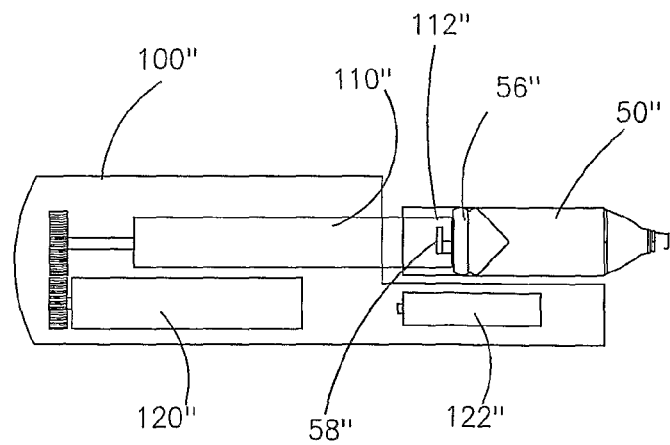

FIG. 15B illustrates a cutaway view of the injector system of FIG. 15A showing the motor and battery power supply.

Figure 15C:
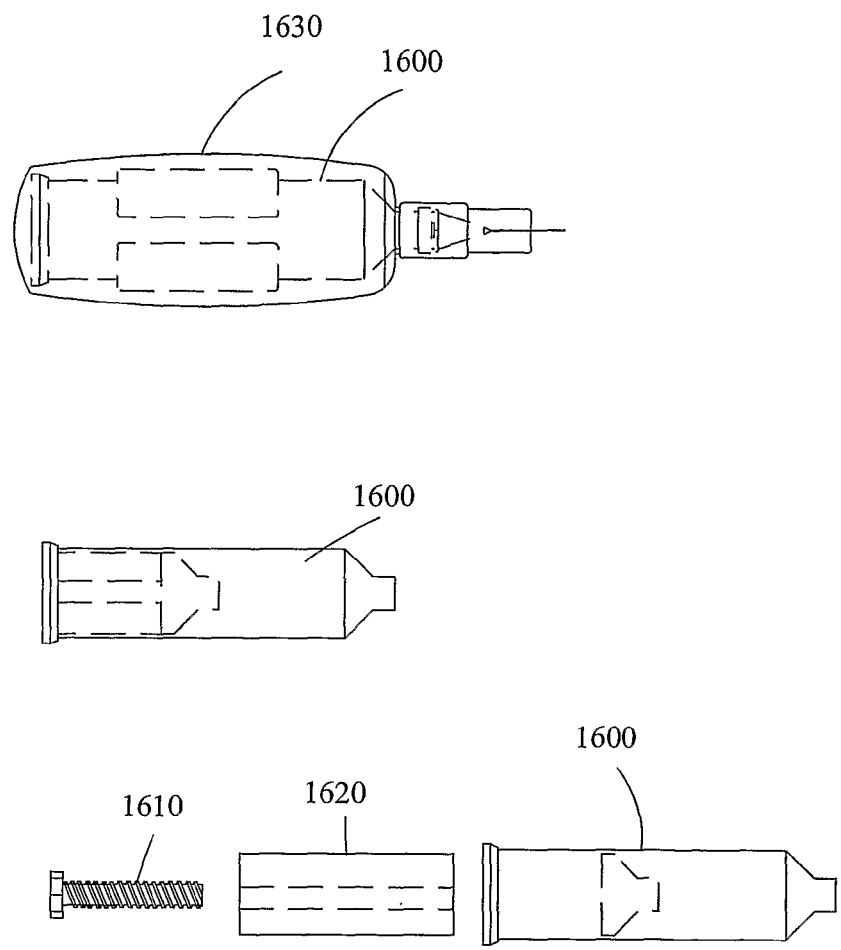

FIG. 15C illustrates another embodiment of an injector system of the present invention.

Figure 15D:
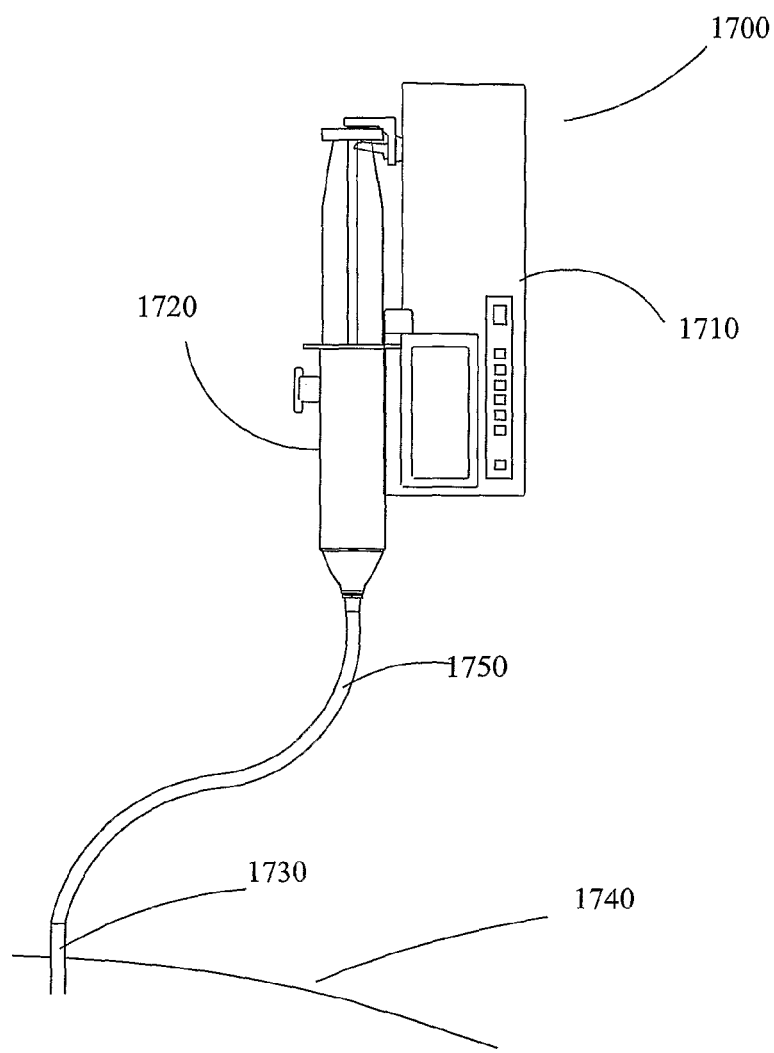

FIG. 15D illustrates an embodiment of an injection or fluid delivery system of the present invention for use, for example, in connection with a stereotactic localization frame.

Figure 15E:
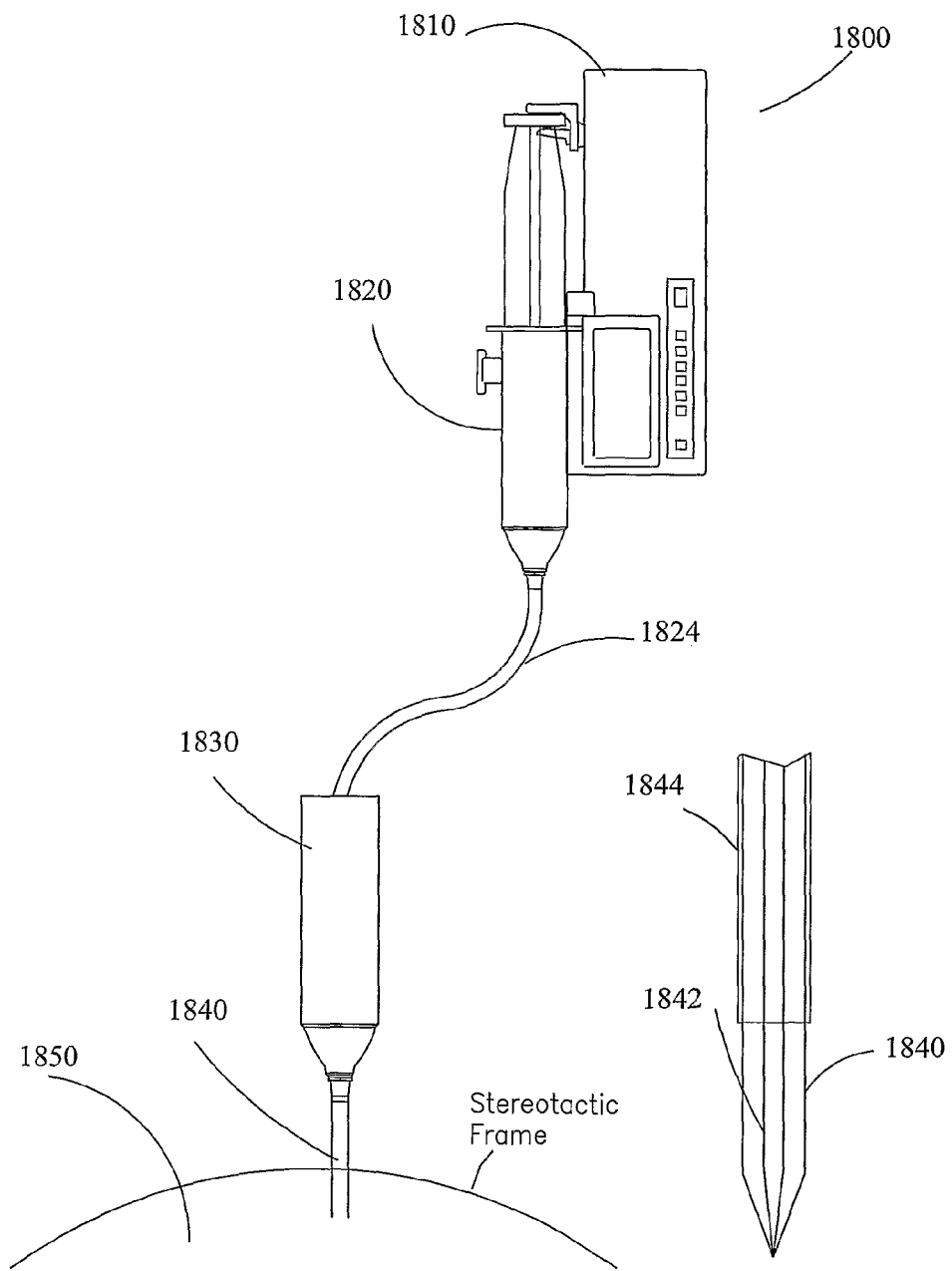

FIG. 15E illustrates another embodiment of an injection or fluid delivery system of the present invention for use, for example, in connection with a stereotactic localization frame.

FIG. 16A illustrates an embodiment of a handheld switch or control assembly for use with an injector system.

FIG. 16B illustrates the switch or control assembly of FIG. 16A in operative connection with the injector system of FIG. 15A.

FIG. 16C illustrates the injector system of FIG. 15A as worn on the arm of an operator, wherein a sterile barrier surrounds the injector system.

FIG. 16D illustrates the injector system of FIG. 16A adapted to be worn on the body of an operator.

FIG. 16E illustrates the injector system of FIG. 15A including embodiment of control and display panels.

FIG. 16F illustrates an embodiment of a head mounted display for use in connection with the injection systems of the present invention.

Figures 17A, 17N:
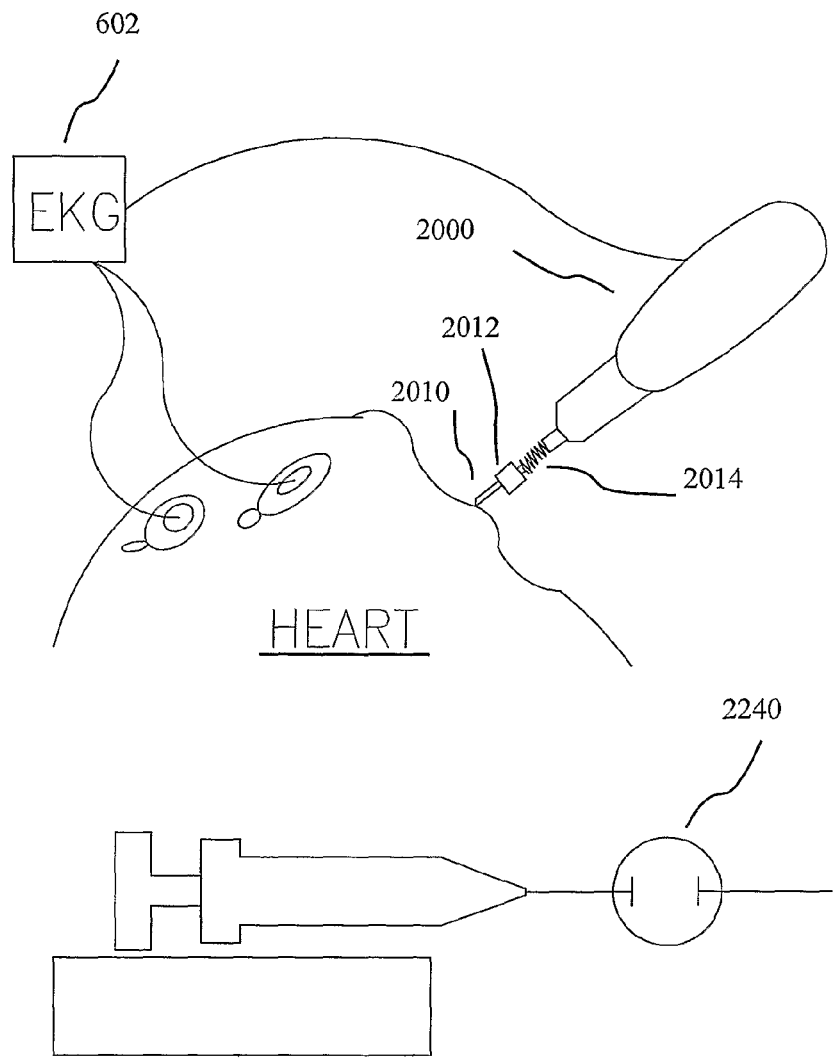

FIG. 17A illustrates an embodiment of system of the present invention in which an electrocardiogram (EKG) can be used to measures heart movement and synchronize injection.

Figure 17B:
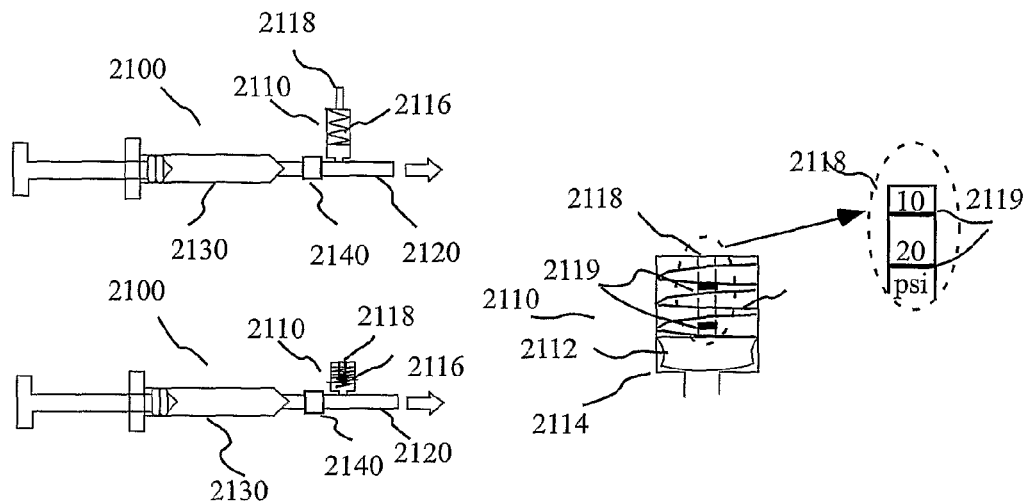

FIG. 17B illustrate an embodiment of a device of the present invention in which an indicator such as a pop-up indicator (for example, a pop-up needle) in fluid connection with a patient interface pops up once a certain threshold pressure is reached.

Figure 17C:
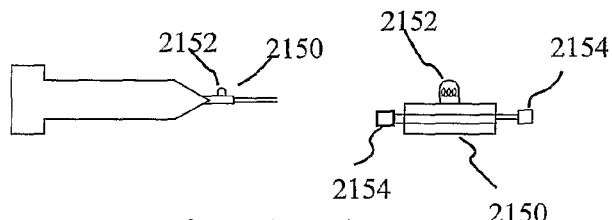

FIG. 17C illustrates the use of a disposable pressure transducer, pressure sensor or pressure switch with an indicator to indicate a certain pressure level.

Figure 17D:
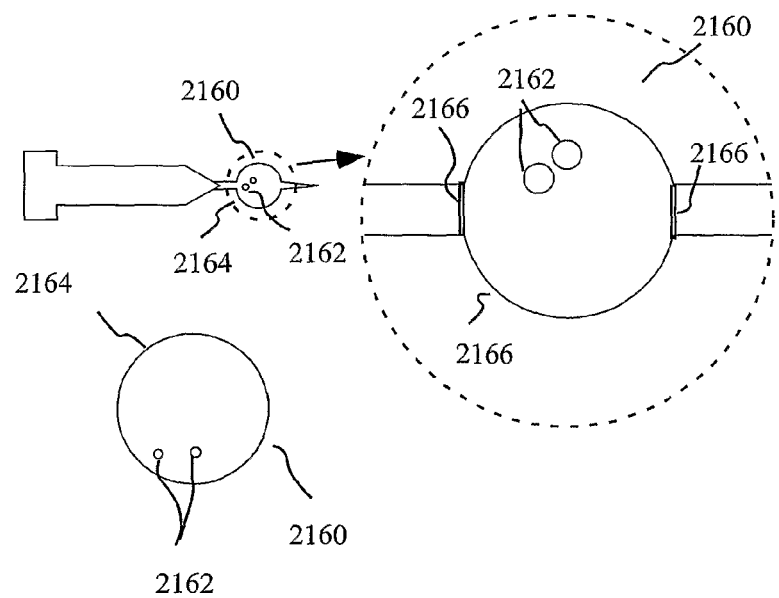
Figure 17E:
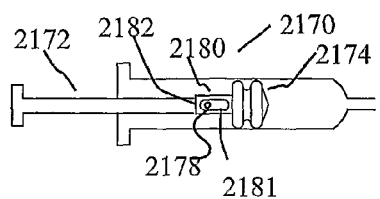

FIG. 17D illustrates a pressure measuring device of the present invention including floating balls (or other indicator elements) in a transparent flow path element or housing that compress and sink (as a result of an increase in density) as pressure increases.

FIGS. 17E through 17H illustrates an embodiment of a syringe device of the present invention including a spring-loaded (or otherwise biased) rubber cover in operative connection with a plunger (which is slidably disposed within the syringe barrel) to measure force/pressure within the syringe barrel mechanically.

Figure 17G:
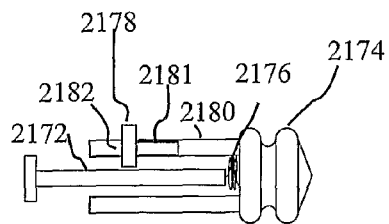
Figure 17F:
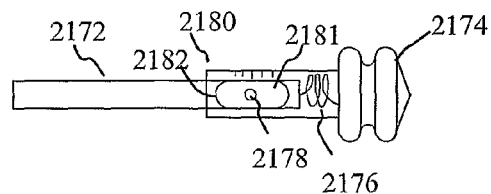
Figure 17H:
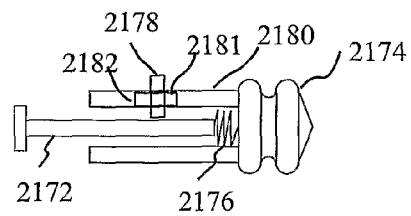
Figure 17I:
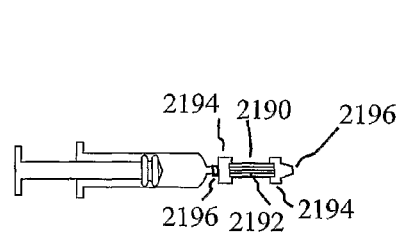
Figure 17J:
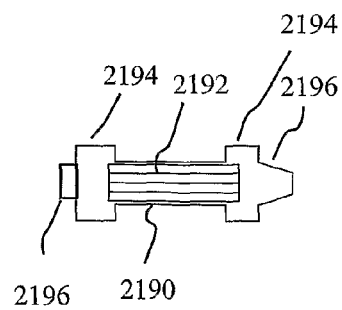
Figure 17K:
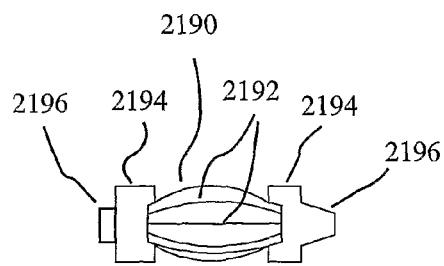

FIGS. 17I through K embodiments of fluid path elements of the present invention including elastic tubing in the fluid path that is, for example, colored on the outside and expands with increasing pressure.

Figure 17L:
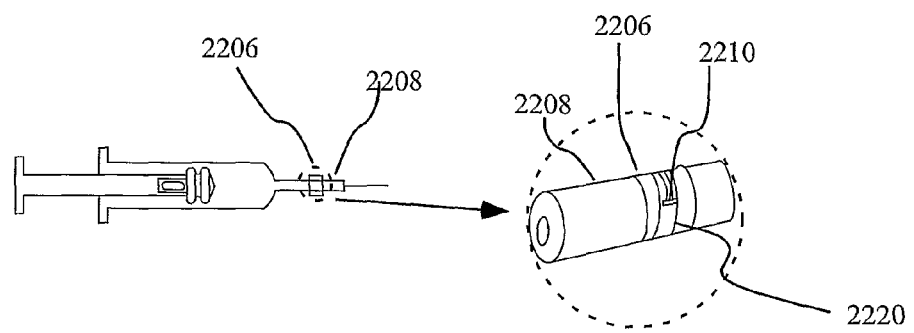
Figure 17M:
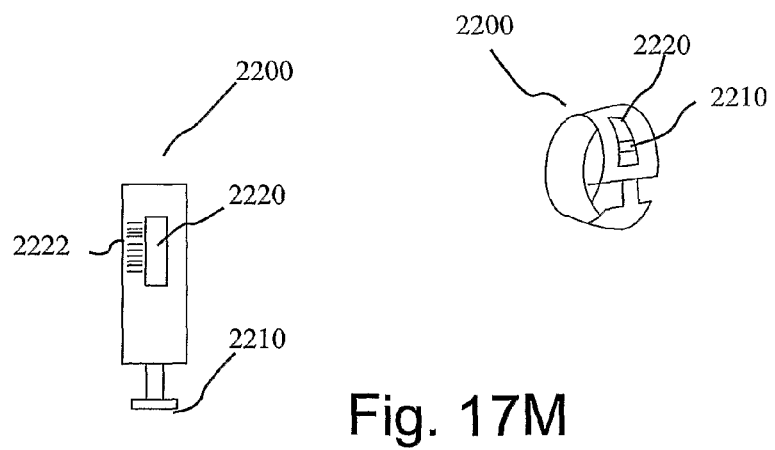

FIGS. 17L through 17M an embodiment of a graduated ring that encompasses an expandable tubing device as, for example, described in connection with FIGS. 17I through K to provide an indication of pressure.

FIG. 17N illustrates an embodiment of a system of the present invention in which a flow meter with a known internal diameter is used to provide a measurement of flow and/or pressure.

Figure 17O:
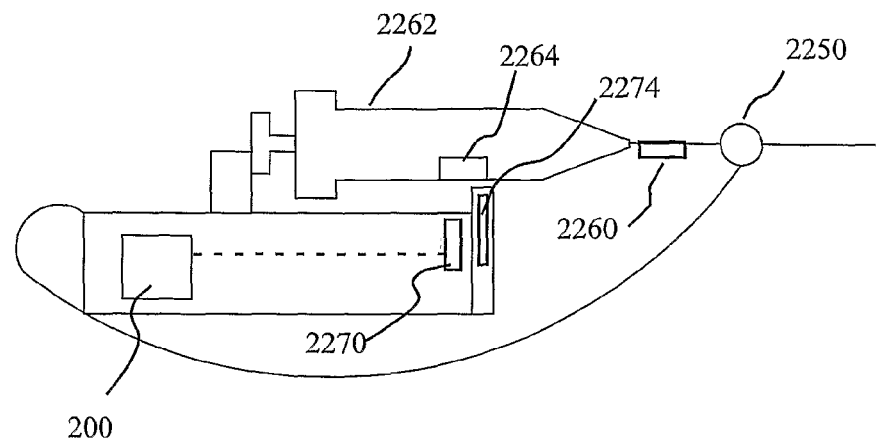

FIG. 17O illustrates the use of one or more pressure transducers to measure pressure and to feed back pressure data to a control system.

Figure 17P:
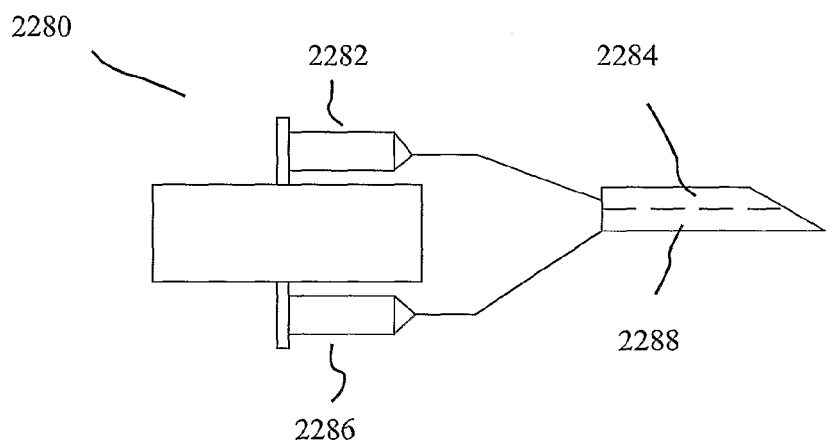

FIG. 17P illustrates a system of the present invention that is adapted to inject a sequence of fluids, for example, at increasing pressure, to drive cells deeper into tissue.

Figure 17Q:
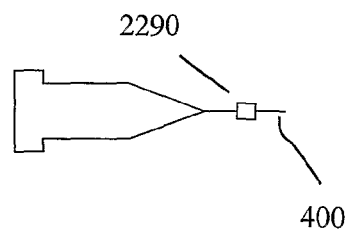

FIG. 17Q illustrates the user of a membrane filter or other control device in fluid connection with a patient interface that will allow fluid to pass only upon buildup of a certain pressure.

Figure 17R:
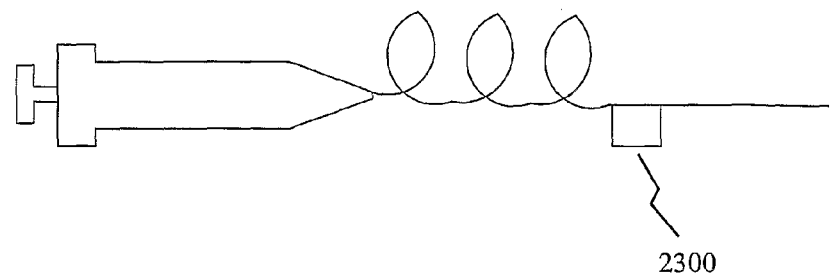

FIG. 17R illustrates use of one or more ultrasonic flow transducers (for example, using the coraolis effect) to measure flow and to assist in break up of clumps.

Figure 17S:
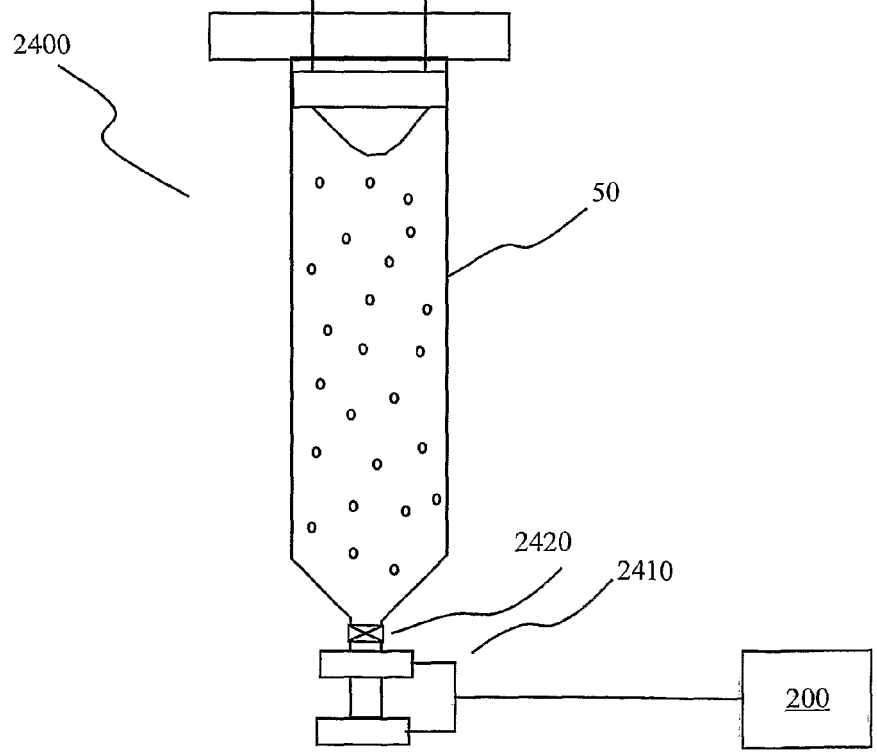

FIG. 17S illustrates an embodiment of a system of the present invention including one or more density measuring devices (based, for example, on the Coriolis effect) in operative connection a container, a fluid path conduit and/or patient interface 400.

Figure 18A:
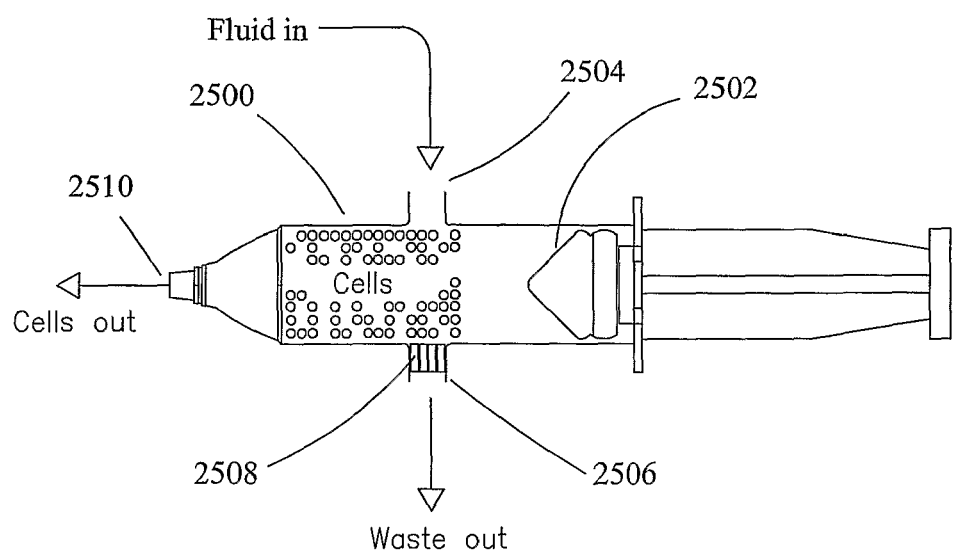

FIG. 18A illustrates an embodiment of a device of the present invention adapted to effect fluid introduction to cells, fluid removal from cells and cell injection.

Figure 18B:
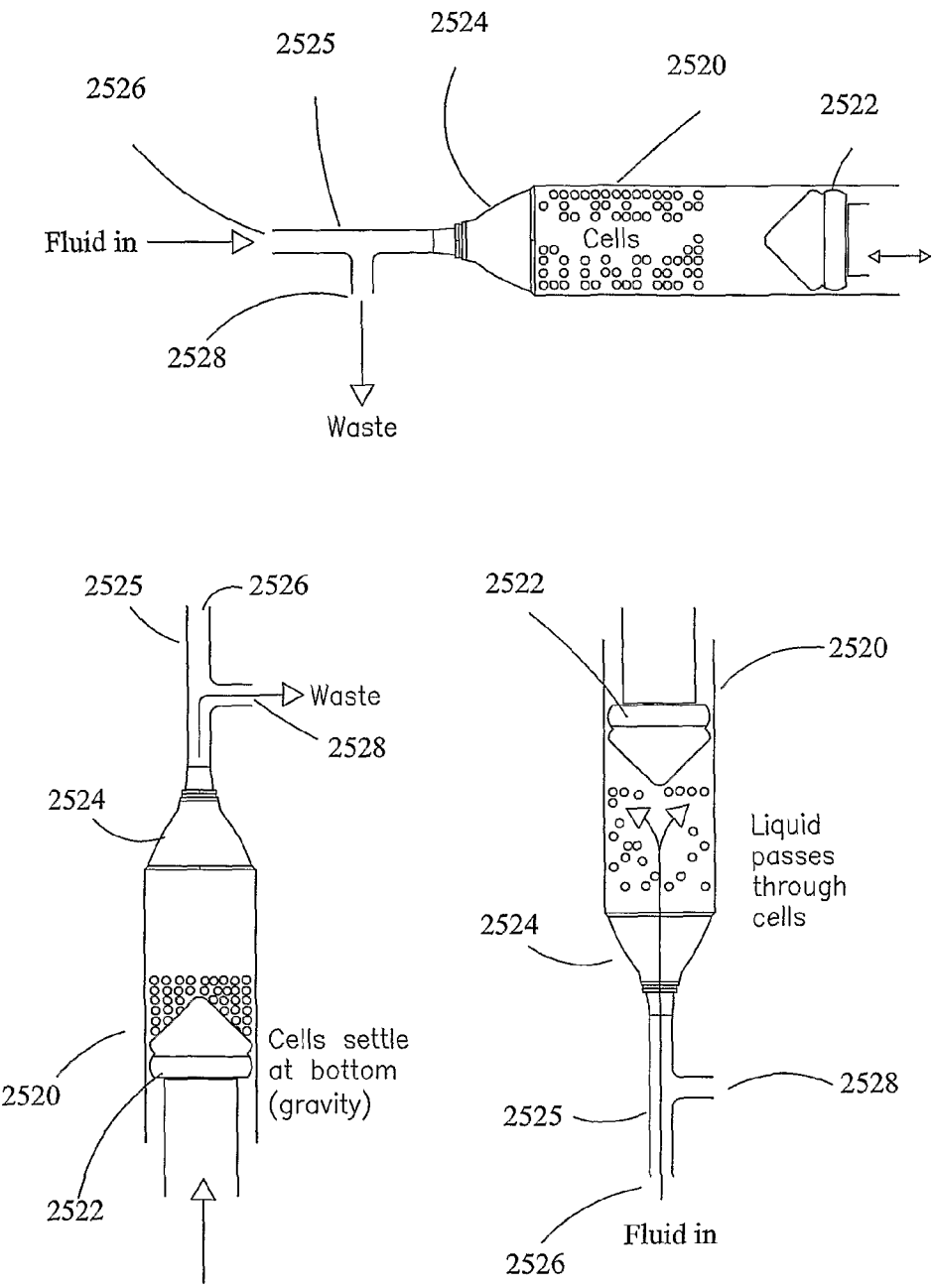

FIG. 18B illustrates another embodiment of a device of the present invention adapted to effect fluid introduction to cells, fluid removal from cells and cell injection.

Figure 18C:
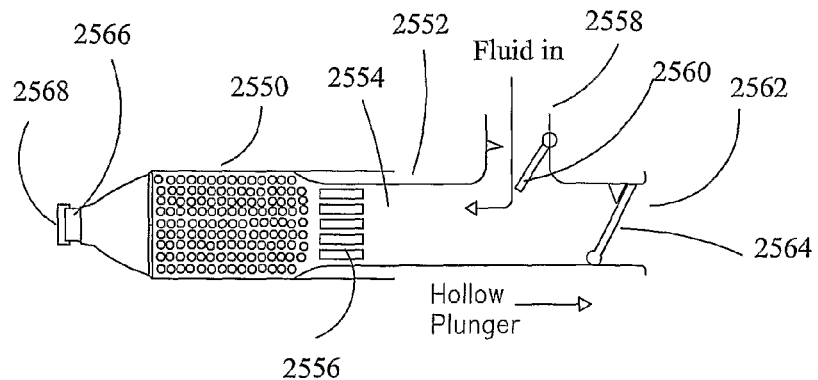

FIG. 18C illustrates another embodiment of a device of the present invention adapted to effect fluid introduction to cells, fluid removal from cells and cell injection wherein buffer or other fluid is being drawn into the device.

Figure 18D:
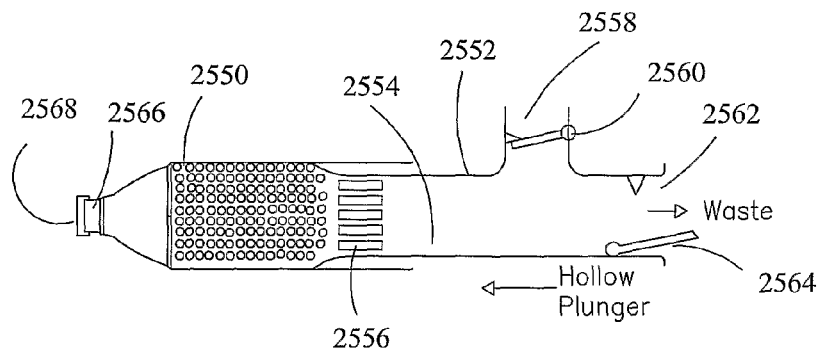

FIG. 18D illustrates the device of FIG. 18C wherein waste is being expelled from the device.

Figure 18E:
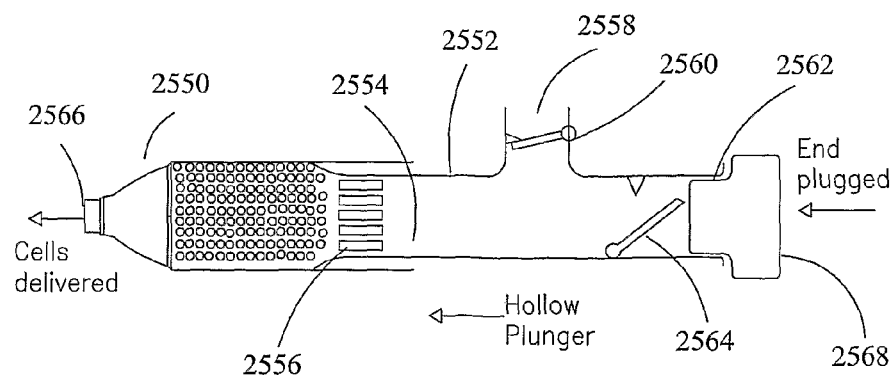

FIG. 18E illustrates the device of FIG. 18C wherein cells are being delivered from the device.

Figure 18F:
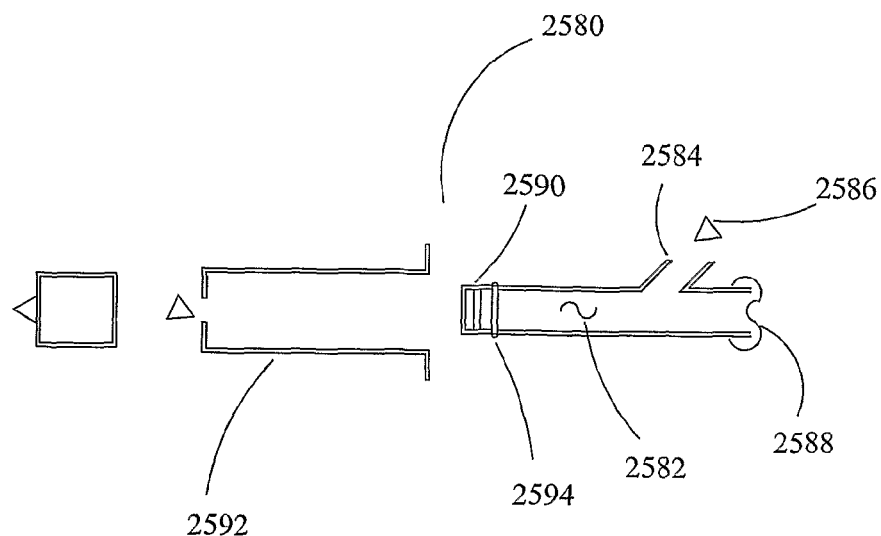

FIG. 18F illustrates another embodiment of a device of the present invention adapted to effect fluid introduction to cells, fluid removal from cells and cell injection wherein buffer or other fluid is being drawn into the device.

Figure 18G:
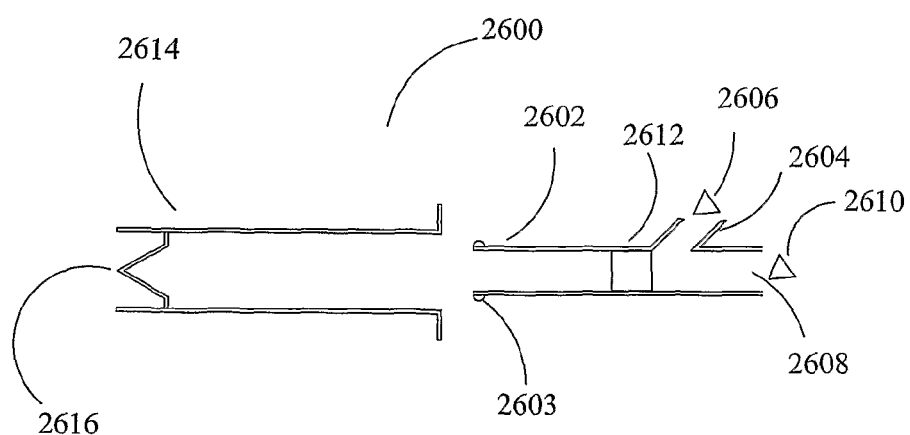

FIG. 18G illustrates another embodiment of a device of the present invention adapted to effect fluid introduction to cells, fluid removal from cells and cell injection wherein buffer or other fluid is being drawn into the device.

Figure 18H:
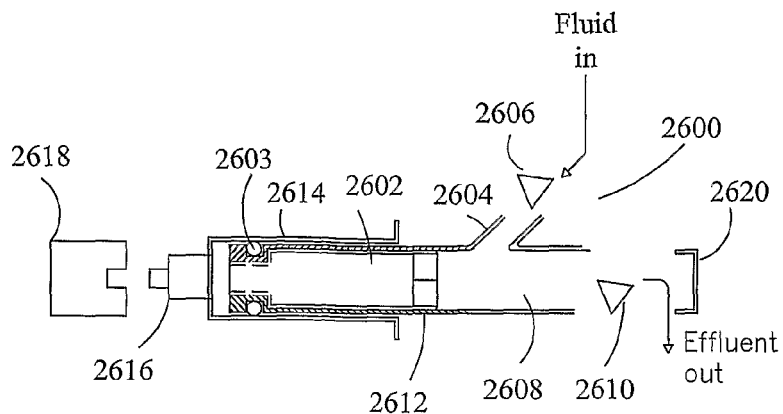

FIG. 18H illustrates the device of FIG. 18G in which the cell chamber is in operative connection with the housing or cylinder.

Figure 18I:
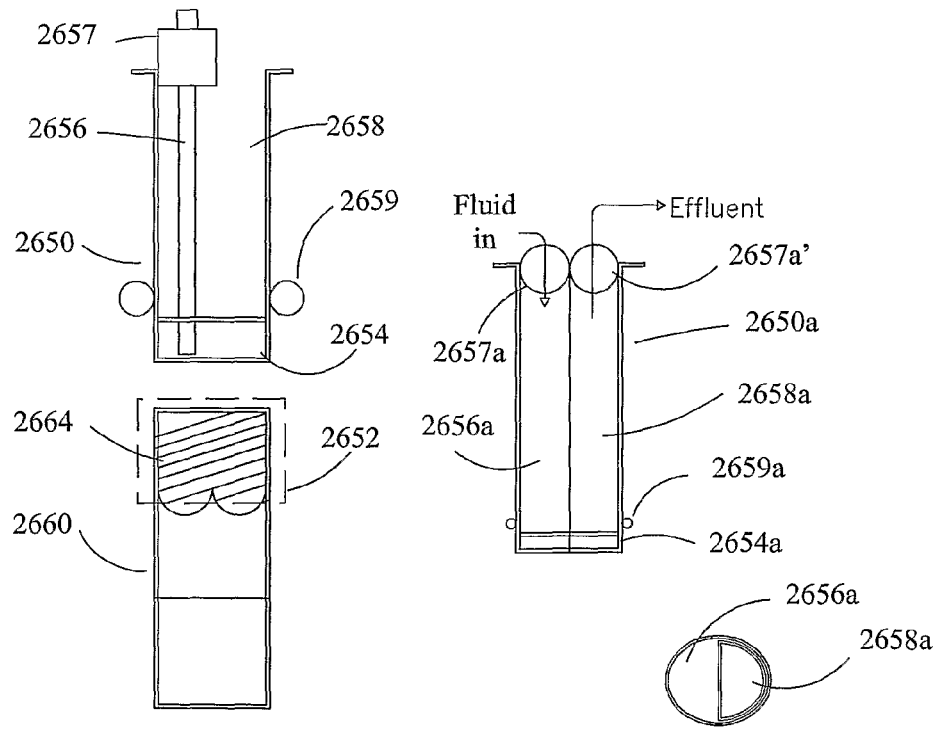

FIG. 18I illustrates an embodiment of a plunger system operable to effect fluid introduction to cells, fluid removal from cells and cell injection in a standard vial such as a cryovial.

DETAILED DESCRIPTION OF THE INVENTION

Figure 2:
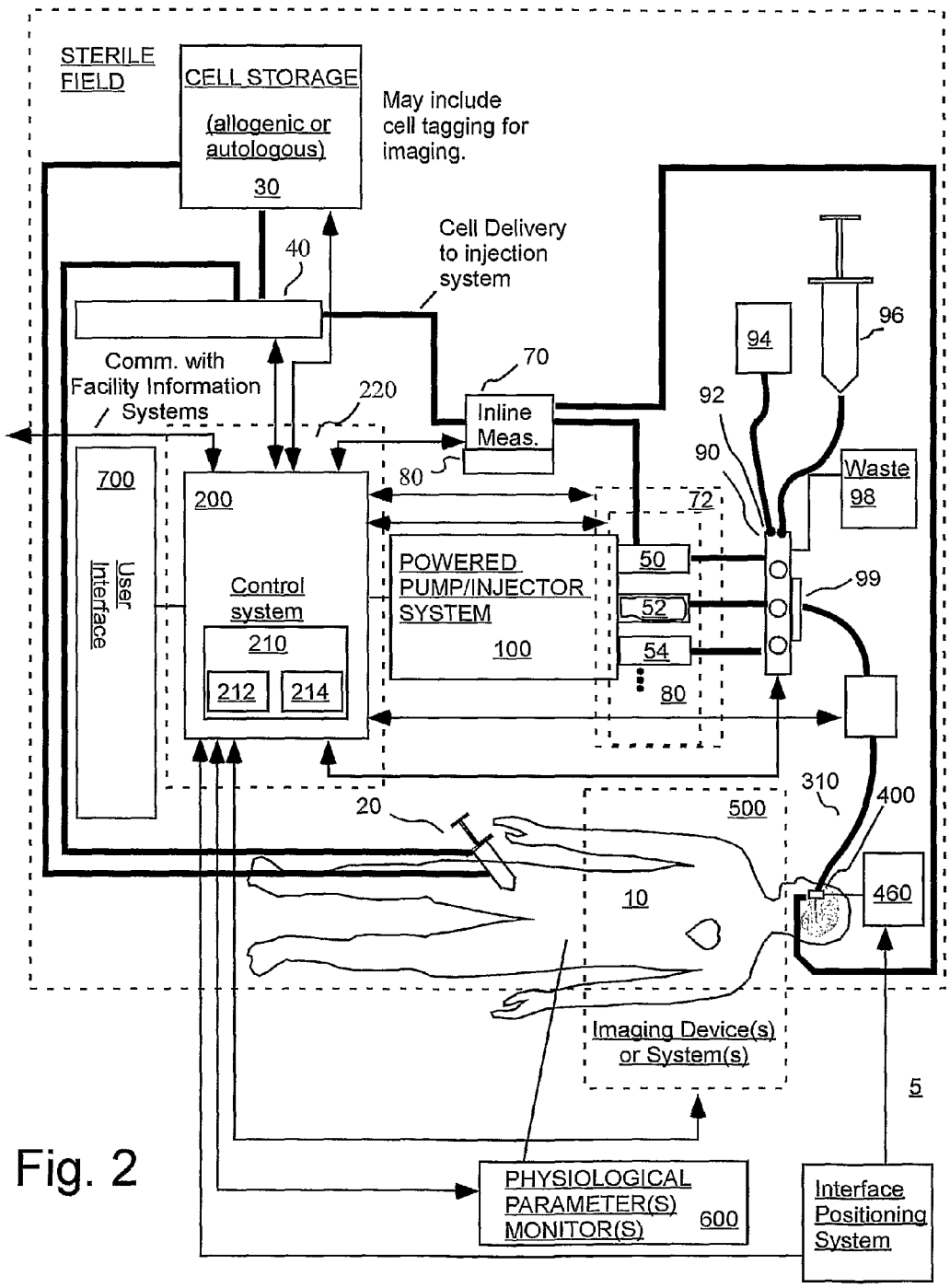
FIG. 2 sets forth several embodiments of systems of the present invention for use in delivery of an injectate or injection fluid, and particularly an injection fluid containing cells, to a brain of a patient FIG. 3 sets forth several other embodiments of systems of the present invention for delivery of an injection fluid, and particularly cells, to the heart of a patient.
Figure 3:
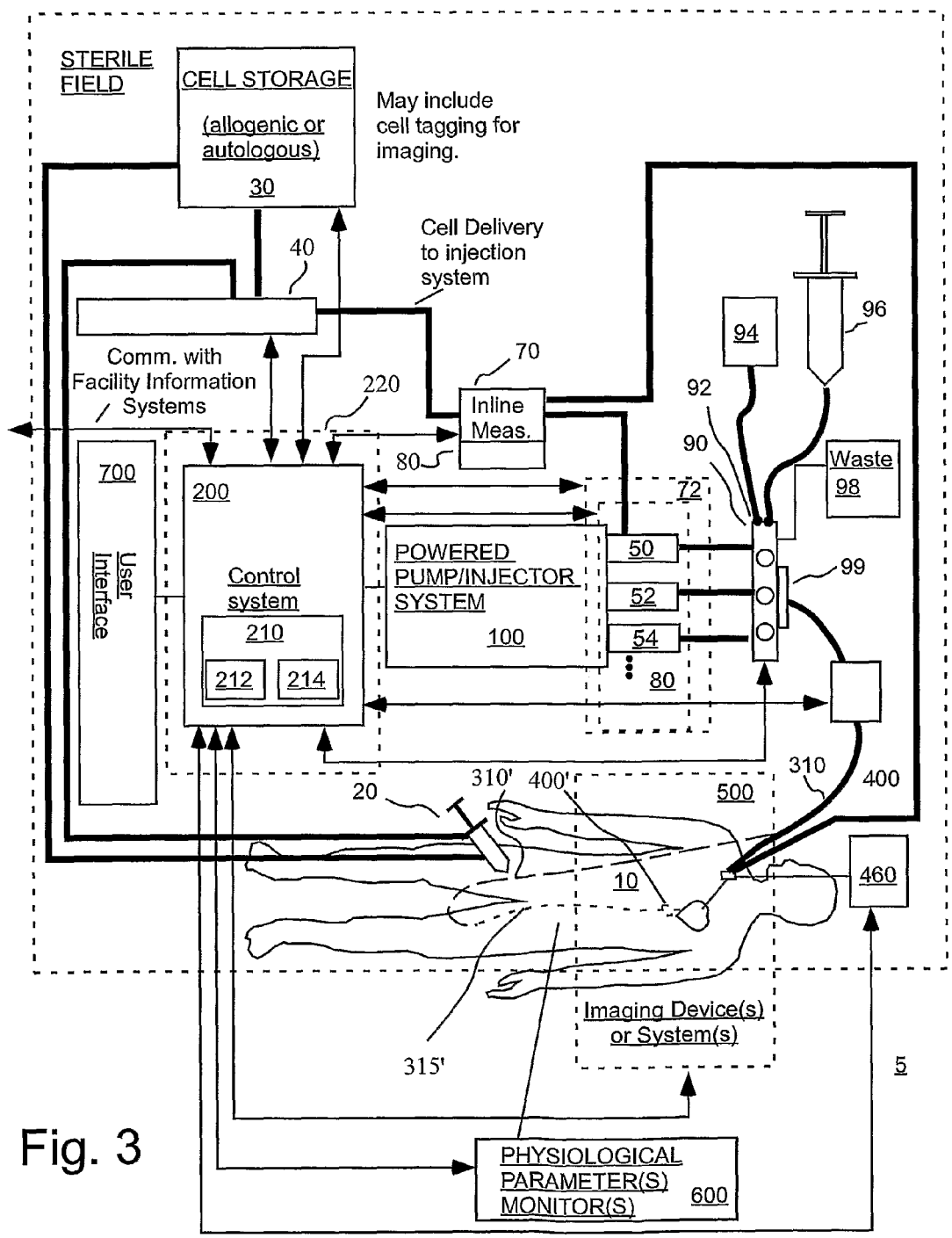
FIG. 3A illustrates an embodiment of a container in operative connection with a cell maintenance unit or system.

FIG. 2 sets forth several embodiments of systems of the present invention for use in delivery of an injectate or injection fluid, and particularly an injection fluid containing cells, to a brain of a patient. FIG. 3 sets forth several embodiments of systems of the present invention for delivery of an injection fluid, and particularly cells, to the heart of a patient. Several embodiments of the present invention are discussed below in detail with respect to delivery of cells to the external heart of a patient. However, one skilled in the art appreciates that the devices, systems and methods of the present invention can be used to deliver many different types of substances to many different tissues, internal to the body as well as to the skin. Moreover, the devices, systems and methods of the present invention are applicable to open surgery or endoscopic needle-based deliveries as well as to catheter-based (for example, intravascular) deliveries.

The systems of FIGS. 2 and 3 are similar in overall architecture and operation, and the systems of the present invention will be described generally with reference to FIG. 3 and with respect to the delivery of cells through the outer surface to the tissue of the heart. In the case that a system of the present invention is to delivery a potentially dangerous or hazardous agent, one or more of the devices, systems and/or methods disclosed in Published PCT International Patent Application WO 2004/091688, the disclosure of which is incorporated herein by reference can be used in the system of the present invention.

In general, cell therapies are believed to work by replacing diseased or dysfunctional cells with healthy, functioning ones. However, the mechanisms of the therapies are not well understood. As described above, therapeutic treatment involves harvesting cells from the body (such as adult stem cells) and later implanting such cells. As discussed above, the techniques are being applied to a wide range of human diseases, including many types of cancer, neurological diseases such as Parkinson's and Lou Gehrig's disease, spinal cord injuries, diabetes, vascular disease, and heart disease. Many factors are considered when selecting an autologous or an allogeneic stem cell transplant. In general, autologous stem cell transplants (since the donor and the recipient are the same person and no immunological differences exist) are safer and simpler than allogeneic (donor cells from a healthy donor other than the recipient) stem cell transplant. However, allogeneic cells can be better characterized and controlled. In addition, it is possible that cell components are necessary or sufficient to achieve a therapeutic response.

FIG. 3 illustrates, for example, the harvesting of autologous bone marrow cells or other cells from a patient 10 using a harvesting device such as syringe 20 before or during an injection procedure. The harvesting of bone marrow cells from the thigh of a patient is discussed, for example, in U.S. Pat. Nos. 6,595,979 and 6,835,193, the disclosure of which are incorporated herein by reference. Such autologous cells or allogeneic cells from a donor can be placed in a cell storage container or facility 30 for use at a later time, which may for example, include incubation, concentration and freezing of the cells and/or other processing. Shortly before delivery to a patient, cells can be removed from cell storage 30 for processing in a cell processing unit 40 and/or other units before delivery (for example, thawing and other processing). Autologous cells can also be harvested and relatively quickly delivered to a patient with or without substantial intervening processing.

In several embodiments of the present invention, cells are delivered to a container 50 (for example, a syringe) in a carrier fluid as known in the art. Cells can also be harvested directly into container 50 from the patient. The contents of container 50 are preferably pressurizable for injection into the tissue of a patient. Prior to delivery of the cell-containing fluid to container 50, measurements relative to effective delivery of cells to heart or other tissue can be made using one or more inline sensor or measuring units or systems 70. Measuring unit 70 can, for example, measure cell count, cell viability, pH, injection fluid density, temperature, nutrient level, gas level, composition etc. Injection parameters and cell maintenance parameters can be determined, changed, and/or controlled via control system 200 based on such measurements. In FIG. 3, container 50 is illustrated as being connected to a powered pump/injector system 100 which is operable, for example, to pressurize the contents of container 50 for injection into the tissue of the patient. Using, for example, connection mechanisms known in the art, container 50 (for example, a syringe) can be removably connectable to powered pump/injector system 100. Harvesting device 20 can, for example, harvest cells directly into container 50 as described above, and any subsequent storage and/or processing of cells can take place in container 50.

Measuring unit 70 and or other sensor measuring unit(s) or system(s) 72 can remain in operative connection with container 50 while container 50 is operatively connected to pump/injector system 100 to continue to monitor the state of the injection fluid prior to and during injection. Moreover, one or more maintenance units or systems 80 can be placed in operative connection with container 50 while container 50 is in operative connection with pump/injector system 100 to maintain cells in a desirable state. For example, the injection fluid in container 50 can be agitated to maintain the injection fluid in a generally homogeneous state. The agitation of a multi-component fluid is discussed in Published PCT International Patent Application Nos. WO 00/53096, WO 00/53242, WO 00/64353, WO 03/053494, WO 03/053554 and WO 03/095000, the disclosures of which are incorporated herein by reference. Moreover, cell heather, cell viability and/or other properties of cells or the cell environment can be maintained by maintenance unit 80. For example, temperature, pH, pressure, nutrients, gases illumination (light energy) etc can be maintained within desirable ranges and waste can be removed. Various aspects of cell maintenance are discussed, for example, in U.S. Pat. No. 6,758,828, the disclosure of which is incorporated herein by reference. A cell maintenance unit or system 80 can also be in place or in fluid connection at one or more places downstream in the fluid path from container 50 such as at patient interface 400. For example, the state of the cells exiting patient interface or already implanted in the tissue can be measure or monitored an a cell maintenance unit 80 used to, for example, deliver maintenance substances (for example, nutrients, gases etc.) for the maintenance of the viability and deliverability of the cells and/or the carrier fluid. Likewise, a cell maintenance unit or system 80 can also be in place or in fluid connection at one or more places upstream in the fluid path from container 50 such as at cell storage container or facility 30 or at cell processing unit 40. The state of the cells can thereby be improved or optimized for delivery to container 50, for delivery of cells to the patient and for survival and/or efficacy of such cells after delivery to the patient. Further injection parameters can be determined and/or controlled to improve or optimize cell health etc. within the fluid path in delivery of cells to the patient and survival and/or efficacy of cells after delivery to the patient. A single cell maintenance unit or system can be provided that is in fluid connection with various fluid path elements. Alternatively, multiple distributed cell maintenance units or systems or a combination of a central and distributed systems can be provided. Monitoring, controlling an maintaining the composition and/or state of a carrier fluid/cell slurry upstream of container 50, within container 50, and downstream of container 50 (including at the exit of patient interface 400 and within the tissue) enables optimization of the conditions of cell delivery not previously possible. Moreover, data can be stored between patients/procedures and learning techniques utilizing, for example, fuzzy logic, neural networks, and artificial intelligence generally, can be used via control system 200 to further enhance or optimize conditions.

Figure 3A:
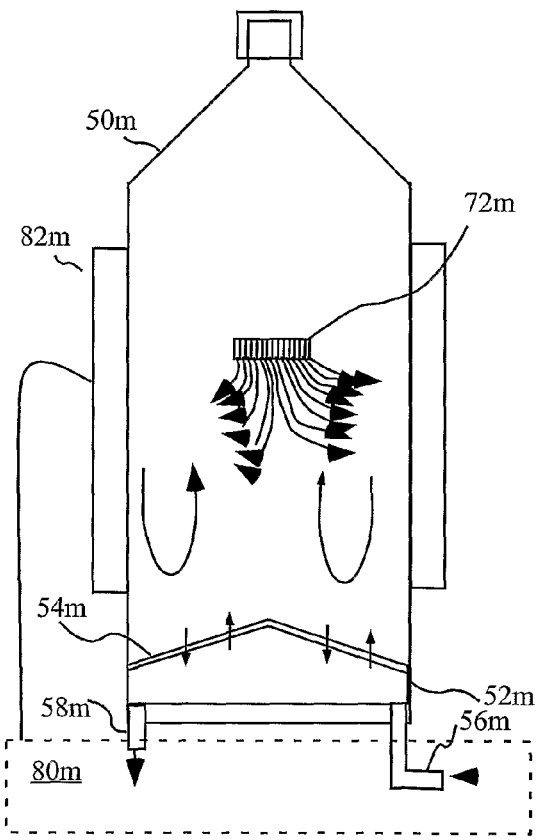

FIG. 3A illustrates an embodiment of a container 50m in operative connection with a cell maintenance unit or system 80m. In the illustrated embodiment container 50m can include a sensor bank or sensor system 72m that is operative to send measurement signals of various parameters of a carrier fluid/cell slurry within container 50m to, for example, control system 200 (portions of which can be distributed to reside within cell maintenance unit 80m). The sensors of sensor bank or system 72m can, for example, be in contact with the fluid within container 50m or can sense certain parameters (for example, optically) through the container wall (which can, for example, be translucent). Control system 200 is in communicative connection with cell maintenance unit 80m to provide control signals thereto, determined at least in part on the basis of the measured parameters provided by sensor bank 72m. A plunger 52m can, for example, include a semipermiable member or a porous filter member 54m in fluid connection with one or more inlets 56m and one or more fluid outlets 58m. Member 54m does not allow cells to pass therethrough (for example, via size exclusion). One or more inlets 56m and one or more outlets 58m are used, for example, introduce various compositions (for example, buffers, nutrients, gases etc.) and carry away various compositions (for example, waste and/or other compositions). Nutrients, gases etc. transport through member 54m to the interior of container 50m while waste products and other undesirable compositions transport through member 54m from the interior of container 50m to exit via outlet 58m. Inlets 56m can, for example, be in fluid connection with a multi-source injector such as injector 100 suitable to deliver fluids thereto. Cell maintenance unit 80m can include an agitation mechanism 82, which is in operative connection with container 50m and is operable to agitate the contents thereof to maintain a relatively homogeneous slurry within container 50m. Various containers suitable for use in the systems of the present invention are set forth, for example, in FIGS. 18A through 18I.

Each of the various systems or units of the present invention can, for example, be in unidirectional or bidirectional communication with a control system 200 that can, for example, include one or more control units or controllers including one or more processors or microprocessors 200, which (as known in the control arts) can include one or more processing units 212 and associated memory storage units 214. Control system 200 can be centralize or distributed within system 5. As illustrated, for example, in FIG. 3, feedback or closed loop communication paths can, for example, be used to control the various components of system 5 before, during and after an injection procedure to control the various components of system 5. Moreover, communication between facility (for example, hospital) information systems and system 5 can be provided via, for example, control system 200. A communication system 220 represented schematically in FIGS. 2 and 3 can effect and/or coordinate communication between the element of system 5. Communication system 220 can included wired and/or wireless communication and related connectors, hubs, switches and the like as known in the analog and digital communication arts.

As also illustrated in FIG. 3, more than one container (for example, syringe) can be placed in operative connection with pump/injector system 100 to inject more than one fluid in the tissue of patient 10. In FIG. 3, three containers 50, 52 (including for example, a fluid-filled collapsible containment) and 54 are illustrated, but less than or more than three containers and associated fluids (which may contain liquid, solid, gel, and/or gaseous components) can be provided. Many type of additional fluids including, but not limited to, flushing or diluents fluids such as saline, viscosity adjusting fluids, imaging contrast fluids, and/or maintenance fluids (for example, nutrient fluids, gases etc.), can be provided. The flow of fluid from various pressurizable containers can, for example, be controlled via a manifold or valve system 90 in fluid connection with containers 50, 52 and 54 and in communicative connection with control system 200. One or more ports 92 can be provided, for example, in manifold system or valve system 90 to provide for fluid connection to other fluid sources which can include on or more other powered pump/injector systems 94 and/or one or more manually operated syringes 96. Manifold system 90 can also include one or more ports through which waste (which may present a biohazard) can be transmitted to an appropriate waste container 98. Manifold system 90 can further include or be in fluid communication with one or more mixers or mixing systems 99 to, for example, effect mixing of one or more fluids.

Injection fluid is delivered from manifold system 90 (or directly from container 50 and other containers in case of a system in which manifold system 90 is absent) through one or more fluid path elements 310 (for example, flexible tubing), each of which can include one or more lumens, to a patient interface 400 (for example, a needle or a catheter) for injection into the patient's tissue. One or more measurement units or systems 74 can be provided in connection with fluid path element 310 or in connection with patient interface 400 for measurement of various variables including fluid flow rate, fluid pressure, fluid density, cell count, cell viability, cell maintenance variables etc. Such information can, for example, be transmitted to controls system 200 and the operation of system components including, for example, pump system 100, cell maintenance unit or system 80, manifold 90 and patient interface 400 can be controlled, at least in part, on the basis of such data or information. System 5 can further include a patient interface positioning control system 460 which can operate to facilitate manual positioning or to partially or fully automate the positioning of patient interface 400.

As discussed above, many embodiments of the present invention are discussed in connection with respect to the delivery of cells, cell components and/or other agents through the outer surface of the body to the tissue of the heart. Once skilled in the art appreciates that the devices, systems and methods of the present invention are also applicable to intravascular delivery methods using catheters and other conduits. In that regard, FIG. 3 illustrates an alternative fluid path 310' in fluid connection with a intravascular catheter 315 and a patient interface 400' (which can include a penetrating member or needless injection mechanism as know in the art).

Various other components or systems can be used in connection with the present invention. For example, one or more imaging devices or system(s) 500 (for example, X-ray systems (including, for example, angiography, venography and urography), computed tomography (CT) systems, magnetic resonance imaging (MRI) systems, ultrasonic imaging systems, light based imaging systems, and positron emission tomography (PET) systems) can be used in connection with the present invention. Imaging systems 500 can, for example, be used to track the position and viability of previously tagged cells which are tagged with a marker that is detectible using imaging system 500, to track the position of patient interface 400 or to monitor one or more patient organs. Likewise, one or more physiological parameter monitors or monitoring systems 600 can be provided to monitor patient physiological parameters including, but not limited to, cardiac function, respiration, blood oxygen level, and blood pressure. Data from monitor(s) 600 can be provided to control system 200 and can be used in controlling the operation of one or more of the components of system 5. Monitor(s) 600 can also be used to simply monitor the state of patient 10 and ensure that the injection procedure does not harm patient 10.

System 5 can also include a user interface system 700 that can, for example, be used to provide user input and/or control into system 5 as well as to provide information (for example, using visual, audible and/or tactile indicators) to the user(s).

Details of various embodiments of a number of the components of and the operative connection of such components within system 5 are set forth below. One skilled in the art appreciates that the various components of the systems of the present invention can be arranged or operatively connected in various manners and that various systems of the present invention need not include all of the components set forth in FIG. 2 and/or FIG. 3.

Although headings and subheadings are provided in the text of the application for organizational purposes, one skilled in the art will appreciate that concepts discussed under one heading or subheading can have applicability in other headings or subheadings and the use of headings and subheading is not meant to limit the invention in any manner.

Patient Interface

Figure 4:
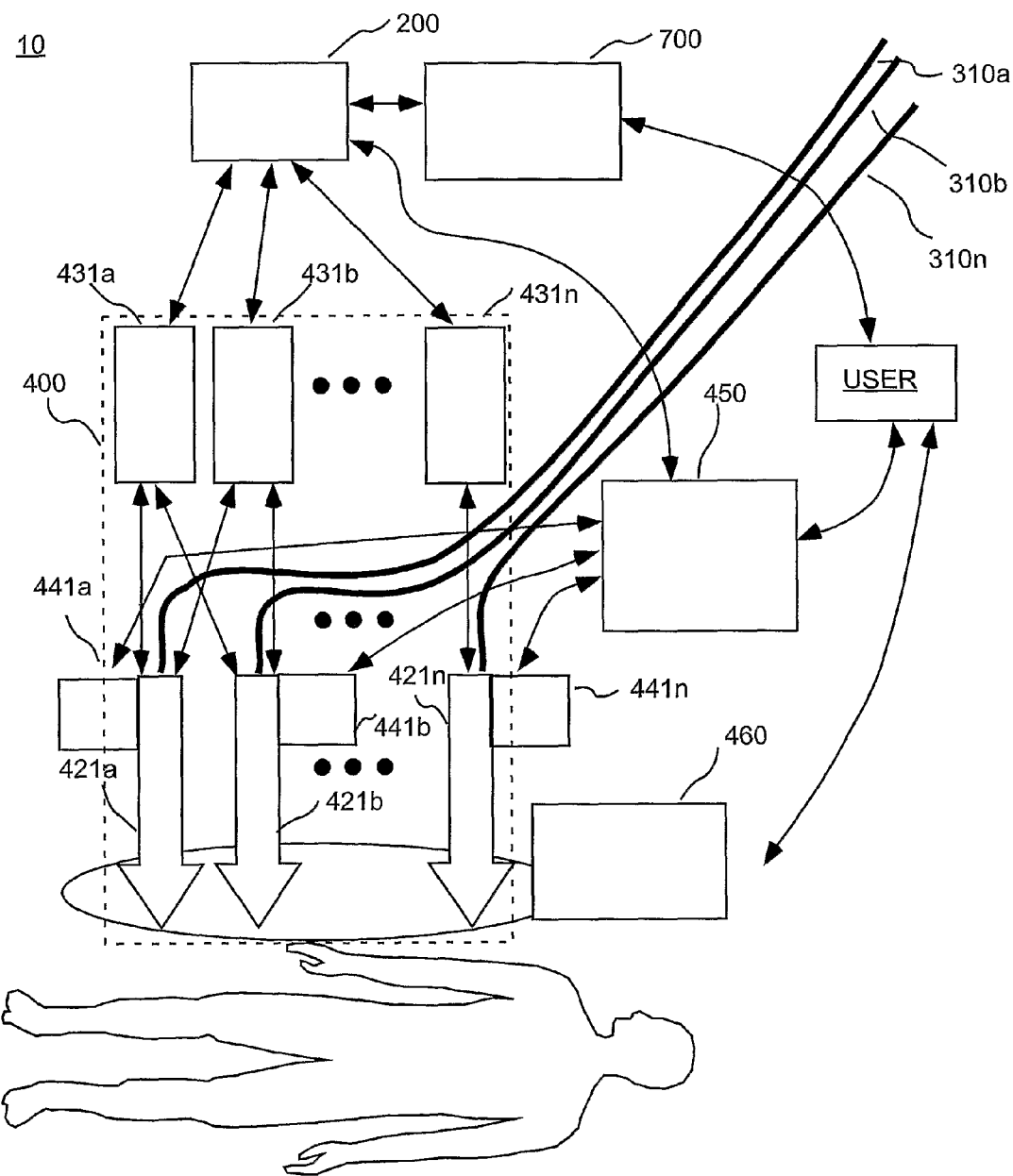
FIG. 4 illustrates a generalized embodiment of a patient interface of the present invention.

In general, patient interface 400 is the component of cell delivery system 5 that interfaces, interacts or interconnects with the patient to deliver a substance to the patient. Patient interface 400 is, for example, shown in operative connection with the patient's heart in FIG. 3 (and in connection with the patient's head/brain in FIG. 2). In a generalized embodiment as illustrated in FIG. 4, patient interface 400 includes one or more effectors 421a, 421b . . . 421n, which can optionally be moved or otherwise altered by one or more actuators 431a, 431b . . . 431n in operative connection with effectors 421a, 421b . . . 421n. Fluid is brought to effectors 421a, 421b . . . 421n through fluid path elements such as conduits 310a, 310b . . . 310n. Actuators 431a, 431b . . . 431n (and effectors 421a, 421b . . . 421n) are in communicative connection with control system 200. One or more sensors 441a, 441b . . . 441n can be in operative connection with effectors 421a, 421b . . . 421n and in communicative connection with control system 200 to provide, for example, feedback control of effectors 421a, 421b . . . 421n. Such communication can, for example, be effected via a sensor interface 450, which can be in communication with sensors 441a, 441b . . . 441n and control system 200. Sensor interface 450 can also be integrated with control system 200. Each component of the system of the present invention can be provided with such a sensor interface (as, for example, described above in connection with sensor bank 72m of container 50m). Operation of actuators 431a, 431b . . . 431 and effectors 421a, 421b . . . 421n can also be controlled, at least in part, on the basis of data provided by other systems sensors and monitors (for example, measuring units 70, 72 and/or 74 and physiological parameter monitor(s) 600).

In current manual systems, there is a single effector—a needle, (or a catheter) a single piece of tubing connecting the needle to an injection fluid source and no actuator connected to a control system. The interface positioning system in current manual systems is generally a needle grip or forceps used by the doctor to manually maneuver the needle.

In one embodiment of the present invention, as discussed further below, one effector can be a single lumen needle or catheter and a second effector can be a depth stop or control mechanism. A fluid path element can be a single piece of tubing in this embodiment and there may be no actuators in operative connection with the control system. In a more sophisticated embodiment of the present invention, as discussed in more detail below, there can be a multi lumen (for example, concentric lumens) needle or catheter with multiple fluid path elements in fluid connection therewith. A depth stop or depth control mechanism can be operated by an actuator. Another actuator such as a grip, ball screw, and motor can, for example, cause the needle to be withdrawn as the injectate is deposited into the tissue.

A. Needles or Catheters—Fluid Dispersal

In the injection of cells into tissue such as the heart to regenerate damaged tissue, the needle or catheter (typically referred to collectively herein as "needle") portion of the patient interface 400 of system 5 preferably satisfies certain criteria. In the case of the heart, for example, the needle must be injected into a moving/beating heart, is preferably able to administer a consistent distribution of cells within the tissue, is preferably able to maintain repeatability in cell viability/concentration, is preferably adapted to prevent clogging of the cells and is preferably able to induce visualization of the target tissue. To satisfy these and other criteria, the present inventors have developed a number of devices providing, among other things, dispersal and retention of fluids within tissue, anchoring and retention of needles within tissue, needle depth and/or needle angle control.

Figure 5:
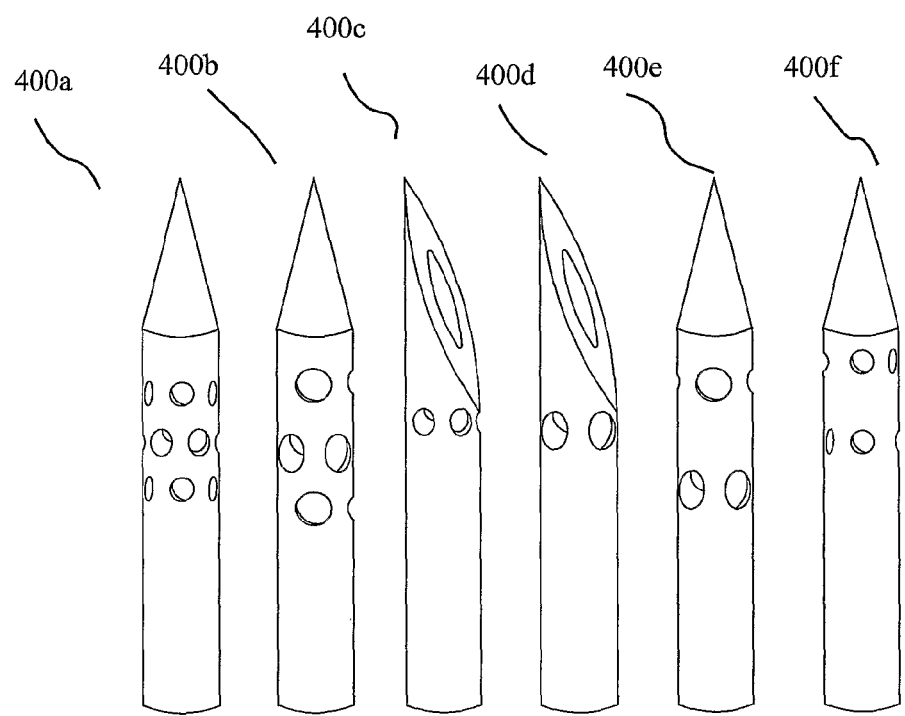
FIG. 5 illustrates several needles with different port configurations for use in the present invention.

The needle is preferably designed with attention to the handing and delivery of cells. Although the exact mechanics of the effect of, for example, autologous bone marrow-derived progenitor cells upon, for example, myocardial tissue remains unclear, it is believed that a wide distribution of the cells within the tissue is beneficial to treatment. The needle can, for example, be designed to enhance the distribution of the progenitor cells. A straight needle with an axial opening will produce a distal straight flow pattern that is less likely to disperse radially. A benefit of needles including one or more side holes is the capability to disperse the fluid radially. As illustrated in FIG. 5, several different needle-tip designs 400a-f including variations in hole location, presence of a distal end opening, number, tip bevel, angle and style can be provided with, for example, an objective to disperse the cells in the largest area possible per injection and/or to provide an even distribution. Design specifications for several needle designs including variations in hole location, number, tip bevel, angle and style are discussed below.

In that regard, in FIG. 6A through 6C illustrate a needle 400g with a 28° inclusive point and multiple side ports 402g. The side port of the present invention can, for example, be oriented orthogonally relative to the main flow lumen of the needle. Angled side holes can also be used. Side ports 402g are staggered in position between rows. In the illustrated embodiment, there are two rows of side ports 402g in which the position of side ports 402g the second or distal row is rotated 90° with respect to the position of side ports 402g in the first or proximal row. Many different number of and configurations of side ports can be used. The hole sizes of the side ports and or number of side ports can vary between rows of side ports and between adjacent side ports. In several embodiments, a relatively small hole can be provided on the distal tip of the needle to, for example, provide for balanced flow out of the side ports of the needle. A small hole on the distal tip can also decrease coring of tissue as compared to a larger hole. Such a hole or port on the distal tip of the needle can also provide for flow in the radial and axial directions to provide for an even distribution of cells.

Figure 6F:
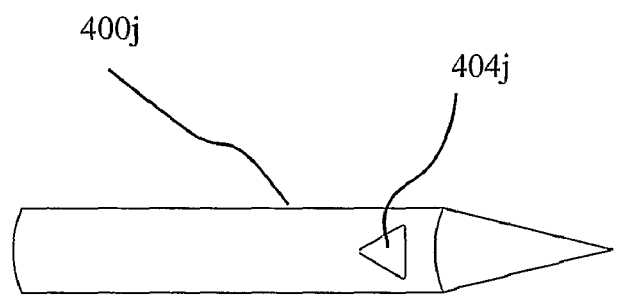
FIG. 6F illustrates a side view of an embodiment of an needle of the present invention including a generally triangular shaped port in which a distal end of the port is wider than the proximal end.
Figure 6E:
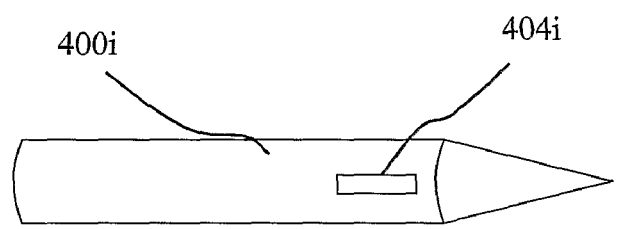
FIG. 6E illustrates a side view of an embodiment of a needle of the present invention including a generally axially oriented slit port.
Figure 6D:
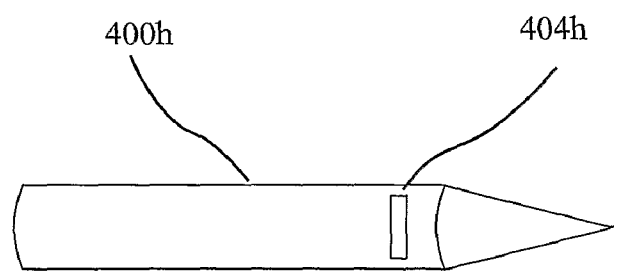
FIG. 6D illustrates a side view of an embodiment of a needle of the present invention including a generally laterally oriented slit port.

FIGS. 6D through 6F illustrate several other injection openings, ports or port patterns for needles of the present invention. For example, slits can be used to produce a more elongated injection pattern. In FIG. 6D, a port or slit 402h oriented generally orthogonal to the axis of needle 400h is formed in needle 400h. FIG. 6E illustrates a needle 400i including a port or slit 402i oriented generally parallel to the axis of needle 400h. Moreover, the port, slot or slit width can be varied over the length of the slit in, for example, a linear or curvilinear manner. FIG. 6F, for example, illustrates a triangular slit, port or hole 404j in a needle 400j in which slit 404j is wider toward a distal end thereof than toward a proximal end thereof. Such a port design may, for example, give more flow distal as compared to standard side holes as a result of the pressure gradient over the axial length of the needle. A plurality of ports of various shapes can be used in a single needle.

Figure 6G:
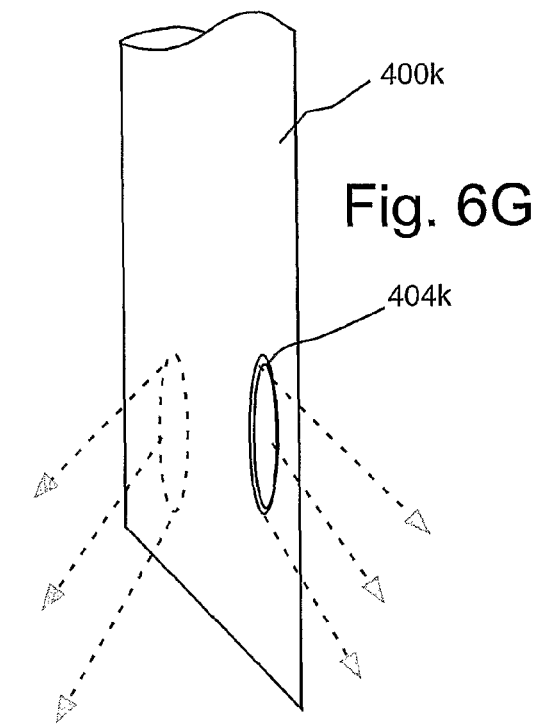
FIG. 6G illustrates a side view of a portion of an embodiment of a needle of the present invention including two opposing extending slot-shaped ports at the same axial position.

FIG. 6G illustrates an embodiment of a needle 400k with elongated or slotted outlets or ports 404k. Slotted outlets or ports can, for example, reduce the likelihood or prevent clogging (via increased area of the opening as compared to smaller circular openings) and provide a more even distribution of cells. In FIG. 6G, two slots or slits 404k were positioned generally oppositely (that is, 180° apart) around the axis of needle 400k. In several embodiments, slots 404k were sufficiently long and narrow to provide a forward projection (that is, toward the distal tip of needle 400k) within the fluid flow as the fluid leaves needle 400k (see dashed arrows in FIG. 6G). Such a forward projection can assist in preventing retrograde flow (or flow that tends to be forced out of the tissue) as discussed in further detail below. If too many slots are provided or if the slots are too wide, there will be insufficient forward momentum in the flow to cause the exit flow to be directed forward (that is, have a forward projection) toward the needle tip.

Figure 6I:
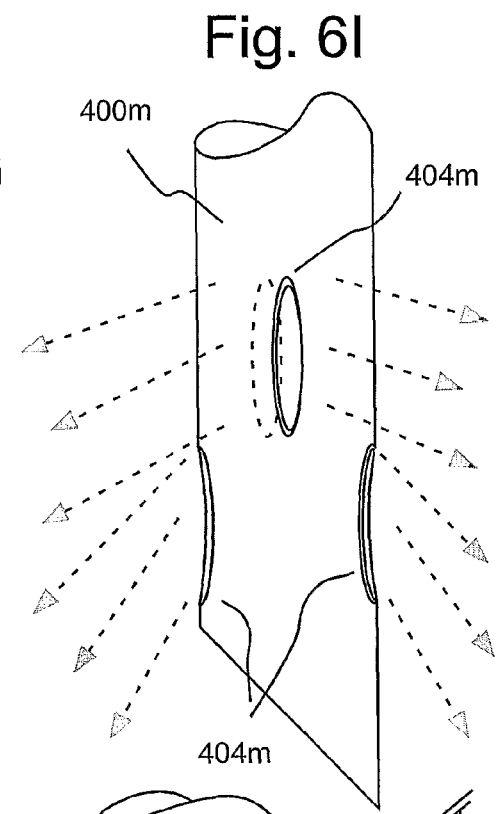
FIG. 6I illustrates a side view of a portion of an embodiment of a needle of the present invention including a first set of two opposing extending slot-shaped ports at a first axial position and a second set of two opposing extending slot-shaped ports at a second axial position, wherein the first set of ports are offset by approximately 90 degrees from the second set of ports.
Figure 6H:
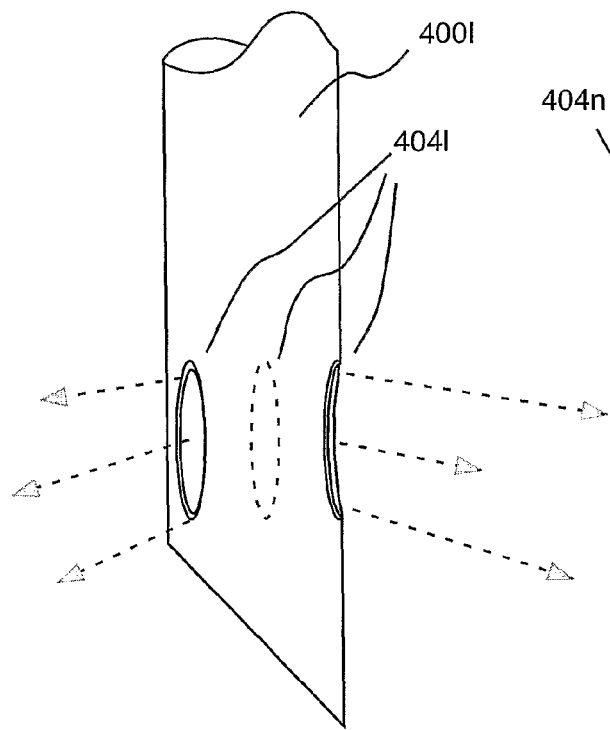
FIG. 6H illustrates a side view of a portion of an embodiment of a needle of the present invention including three extending slot-shaped ports at the same axial position which are separate by approximately 120 degrees around the circumference of the needle.

For example, in FIG. 6H, three slots 404l (of generally the same size as provided in FIG. 6G were positioned at different radial positions around the axis of a needle 400l, but at the same axial (forward/rearward) position on needle 400l. In the illustrated embodiment, each slot 404l is positioned approximately 120° around the axis of needle 400l from the adjacent slots 404l. As illustrated with the dashed arrows in FIG. 6H, the forward element in the flow exiting needle 400l was found to be less than that in the embodiment of FIG. 6G.

To provide an even distribution of flow around the circumference of the needle, rows of offset slots 404m can be used as illustrated, for example, in FIG. 6I. In the illustrated embodiment, two rows with two opposing slots 404m in each row were used. The position of the slots between the rows was rotated approximately 90° about the axis of needle 400m. In the embodiment of FIG. 6I, it was found that the forward projecting element of the radially outward flow was increased as compared to the embodiment of FIG. 6H.

In several studies of each of the embodiments of FIGS. 6G through 6I, the slots were approximately 0.008 inches wide and 0.013 inches long. A flow rate of approximately 0.5 ml/sec was used in the studies. The tips of the needles of FIGS. 6G through 6I were closed. Open ended needles can be used, but closed ends provides less chance of needle tip clogging as a result of coring.

Figure 6J:
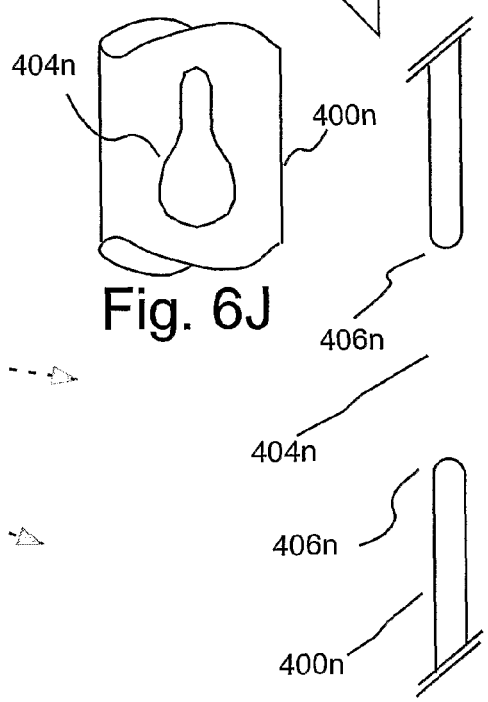
FIG. 6J illustrates a side view of a portion of an embodiment of a needle of the present invention including a generally tear drop shaped port in which a distal end of the slit port is wider than the proximal end.
Figure 6K:
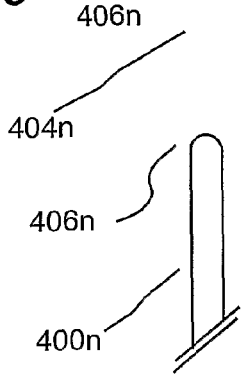
FIG. 6K illustrates a side view of an embodiment of a port of a needle of the present invention wherein walls of the port are radiused or rounded to reduce or eliminate cell (or other injection agent) damage.

Ports that vary in size over the length and/or width thereof can also be used. Slots having, for example, a triangular or tear drop shape (see, for example, slot 404n of FIG. 6J), wherein a rearward portion of the slot has a width less than a forward portion of the slot, can be used to provide a more even distribution of flow from the slot as the pressure upstream (rearward or proximal) is higher than the pressure downstream (forward or distal). As illustrated in FIG. 6J the inside of needle 400n can, for example, be electropolished to create smooth surfaces and rounded edges 406n to reduce or prevent cell damage. Coatings (preferably biocompatible coatings) can additionally or alternatively be used to reduce or prevent cell damage.

Figure 6L:
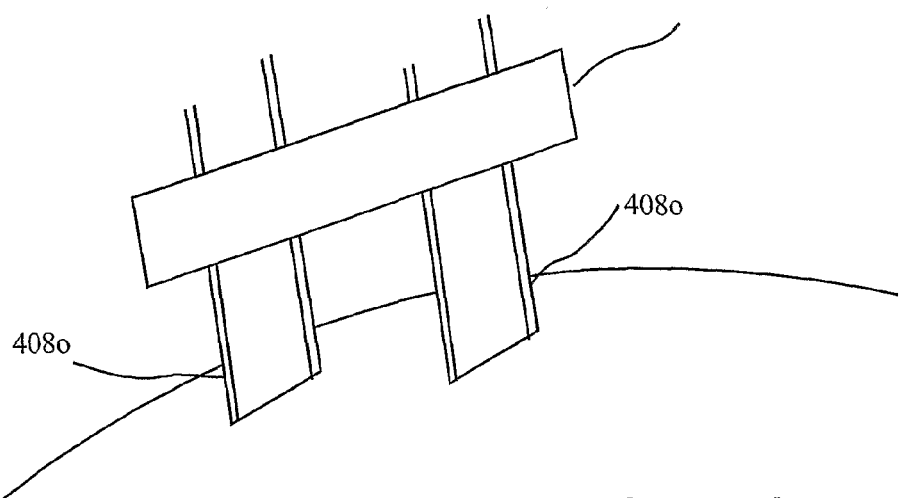
FIG. 6L illustrates a perspective view of a patient interface of the present invention including two needles.
Figure 6M:
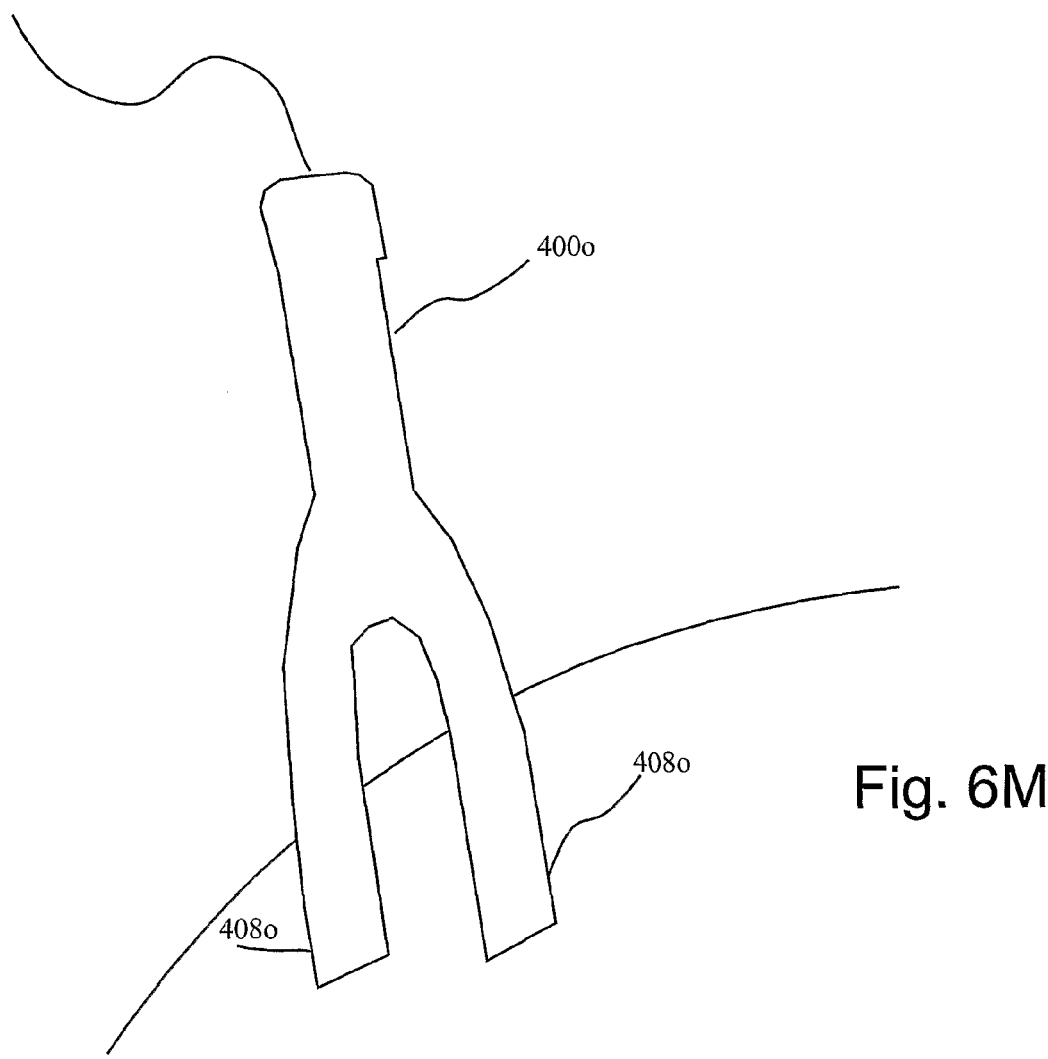
FIG. 6M illustrates a perspective view of a patient interface of the present invention including two needles and including a depth control mechanism extending between the needles.
Figure 6N:
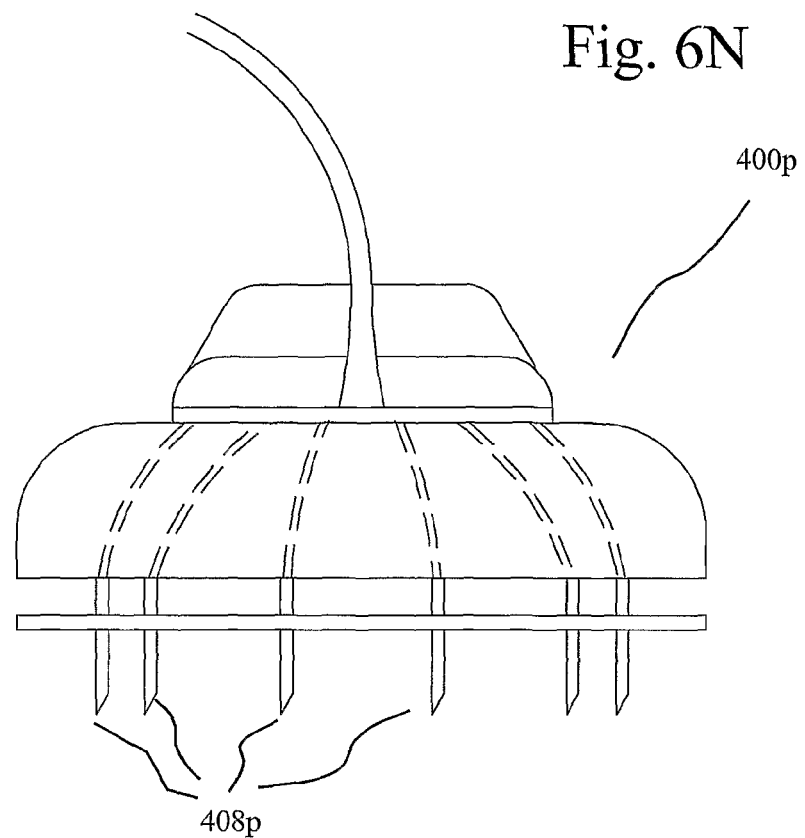
FIG. 6N illustrates a side view of a patient interface of the present invention including an array of a plurality of needles.

Fluid dispersal can also be enhanced by providing multiple needles. For example, FIGS. 6L and 6M illustrates devices including a needle or lumen 400o that forks to create two injection needles 408o. In FIG. 6M, a cross member 409o extending between needles 408o contacts the tissue and acts as a depth stop to control the depth of penetration of needles 408o. The axial position of depth stop 409o can be adjusted to adjust the depth of penetration. Two needles or tips double the number of points of entry of the fluid into the tissue. By increasing the number of points of entry, this design can widen the distribution of fluid in the tissue. As discussed further below, more than two needles/tips can be provided. Moreover, a plurality of needles can be arranged in arrays. For example, FIG. 6N illustrates a large needle manifold 400p including an array of needles 408p with an adjustable depth stop. Depth stops are discussed in greater detail below.

Figure 6O:
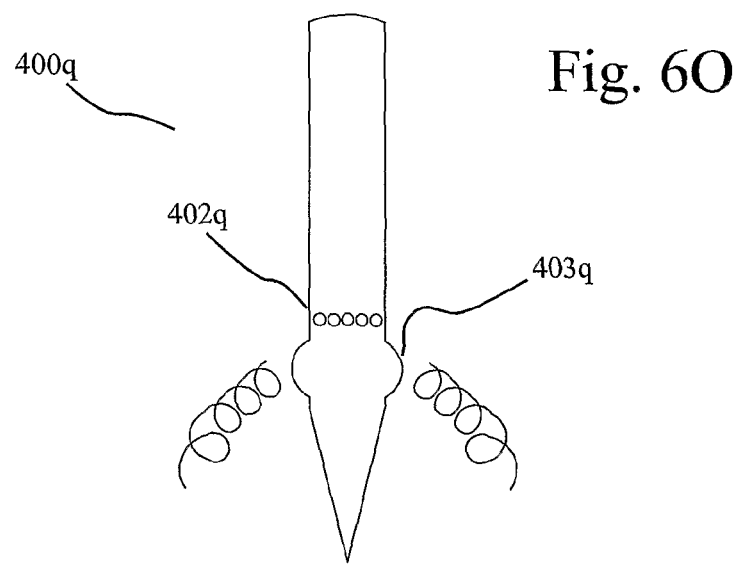
FIG. 6O illustrates a side view of an embodiment of a needle of the present invention including a convex curved surface positioned distal from several ports to create flow patterns resulting from a reverse Coanda effect.

FIG. 6O illustrates a needle 400q which takes advantage of the reverse Coanda effect. In that regard, side holes or ports 402q are placed proximally to a nub or curved surface 403q. Injection fluid flows distally around nub 403q. This effect can produce a dispersed radial pattern and may reduce the likelihood of retrograde flow back.

B. Tissue Access Assurance, Anchoring and/or Retention

In several embodiments of the present invention, one or more mechanisms are provided to deliver fluid to tissue such as the myocardium during surgical procedures in which the heart remains beating. To increase the ease of use of the devices of the present invention and maintain depth-of-injection accuracy, mechanisms were developed to secure the patient interfaces of the present invention to the tissue during injection or to assure operative connection of the patient interfaces of the present invention with the tissue during injection. Such mechanisms also reduce fluid loss by ensuring the fluid is delivered inside the tissue over the course of the injection.

An anchoring or retention function can, for example, be performed through the use of mechanical anchors. For example, FIGS. 7A(1) and 7A(2) illustrate devices including one or more wire stabilizers and at least one cell delivery needle. In FIG. 7A(1), device 800 includes three injection lumens or needles 804. A stationary or a movable/adjustable depth gage 806 actuated by the operator can also be provided. Preformed small wires 808 hold needle device 800 in place while the stem cells and/or other agents are injected through, for example, a single or, multiple needles 804 or an articulating array of small needles. Needles 804 can, for example, form a radial flow pattern. Anchor wires 808 can from curved sharps that extended into the tissue around needle(s) 804 just prior to injection, to hold needle(s) 804 secure into the tissue to be injected. Like other anchoring mechanisms, a benefit of this device lies in the array of small wires 808 that penetrate the heart muscle and hold the device in place while injecting through needle(s) 804, reducing the possibility that needle(s) 804 will move during injection and ensuring a constant depth of injection. The device also reduces the possibility of fluid loss by preventing needle 804 from being removed prior to completion of fluid delivery. FIG. 7A(2) illustrates device 800 with just a single injection needle 804 and three anchor wires 808 both attached and detached from tissue.

Figure 7B:
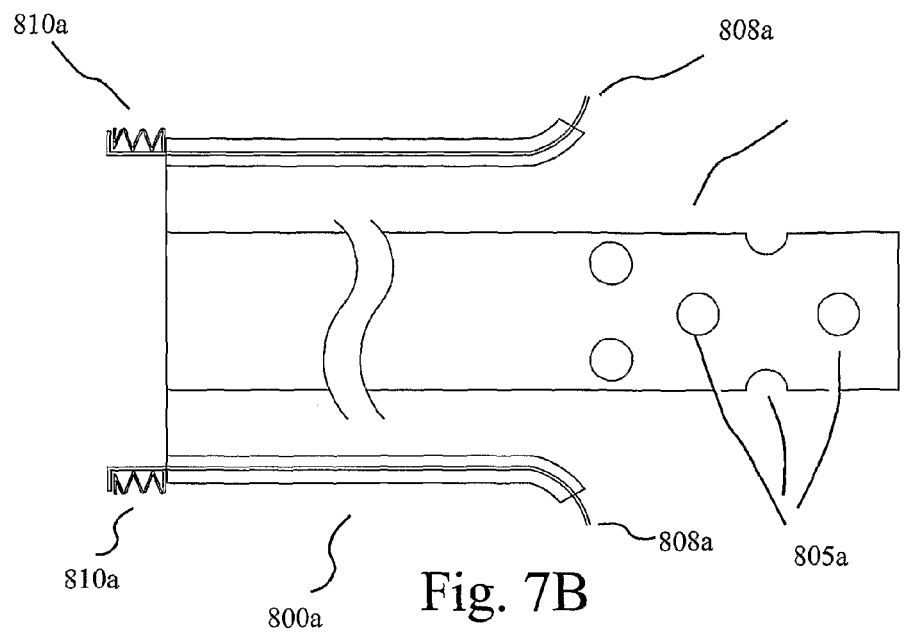
FIG. 7B illustrates another embodiment of a patient interface of the present invention including anchor or stabilization members.

FIG. 7B illustrates a device 800a that is similar in operation to device 800 of FIG. 7A, but includes wire radial grabbers or anchors 808a that grab and hold the heart muscle or other tissue while injecting the cells via a needle 804a. Wire grabbers 808a can, for example, be attached to a spring mechanism 810a that unfolds and grabs the muscle. Flow is provided through center needle 804a with side holes 805a.

Figure 7C:
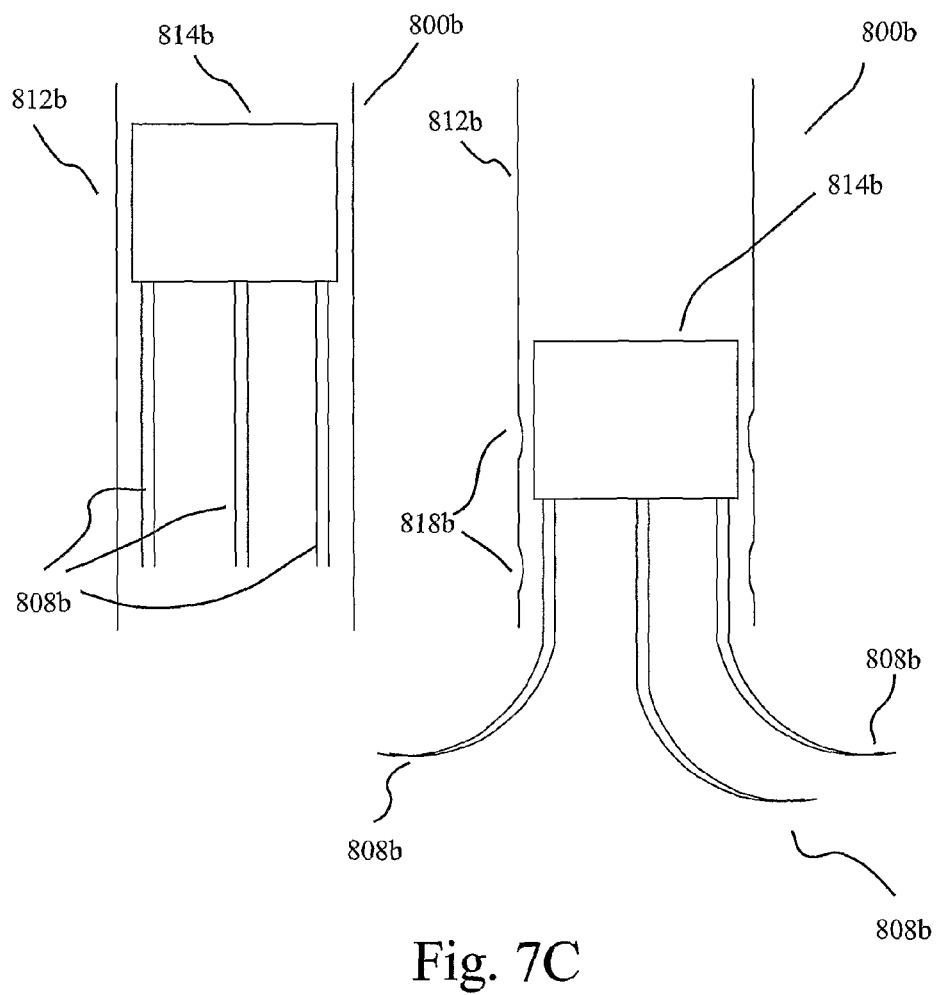
FIG. 7C illustrates another embodiment of a patient interface of the present invention including anchor or stabilization members.

FIGS. 7C(1) and 7C(2) also illustrates a needle 800b including anchoring wires 808b. In this embodiment, a needle sheath 812b covers wires 808b, which can, for example, be spring loaded. Drawing sheath 812b upward or rearward (compare FIG. 7C(2) to FIG. 7C(2)) springs wires 808b open and anchors the device in place. A piston 814b blocks the end hole 816b, which lets stem cells and/or other agents flow out of side ports 818b (see FIG. 7C(2), in which wires 808 are illustrated in their deployed position). Benefits of this embodiment include automatic anchoring upon sheath removal and side hole injection flow.

FIG. 7D(1) illustrates a needle device 800c including a two-lumen tube, lumen or needle 804c with exit side holes 818c and a balloon 820c to hold needle 804c in place. In this embodiment, needle 804c is inserted into the heart muscle or other tissue, balloon 820c is inflated via a first lumen in operative connection with a first syringe 824c to hold needle 804c in place. Cells and/or other agents are injected through a second (for example, center) lumen of needle 804c, which is in operative connection with a second syringe 826c. FIG. 7D(2) further illustrates the operation of a needle device 800c. The inflation of balloon 820c (via an air channel 828c illustrated in FIG. 7D(2)) adapts to the path of least resistance, so less tissue damage occurs while needle 804c is still secured to the tissue of, for example, the beating heart. Another benefit of this device is anchoring balloon 820c, which not only anchors needle 804c, but also stops retrograde flowback of the cells and/or other agents, which is discussed further below.

FIG. 7D(3) illustrates a "leaking balloon" device 800d including a distally attached balloon 820d with side holes 830d. After insertion of needle 804d into the heart muscle or other tissue, balloon 820d is inflated and anchors needle 804d in place. The cells and/or other agents are injected into balloon 820d and flow out the side holes 830d in a generally radial direction. Balloon 820d seals the needle cavity, thereby reducing or eliminating retrograde flow back.

Device 800e of FIG. 7D(4) is similar in operation to device 800d of FIG. 7D(3). In the embodiment of FIG. 7D(4), device 800e includes a collar 820e that expands when stem cells and/or other agents are injected. Expanded collar 820e acts as an anchor while injecting. Needle 804e has side ports or holes 805e and injection fluid/cells flow out of needle 804e past expanded collar 820e. Collar 820e may be visualized as a V-shaped member (in cross-section), attached proximally to needle 804e. Collar 820e opens distally and the flow exits needle 804e at the open end of collar 820e. Collar 820e can, for example, be formed of a flexible polymeric material that expands as a result of fluid pressure.

Device 800f of FIG. 7D(5) is similar in operation to device 800e in that it has a similarly shaped collar 820e. In the embodiment of FIG. 7D(5), collar 720e is made of a material that is preshaped and, when opened, returns to its original opened shape. As needle 804r of device 800f is inserted into the tissue (for example, the heart), a sheath 823f is forced or drawn rearward or back, springing open preshaped collar 820f. Open collar 820f acts as an anchor while injecting. The fluid flow is similar that of device 800e described above in that it exits needle 804f through side ports or holes 805e and flows distally through open collar 820f. After the injection, sheath 823f is moved forward, forcing collar 820f to close inside sheath 823f.

Figure 7E:
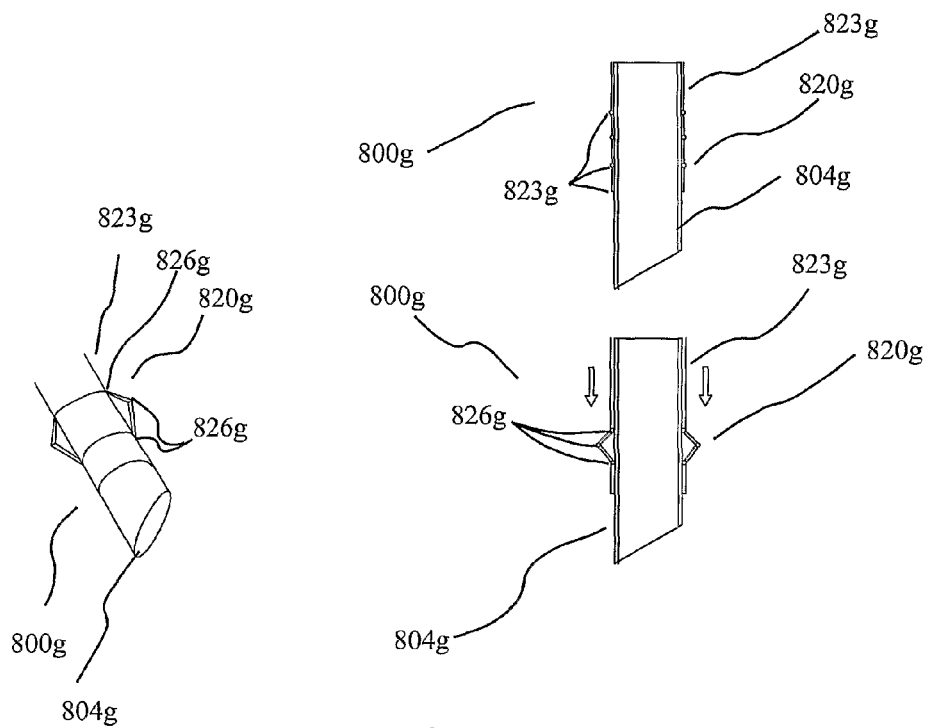
FIG. 7E illustrates another embodiment of a patient interface of the present invention in which an expanding stabilization member is in an expanded and a contracted state.

FIG. 7E illustrates another needle device 800g including a mechanical needle retention device that operates in a similar manner to the inflatable balloon embodiments discussed above. In this embodiment, needle 804g is surrounded by an external sleeve 823g. Moving sleeve 823g toward the tip of needle 804g "pops out" or actuates a mechanical retention member 820g. Retention member 820g can, for example include several hinge members 826g that causes retention member 820g to fold and extend radially outward.

Figure 7F:
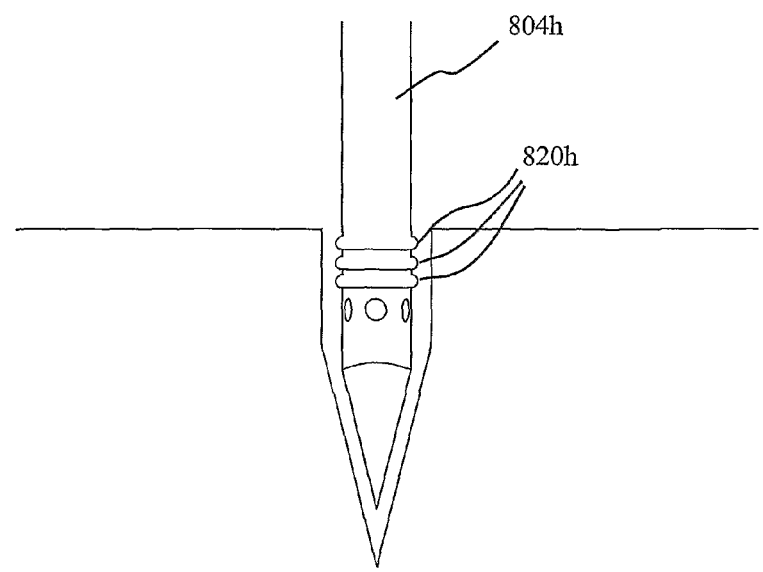
FIG. 7F illustrates another embodiment of a patient interface of the present invention including ribbing to anchor or stabilize the patient interface within tissue.

FIG. 7F illustrates a needle 804h including one or more circular rings 820h around needle 804h. Rings 820h can act as an anchor to hold needle 804h in place while injecting cells and/or other agents. Rings 820h also acts as a seal to prevent retrograde flow back of the fluid. Rings 820h can also provide a visible depth gage.

Figure 7G:
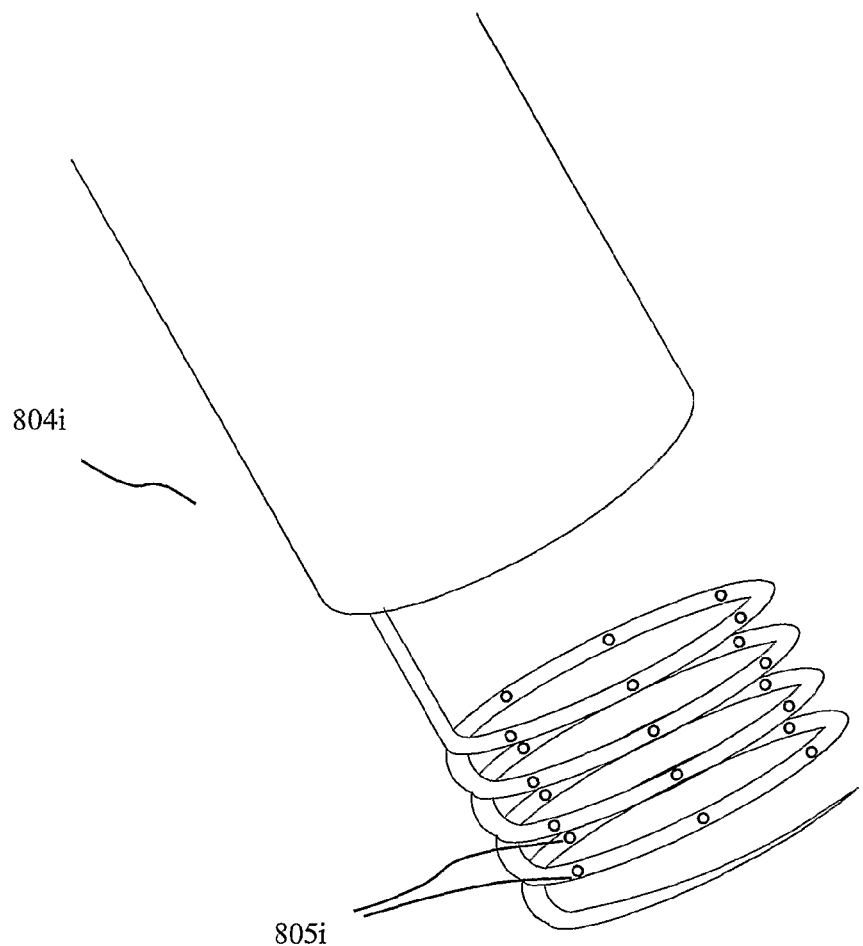
FIG. 7G illustrates another embodiment of a patient interface of the present invention including a helical or spiral penetrating member.

The needles of the present invention can also be shaped to provide for secure attachment to the tissue. FIG. 7G, for example, illustrates a corkscrew- or spiral-shaped needle 804i operable to secure needle 804i to tissue during the injection. Spiral needle 804i can be either rigid or compliant. A stiff spiral will powerfully secure needle 804i into the injection site, eliminating the possibility that it will slip or otherwise "come loose" from the injection site during delivery of the fluid. A more compliant spiral is able to move and "flex" with the tissue (for example, the beating heart), easing strain on the tissue and ensuring that a constant injection depth is maintained throughout fluid delivery. The stiffness or compliance of a needle can be readily optimized for a particular purpose. Holes or ports 805i can be distributed along the length of the spiral needle that is inserted into the tissue to distribute the injection fluid.

FIG. 7H(1) illustrates a device 800j including a set of pincer needles 804j that are operable to hold fast to the injection site. Each of the pincers 804j can include a plurality of side ports 805j. Device 800j helps to ensure, for example, that as the heart moves device 800j will not be mistakenly withdrawn from the injection site during fluid delivery, reducing the possibility of fluid loss or incorrect injection depth. FIG. 7H(2) illustrates a hook-shaped or curved needle 804k that allows needle 804k to secure itself to the tissue. The curved shape of needle 804k also provides for substantial needle-tissue contact, while limiting the depth of insertion.

FIG. 7H(3) illustrates a device 800l including one or more flexible needles 804l that are activated by the injection pressure of the fluid injectate. Fluid is injected down the tube or lumen 802l of the device and pushes a flange 832l that opens flexible needles 804l to anchor device 800l. As needles 804l are opened, the cells and/or other agents are injected. The operation of device 800l can increase the area of cell dispersion, providing for continuous dispersion of fluid from the start of needles 804l opening to full extension.

Figure 7I:
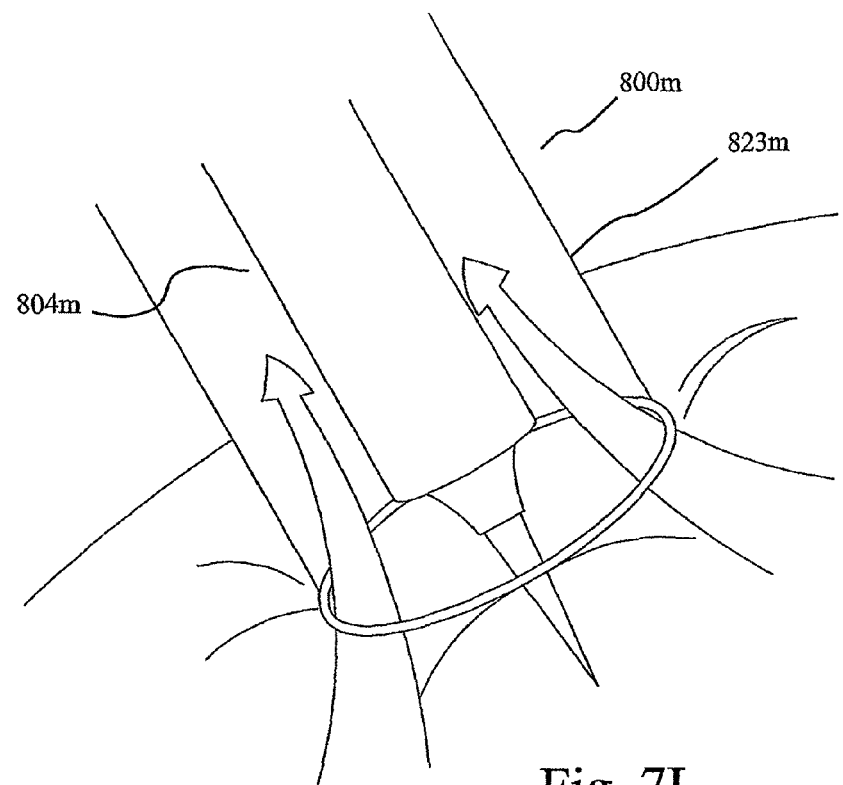
FIG. 7I illustrates another embodiment of a patient interface of the present invention in which a vacuum source is used to stabilized the penetrating member in tissue.

FIG. 7I illustrates the use of suction or vacuum, drawn within the volume between a sheath 823m around needle 804m at the time of the injection to secure needle 804m onto the tissue to be injected. Like the mechanical anchoring and retention devices described above, the suction reduces the possibility that needle 804m will move during injection, ensuring a constant depth of injection and reducing the possibility of fluid loss. It also reduces the possibility of fluid loss by preventing needle 804m from being removed prior to completion of fluid delivery.

Figure 7J:
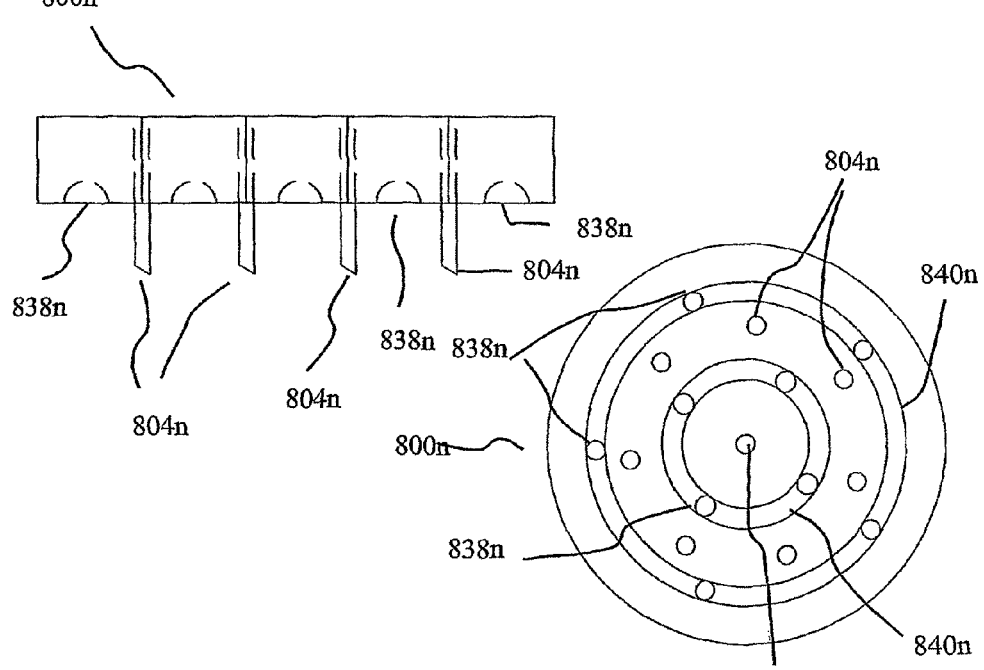
FIG. 7J illustrates another embodiment of a patient interface of the present invention in which a vacuum source in operative connection with a plurality of vacuum ports is used to stabilized the penetrating member in tissue.

FIG. 7J illustrates a vacuum ported needle array 800n with suction ports 838n in groves 840n around a circle array of needles 804n. Suction holds device 800n in place while injecting cells and/or other agents. Needles 804n can be provided with various lengths depending on muscle thickness. Benefits of device 800n include the ability to hold device 800n in place while injecting cells and/or other agents into a large area of muscle.

Figure 7K:
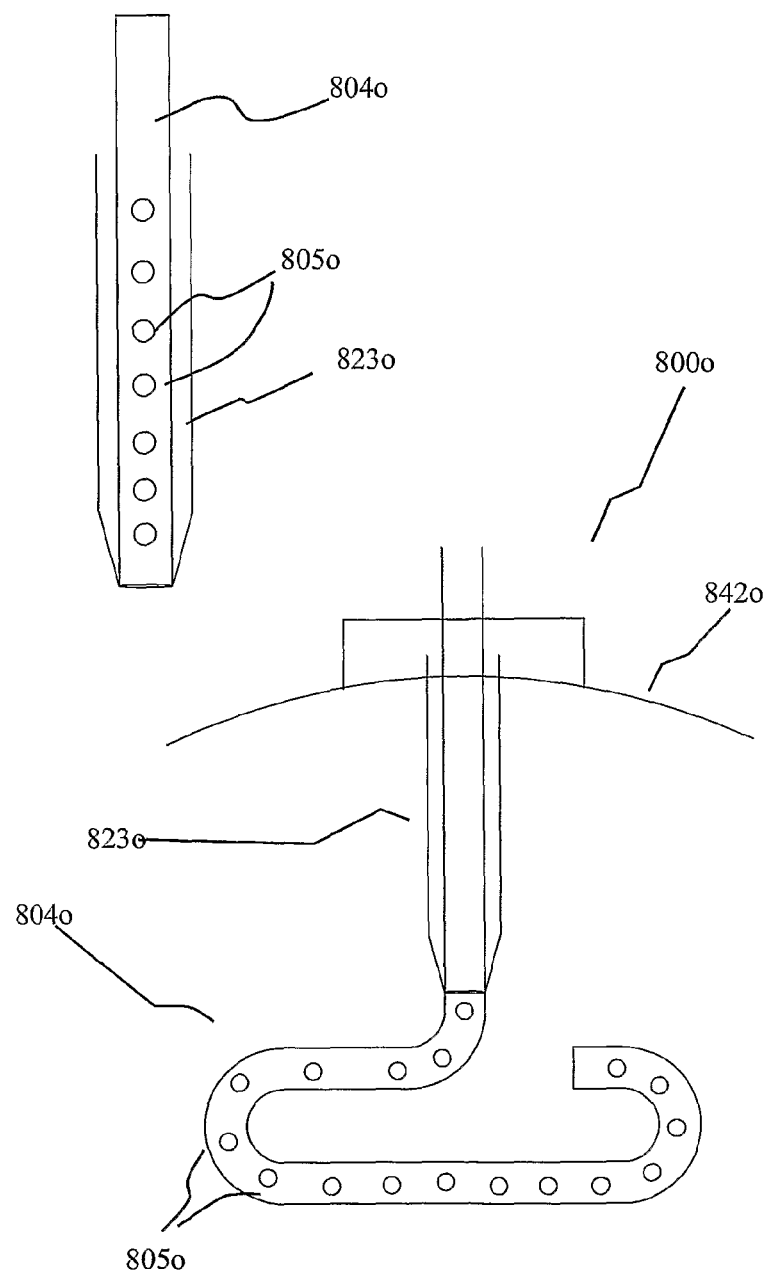
FIG. 7K illustrates another embodiment of a patient interface of the present invention in which a penetrating member having a memory shape is used to anchor or stabilize the penetrating member in tissue in which the penetrating member is illustrated in a retracted and deployed state.

FIG. 7K illustrates a device 800o in which a needle 804o is held in place by a formable suction cup 842o. A sheath 823o encapsulates needle 804o. Upon rearward movement of sheath 823o relative to needle 804o, needle 804o changes shape or expands and forms, for example, a needle ring or other curved shape. The needle has side ports or holes 805o for radially distributed fluid delivery. Needle 804o can, for example, be formed out of a shape memory alloy such as Nitinol (a nickel-titanium shape memory alloy) with a predetermined shape.

FIG. 7L illustrates a needle array device 800p including an adhesive pad 846p for retention of pad 846p on the tissue. Needle array device 800p can include a colored dye for location marking (marking is discussed further below). Multiple needles 804p inject cells and/or other agents into tissue, while adhesive pad 846p holds device 800p in connection with the tissue and marks the location of each injection area 850p with dye, providing location mapping.

FIG. 17l(1) illustrates an embodiment of a device 800p' including a flexible cover 846p' including a hydrophilic layer that is adapted to adhere (without an adhesive or glue thereon) to a moist surface of tissue. After an injection via needles 804p' is effected, cover 846p' can be removed from connection with the tissue (for example, via a peeling action thereof) to remove device 800p' from connection with the tissue.

In addition to attachment of needles to tissue via, for example, mechanical anchors, suction, and/or adhesion, assurance of access to tissue or appropriate tissue contact can be provide through a number of other mechanisms. For example, an automated "firing" or injection of injectate or injection fluid can be initiate upon contact with tissue. FIG. 7M, for example, illustrates a device 800q that operates in a manner somewhat similar to a nail gun. Injection flow is started when a moveable needle cap 852q is pressed against, for example, the heart muscle with a predetermined force, such that needle cap 852q is moved rearward to contact a contact member 854q. A spring or other force applying or biasing element 856q can be used to set the force required to active injection. This force can be made adjustable. Injection flow can be stopped automatically when needle 804q is withdrawn and injection cap 852q is force out of contact with contact element 854q by element 856q.

Figure 7N:
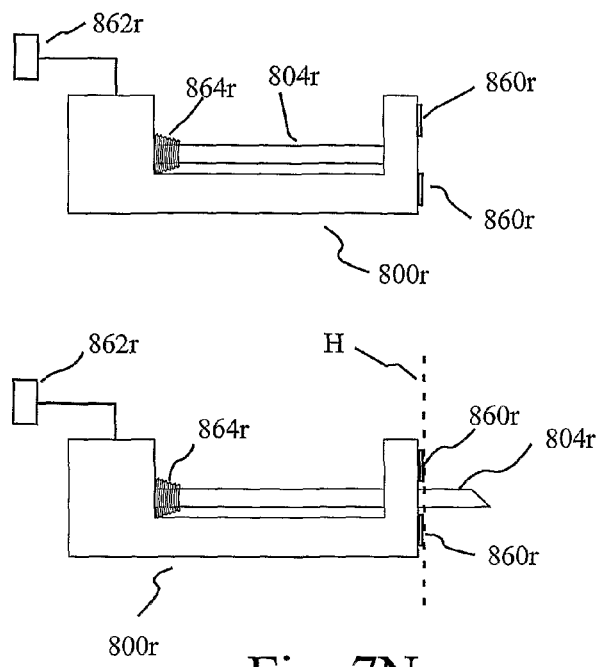
FIG. 7N illustrates an embodiment of a patient interface of the present invention in which contact with moist tissue causes initiation of an injection process via contact of one or more electrical contacts with the tissue.

FIG. 7N illustrates a device 800r including conductive metal contacts 860r that when contacted with a wet (that is, electrically conductive) surface, close a circuit, providing indication that the surface of the tissue (for example, heart H as illustrated in the lower portion of FIG. 7N) is in contact. Alternatively, device 800r could sense the heart's electrical signals to verify contact. Indication of contact can, for example, arm device 800r. Once device 800r is armed, needle 804r can automatically extend or extend into the tissue to a predetermined maximum depth when an injection button 862r is pressed. Activation of button 862r or other actuating element can, for example, activate a needle extension mechanism 864r. In one embodiment, discussed in greater detail below, at maximum depth a portion of the dose is delivered. Then the needle can be pulled back or rearward, delivering the remaining dose (and/or one or more other fluids) as it retracts. Finally, when the needle exits the tissue, a plunger can pull back slightly to prevent capacitance leakage.

Figure 7O:
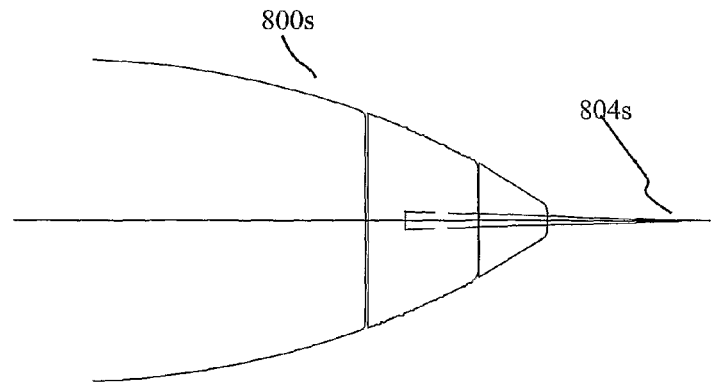
FIG. 7O illustrates an embodiment of a patient interface of the present invention in which the penetrating member is in connection with the remainder of the patient interface via a movable or compliant connection such as a spring connection.
Figure 7O:
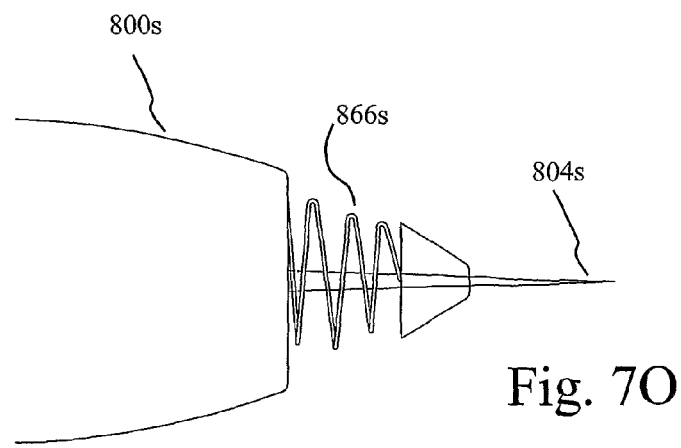

FIG. 7O illustrates a device 800s including one or more compliant or movable needle tips 804s to help ensure needle tip 804s remains in appropriate contact with, for example, a supple, moving injection site such as a beating heart. Compliant needle tip 804s can move axially, along the direction of needle tip 804s, rotate and flex distally according to the motion of the tissue at the injection site, or both. The supple movable nature of needle tip 804s can ensure that as the heart moves, needle tip 804s will not be mistakenly withdrawn from the injection site during fluid delivery, reducing the possibility of fluid loss or incorrect injection depth. In the illustrated embodiment, needle tip 804s is made moveable via connection with a flexing coil member 866s.

Figures 7P, 7Q:
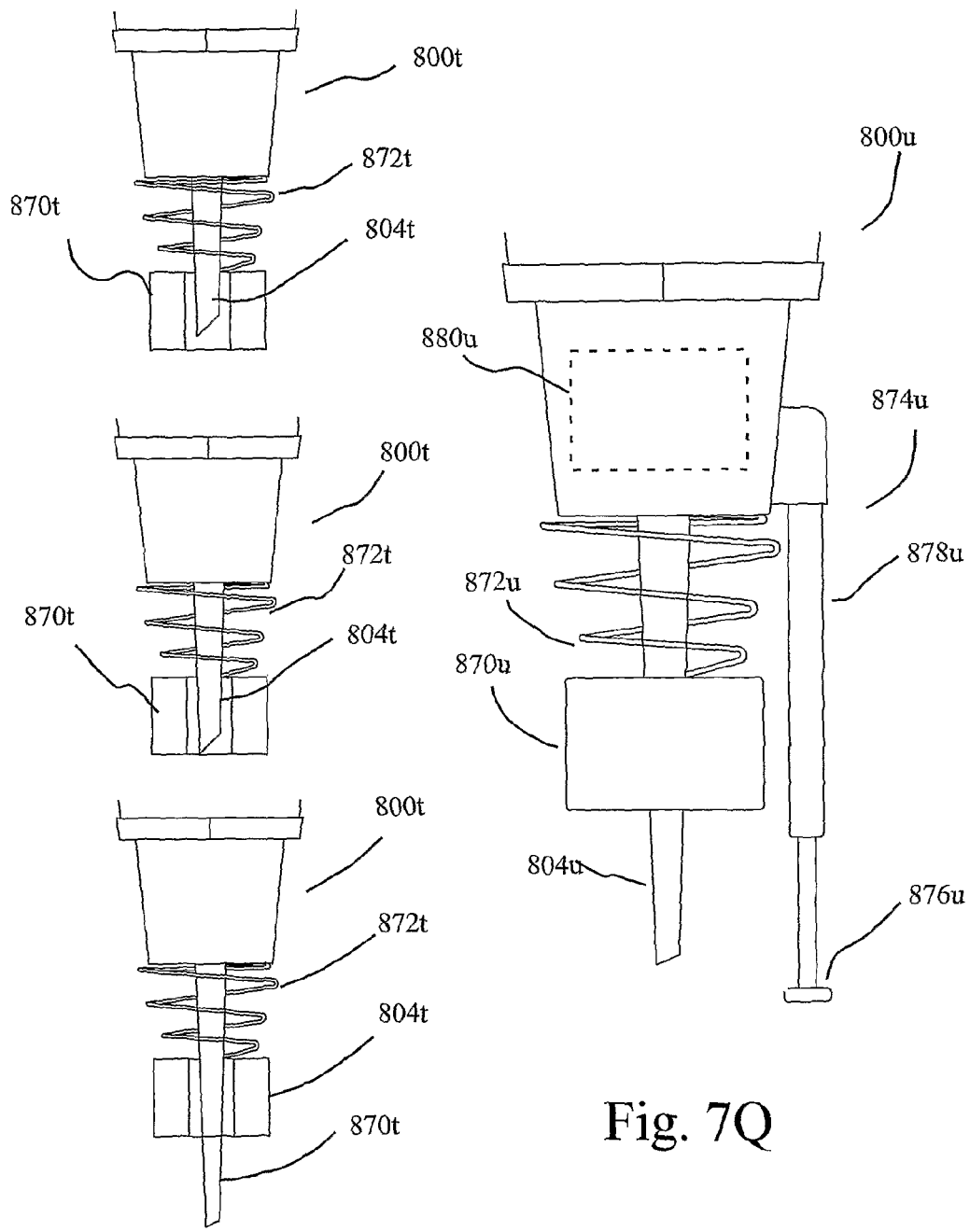
FIG. 7P illustrates an embodiment of a patient interface of the present invention in which a depth control mechanism is in operative connection with the penetrating member and is in connection with the remainder of the patient interface via a movable or compliant connection such as a spring connection.
FIG. 7Q illustrates an embodiment of a patient interface of the present invention including a sensor to detect contact with tissue.

FIG. 7P illustrates another embodiment of a "compliant" device 800t of the present invention. As a depth stop 870t of device 800t is brought into contact with tissue (for example, heart tissue H) and device 800t is "armed", depth stop 870t is force rearward and, holding in position, causes needle 804t to fire (move forward) into tissue to a predetermined depth and deliver fluid. Thus, the injection commences at a desired depth. In the illustrated embodiment, depth stop 870t is movably connected within device 800t via a spring element 872t.

FIG. 7Q illustrates an embodiment of a device 800u including a "shock absorbing" or other sensor 874u that tracks tissue (for example, heart) motion by contact of a movable contact member or element 876u with the tissue. Contact member 876u can, for example, be positioned on the end of a shaft slidably disposed within a sheath 878u of sensor 874u. Sensor 874u translates the motion of contact member 876u to a depth stop device 870u and a needle tip 804u via, for example, a control system 880u. The position of depth stop device 870u and needle tip 804u can be controlled in a manner corresponding or tracking the change in position of the tissue. Similar to the embodiment of FIG. 7P, depth stop 870u is connected within device 800t via a spring element 872u. Constant and gentle tracking of, for example, the heart surface via sensor 870u reduces "gapping" and leaking during injection, improving the accuracy of the injection and reducing the possibility of fluid loss during injection.

Figure 7R:
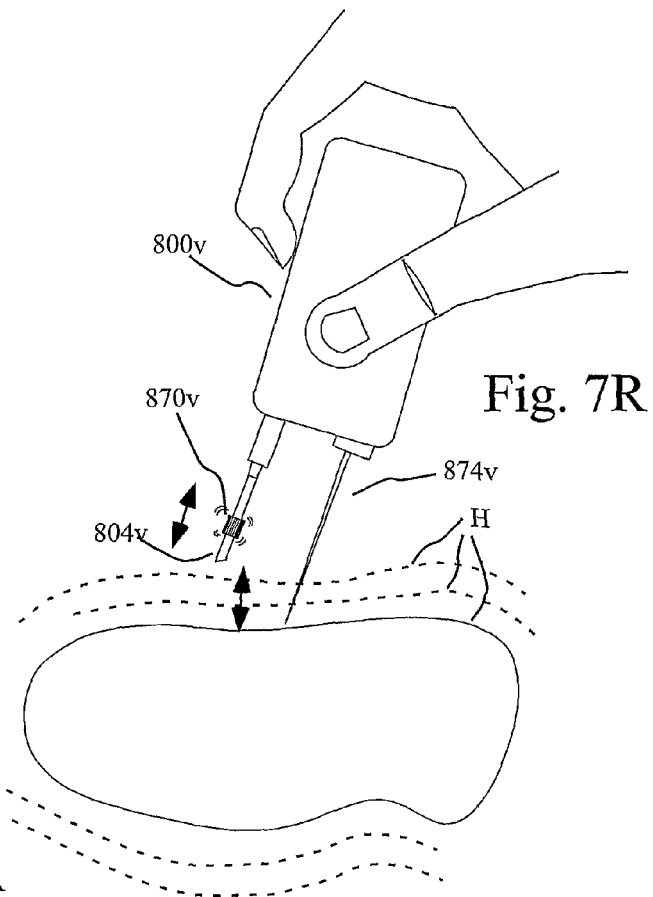
FIG. 7R illustrates an embodiment of a patient interface of the present invention including a sensor to detect contact with tissue and/or movement of tissue (for example, a beating heart) relative to the patient interface.

FIG. 7R illustrates another embodiment of a device 800v that automatically measures heart movement and synchronizes, needle position, needle penetration and/or injection timing therewith. Device 800v can, for example, include a sensor 874v such as a laser equipped sensor or wire feeler to determine the distance between device 800t (or some point thereon) and a surface H of the beating heart. Needle 804v and an attached or associated depth stop device 870v (via, for example, a control system 880v in operative connection with sensor 874v and needle 804v) can be movable to automatically mirror the movement of the heart surface, resulting in more accurate depth control and more gentle and accurate needle positioning. Injection can be timed to correspond to a desirable phase of the cardiac cycle.

C. Needle Movement or Articulation

Figure 8A:
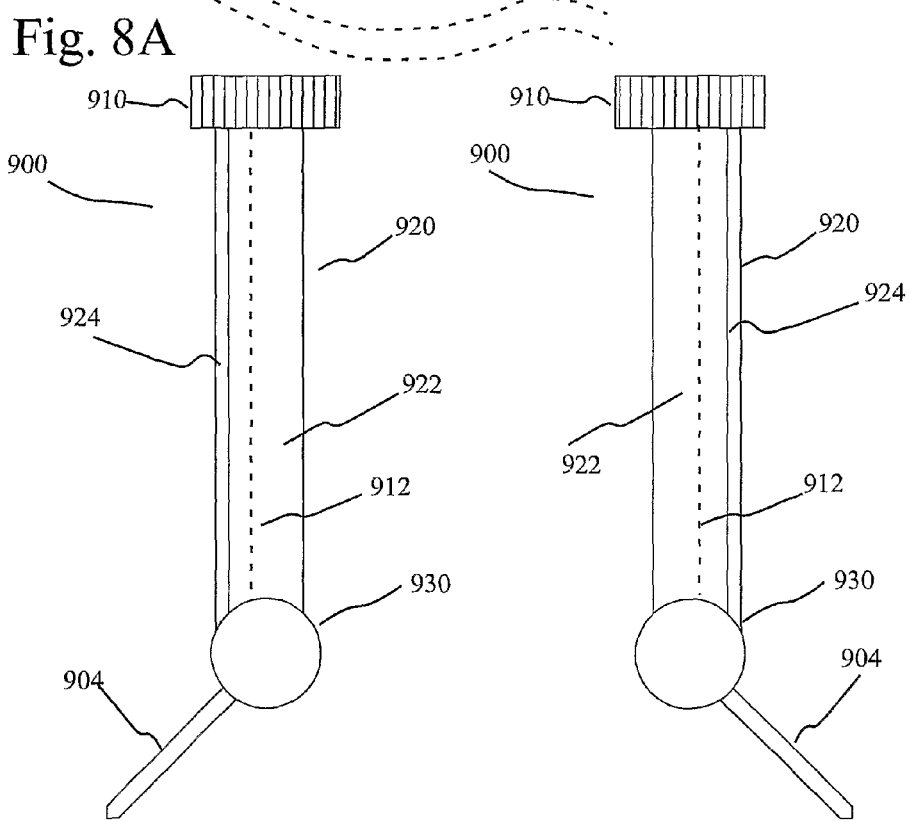
FIG. 8A illustrates an embodiment of a patient interface of the present invention in which a penetrating member of the patient interface can articulate relative to an extending portion of penetrating member.

FIG. 8A illustrates an embodiment of a device 900 including a moving or articulating needle 904 that, for example, enables the tip thereof to rotate approximately 120 degrees. Device 900 can, for example, include a thumb wheel 910 or other control mechanism that attaches by connector 912 such as a wire to the needle 904. In the illustrated embodiment, thumb wheel 910 is attached to a first end of a conduit or tube 920. Conduit 920 includes a first lumen 922 through which connector 912 passes and a second lumen 924, which is in fluid contact with needle 904 for transport of fluid thereto. A joint 930 such as a ball joint or a flexing section is connected to a second end of conduit 920. Needle 904 can be rotated by moving thumb wheel 910. Device 900, for example, provides the benefit of maneuverability around the heart, whereas maneuverability of a straight needle is quite limited.

Figure 8B:
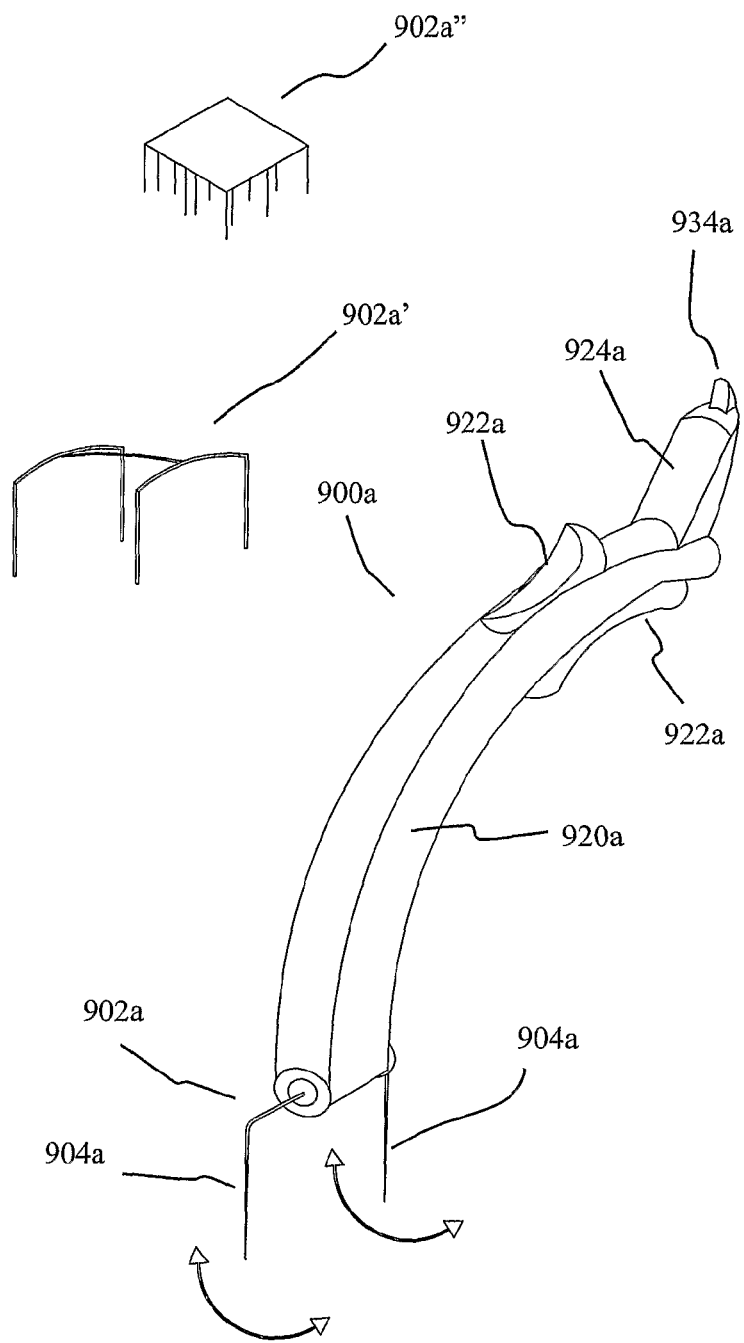
FIG. 8B illustrates another embodiment of a patient interface in which a penetrating portion of the patient interface can articulate relative to an extending portion of the penetrating member and several multi-needle penetrating portions for use therewith.

FIG. 8B illustrates an embodiment a device 900a of the present invention that provides a combination of an articulating needle head 902a with a multi-tip needle 904a. Articulating head 902a, for example, allows needle tips 904a to generally perpendicularly enter tissue without requiring movement of a handle 920a of device 900a—particularly beneficial, for example, during thoroscopic procedures. Two or more needle tips 904a can double, triple, quadruple etc. the number of points of entry of the fluid into the tissue. FIG. 8B also illustrated a four-needle tip reticulating needle head 902a' and a multi-needle array reticulating needle heat 902a". Such needle heads can, for example, be removably attachable to handle 920a. By increasing the number of points of entry, this embodiment widens the distribution of fluid in the tissue. Multiple-tipped needles, including needle arrays, can be utilized to take further advantage of this increase in distribution. Handle 920a can, for example, include finger grips 922a to facilitate grasping thereof. A lever or other control mechanism 924a can be provided to control the position of needle head 902a and thereby the position of needle tips 904a. An actuating element such as a button 934a can be provided to initiate injection.

D. Injection Depth Control

In several embodiments, the present invention provides depth stops or injection depth control devices to provide for injection of a therapeutic fluid (including, for example, cells) into tissue such as the myocardium. In that regard, because of variations in the thickness of the myocardium, methods and devices for limiting the depth of injection are necessary to insure consistent fluid delivery and to prevent potentially harmful intraventricular injections. In several embodiments, upon insertion of the needle, a depth stop contacts the surface of the myocardium, preventing injection beyond a specified depth. Based on a typical myocardium tissue depth of 4 to 14 mm, a total range of motion for the depth regulating or control devices in several embodiments of the present invention was established to be approximately 2-8 mm and, particularly in the range of approximately 4-8 mm, inclusive. One skilled in the art appreciates however that the depth control devices of the present invention can operate over a wide range of tissue depth penetration. The depth control devices can, for example, operatively connect to patient interface 400 (for example, a needle). The depth control devices of the present invention can be adjustable (for example, manually or via control system 200) during the procedure for which the injections are required. Further, the position of a penetrating member or needle relative to a fixed depth control device can be adjusted to control penetration depth. The depth control devices of the present invention are preferably constructed of materials appropriate and suitable to its medical purpose.

Figure 9A:
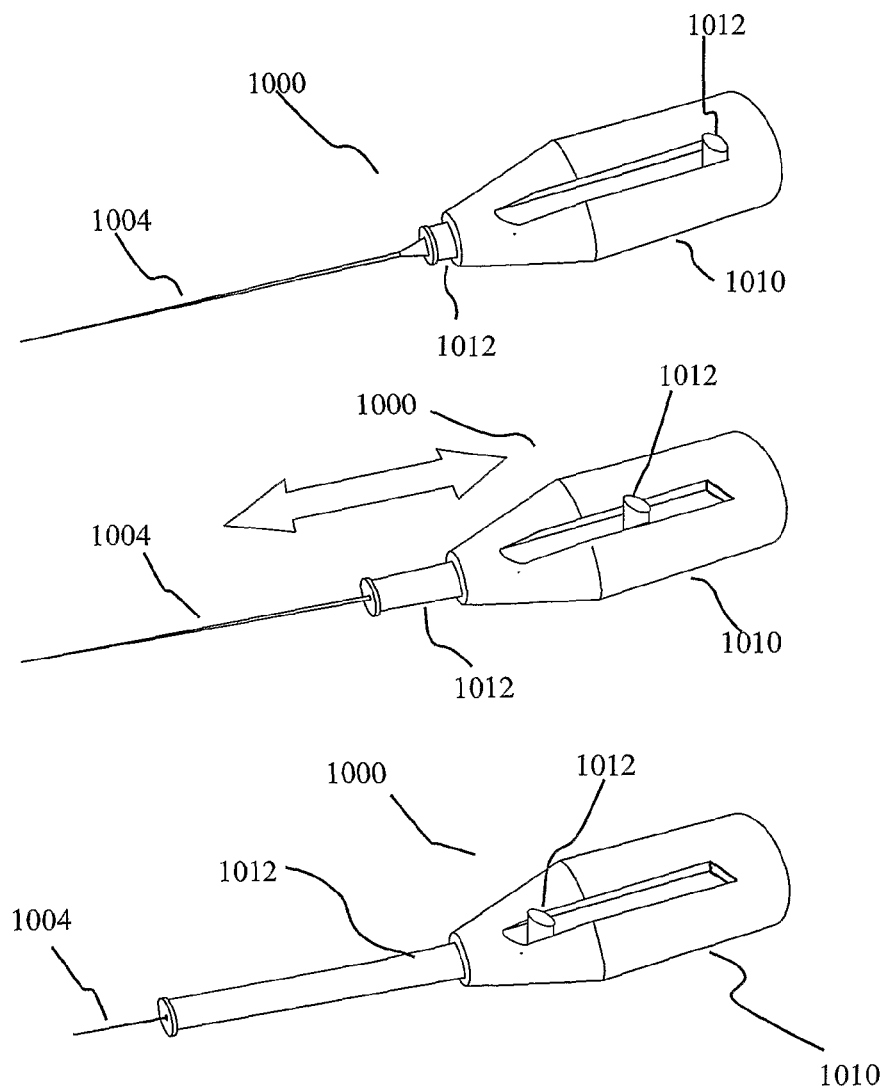
FIG. 9A illustrates an embodiment of a patient interface of the present invention including a movable sheath depth control mechanism in which the sheath is depicted in several positions corresponding to several different needle penetration depths.

FIG. 9A illustrates an embodiment of a device 1000 of the present invention including a depth control device 1010 including a sliding sheath 1012 that can, for example, be manually extended and retracted around a needle 1004 via the position of a control lever or other control member 1014. A series of interlocking mechanical features (not shown) can, for example, index the location of sliding needle sheath 1012 in discrete, graduated locations. At each location, a different length needle 1004 is exposed beyond the leading or forward edge of sheath 1012. Upon insertion of needle 1004, sheath 1012 will press against the tissue, only allowing the protruding portion of needle 1004 to enter the tissue.

FIGS. 9A(1) and 9A(2) illustrate another embodiment of a depth control device 1010a including a sliding sheath 1012a or indicator to control depth of penetration. In this embodiment, the indicator sheath 1012a can be slid axially along a needle 1004a and locked at a desired position. A smooth, pipette-like transition region 1020a is provided between a lumen 1030a of conduit or tube 1032a and a lumen 1006a of needle 1004a to reduce/eliminate turbulence of cell/liquid mixture from lumen 1030a of tube 1032a to lumen 1006a of needle 1004a (such "smooth" or gradual transitions are discussed in further detail below). A reservoir 1040*a* is provided for applying an adhesive bonding material between needle 1004*a* and sliding sheath 1012*a*. A built-in depth stop abutment 1042*a* is provided so that the range of motion of sliding sheath 1012*a* is limited and the user cannot extend needle 1004*a* beyond a limit set by detents 1044*a*. Detents 1044*a* engage locking components 1048*a* of sliding sheath 1012*a* at fixed locations to control needle extension past a forward indicator surface 1014*a* of sliding sheath 1012*a*. Forward indicator surface 1014*a* preferably has a controlled surface area to allow the user to see the injection site. By abutting the tissue surface, indicator surface 1014*a* prevents needle 1004*a* from being injected too far into the tissue. The mechanism also includes one or more lock members 1048*a*, which when engaged with detents 1044*a*, prevents sliding sheath 1012*a* from moving out of its current setting under normal loads. Device 1010*a* can, for example, be adjusted, locked and unlocked using one hand by moving sliding sheath 1012*a* and extending or retracting lock components 1048*a* (which can be positioned on the end of flexing arms 1050*a*) via an actuating mechanism 1052*a*. In several representative embodiments, device 1010*a* is designed to pass through a trocar having an inner diameter of at least 10 mm.

FIG. 9A(3) illustrates an embodiment of a depth control device 1010*b* in operative connection with a needle 1004*b* similar in operation to device 1010*b* of FIGS. 9A(1) and 9A(2), but further including a flattened area 1016*b* on a forward end and/or a flattened area 1016*b*' on a rearward end of depth control device 1010*b* so that a surgeon can more easily grip depth control device 1010*b* with, for example, forceps, clamps, or other similar surgical grasping tools.

FIG. 9A(4) illustrates an embodiment of a depth control device 1010*c* in operative connection with a needle 1004*c* in which a rack 1044*c* is connected to an adjustable needle sheath or stop 1012*c*. Rack 1044*c* fits within a housing 1052*c* and can, for example, be spring loaded by a leaf spring 1045*c* (or otherwise biased) against fixed stops 1054*c* (triangle-shaped stops in the illustrated embodiment) formed in a top of housing 1052*c*. By pressing down upon rack 1044*c* (for example, through an opening 1056*c* suitably dimensioned to allow access by, for example, an operators thumb), the operator can disengage rack 1044*c* from stops 1054*c* of housing 1052*c*. Rack 1044*c* can then be pushed forward or backward to change the position/setting of needle sheath 1012*c*. An indicator 1058*c* and gradations 1060*c* can be provided to indicate the selected setting.

FIGS. 9A(5)(a)-(d) illustrates an embodiment of a depth control device 1010*d* including an adjustable needle indicator 1012*d*. As illustrated in FIG. 9A(5)(c) smooth, pipette-like transition region 1020*d* is provided between a lumen 1030*d* of conduit or tube 1032*d* and a lumen 1006*d* of needle 1004*d* to reduce or eliminate turbulence of cell/liquid mixture from lumen 1030*d* of tube 1032*d* to lumen 1006*d* of needle 1004*d*. A built-in depth stop abutment 1042*d* is provided so that the range of motion of actuator 1060*d* is limited and the user cannot extend needle 1004*d* beyond a limit set by detents 1044*d*. A reservoir 1040*d* is provided for applying an adhesive bonding material between needle 1004*d* and sliding actuator 1060*d*. An actuator 1060*d* includes teeth 1062*d* which are biased in place between stops 1044*d* formed in an upper housing section 1064*d*' (which is attached to lower housing section 1064*d*'' to form housing 1064*d*) via a cantilevered section 1066*d* of actuator 1060*d*. This feature allows the user to index the position back and forth while depressing the button. When not pressing on actuator 1060*d*, forces acting along needle 1004*d* cannot move needle 1004*d* out of position. As described above, the indicator surface can have a controlled surface area to allow the user to see the injection site. Abutment of a forward end 1016*d* of indicator 1012*d* prevents needle 1004*d* from being injected too far into the tissue. Device 1010*d* can, for example, be held by forceps using a forward flattened surface 1018*d* near needle 1004*d*. Device 1010*d* is actuated by depressing textured actuator 1060*d* and sliding it forward or backwards. Once in or near a desired position the user removes the downward force on button 1060*d* and teeth 1062*d* click into place into one of indexed stops 1044*d* (see, for example, FIG. 9A(5)(d), thus holding device 1010*d* at the set position. Device 1010*d* can be designed, for example, to pass through a trocar with an inner diameter of at least 11 mm (a taller button can provide more tactile feel to the end user).

The embodiments described above including a rack or similar mechanisms can, for example, be made infinitely variable by, for example, providing engaging friction surfaces that are biased together but releasable upon application of a force rather than finite stopping or abutment elements such as teeth.

Figure 9B:
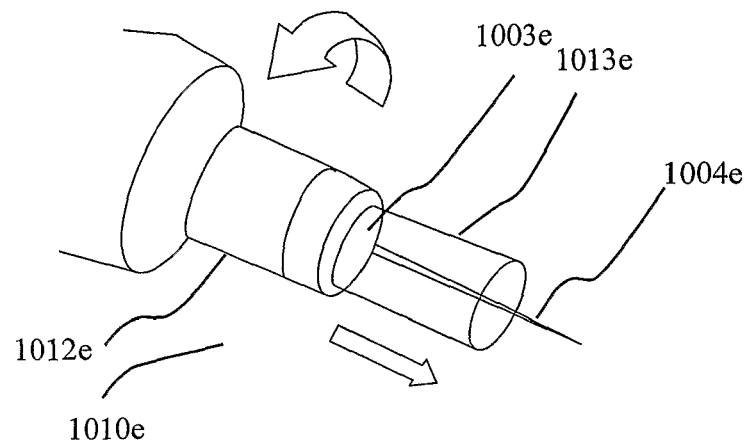
FIG. 9B illustrates an embodiment of a patient interface device of the present invention including an adjustable depth control device in which rotation causes extension or retraction of a sheath surrounding a needle.
Figure 9B:
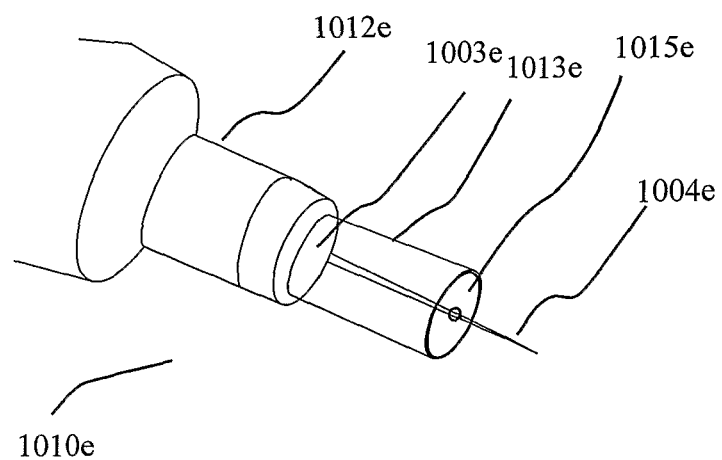

FIG. 9B illustrates a depth control device 1010*e* including an external sheath 1012*e*, connected to a needle hub 1003*e*. Sheath 1012*e* is rotated to move a transparent, adjustable sleeve 1013*e* along the length of needle 1004*e* to an infinite number of locations. Making sleeve 1013*e* clear or transparent minimizes visual obstruction while allowing for the largest diameter possible. Rotations of sleeve 1013*e* in either direction will extend or contract sleeve 1013*e* according to the amount and direction of rotation, exposing different lengths of needle 1004*e* for insertion into the injection site. A dam, barrier 1015*e* or other mechanism (for example, an elastomeric septum through which needle 1004*e* is slidable) can be provided at the distal end of the sleeve 1013*e* of device 1010*e* (and other devices of the present invention) to prevent fluid from entering the space between the inner wall of sleeve 1013*e* and needle 1004*e*.

FIG. 9B(1) illustrates an embodiment of a depth control mechanism 1010*f* that operates similarly to a clicking ballpoint pen. In that regard, in one embodiment, as an operator pushes a control button 1060*f*, a needle stop sheath 1012 *f* advances forward and turns (for example) $\frac{1}{6}^{th}$ of a revolution. When the needle stop sheath 1012*f* returns rearward upon release of button 1060*f*, one of a plurality of depth step grooves 1017*f* engages an indexing stop 1065*f*. Needle stop sheath 1012*f* is preferably biased (for example, via a spring 1019*f*) so that it returns rearward. The length of engaging depth step groove 1017*f* determines how far rearward needle stop sheath 1012*f* is allowed to travel. The predetermined lengths of depth stop grooves 1017*f* can correspond to a graduate indicator 1018*f* on needle stop sheath 1012*f* which can, for example, align with a magnifying window 1067*f* to display the needle stop setting that is selected.

FIG. 9B(2) illustrates an embodiment of a depth stop control device 1010*g* including an eccentrically mounted control or thumb wheel 1060*g* that provides variable depth stop control. An eccentric axle 1062*g* of wheel 1060*g* is attached to a housing 1064*g* which is in operative connection with tubing 1068*g* in fluid connection with a source of injectate (not shown in FIG. 9B(2) and with a needle 1004*g*. In one embodiment, a pin 1070*g* is in operative connection with needle 1040*g* and positioned within a groove 1072*g* in wheel 1064*g*. Rotation of wheel 1060*g* about eccentrically positioned wheel axis 1062*g* causes pin 1070*g* to move within groove 1072*g* and thereby move axially within housing 1064*g* to adjust the length of needle 1040*g* extending beyond a forward surface 1074*g* of needle stop housing 1064*g*. The position of wheel 1060g can be infinitely adjustable or stops can be provided to provide finite adjustment positions.

FIGS. 9B(3) and 9B(4) illustrate an embodiment of a depth stop control mechanism 1010h wherein an eccentrically mounted wheel 1060h itself provide a depth stop surface. In FIG. 9B(3) wheel 1060h is rotated about its eccentrically positioned axle 1062h so that a minimum penetration depth for needle 1004h is set, while in FIG. 9B(4) wheel 1060h is rotated about its eccentrically positioned axle 1062h so that a maximum/penetration depth is set.

FIG. 9C illustrates an embodiment of a depth control device 1010i including a contact member 1012i in the form of, for example, a "halo" or annual member that rides over needle 1004i, indexing penetration depth by restricting the depth needle 1004i can be inserted into the tissue. When placed in contact with the tissue, halo 1012i can slide (for example, via a sliding extending member 1011i that is slidable attached to a housing 1020i) to a preset "stopping point", restricting needle 1004i to a specific depth in the tissue and allowing an injection dose to be successfully administered by either manual or automated means. The minimally obstructive structure of this embodiment enhances visibility of the injection site, increasing accuracy and reducing the possibility of user error.

FIG. 9D illustrates an embodiment of a depth control device 1010j including a fitting 1012j that is pressed over, for example, a standard needle hub 1003j to a specific depth, exposing a known length of needle 1004j. Fitting 1012j can, for example, be fixedly attached and not adjustable. Fitting allows 1012j only a predetermined length of needle 1004j to be inserted into the tissue via abutment of a forward surface 1016j with the tissue.

Figure 9E:
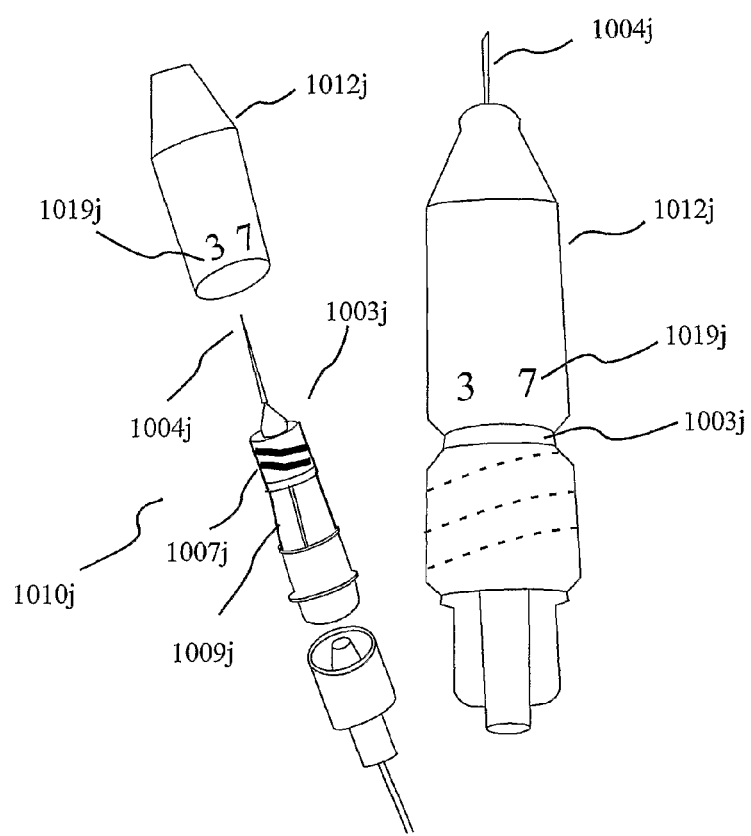
FIG. 9E illustrates an embodiment of a patient interface including an adjustable depth control mechanism in both an assembled and exploded view, wherein a sheath surrounding the penetrating member or needle is rotatable on a needle hub to adjust the position of the sheath relative to the needle.

FIG. 9E illustrates an embodiment of a depth control device 1010k including a clear or transparent sheath 1012j that slides over and onto external threads 1007j on a custom designed needle hub 1003j. Rotating sheath 1012j relative to hub 1003j causes sheath 1012j to ride rearward and forward on the threads 1007j, automatically indexing at known locations via interlocking mechanical features 1009j on the outside of needle hub 1003j. External ridges on rotatable sheath 1012j facilitate gripping and ease of rotation for the user. Numbers 1019j printed on the outside of rotating sheath 1012j indicate the currently exposed length (for example, in millimeters) of needle 1004j to the user.

Figure 9F:
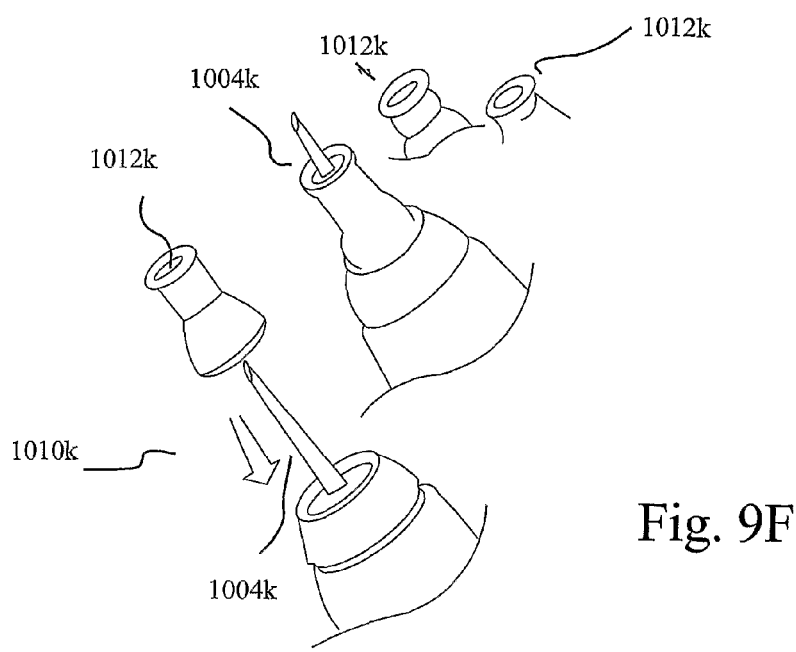
FIG. 9F illustrates an embodiment of a patient interface system of the present invention including a plurality of different depth control mechanisms.

FIG. 9F illustrates an embodiment of a depth control device or system 1010k including individual, removable depth stop contact members 1012k that are snapped over needle 1004k, exposing the tip of needle 1004k at different lengths and/or angles (via angled forward surface or edge 1016k on certain depth stop contact members 1012k) relative to forward edge 1016k of depth stop contact member 1012k. Alphanumeric and/or color-coded markings can indicate the different angles and depths of contact members 1012k to the user. Multiple contact members 1012k can be used throughout a single procedure, allowing the user to manually constrain the injections to a wide range of parameters (depth, angle, etc. . . . ).

Figure 9G:
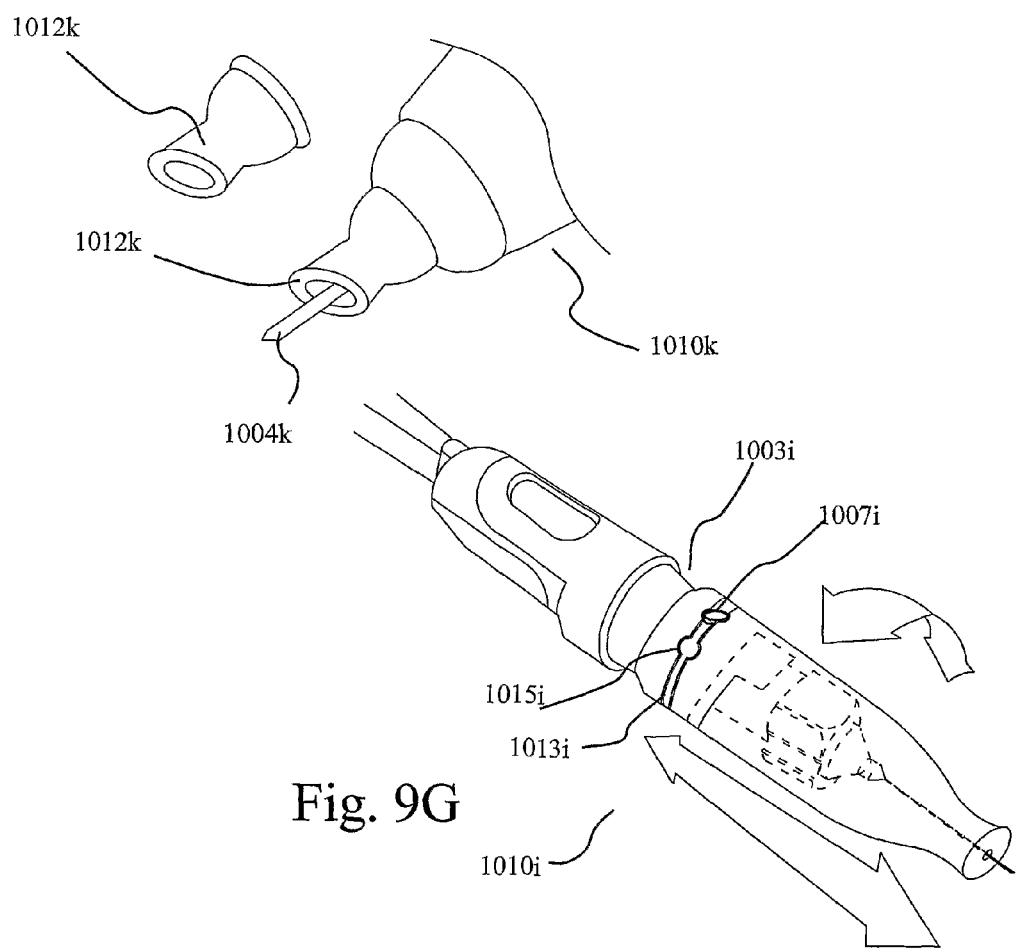
FIG. 9G illustrates another embodiment of a patient interface including an adjustable depth control mechanism including a sheath surrounding the penetrating member or needle that is rotatable on a needle hub to adjust the position of the sheath relative to the needle.

FIG. 9G illustrates an embodiment of a depth control device 1010l including a spiral groove 1013l in the depth stop sheath 1012l that rides on a stationary post 1007l on a needle hub 1003l. Rotating depth stop sheath 1012l causes it to extend and retract, altering the length of exposed needle 1004l and regulating depth of penetration. Small variations in the size of the depth stop groove 1013l form position stops 1015l, corresponding generally to the size or diameter of post 1007l on needle hub 1003l, index the location of depth stop sheath 1012l in known locations indicated, for example, by numeric markings on depth stop sheath 1012l.

FIGS. 9G(1) and 9G(2) illustrate another embodiment of a depth control device 1010m. As described above a reservoir 1020m can be provided for applying an adhesive bonding material between needle 1004m and a sliding member 1030m to firmly attached needle 1004m to sliding member 1020m. A built-in depth stop 1032m limits the forward motion of sliding member 1030m so the user cannot extend needle 1004m beyond the limit set by detents 1042m formed in a housing 1040m. A spring or other biasing member 1050m provides a load on a pin 1060m to control the set position of needle 1004m past a forward indicator surface 1044m of housing 1040m. As described above, indicator surface 1044m can have a controlled shape and/or surface area to allow the user to see the injection site, and abutment of tissue with indicator surface 10044m prevents needle 1004m from being injected too far into the tissue. Device 1010m can, for example, be held by clamps (for example, hemostats) around the outer surface of housing 1040m during, for example, a heart procedure (such as open hear surgery or thoracic surgery through the chest wall). In several embodiments, the needle depth position does not change during use. Fixed positions corresponding to a penetration depth of, for example, 4 mm, 6 mm and 8 mm can be provided. The position setting of device 1010m can be set using one hand through a twisting and sliding motion sliding member 1030m while holding the outer housing 1040m and an upper knob of flange 1046m where tubing 1048m enters device 1010m. In one representative embodiment, device 1010m can, for example, pass through a trocar having an inner diameter of at least 10 mm.

Figure 9H:
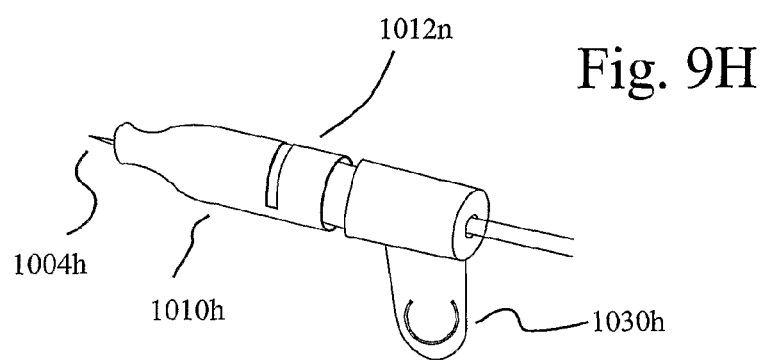
FIG. 9H illustrates a perspective view of another embodiment of a patient interface including an adjustable depth control mechanism and a "butterfly" portion to facilitate grassing thereof.

FIG. 9H illustrates an embodiment of a depth control device 1010n including a standard needle hub that can be snapped into a custom depth stop subassembly 1012n including an integral butterfly 1020n. Butterfly element 1020n is suitable for grip with either fingers or other suitable gripping surgical instrument (for example, a clamping device such as hemostats), improving control of needle 1004n.

Figure 9I:
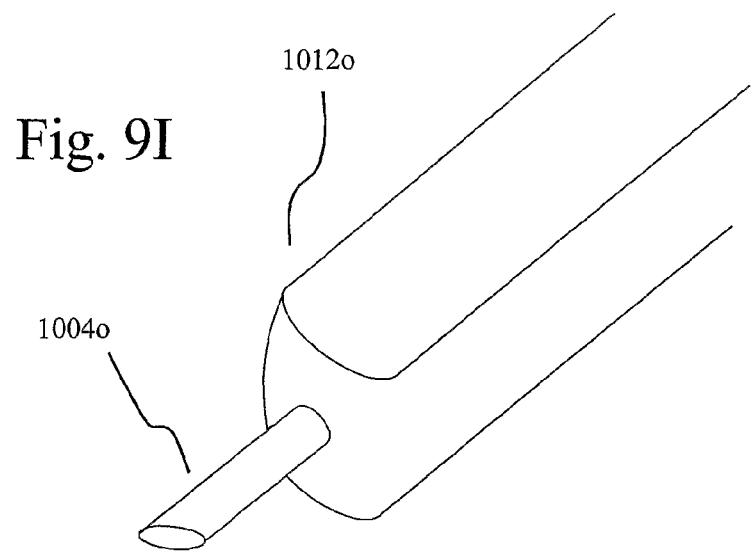
FIG. 9I illustrates a perspective view of another embodiment of a patient interface including a needle or penetrating member that is adjustable in position relative to a curved depth control mechanism.
Figure 9J:
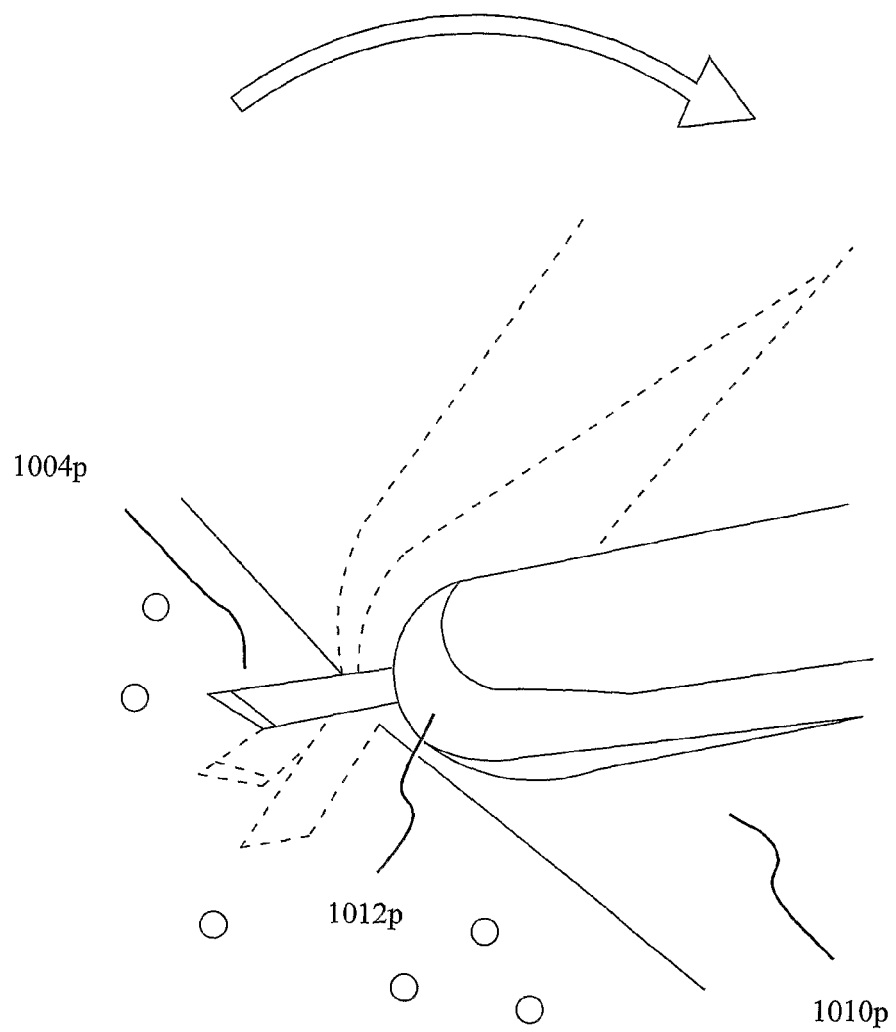
FIG. 9J illustrates a perspective view of another embodiment of a patient interface including a needle or penetrating member that is adjustable in position relative to a curved depth control mechanism.

FIG. 9I illustrates an embodiment of a depth control device 1010o including a needle 1004o that adjusts in and out of a stationary depth stop 1012o. In the illustrated embodiment, depth stop 1012o is rounded or bull-nose shaped. FIG. 9J illustrates another embodiment of a depth control device 1010p including a needle 1004p that adjusts in and out of a stationary depth stop 1012p. In the embodiment of FIG. 9J depth stop 1012o is generally domed-shaped.

Figure 9K:
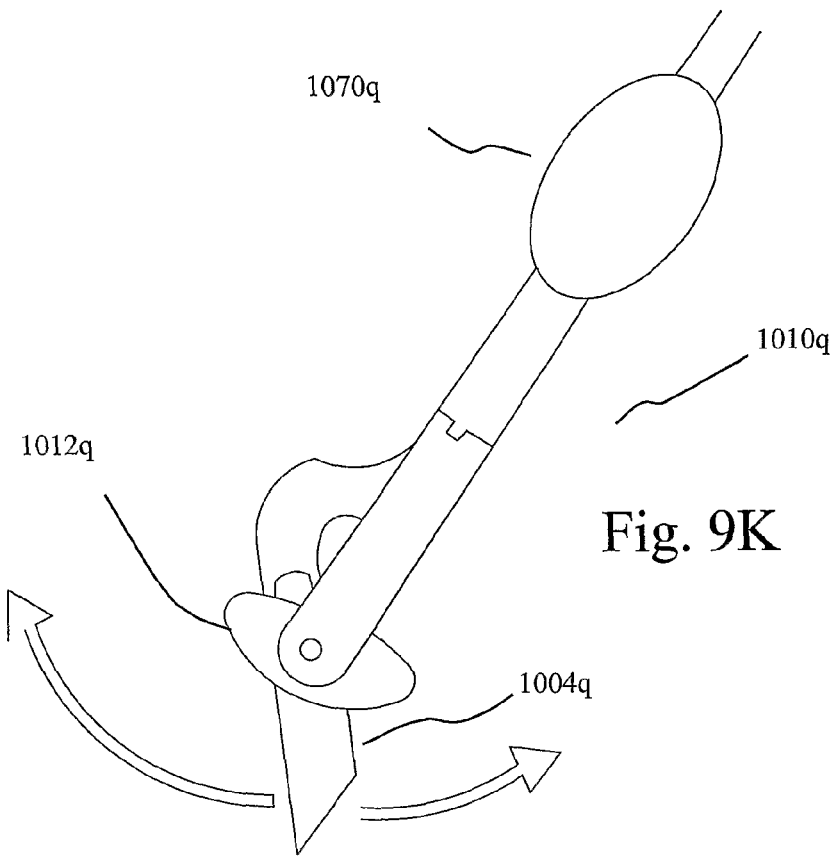
FIG. 9K illustrates a perspective view of another embodiment of a patient interface including a curved needle or penetrating member that is adjustable in position relative to a curved depth control mechanism.

FIG. 9K illustrates an embodiment of a depth control device 1010q including a needle 1004q that moves or articulates relative to a handle 1070q, allowing the user to adjust the angle of needle 1004q. Increasing or decreasing the angle of needle 1004q can adjust the depth of needle penetration perpendicular to the tissue surface. A curved depth stop 1012q contacts the tissue to limit penetration of needle 1004q.

Figure 9L:
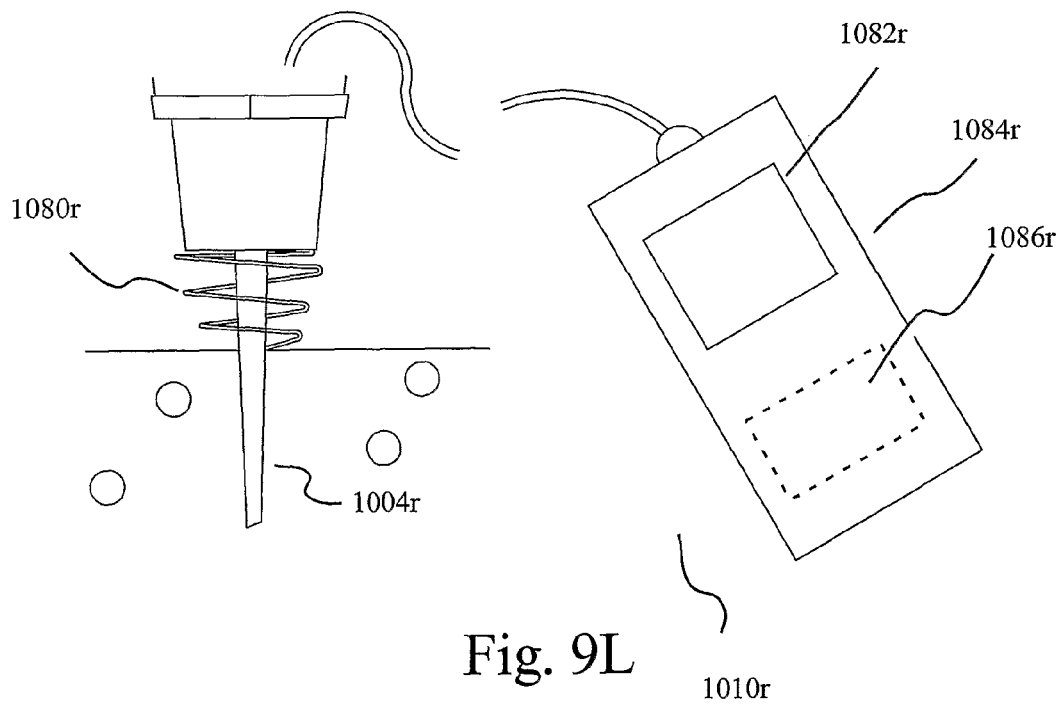
FIG. 9L illustrates an embodiment of a depth control device including a mechanism that measures/indicates the depth of needle penetration by detecting the amount of deformation or compression of a spring or other element.

In addition to mechanical or contacting depth stops as discussed in connection with the above embodiments, various sensor mechanisms can be provided to ensure that injection is made at a desire depth. For example, FIG. 9L illustrates an embodiment of a depth control device 1010r including a mechanism that measure/indicates the depth of needle penetration by detecting the amount of deformation or compression of a spring or other element 1080r surrounding the tip of needle 1004r and translating that into a distance displayed to the user on a display 1082r of a measurement unit 1084r that can, for example, comprise a processor 1086r such as a microprocessor and can be part of or in communication with control system 200. As clear to one skilled in the art, many measuring or sensing mechanisms can be used to measure depth of penetration.

Figure 9M:
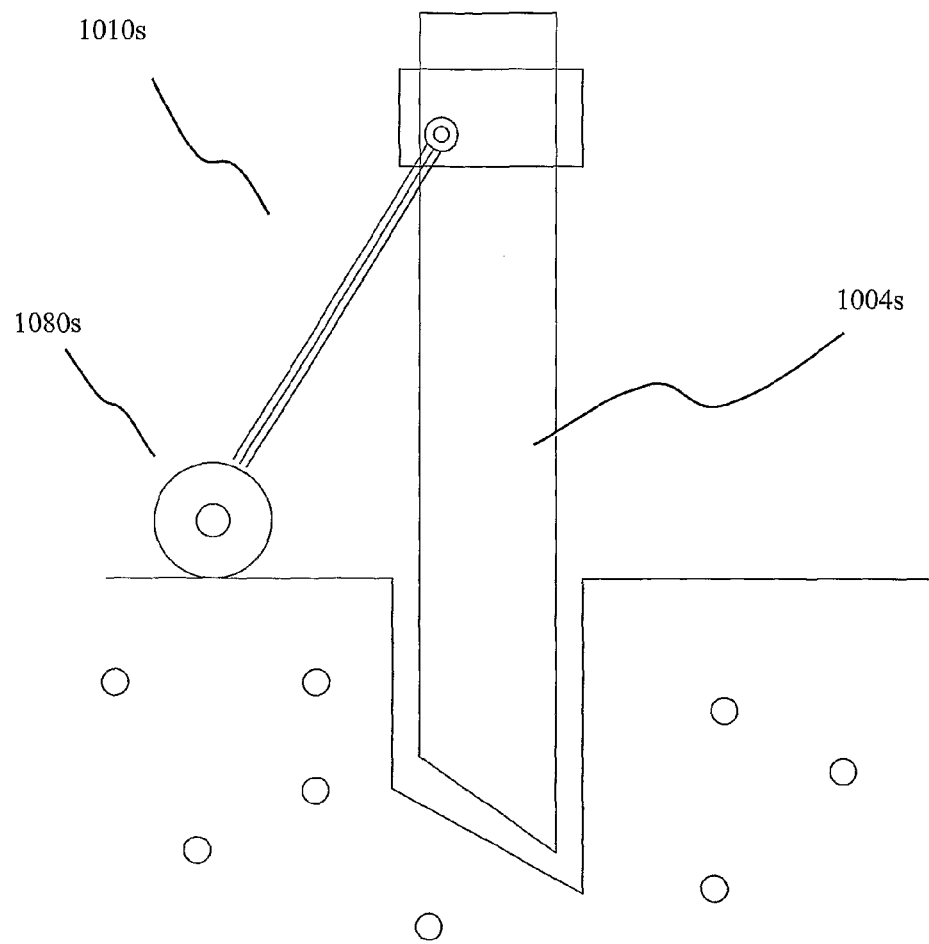
FIG. 9M illustrates an embodiment of a depth control device including a mechanism that measures/indicates the depth of needle penetration.

FIG. 9M illustrates an embodiment of a depth control device 1010s wherein an energy assist mechanism provides, for example, needle vibration to enable/facilitate penetration of tissue. Needle 1004s can, for example, include a blunt tip that is non-penetrating or non-piercing without energy assist. Once vibration (or other energy assist) stops, needle 1004s no longer penetrates the tissue. A depth monitor or sensor 1080s can be provided to shut off vibration (or other energy assist) when an appropriate depth is reached. Energy assisted needles are, for example, discussed in Published PCT International. Patent Application No. WO 05/086874, the disclosure of which is incorporated herein by reference.

Figure 9N:
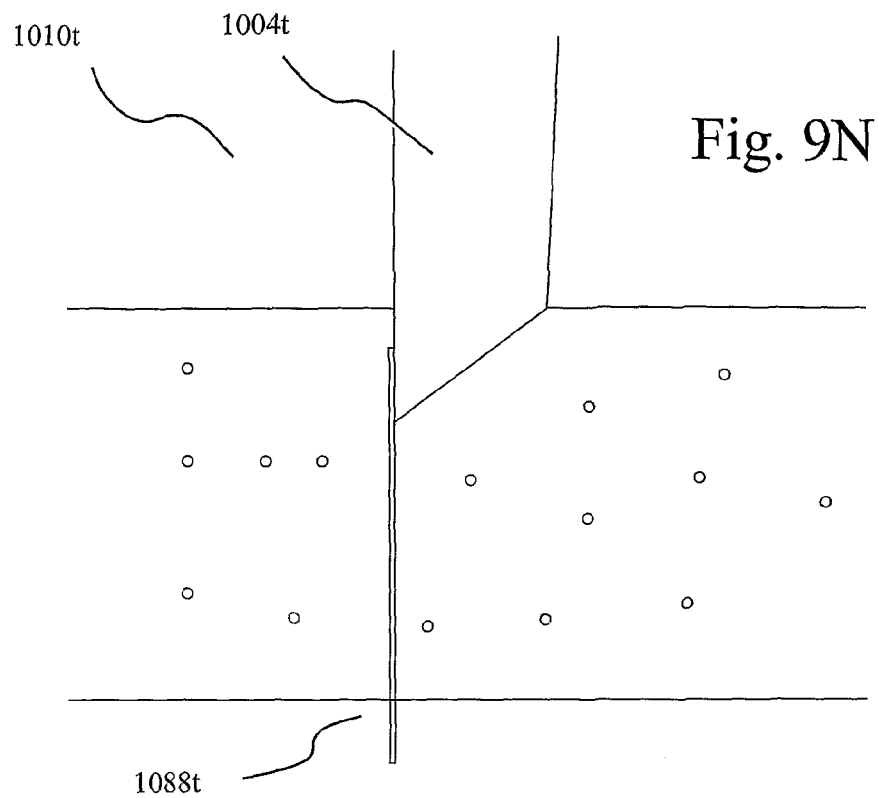
FIG. 9N illustrates an embodiment of a depth control device including a mechanism that limits the depth of needle penetration by detecting passage of a penetrating element through a layer of tissue (for example, the myocardium).

FIG. 9N illustrates an embodiment of a depth control device 1010t including a piercing element 1088t that automatically signals when penetration of needle 1004s is to be stopped. During operation, piercing element 1088t goes through a certain defined point or layer in tissue such as the myocardium and detects entrance into an area such as a ventricle. A signal is transmitted upon entrance into the ventricle (as determined, for example, by a reduction in resisting force) to, for example, control system 200. Upon transmission of that signal, needle penetration can be ceased. Preferably, piercing element 1088t has a very small diameter so that depth detection can be provided without excess tissue damage.

Figure 9O:
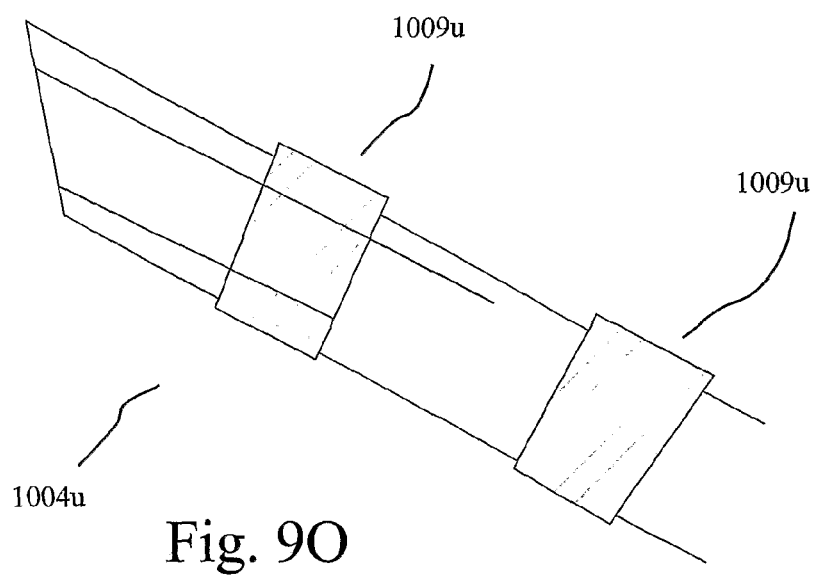
FIG. 9O illustrates an embodiment of a needle or penetrating member of the present invention including indicators adapted to be visible in an imaging system to assist in guidance of and determination of the depth of penetration of the needle.

Depth control can additionally or alternatively be effected by providing, for example, incremented indicators or other indicators on the needle to indicate depth of penetration. By, for example, etching annular indicators 1009u in a needle 1004u at even increments as illustrated in FIG. 9O, doctors are provided with a visual reference for needle insertion depth. Moreover, such etching may be detectable using an imaging unit such as an ultrasonic imaging unit as well. Alternatively or additionally, indicators 1009u can includes spaced electrodes or other sensors that provide a measurement of the depth of penetration of needle 1004u. Needle 1004u can, for example, be in a retracted state and be extended in a controlled manner to a desired penetration depth as determined, at least in part, by feedback from electrodes 1009u.

Figure 9P:
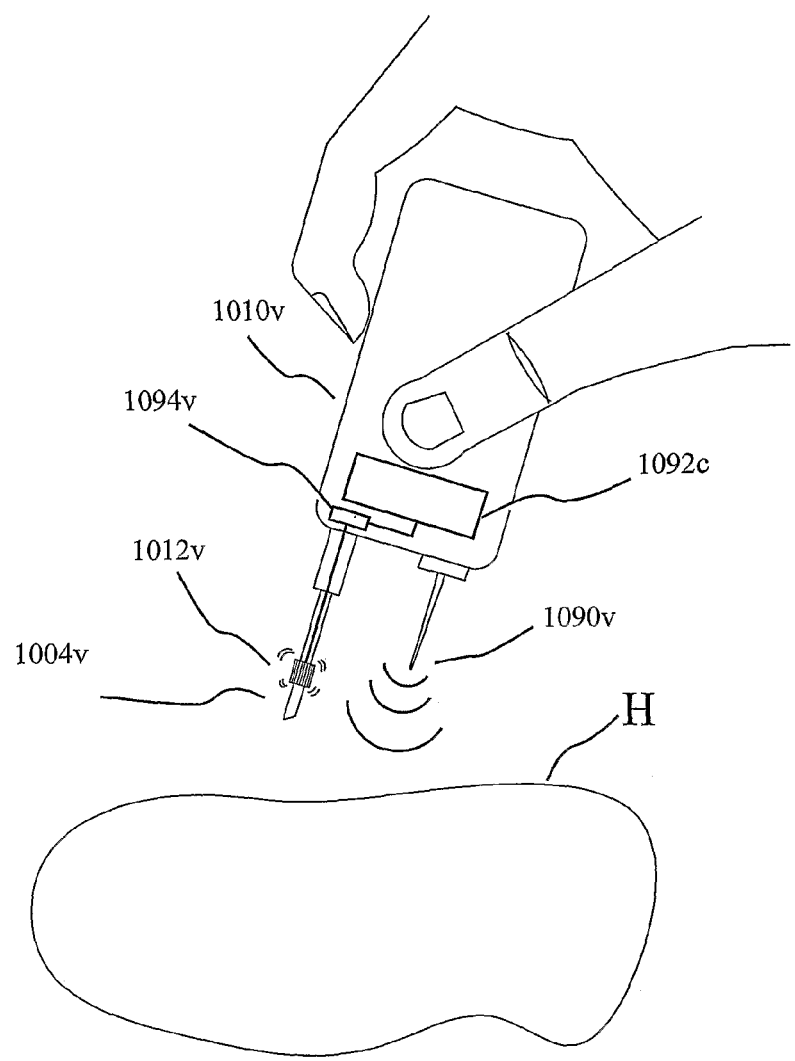
FIG. 9P illustrates an embodiment of a depth control device of the present invention including a sensor mechanism that measures/indicates the thickness of target tissue.

FIG. 9P illustrates an embodiment of a device 1010v of the present invention including an adjustable depth stop 1012v (as, for example, described for several embodiments above) in operative connection with a needle 1004v. Device 1010v also includes a sensor 1088v operative to measure the thickness of tissue to be penetrated by needle 1004v. Sensor 1090v can, for example, include a piercing member such as element 1088t of FIG. 9N, which can, for example, contact a layer in tissue such as the myocardium of heart H and detects entrance into an area such as a ventricle to provide a determination of tissue thickness. Sensor 1090v can also or alternatively include an ultrasound probe operable in connection with a controller 1092v to measure tissue thickness. In that regard, sensor 1090v can, for example, be in communicative connection with controller 1092v. which can, for example, be in communicative connection with or a part of control system 200. Controller 1092v (which can, for example, include a microprocessor) can be in communicative connection with an actuator 1094v (for example, a motor) in operative connection with adjustable depth stop 1012v. Once the thickness of the tissue (for example, heart tissue H) has been determined. Actuator 1094v can be used to adjust the position of depth stop 1004v to provide a desired depth of penetration of needle 1004v (for example, so that needle 1004v does not pass through the myocardium and into a ventricle).

E. Backflow or Retrograde Prevention, Fluid Retention and Fluid Targeting

An issue that arises when injecting an injection fluid such as a cell-bearing fluid into tissue or organs is the propensity of the fluid to retrograde or backflow from the injection site. There are several risks associated with backflow or retrograde. For example, the number of properly placed cells is significantly reduced by retrograde, which can diminish the clinical effectiveness of specific cell delivery. Further, if several sites are injected within a single organ or tissue, the amount of viable cells in each injection may vary significantly resulting in poor overall clinical effectiveness. The cells contained in the retrograde fluid may also be hazardous to the surrounding tissue or hazardous to the clinicians and other attending personnel. Several embodiments of the present invention for prevention of backflow or retrograde include one or more mechanical members, either on the needle or close to the needle, that are operate like a plug or cause a seal between the needle and the tissue to reduce the amount of retrograde flow. Several such embodiments are briefly discussed above.

Figure 10A:
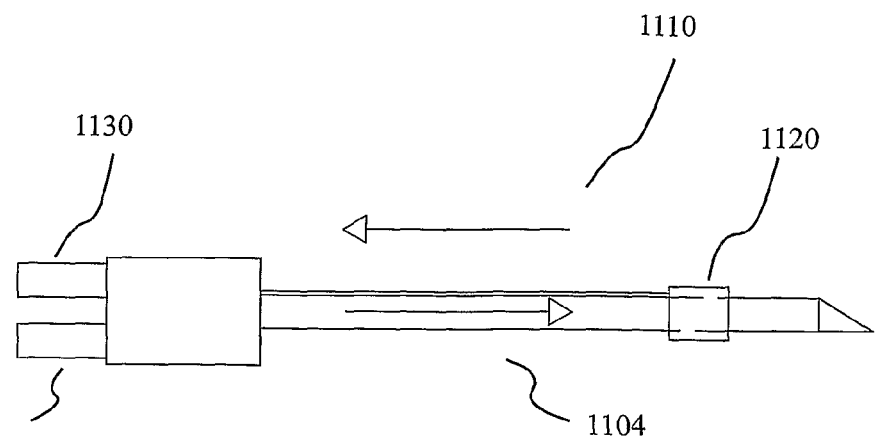
FIG. 10A illustrates an embodiment of a device of the present invention including a porous filter member in operative connection with a vacuum source in the vicinity of the distal end of a penetrating member.

FIG. 10A illustrates an embodiment of a device 1110 including a needle 1104 (which can be a multiple lumen needle) including a porous wall section 1120 that is in fluid connection with a vacuum source 1130. As the cells and carrier fluid from a fluid source 1140 in fluid connection with needle 1104 exit the end of needle 1104, the fluid is drawn away from the injection site by applying vacuum to porous wall section 1120, which functions as a filter. The fluid can easily pass through porous wall section 1140, however the cells cannot pass through this section because of their size (~7 micron). The pore size of porous wall section 1140 or other filter can, for example, range from 4 to 10 micron. In another embodiment porous section 1140 is not attached to the vacuum source. As the cells and carrier fluid accumulate at the end of the needle, the pressure differential causes the fluid to exit the through porous section 1149 and be captured in a container (incorporated similarly to vacuum source 1130) in the proximal end of the needle.

Figure 10B:
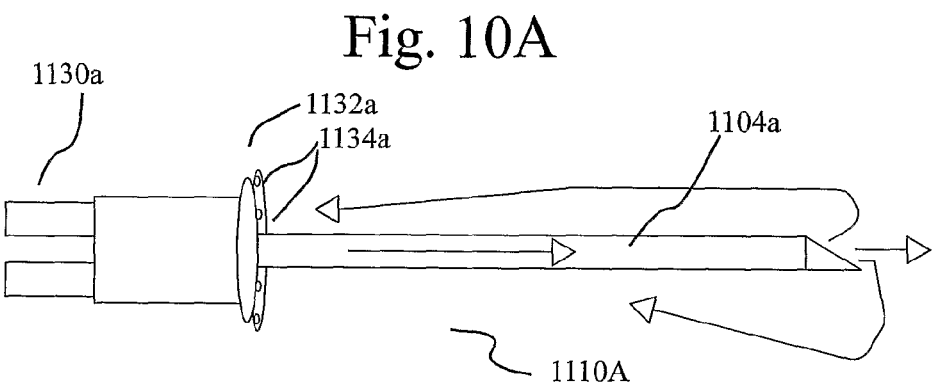
FIG. 10B illustrates an embodiment of a device of the present invention including a ported member that contacts the tissue and is in fluid connection with a vacuum source.

FIG. 10B illustrates an embodiment of a device 1110a of the present invention in which a ring 1132a is positioned circumferentially about needle 1104a. Ring 1132a has at least one hole or port 1134a in fluid connection with a vacuum source 1130a. When properly positioned during an injection, hole(s) 1134a have direct contact with the tissue. As needle 1104a is placed in the injection site, ring 1132a makes contact with the tissue. As the injection is started, vacuum is initiated, which assists in drawing the fluid through the tissue, thereby improving cell distribution, while minimizing retrograde flow outside of the target tissue. Additionally or alternatively, a multineedle array such as illustrated in FIG. 6N can be used in which one or more needles are used to inject fluid/cells and one or more other penetrating needles are used to apply suction within the tissue to draw fluid into the tissue.

Backflow can also be prevented by application of a sealing element. For example, a fibrin adhesive sealant or a polymeric film can be applied. Likewise, collagen/gelatin or other plug can be inserted at the injection site. The devices of the present invention can, for example, accomplish this application automatically after needle withdrawal or manually by the clinician. The use of various plugs or sealing element is, for example, discussed in U.S. Patent Application No. 2003/0109899, the disclosure of which is incorporated herein by reference.

Figure 10C:
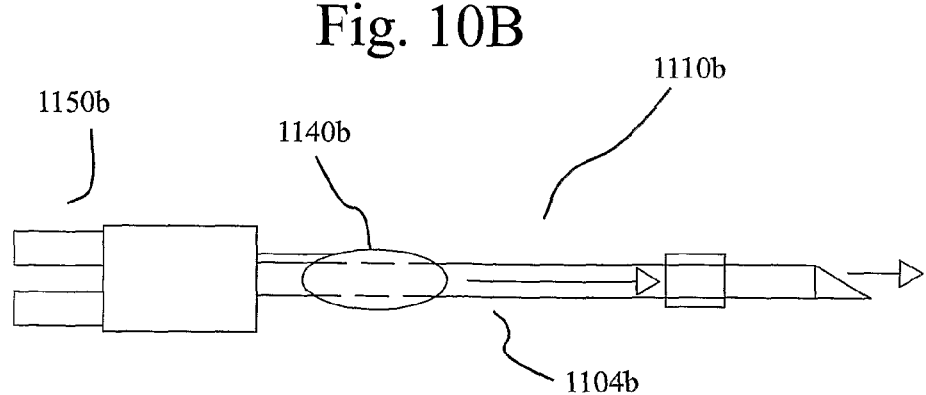
FIG. 10C illustrates an embodiment of a device of the present invention including a penetrating member or needle with an attached small balloon or other expanding member, which is in communication with a source of inflation fluid.

FIG. 10C illustrates an embodiment of a device 1110b of the present invention including a needle 1104b with an attached small balloon or other expanding member 1140b, which is in communication with a source of inflation fluid 1150b. Small balloon 1140b can, for example, be circumferentially attached to the shaft of needle 1104b. Once needle 1140b is inserted into the tissue, balloon 1140b is inflated to a specified diameter or pressure. When inflated, balloon 1140b acts as a stop to prevent backflow of fluid from the injection site. This may also help maintain the isolated injection pressure, such that it will aid in dispersing the cells more broadly into the tissue, effecting a better clinical outcome. Balloon 1140b can be fully in the tissue, partly in and partly out, or almost totally out of the tissue. The shape of balloon 1140b can, for example, be determined by it's designed penetration depth at inflation. For a fully inflated balloon, balloon 1140b is preferably relatively thin and uniform. For a barely inserted balloon, balloon 1140b is preferably more round to act like a plug applied to the outside of the tissue. For a partially inserted balloon, balloon 1140 can, for example, have a conical wedge, tapered, or stepped shape.

Although materials, such as polyurethane, silicone or other materials can be used for balloon 1140b, polyethylene terephthalate PET provides an advantage as a result of its "heat setting" characteristic. Heat setting refers generally to the ability of PET to "remember" a dimension when blow molded, such that it will not continue to inflate (or grow in diameter) when pressure is applied. This characteristic is important for this type of application, because tissue damage may occur if balloon 1140b is over-expanded. The characteristic of heat setting is used in PET beverage bottles, as well as in angioplasty medical balloons.

In another embodiment, after cell delivery, and prior to removing the needle from the injection site, a bolus of a diluent or flushing fluid such as saline is delivered into the tissue. This saline bolus improves dispersement the cells by pushing them deeper into the tissue and increasing the overall effectiveness of the procedure.

Figure 10D:
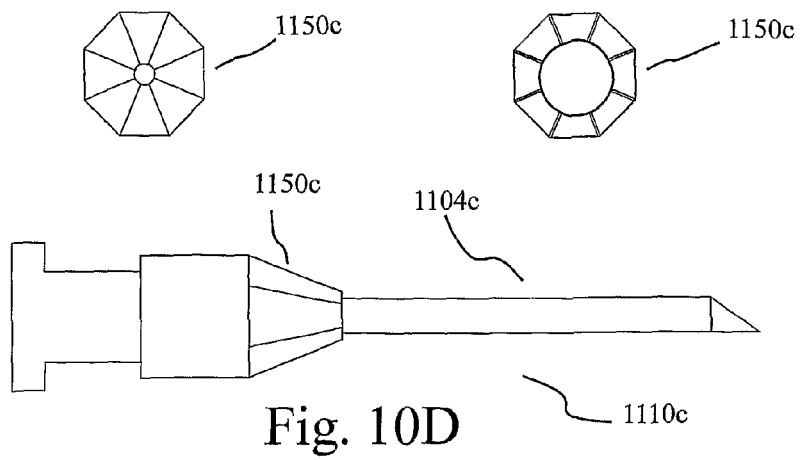
FIG. 10D illustrates an embodiment of a device of the present invention including a sealing member in operative connection with a penetrating member or needle to apply force to tissue and limit backflow.

FIG. 10D illustrates another embodiment of a device 1110c of the present invention in which tissue around an injection site is mechanically held to prevent retrograde flow. There are a number of manners for mechanically sealing the tissue around the needle during an injection. In one example, a flat, dish-shaped device can be held against the tissue during the injection (and for a period of time after the injection—while pressure equilibration takes place) to prevent fluid from escaping the injection site. Alternatively, a colet-like device 1150c can trap the tissue within its grasp and apply a closing force (a radially inward force in the illustrated embodiment) as illustrated in FIG. 10D. The operation of collet 1150c can be an automatic function, triggered by tissue contact, or manually operated by the clinician. As illustrated in FIG. 10D collet 1150c can be located proximal to the tip of needle 1104c. The upper left portion of FIG. 10D illustrates a front view of collet 1150c in a closed state, while the upper right portion of FIG. 10D illustrates a front of collet 1150c in an open state.

In a further embodiment as illustrate in FIG. 10D(1), a film 1154d (preferably a biocompatible film) is attached to tissue T (for example, via an adhesive) as needle 1104d is placed. Film 1154d is attached in a manner to act as a seal around needle and prevent retrograde flow during the injection. Biofilm 1154d can be biodegradable such that it slowly degrades (for example, dissolves) over time as the wound heals. Biodegradable polymers and adhesives are disclosed, for example, discussed in Published U.S. Patent Application No. US-2004-0170597, the disclosure of which is incorporated herein by reference. This film could also serve a marking or indication function as discussed elsewhere.

Figure 10G:
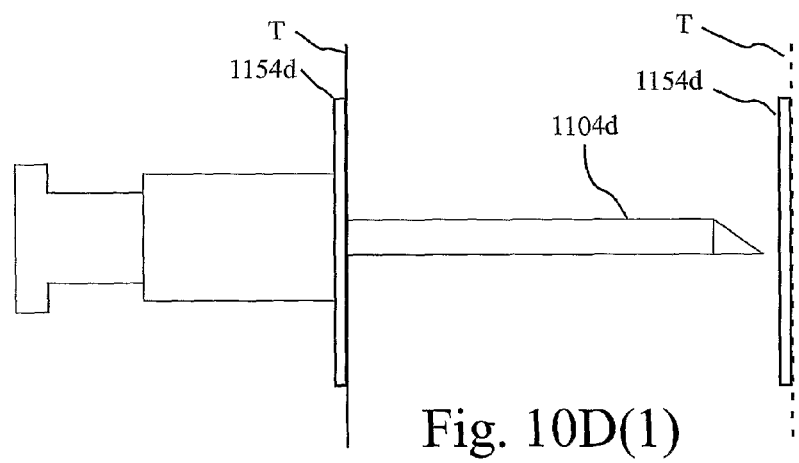
FIG. 10G illustrates an embodiment of a device of the present invention including a plurality of injecting syringe elements.
Figure 10G:
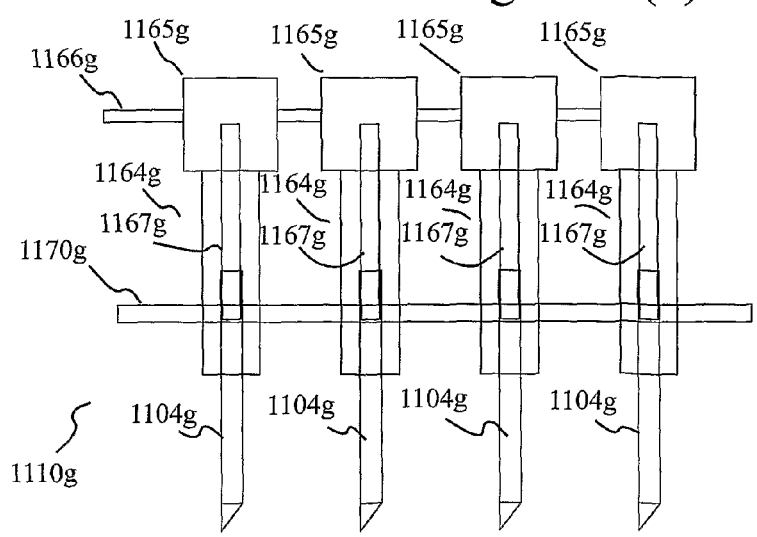
Figure 10E:
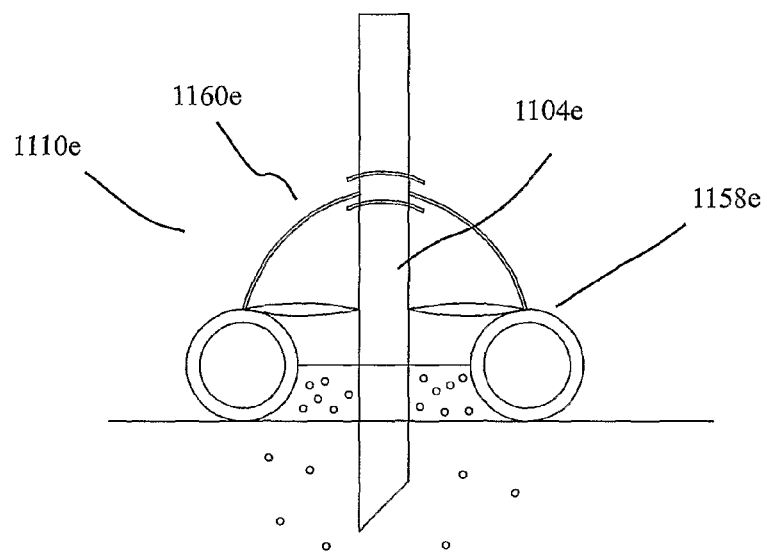
FIG. 10E illustrates a side view and a perspective view of an embodiment of a device of the present invention including a containment member that surrounds an injection site.
Figure 10E:
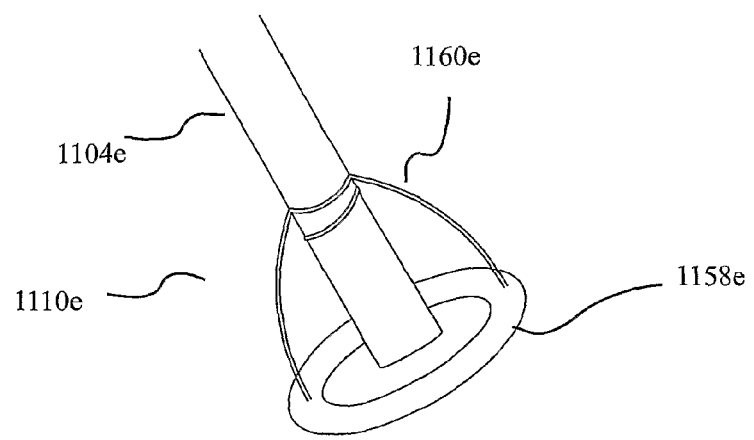

FIGS. 10E and 10E(1) illustrate a device 1110e in which, for example, a soft pillow ring 1158e and connected enclosure 1160e are mounted to a needle 1104e. Upon contact with tissue T, ring 1158e can deform to conform to the shape of the tissue surface and can form a sealing engagement therewith. Fluid that seeps from the injection site is retained by ring 1158e, increasing the likelihood that the injected fluid will return to the injection site and be retained within the tissue.

Figure 10F:
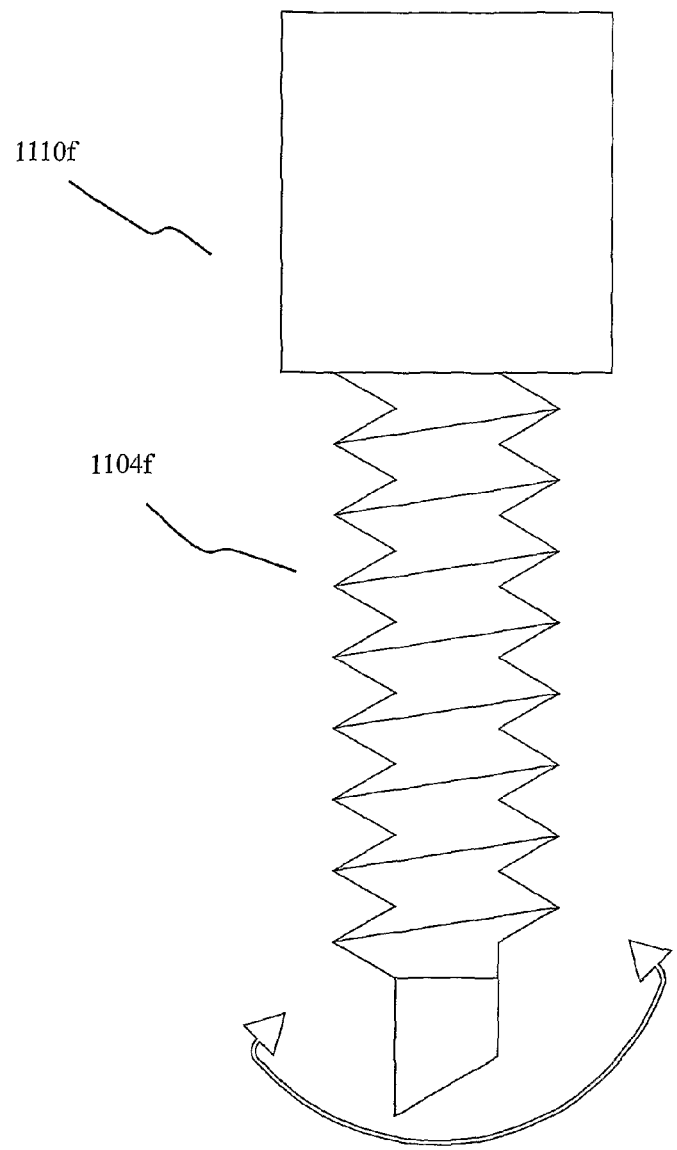
FIG. 10F illustrates an embodiment of a threading, rotating penetrating member or needle of the present invention.

The shape of the needle can also improve fluid retention. For example, FIG. 10F illustrates an embodiment of a device 1110f of the present invention including a free-spinning, threaded needle 1104f that creates a torturous path or track upon insertion into tissue that prevents injected material from readily flowing up the side of needle 1104f and out of the tissue. Such a threaded needle 1104f also assists in placing needle 1104f in secure connection with the tissue.

Alternatively, the injection protocol can be modified to enhance fluid retention, for example, by injecting the injection fluid, then delaying the needle withdrawal until the fluid is dispersed into the tissue. This delay may only be a few seconds and can be monitored by control system 200. After the injection, a second timer or timing function can start a count down. When complete, an audible (or other type of) indication or alarm can be activated signaling that the needle can be withdrawn.

Other methodologies can also aid in the dispersion and retention of cells. An example is the pulsing of the injectate flow rate at a given frequency to drive the cells deeper into the tissue. This methodology operates similarly to a concrete vibrator, which is used to eliminate voids in the slurry. Another method is a slow injection, which allows capillary action to distribute the cells with minimal backflow. Potentially, this approach can be accomplished by using a distribution system, which includes a series of tubes with needles that are all placed in operative connection with pump system 100 at the same time. The fluid is then slowly infused into the tissue to mitigate retrograde flow. As illustrated in device 1110g of FIG. 10G, to eliminate uneven or volume inaccuracy as a result of pressure differentials, individual needle assemblies 1164g can include a piston 1167g and an actuator 1165g (for example, an electrical or hydraulic—using, for example, saline supplied via a manifold system 1166g) actuator) to inject the fluid through needles 1104g. Such individual control can provide volume accuracy for each injection site. Fluid can, for example, be supplied to needle assemblies 1164g via a manifold systems 1170g.

Figure 10H:
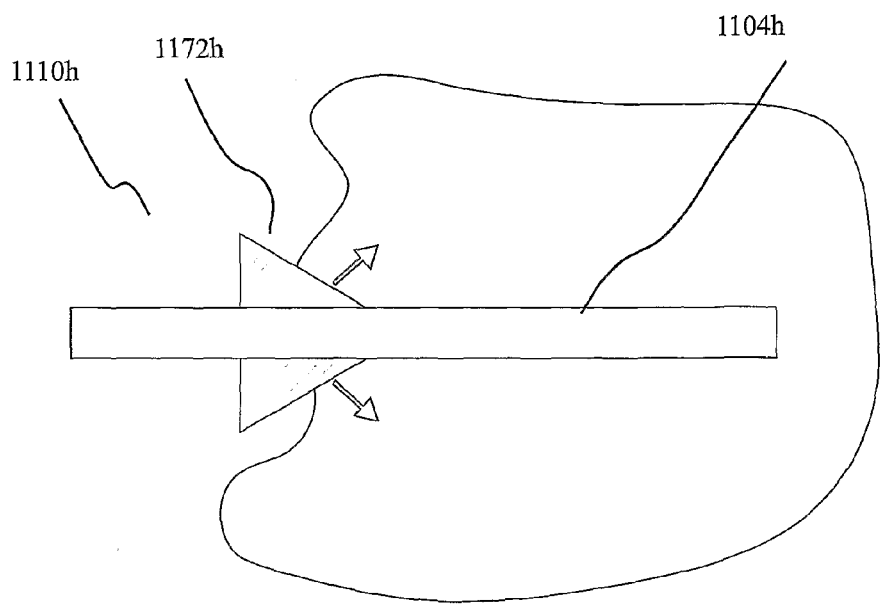
FIG. 10H illustrates an embodiment of a device of the present invention including a wedge shaped sealing member in operative connection with a penetrating member or needle.
Figure 10I:
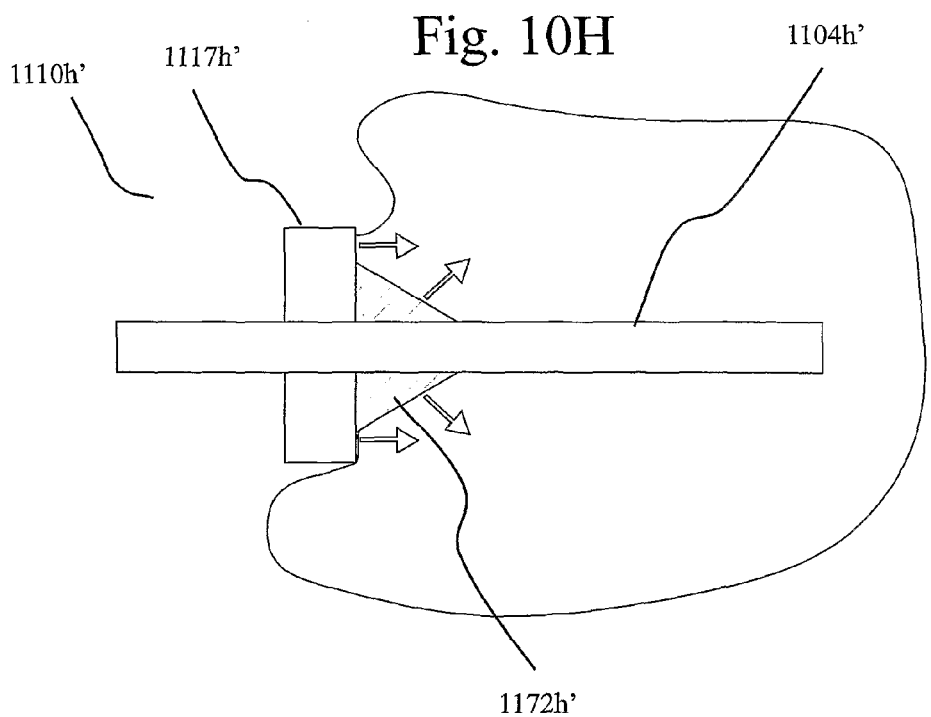
FIG. 10I illustrates another embodiment of a device of the present invention including a wedge shaped sealing member in operative connection with depth control mechanism and a penetrating member or needle.

FIG. 10H illustrates another embodiment of a device 1110h including a mechanism for reducing leakage of injected fluid which includes a tapered or conical member 1172h that is fixed or slidable on a needle 1104h or a catheter, so that when needle 1104h is in the correct place in the tissue, conical member 1172h is slid forward to increase the pressure on the tissue and reduce the leakage of injected fluid. FIG. 10I illustrates incorporation of the tapered or conical member 1172h into a depth stop or penetration depth control mechanism 1174h in device 1110h'. The forward flat surface of depth control mechanism 1174h provides the depth stop function and tapered or conical section 1172h provides increased pressure to reduce back flow.

F. Cavity Creation

Injection fluid/cell distribution and retention can also be enhanced and retrograde flow decreased through cavity creation in the tissue prior to, during or after injection. In that regard, a cavity (that is an open volume) of some size and shape in tissue can be created as a repository for injected cells.

Cavities can be produced in several ways in, for example, the outer wall of the heart during thoracotomy (or percutaneously) or the inner wall of the heart (endocardium; generally through the use of catheter-based systems). For example, cavities can be created using a fluid jet (for example, containing cells in a fluid medium). Cavities can also be formed using a fluid jet from primary port or a secondary port using a fluid not containing cells. Such a non-cell-bearing fluid can be used to create cavities with much higher flow rate than the flow rate at which the cells are delivered, thereby preserving the biological integrity of the cells. Cells can, for example, be delivered after cavity formation through another, lower pressure, port. Cavities can also be created by application of energy to disrupt or ablate tissue (for example, myocardial tissue). Examples of suitable energy include, but are not limited to, ultrasound, laser light, RF or microwave energy, thermal heating, and/or cryogenic cooling. Cavities can also be created by simple mechanical disruption or dissection of tissue, such as with any number of mechanical member including, for example, a dilator, forceps, or dilatation balloon. Cells can also be embedded in a plug of, for example, an elastic solid or a gel which is then deposited into the cavity created by the plug itself.

A number of known cavity forming methods and devices can be adapted for use in connection with delivery of therapeutic agents (including, for example, cell therapy). For example, U.S. Pat. No. 6,344,027, the disclosure of which is incorporated herein by reference, discloses a water jet catheter for creating holes or cavities in the endocardium. The clinical purpose set froth in U.S. Pat. No. 6,344,027 is to apply TMR therapy (Transcatheter Myocardial Revascularization) to the heart. The same or a similar technique can, however, be used to create cavities in the heart wall for deposition of therapeutic medications, including, but not limited to, cells, proteins, or gene vectors. U.S. Pat. No. 6,224,566, the disclosure of which is incorporated herein by reference, discloses a similar TMR system that creates cavities in tissue using laser light delivered through fiber optics in a catheter. U.S. Pat. No. 5,840,059, the disclosure of which is incorporated herein by reference, discloses a system using laser energy through an optical fiber delivered via vascular catheter to burn a channel in the myocardium inner wall. A separate set of lumens can be used to delivery therapeutic agents into the channels. U.S. Pat. No. 6,199,554, the disclosure of which is incorporated herein by reference, discloses a method for combining therapy with controlled injury to the myocardium.

Figures 11A, 11B:
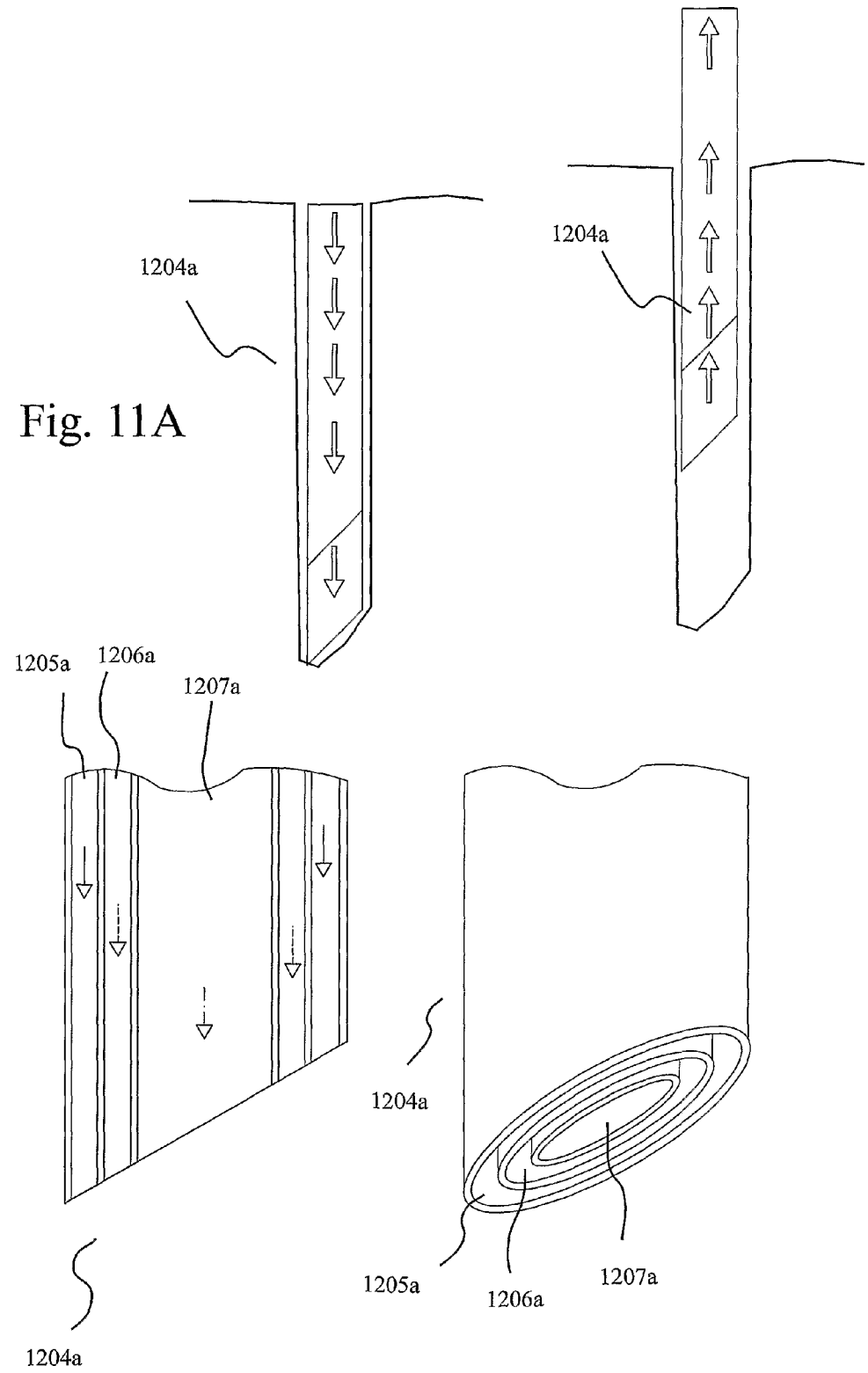
FIG. 11A illustrates use of a penetrating member or needle as a cavity creation device.
FIG. 11B illustrates a side cutaway view and a perspective view of an embodiment of a multi-lumen penetrating member of needle of the present invention.

FIG. 11A illustrates that a needle member 1204 itself can be used in cavity formation and reduction of retrograde flow. In that regard, needle 1204 can first be inserted into the tissue to a maximum depth and then withdrawn creating a cavity forward of needle 1204. Cells and/or other therapeutic agents can be injected continuously as the needle is withdrawn or injected at one or more discrete times. The cavity formed by the removal of needle 1204 is thereby filled with injection fluid. Fluid has more tissue access (as compared to the case of injection while maintaining maximum needle penetration depth) as needle 1204 withdraws because needle 1204 is not blocking tissue and the tissue void is larger. Rotating needle 1204 slightly upon insertion may increase the size of the cavity. Likewise, use of an irregular needle, a threaded needle as described in FIG. 10F or a cork-screw shaped needle as described in FIG. 7G can create a cavity of, for example, increased diameter and/or length. One or more penetrating members (which can be extendible and/or retractable independent of the motion of the needle) other than the needle (see, for example, FIG. 7A(2)) can also be used to create cavities. Such penetrating members can, for example, be positioned along one or more needles or within one or more needle lumens. Moreover, multiple needles (as, for example, described in connection with FIG. 7A(1)) can be used to simultaneously create multiple cavities into which injection fluid is injected.

Multiple cavities (including, volumes such as channels or fissures) can be created in the heart muscle or other tissue using high velocity fluid jets, radiation, or simple mechanical disruption with a tissue dilator or similar instrument as described above. A lumen can, for example, terminate in multiple nozzles, like a showerhead, to first distribute ablation channels over a wider area of the heart. Suction can be provided via the same lumen or through a separate (and potentially dedicated) lumen to remove the cavity creating fluid (for example, saline) and to free volume for a later injection or injections of therapeutic agent. A second injection can immediately follow through the same lumen or through a separate (and potentially dedicated) lumen. Such lumens can be positioned adjacent each other or in a concentric arrangement. A needle 1204a including a concentric arrangement of three lumens 1205a, 1206a and 1207a is, for example, set forth in FIG. 11B. A fluid solution other than a cell-bearing fluid can, for example, be delivered which contains nutrients and growth factors, which are injected into the pre-formed channels. In another injection or step, cells can be delivered carefully through the first or second lumen or through a third, dedicated set of lumens, which are preferably designed to minimize shear stress on the cells as they are delivered into the nutrient solutions already deposited into the pre-formed channels. Control system 200 can control the fluid delivery and, for example, synchronize fluid delivery with the diastolic interval of the cardiac cycle (discussed in more detail below). Such synchronization enables the injection of nutrients, growth factors, and cells during diastole and can minimize ejection of materials from the channels as the heart muscle contracts.

Multiple lumen systems as, for example, illustrated in FIG. 11B can be used to deliver many substances other than the primary therapeutic fluid, including but not limited buffers that protect the primary therapeutic material from damage, liquids that push the primary therapeutic fluid to further depth in the tissue, more viscous fluids or even solids or quasi-solids, that act to cap the therapy site, or color, radiological or other markers that allow the user to keep track of the injection visually or with a secondary sensing device. For example, a "protecting" or other fluid can be introduced through an outer lumen and cells or other agents introduced through an inner lumen. Also, cells or other agents can be introduced through an outer lumen and another fluid can be introduced via an inner lumen to force the cells into voids in the tissue.

In the case where the cells are to secret chemicals, they are typically placed in a number of locations so that their secretions cover target area, generally counting on diffusion for dispersion of the chemicals throughout the desired tissue. The larger the target regions, the more locations where cells need to be deployed, and thence the more needle penetration that are required. In the case of injection into the brain, assuming the injections are done stereotactically with straight needles, the more needle penetrations needed, the greater the risk of serious complications such as bleeding.

Curved needles can, for example, be used to reduce the number of needle penetrations. In the case of the brain, the majority of the path through the brain can be traversed by a straight needle and then a second smaller, curved needle can be chosen from a set with various curvatures to traverse the remaining distance. Curved tubes or needles are used for example in laparoscopic surgery and to infuse saline and supply electrical energy in RF ablation.

As described above, a controlled injection can be effected as the needle is withdrawn, so that a line of cells is deposited in the needle track. There are many ways to accomplish this result. The withdrawal can be controlled via, for example, injector 100 using computer control via control system 200 so that injection rate and position can be controlled and synchronized. Alternatively, the position of the needle can be controlled by the surgeon, and a measured position can be provided to injector 100 and/or control system 200, so that, within programmed safety limits, the desired delivery profile is achieved as the surgeon moves the needles out (or optionally in.)

Furthermore, one can take advantage of anisotropic flow or diffusion within tissue to cover a desired target region with the fewest needle penetrations possible. For example, in the case where cells are secreting chemicals that are helpful to the brain or other tissue, it can be beneficial to target the cell (or other agents) to "upstream" regions of the target organ so that both the bulk motion (of, for example, cerebrospinal fluid or CSF) and/or diffusion anisotropy preferentially carry the chemicals to the remainder of the targeted area.

For example, CSF moves through the brain such that there is a net flow and a diffusion component to its motion. In regions of the brain where there are nerve bundles (parallel arrangements of axons), diffusion and flow is easier along the direction of the bundle. Diffusion tensor imaging (DTI) is an MRI technique that allows visualization of the diffusion directions. Studies of a particular patient and/or studies of a plurality of patients/healthy subjects can be used to determine patterns of anisotropic flow and/or diffusion in a particular organ or tissue area. If for example, diffusion is preferentially in a first direction such as the vertical, then a generally orthogonal or horizontal line of deposition can be preferable. A curved needle can be used to deposit a curved "line", taking advantage of the preferred diffusion direction.

Fluid Path and Fluid Flow

A. Cell Protection and Viability in Fluid Path Elements

In general, any component with which the injection fluid comes into contact during the injection procedure is considered part of the fluid path. With reference to FIG. 3, for example, in the fluid delivery stage, the fluid path for the injection fluid (including, for example, cells) can, for example, include container 50, manifold system 90, mixing system 99, conduit 310, fluid contacting portions of inline measurement unit or system 74 (if any), patient interface 400 and any intervening conduits of connectors.

Within the fluid path (in the fluid delivery state or elsewhere—for example, in the cell harvesting, cell storage, cell processing or any intermediate stages) turbulent stresses contribute strongly to mechanical trauma of cells. Conditions that contribute to or promote turbulence include wall irregularities, abrupt changes in tube dimensions, and disturbed flow upstream of a region of interest are common in current practice, as illustrated in the luer connector in FIG. 1B. In this invention, cell damage resulting from hydrodynamic forces during handling and delivery of injection fluid are preferably minimized by reducing the occurrence of or eliminating such conditions to, for example, improve therapeutic value. In that regard, cumulative and peak shear stresses are preferably reduced or minimized. It is desirable to eliminate turbulence and areas of negative pressure (eddies) in the flow. Laminar flow is desirable. However, even damaged or dead cells my have therapeutic value in some instances, such as myocardial regeneration, whereas dead cells appear to have no value in other instances, such as the treatment of Parkinson's disease.

Figure 12A:
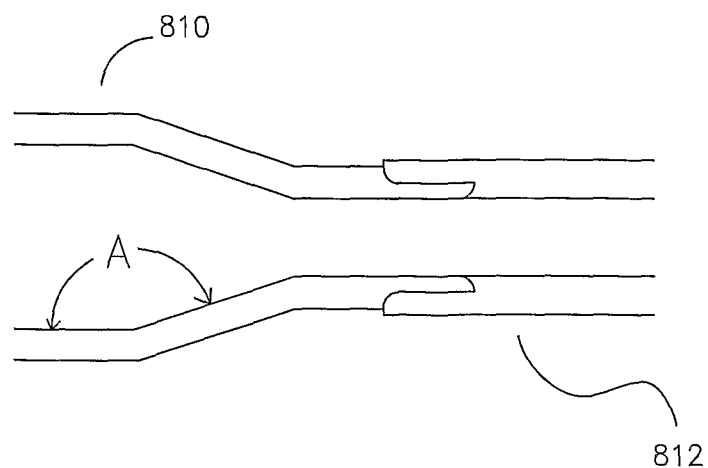
FIG. 12A illustrates an embodiment of a fluid path of the present invention providing for a gradual transition between inner diameters.
Figure 12B:
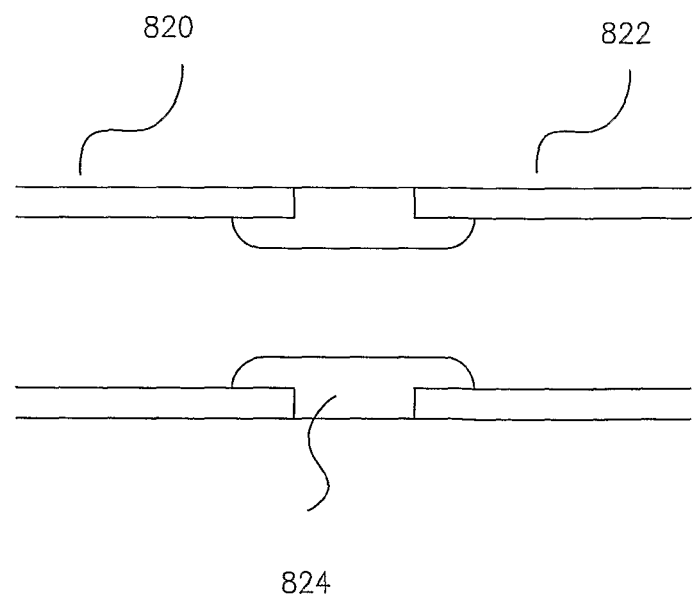
FIG. 12B illustrates an embodiment of a fluid path of the present invention including a connector providing for a curved, rounded or radiused transitions.
Figure 12C:
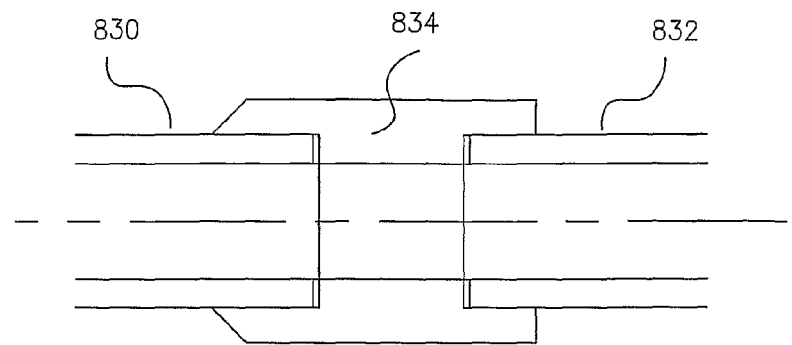
FIG. 12C illustrates the use of an intervening fitting or connector of the present invention to create a smooth transition between tubing and a needle.
Figure 12D:
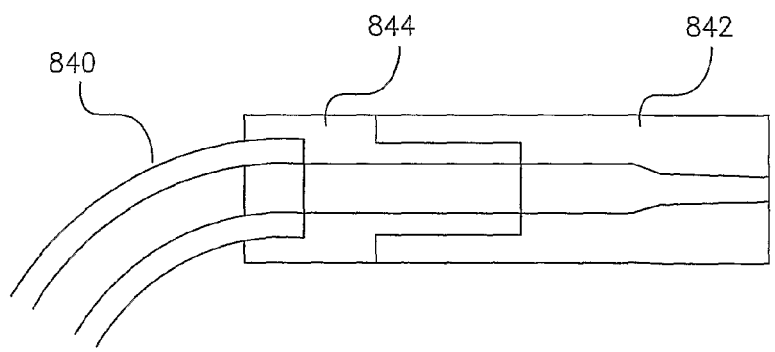
FIG. 12D illustrates use of another fitting, transition or connector of the present invention to connect a first section and a second section to provide for smooth internal diameters in the fluid path.

Hydrodynamic forces can, for example, be reduced by providing for gradual transition within and between all fluid path element. For example, FIG. 12A provides an example of a relatively gradual transition from a large radius section 1310 to a smaller radius section 1312. All edges or corners are preferably rounded or radiused as illustrated in FIG. 12B, in which a first section 1320 is connected to a second section 1322 via a connector 1324 providing for radiused or rounded edges. In any area in which two fluid path elements are joined, the joints are preferably butted to reduce or eliminates sharp transitions or to provide for smooth internal diameters. For example, FIG. 12C illustrates the use of an intervening fitting 1334 to create a smooth transition between tubing 1330 and a needle 1332. FIG. 12D illustrates the use of another fitting, transition or connector 1344 connecting a first section 1340 and a second section 1344 to provide for smooth internal diameters in the fluid path. To ease the need to have very tight manufacturing tolerances, it is preferable that the fitting be relatively elastic so that it can accommodate the variations in ID and OD of the parts being mated. Alternatively, one of the other fluid path elements can be relatively more flexible and so adapt to the variations in the fitting. Assembly of one or more of the parts via insert molding can provide advantages because the variations can be accommodated in the molding process.

In most medical applications for the injection of fluid, tubing sets have no specific requirements other than containing system pressure without leaking and compatibility with the injection fluids. However, in certain applications that have more specific requirements including, but not limited to, cell delivery, delivery of ultrasound contrast and delivery of nuclear medicine, current tubing sets and connectors for use therewith (for example, Luer fittings) have serious shortfalls.

As described herein, in the case of delivery of cells, there is a sensitivity to shear stresses induced in the cells. Moreover, there is a sensitivity to lost volume (as relatively small volumes are delivered). Further, trapped material left in a connector can present a biohazard. Similarly, in delivery of ultrasound contrast there is a sensitivity to lost volume as small volumes are typically delivered. Moreover, standard or conventional fittings used in the industry have areas where bubbles can collect and not be delivered to the patient. Nuclear medicine also uses relatively small volumes. Moreover, any trapped material left in a connector presents a radioactive hazard.

To limit loss, it is desirable to use the smallest diameter of tubing possible In the case of cell delivery, however, care must be taken to avoid excessive shear. Currently most low-pressure tubing sets have a bore diameter on the order of approximately 0.060 inches. For certain applications the tube diameter can be on the order of approximately 0.020-inch diameter. This reduction in diameter reduces volumetric loss and increases flow velocity to assist in prevention of adherence of cells (or bubbles etc.) on the walls of the tubing. The length of the tubing is also preferably minimized.

Currently, luer fitting are widely used as connectors in connection with medical tubing sets and other medical components. The design of luer fittings cause the formation of small volumes of fluid that are not in the direct fluid path. That is, there are small volumes in the luer connector wherein material can collect and not be removed by a flush. These common luer fittings are not designed to maintain constant uniform diameter throughout the system.

As illustrated, for example, in FIG. 12E through 12H, the present invention provides a number of other fittings or connectors that provide for relatively low fluid loss. Such connectors also preferably provide for smooth transition between fluid path element to reduce turbulence. In several embodiments of fittings or connectors of the present invention, a face seal can be used. In such an embodiment, the fitting includes flat faces that are mated together to make a seal. The faces can include compressible sealing elements. To reduce the likelihood of leaking, an annular seal (such as an o-ring) can be used. Use of an annular seal can provide for use of the connector at relatively high pressures with little tightening torque.

Figure 12E:
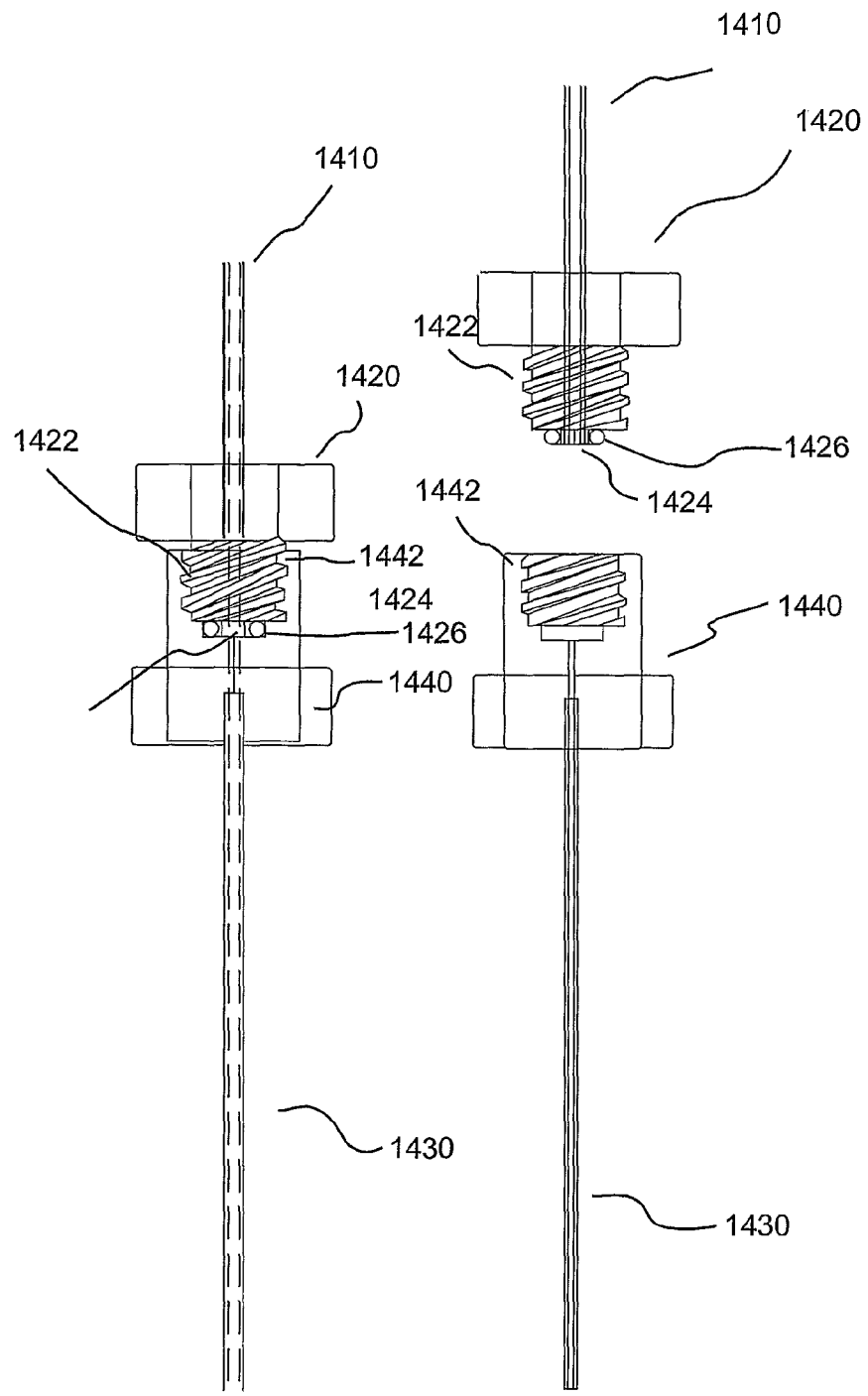
FIG. 12E illustrates a fitting or connector of the present invention that provides for relatively smooth transitions and low fluid loss.

In the embodiment of FIG. 12E, a first tubing section 1410 (for example, a small diameter tubing section) is connected to or terminated by a male fitting 1420. Male fitting 1420 includes, for example, a connection mechanism such as threading 1422. An end 1424 of male fitting 1420 includes (or has in operative connection therewith) a sealing member such as an O-ring 1426. A second tubing section 1430 (for example, a small diameter tubing section) is connected to or terminated by a female fitting 1440. Female fitting 1440 includes, for example, a cooperating connection mechanism such as cooperating threading 1442. As illustrated in the left side of FIG. 12E, preferably there is no significant area change or change in inner diameter upon connection of male fitting 1420 and female fitting 1440.

Figure 12F:
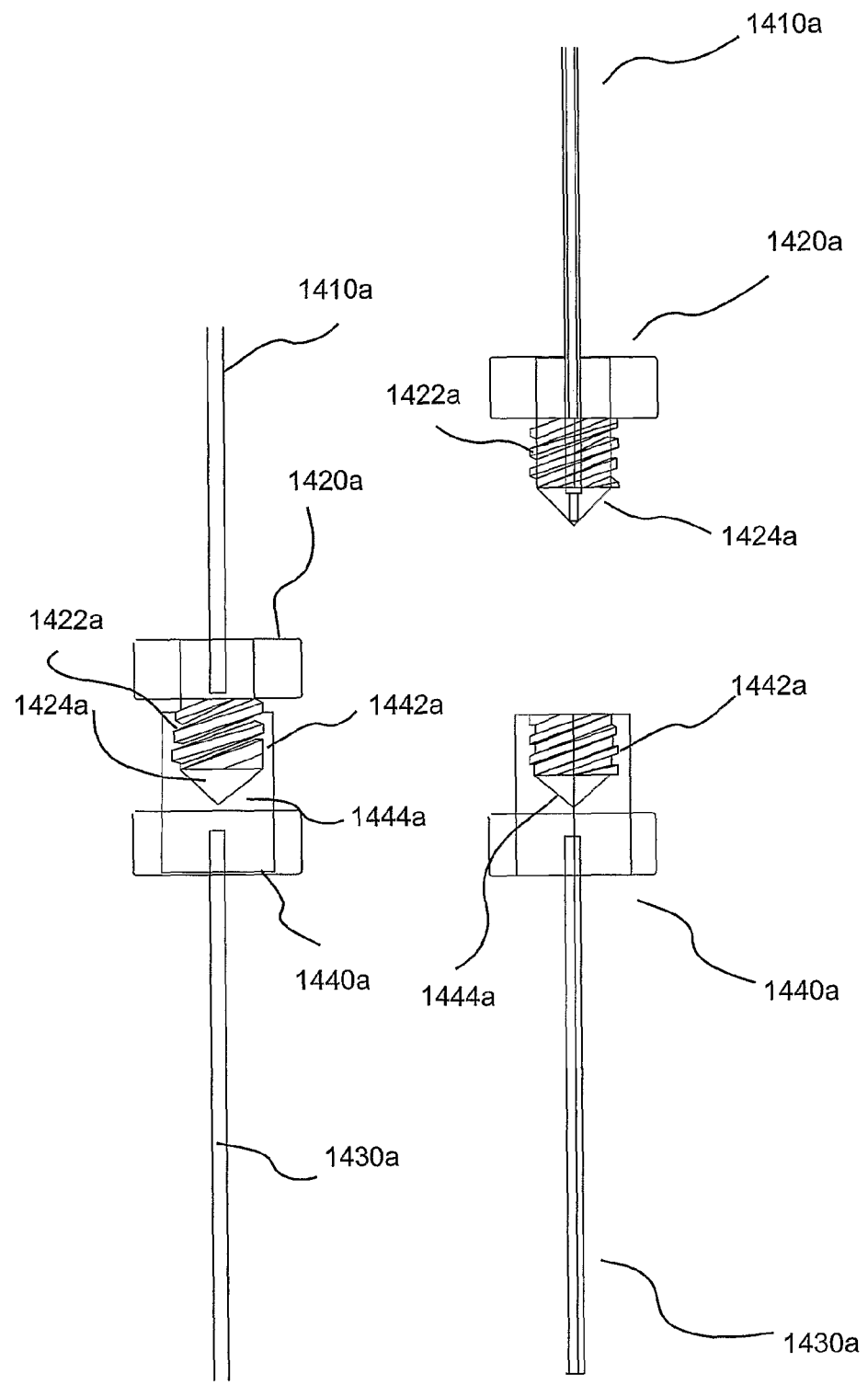
FIG. 12F illustrates another fitting or connector of the present invention that provides for relatively smooth transitions and low fluid loss.

In the embodiment of FIG. 12F, a first tubing section 1410*a* (for example, a small diameter tubing section) is connected to or terminated by a male fitting 1420*a*. Male fitting 1420*a* includes, for example, a connection mechanism such as threading 1422*a*. An end 1424*a* of male fitting 1420*a* is angled or tapered. A second tubing section 1430*a* (for example, a small diameter tubing section) is connected to or terminated by a female fitting 1440*a*. Female fitting 1440*a* includes, for example, a cooperating connection mechanism such as cooperating threading 1442*a*. Female fitting 1440*a* further includes a seating 1444*a* adapted to seat tapered end 1424*a* of male fitting 1420*a*. Seating 1444*a* can, for example, have a taper angle generally the same as or slightly greater than the taper angle of tapered end 1424*a* of male fitting 1420*a*. As illustrated in the left side of FIG. 12G, preferably there is no significant area change or change in inner diameter upon connection of male fitting 1420*a* and female fitting 1440*a*. Male connector 1420*a* and female connector 1440*a* (or portions thereof) can be formed of a resilient or somewhat compliant material to assist in forming a sealed connection.

Figure 1A:
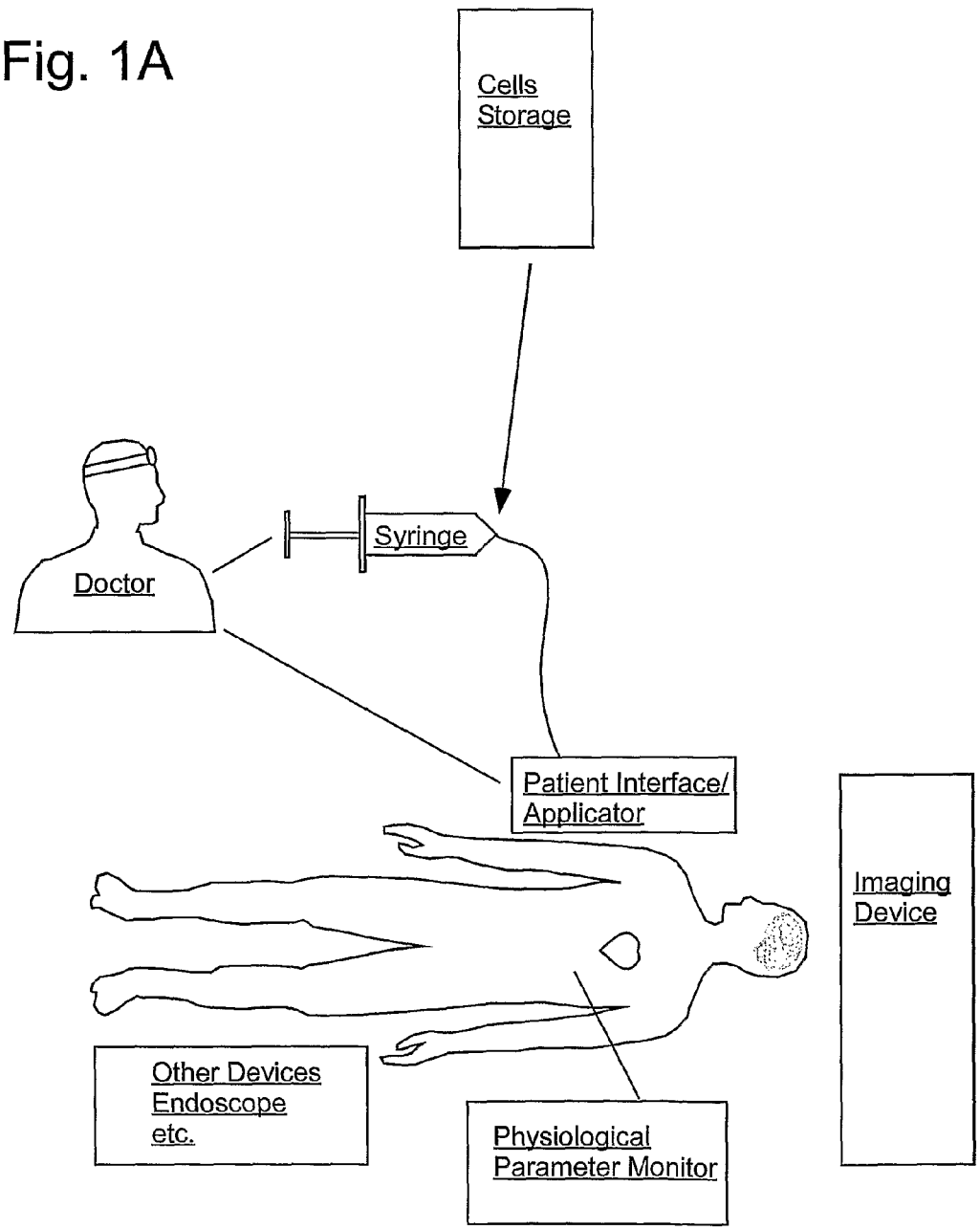
FIG. 1A illustrates a block diagram of an embodiment of a currently available system and method for injection of cells.
Figure 1B:
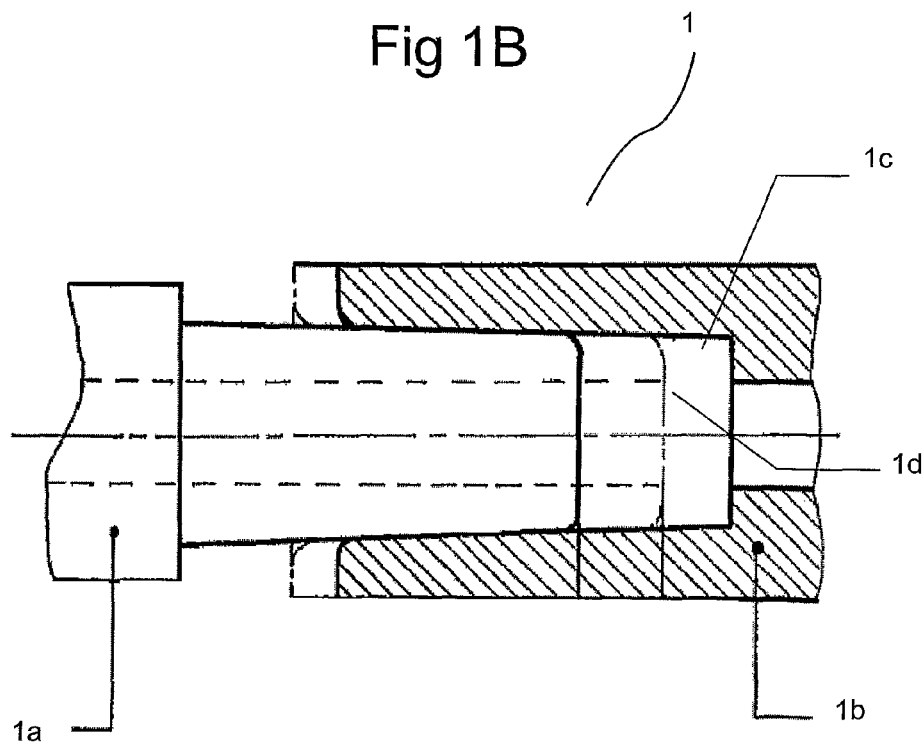
FIG. 1B illustrates an embodiment of a standard luer connector.
Figure 12G:
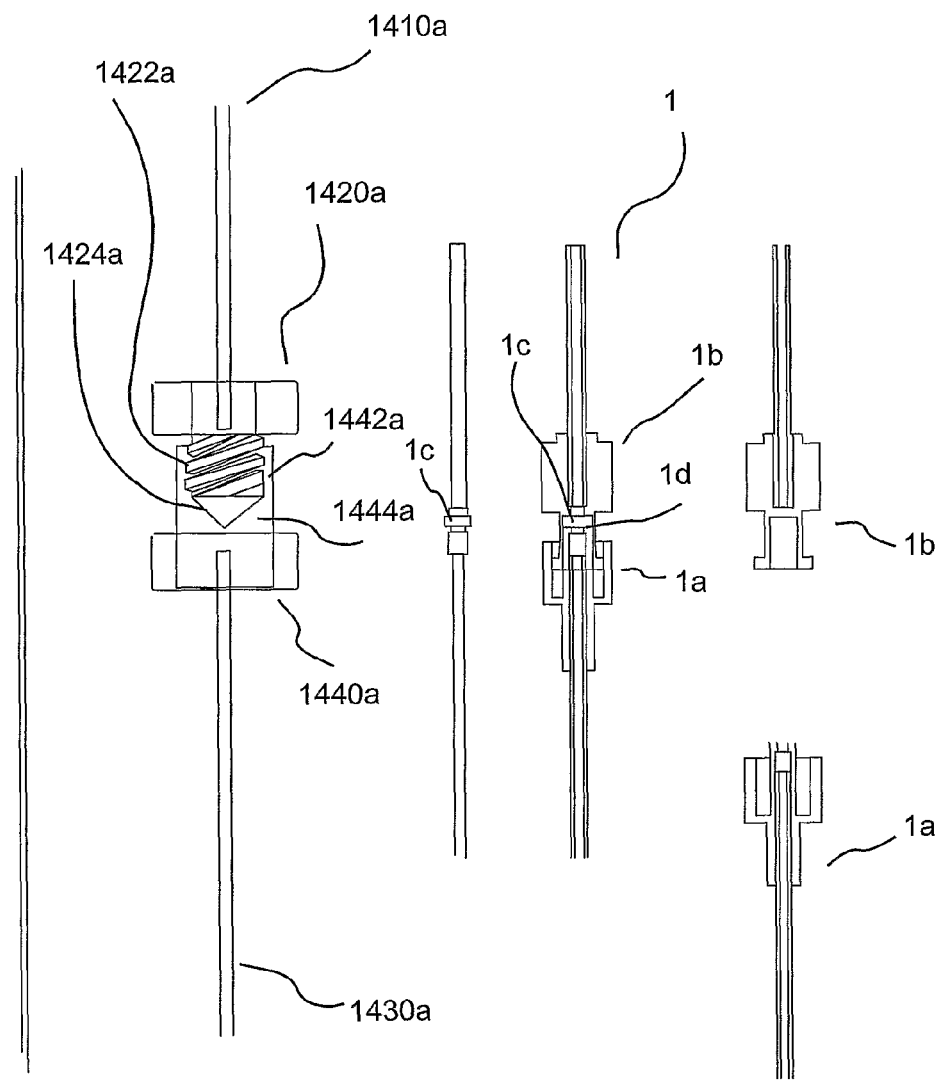
FIG. 12G illustrates a comparison of the fitting or connector of FIG. 5F with a standard luer connector.

FIG. 12G, on the right side thereof, illustrates standard luer connector 1 (as illustrated in FIG. 1B) in a disconnected state and in a connected state. A cross-section of the fluid path created upon connection of male luer connector 1*a* and female luer connector 1*b*, clearly showing the resultant lost volume region 1*c* and resultant sharp transitions, is also illustrated. For comparison, the left side of FIG. 12G illustrates the male connector 1420*a* and female connector 1440*a* of FIG. 12F in a connected state as well as a cross-section of the resultant fluid path, illustrating that there is no lost volume region or sharp transitions in inner diameter.

Figure 12H:
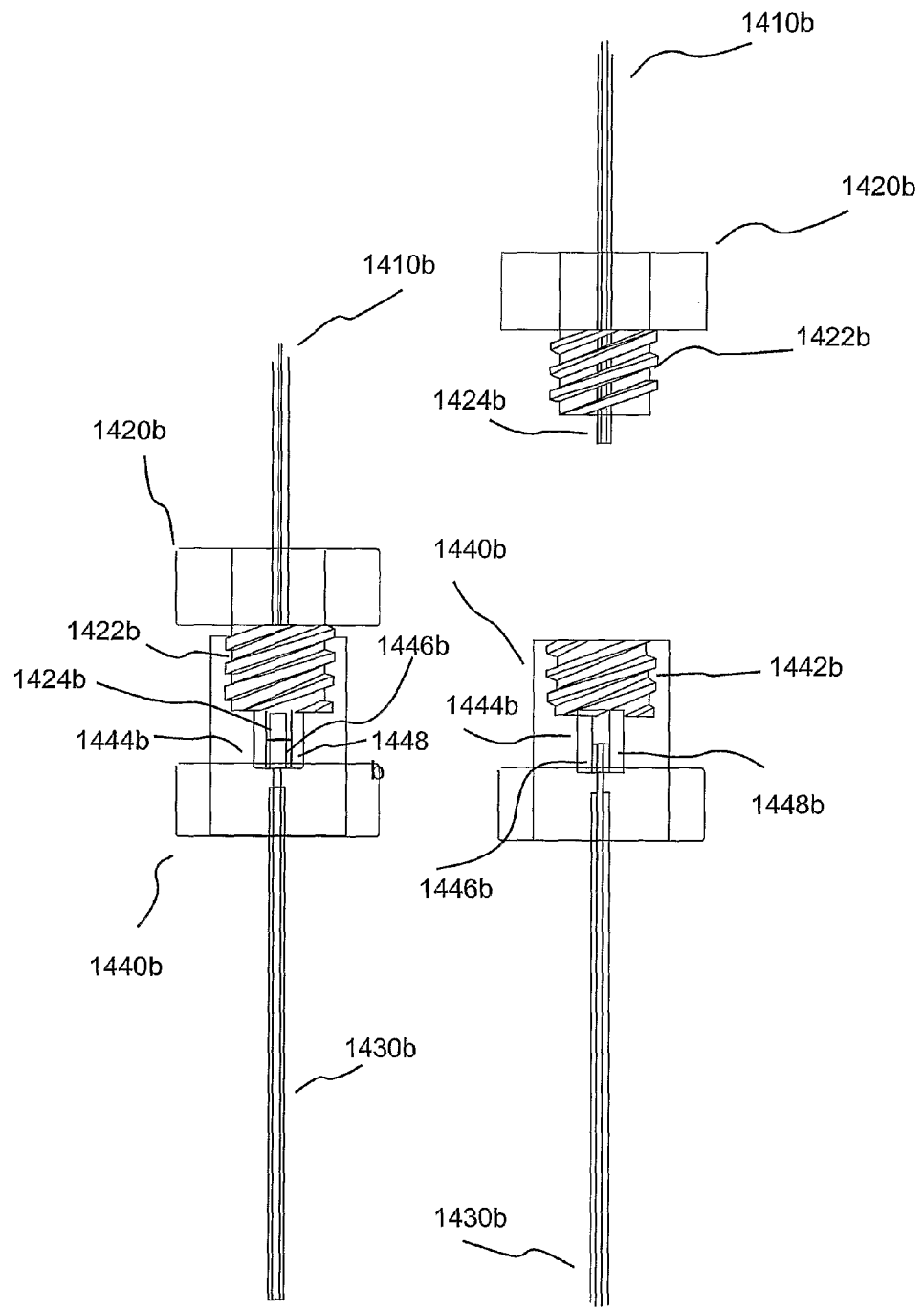
FIG. 12H illustrates another fitting or connector of the present invention that provides for relatively smooth transitions and low fluid loss.

In the embodiment of FIG. 12H, a first tubing section 1410*b* (for example, a small diameter tubing section) is connected to or terminated by a male fitting 1420*b*. Male fitting 1420*b* includes, for example, a connection mechanism such as threading 1422*a*. Male fitting 1420*b* further includes and extending end member 1424*b*. A second tubing section 1430*b* (for example, a small diameter tubing section) is connected to or terminated by a female fitting 1440*b*. Female fitting 1440*b* includes, for example, a cooperating connection mechanism such as cooperating threading 1442*b*. Female fitting 1440*a* further includes a seating 1444*b* adapted to seat extending end member 1424*b* of male fitting 1420*b*. Seating 1444*b* can, for example, including an extending member 1446*b* adapted to mate with extending member 1424*b* of male fitting 1420*b*. Seating 1444*b* further includes a flexible sealing member 1448*b* (for example, an elastomeric sleeve member) to encompass and assist in forming a sealing connection of extending members 1424*b* and 1446*b*. As illustrated in the left side of FIG. 12H, preferably there is no significant area change or change in inner diameter upon connection of male fitting 1420*b* and female fitting 1440*b*.

FIG. 12I illustrates an embodiment of a luer-type fitting or connector 1450 having a through bore 1452 sized to match the outside diameter of tubing 1460 connected to fitting 1450. Tubing 1460 can, for example, be glued into luer-type fitting 1450 in a position that allows a front face 1462 of tubing 1460 to compress and seal against a front face 1472 of a syringe 1470 (or other flow path element). This compressing abutment prevents fluid from entering a dead space area 1454 of fitting 1450. Fitting 1450 further includes a tapered female portion 1456 that mates with a tapered male portion 1474 of syringe 1470.

FIG. 12J illustrates an embodiment of a luer-type fitting or connector 1450*a* having a sliding component 1452*a*. A seal is made at a face 1454*a* of sliding component 1452*a* and tip or front face 1472 of syringe 1470 (or other flow path element). No seal is made at the luer tapers in this embodiment. A smooth transition is provided for the fluid path from syringe 1470 to sliding component 1452*a*. A smooth transition is also provided for the fluid path from sliding component 1452*a* to tube 1460*a* connected to fitting 1450*a*. In the illustrated embodiment, an O-ring or other biasing member 956*a* at the rear of sliding component 1452*a* provides spring compression or biasing force to hold face 1454*a* of sliding component 1452*a* against syringe face 1472.

FIG. 12K illustrates another embodiment of a luer-type fitting or connector 1450*b* which provides functionality similar to that provided by fitting 1450*a* of FIG. 12J, but with no moving parts. A seal is made at a face 1454*b* on the interior of luer-type fitting 1450*b* and tip face 1472 of syringe 1470 (or other fluid path element). No seal is made at the luer tapers. A smooth transition is provided for the fluid path from syringe 1470 to luer fitting interior face 1454*b*. A smooth or gradual transition is also provided for the fluid path from luer-type fitting 1450*b* to tube 1460*b*. In that regard, the flow path within fitting 1450*b* includes a tapered or angled region 1456*b* having a first diameter approximately equal to the inner diameter of tube 1460*b* and a second inner diameter approximately equal to the inner diameter of the syringe tip opening. A swivel nut (not shown in FIG. 12K, but see FIG. 12J) on the syringe tightens onto luer threads pulling face 1454*b* of luer-type fitting 1450*b* and syringe face 1472 together and creating a seal.

FIG. 12L illustrates another embodiment of luer-type fitting or connector 1450*c* having an internal protrusion or extending member 1452*c* that fits within the inner diameter of the syringe tip fluid path (or other fluid path element). A smooth or gradual transition is provided by tapered or angled region or section 1456*c* within protrusion 1452*c* for the fluid path from syringe 1470 to luer-type fitting interior face 1454*b*. A smooth transition is also provided for the fluid path from luer-type fitting 1450*c* to tube 1460*c* via tapered region 1456*c*. In that regard, tapered or angled region 1456*c* has a first diameter approximately equal to the inner diameter of tube 1460*b* and a second inner diameter approximately equal (or slightly smaller than) to the inner diameter of the inner diameter of the syringe tip opening. A seal is created via standard luer taper.

In another embodiment, two mating tapered elements are used. The tapered elements preferably have a greater angle of taper than a Luer connection (approximately 6 deg). In several embodiments, the taper is in excess of 25 degrees. For example, in one embodiment a taper on the order of 45 deg can be used. The male part of the taper can include a smaller angle of taper than the female taper, (for example, about 5 degrees). The difference in taper allows contact in the center over a small area to provide a reliable seal with relatively little tightening torque.

In any fluid path element in which the injection fluid passes through an opening, port or hole, the opening, port or hole is preferably dimensioned and constructed to reduce or minimize cell trauma arising, for example, from shear. An example, of the passage of the injection fluid through an opening, port or hole is the injection of the injection fluid through holes in the needle(s) as described above. Such needle holes 1480 can, for example, be shaped in a way that resembles a depressed ring when viewed face on as illustrated in FIG. 12L (1). This shape reduces shear, thus increasing cell viability. This shape also allows access to the surface of more tissue. FIG. 12M illustrates an embodiment of a needle wherein the interior circumference of the needle hole 1482 is rounded to decrease cell damage arising from shear stresses. FIG. 12N illustrates a needle with dimpled injection side holes or ports 1484 to reduce the amount of shear as the cells exit the side holes. Since the cells typically concentrate toward the center of the needle in laminar flow, a dimpled port or hole, which extends toward the center of the needle, allows the more centrally located cells to exit first, optimizing the amount of stem cells per hole. Softening the edges of the dimpled ports or holes 1484' reduces the amount of shear as compared to sharply or quickly transitioning hole edges.

Many short-term blood-contacting devices are catheters or introducers that also require a lubricious surface. Because anti-adherent, blood-compatible coatings are often hydrogels that are lubricious when wet, they can simultaneously provide the dual surface enhancements of lubricity and hemocompatibility. Most medical grade silicones are, for example, not detrimental to cell viability and suitable for use herein. Dow Corning grease and mineral oils are acceptable lubricants.

Cells such as stem cells will adhere to surfaces such as the surface of container 50 and other fluid path elements. For applications requiring short-term blood compatibility, it is desirable that the fluid path element repel, for example, platelets, proteins, cells, or other fouling materials. A non-adherent material (polypropylene and polyethylene are examples of suitable non-adherent materials) is preferably used along with other materials that have hydrophobic coatings.

Moreover, minimizing contact area with foreign surfaces is desirable. Most fluid-contacting medical devices are made of synthetic materials. When cells contact these materials foreign to the body, a number of adverse reaction are triggered (for example, platelet activation and complement activation) that eventually lead to fibrin production and clot formation. Contact with any surface is thus preferably reduced or minimized.

Further, impurities are preferably reduced, minimized or eliminated. For example, high surface tension is detrimental to cells. Any surfactants should thus be avoided. The presence of detergents is particularly detrimental.

Altering the viscosity of the fluid also may enhance cell survival by avoiding turbulent flow. Likewise, flow profiles designed to disrupt clumping and adherence can be used. Stem cells will, for example, clump together if allowed to settle and will adhere to a syringe surface. To initiate flow in these cases a minimum shear rate must first be overcome (toothpaste is an extreme example). The flow profile can, for example, be designed to inject with an initial pulse followed by a sustaining steady flow rate. Alternatively or additionally, motion can be induced in container 50 (for example, a syringe) or other flow path elements to prevent adherence. The flow profile can also or alternatively be reversed periodically (pull-back) to disrupt clumping, for example, where the fluid path narrows. Such pulsatile motion can, for example, be similar to the action of a heart and may enhance cell viability. A high frequency pulse can also or alternatively be superimposed onto the desired flow profile to prevent clumps from forming. This flow profile can, for example, be similar to the vibrations used in material handling applications where the frequency is selected to match the natural frequency of the fluid particles.

Scaffolding can also protect cells. Scaffolds can, for example, include proteins or a meshwork of fibers that help support the cell, give it physical protection, reduce local shear forces, and provide an attachment point for cells. Polymerizing holds the cells together. Collagen is a successful and popular protein based matrix (scaffold). Porous or other beads may also be added to the injection fluid to provide protection.

Bacteriological and fungal infections are a common cause of cell culture failure. Typical bacterial contamination is seen as a white haze and fungal contamination appears as a fuzz ball. In either case, the contamination changes the pH of the media, which kills the cells. Using disposable fluid path elements provides a significant preventative measure in the elimination of bacterial and fungal infections. Typically, container 50, patient interface 400 and all fluid-contacting fluid path components therebetween will be disposable after a single injection procedure in connection with a single patient.

B. Fluid Path and System Capacitance/Delivery Efficiency.

In the delivery of, for example, stem cells into tissue such as the heart muscle or the brain, it can be desirable to deliver a sharp bolus of cells in, for example, ten or more locations. Efficient transfer of cells to the muscle or the brain is important because of the limited quantity of cells available. The pressure required to deliver a bolus might not be available if there is too much capacitance in the system. Capacitance can defined as the ability of the system or an element of the system to increase in volume during pressurization, and then to relax to normal after pressurization. System capacitance can work like a spring absorbing pressure and releasing it when the pressure or restriction on the other side (increase load from heart muscle) of the needle is removed. The absorbing of pressure and subsequent release is why a system with a lot of capacitance will continue to deliver fluid or drip when a needle is withdrawn from the injection site. This dripping decreases the efficiency of the cells delivered, for example, to the heart and cells can be leaked into undesirable locations.

A certain level of capacitance in a fluid delivery system may be desirable, however, in certain circumstances. For example, if cells are damaged at a known shear force, the system can be designed to have enough capacitance to prevent the pressure from rising to the level that would cause shear to occur in the cells.

Figure 13A:
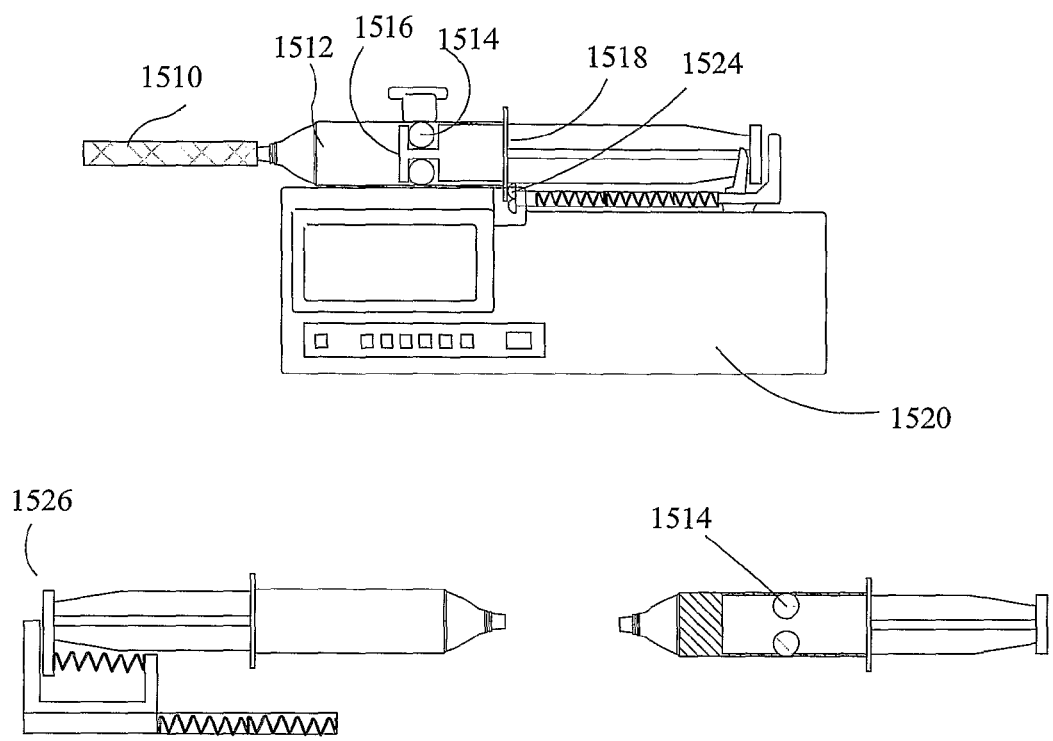
FIG. 13A illustrates a relatively low capacitance delivery system of the present invention including a braided or otherwise stiffened connector tubing.

However, excessive capacitance is undesirable. Capacitance reduction can, for example, be accomplished in several ways: As set forth in FIG. 13A, a braided or otherwise "stiffened" (for example, having thickened wall) connector tubing 1510 connector tubing can be used. The fabrication material for container or syringe 1512 of FIG. 13A and other fluid path elements can be chosen to be stiff (for example, polycarbonate can be chosen rather than, for example, polypropylene—as polypropylene expands more under pressure). Alternatively or additionally, the wall thickness of syringe 1512 can be increased. O-rings 1514 or other sealing rings can be used around the perimeter of syringe plunger 1516 rather than elastomeric plunger covers. In that regard, elastomeric (for example, rubber) plunger covers can flex resulting in increased capacitance. TEFLON® seals can also be used in the syringe plunger. A tight fit of syringe flange 1518 in injector system 1520 can be provided, or a syringe sensor can spring load the flange forward (instead of rearward) as represented by element 1524 in FIG. 13A. Air causes capacitance because of its compressibility, therefore the efficiency of air removal from the system can also be improved. For example, a membrane that allows air to pass but prevents fluid from passing can be provided. Such a membrane can, for example, work at low pressure provided that the pressure is less than the membrane breakdown pressure of the filter. As represented by designation 1526, backlash can be removed from system wherever possible. For example, the plunger can be spring loaded to reduce or eliminate backlash.

It may be also desirable to control the amount of capacitance of a system to protect the cells from exposure to damaging shear forces. If stem cells are destroyed at a know shear force, one can determine what pressure will develop that shear force for a known system configuration, i.e. if the disposable set is defined and a maximum shear force is established, then a maximum system pressure can be determined to reduce or eliminate the chance of exceeding the maximum shear force. As set forth in FIG. 13B, the system can include silicone tubing or other compliant tubing 1510b that allows only a defined amount of pressure to be delivered before it yields (for example, causing it to bulge) and limits the pressure. A maximum pressure setting can be set on an injector or pump system such as system 100 which can, for example, deliver to the maximum pressure and hold that pressure. As illustrated in FIG. 13C, a separate spring loaded vessel (for example, a syringe 1530c including a plunger 1532c loaded by a spring 1534c retained within syringe 1530c with, for example, a mechanical abutment or stop 1536c on the rearward end of syringe 1530c) can be provided to absorb pressure and to provide an indication to the operator that the desired pressure has been exceeded. This can, for example, be useful for the operator to determine when it is safe to remove the needle from the heart, brain or other tissue. If the pressure spikes and spring loaded plunger/indicator 1534c moves, then the operator can hold the device in the tissue until the pressure drops and spring loaded plunger 1534c returns to its original state (indicating that all the cells have been delivered to the tissue).

FIG. 13D illustrates a syringe 1540 including spring isolated plunger 1542 designed such that an operatively connected spring or other biasing member 1544 will not compress under a predefined threshold load. However, if pressure in syringe 1540 exceeds a threshold, spring 1544 will compress, limiting the pressure that can be developed in syringe 1544.

As illustrated in FIG. 13E, a normally closed, a pushbutton valve can be provided to activate pump system such as pump or injector system 100 and open fluid passage to needle 400: A normally closed push-button valve between the container/syringe 50 and the patient interface/needle 400 can, for example, have an electrical switch to initiate the pump system 100. By pressing or otherwise activating this valve, the fluid passage to the needle is opened and an electrical switch triggers injector/pump system 100. When the button is released, injector 100 can, for example, stop and the valve close. If the button is held down, injector 100 stops at a predetermined volume. Any dripping from the tip of needle 400 as a result of system capacitance is eliminated because the valve is closed and will not allow fluid to pass to needle 400. This embodiment can reduce the amount of wasted cells.

FIGS. 13F and 13G illustrate the use of a one-way check valve 1552, respectively, in a needle 1550, respectively. When the needle is placed in tissue (see FIG. 13F) such as in the heart, an activation rod 1554, respectively, is pushed rearward and check valve 1552, respectively, is opened. When needle 1550 is withdrawn from the tissue (see FIG. 13G), activation rod returns 1554 to a relaxed or unstressed state and check valve 1552 is closed, thereby preventing fluid leakage.

FIG. 13H illustrates reduction in capacitance by reducing the total volume of the system (as in comparing the injection system of the right side of FIG. 13H with that of the left side thereof). For example, the size of container/syringe 50 can be reduced and the length of fluid path 310 can be shortened. FIG. 13I illustrates the use of increase wall thickness (in for example, two syringe 50 and 50a) to reduce fluid path element capacitance.

FIGS. 13J through 13N illustrate an embodiment of a syringe 1560 in which capacitance is substantially reduced or eliminated. As described above, capacitance can negatively impacts fluid delivery precision. Excessive capacitance delays fluid movement while the system expands as a result of hydraulic pressure. Subsequently, at the end of the injection, fluid will slowly exit or dribble while the system deflates as a result of pressure loss. This expansion and deflation prevents precise and controlled delivery. Specifically, with cell delivery, uncontrolled capacitance causes a slow continuation of exudates to exit the device without the proper force to deliver the cells to the target tissue. In the extreme case the exudates may even continue after the device is removed from the tissue, potentially exposing other, non-target tissue or clinicians to an unsafe condition.

In the embodiment of FIGS. 13J through 13N, the syringe barrel is designed for minimum strain or radial defection during the maximum pressurization. This can, for example, be accomplished by appropriate material selection and dimensioning as discussed above. Tensile strength, modulus of elasticity, and environmental conditions are important characteristics. As an example, in one embodiment using polycarbonate and given a radial stress of 115 psi, the maximum radial deflection is 0.001 inches, corresponding to a total volume increase of 0.10 mL within a 17 mL total volume syringe. Use of a solid, non-elastomeric plunger 1562 with, for example, an O-ring side sealing member 1564 also helps minimize capacitance. Such a plunger minimizes fluid contact with an elastic surface (as, for example, compared to a plunger with an elastomeric cover of the forward and side surfaces thereof), while providing a seal against leakage. As described above, delivery tube can also designed and constructed to minimize capacitance. Syringe 1560 of FIGS. 13J through 13N, is preferably fabricated from an optically clear polymer such as polycarbonate to ensure visibility of the fluid contents. The material of syringe 1560 is also preferably blood- and cell-contact compatible. Optionally, the internal aspects of the fluid path and fluid path elements (including syringe 1560 and other fluid path elements) may have a lubricious coating, such as HYDROMER® (a hydrogel material made by the interaction of poly-vinylpyrrolidone with one of several, isocyanate prepolymers) available from Hydromer, Inc. of Branchburg, N.J. to, for example, reduce friction and/or maintain cell viability. Coatings can also be used to reduce plating or wall adherence. The internal aspects of the barrel are preferably adapted to minimize fluid turbulence and cell viability by, for example, providing radii at diameter transitions, as well as non-acute angles. A connector such as a male luer connector or fitting or a fitting of the present invention as described herein can be provided incorporating a rotating nut to aid in attaching the disposable tubing.

A distal angle of a forward section 1566 of plunger 1562 can be slightly smaller than the distal angle of a transition region 1568 of the syringe barrel (see FIG. 13J). This angle mismatch provides a channel for cells to exude through distal opening or syringe tip 1570 without getting trapped against the interior barrel angle. Typically, conventional syringe designs incorporate matching angles between the plunger and barrel. However, this arrangement causes both surfaces to touch simultaneously over a substantial portion thereof. While, such angle matching is a good design for most non-viable fluids, angle matching could damage cells caught between the two surfaces and lower the overall effectiveness of cell therapy. The described mismatch preferably minimizes the amount of residual fluid, while maintaining cell viability. One or more other abutment elements 1572 (see FIG. 13J) can additionally or alternatively be used to prevent mating of a forward surface of the plunger over a substantial area thereof with a surface of the transition region of the syringe.

Figure 13O:
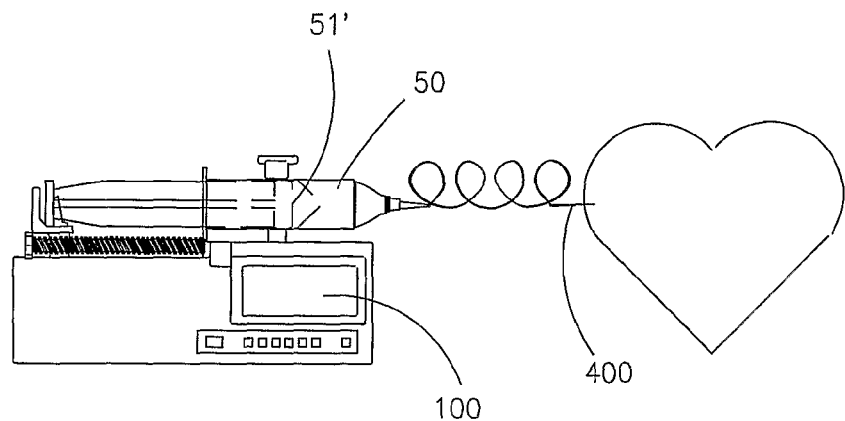
FIG. 13B illustrates an embodiment of a delivery system of the present invention including silicone tubing or other compliant tubing that allows only a defined amount of pressure to be delivered before it yields, thereby limiting the system pressure.
FIG. 13C illustrates a delivery system of the present invention including a separate spring loaded vessel to absorb pressure and to provide an indication to the operator that the desired pressure has been exceeded.
FIG. 13D illustrates a syringe including a spring isolated plunger designed such that an operatively connected spring or other biasing member will not compress under a predefined threshold load.
FIG. 13E illustrates a delivery system of the present invention including a normally closed, push-button valve to activate a pump system or injector system and open fluid passage to a needle.
FIG. 13F illustrates the use of a one-way check valve in a needle of the present invention in which the needle is placed in tissue.
FIG. 13G illustrates the use of the needle of FIG. 13F in which the needle outside of the tissue.
FIG. 13H illustrates a delivery system of the present invention in which capacitance is reduced by reducing the total volume of the system.
FIG. 13I illustrates decreasing of capacitance of a fluid path element by increasing wall thickness.
FIG. 13J illustrates a transparent or hidden line view an embodiment of a syringe of the present invention in which capacitance is substantially reduced or eliminated and wherein the syringe plunger is in a forward position.
FIG. 13K illustrates a side view of the syringe of FIG. 13J.
FIG. 13L illustrates a cross-sectional view of the syringe of FIG. 13J.
FIG. 13M illustrates another transparent or hidden line view of the syringe of FIG. 13J wherein the syringe plunger is in a rearward position.
Figures 13P, 13Q:
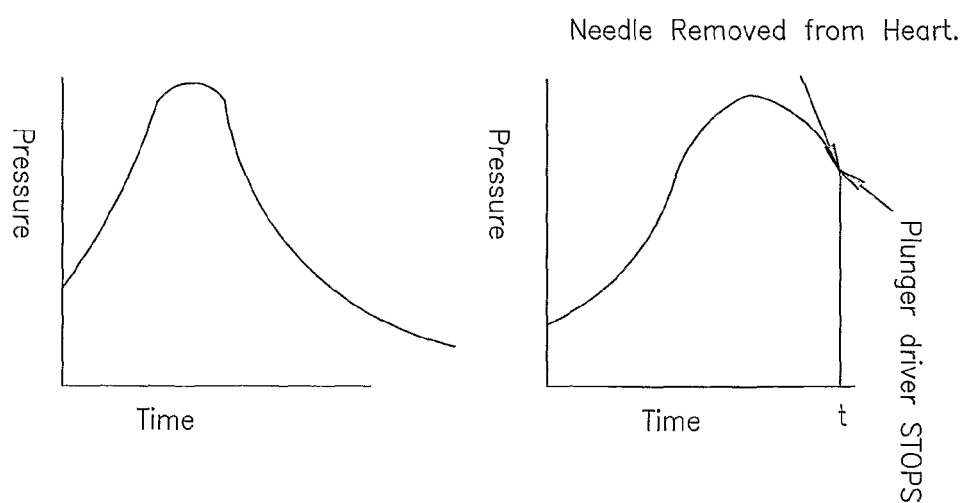

When injecting into tissue with a system having capacitance, the pressure can ramp up quickly and gradually drop as the capacitance is taken up and fluid is injected into tissue (for example, the heart or the brain—see FIG. 13O). Once needle 400 is removed from the tissue, the pressure will drop suddenly as the tissue restriction to flow has been removed. When the pressure drops (as, for example, sensed by a pressure sensor 51'), the drive of pump system 100 can be reversed (for example, by moving a drive member in operative connection with a plunger in container/syringe 50 in a rearward direction), thereby stopping fluid from leaking out of patient interface/needle 400. Pressure sensing in injector systems is, for example, discussed in U.S. Pat. Nos. 6,673,033, 6,520,930 6,488,661, 5,808,203 and PCT International Patent Application Publication No. WO 00/06233, the disclosures of which are incorporated herein by reference. Pump system or injector 100 can be programmed to reverse or retract a certain amount at the end of an injection to relieve residual pressure from the system capacitance. FIG. 13P illustrates a graphical representation of a pressure profile with needle 400 within the tissue. FIG. 13Q illustrates a pressure profile with system capacitance and needle 400 removed from the tissue at time t.

C. Fluid Viscosity

In the case of cell therapy, the injectate or injection fluid typically includes at least one cellular component and a liquid or carrier component. Preferably the cellular component includes live, and undamaged cells, but damaged cells as well as dead cells can have therapeutic value also. The viscosity of the injectate can vary significantly. As discussed briefly above, cells and certain other agents (for example, cells supported on microspheres) do not behave like uniformly dispersed particles in a fluid. Among the problems arising in the fluid transport of cells and certain other agents are tendencies to clump together, to settle, to plate or adhere to walls of the fluid path and/or to stay in place while liquid flows through the "packed" cells (if flow velocities are sufficiently low). A number of approaches to address these problems are discussed above.

As also briefly discussed above, in several embodiments of the present invention viscosity can be used to reduce the significance of or overcome one or more of the problems listed above as well as other problems. Blood is a non Newtonian fluid, meaning that the viscosity is a function of flow velocity and thus the conditions of measurement. Blood at a normal hematocrit has a viscosity of about 4 centipoise at 37° C. under common ex-vivo test conditions. The viscosity of water is approximately 1 centipoise at 20° C. The viscosity of plasma is in between the viscosity of blood and the viscosity of water. A significant component of plasma is albumin, a large protein, which partly explains why plasma's viscosity is greater than that of water. As the concentration of albumin is increased, the plasma becomes more viscous.

If the fluid in the injectate is increased in viscosity, several benefits are realized. For example, the cells will tend to settle more slowly. If the density is increased at the same time, the tendency to settle will be decreased as well. As a result, for example, little or no agitation may be require to maintain the injectate in a homogeneous state. With regard to flow characteristics, a greater force is generally required to pull the cells off the walls and to break up the clumps or packing of the cells. With a more viscous fluid, the pressure at the injection site (commonly the tip of patient interface/needle 400) will be much greater before it starts leaking back the needle track, causing more of a cavity to be created in the tissue for deposition of injectate. Further, the more viscous injectate cannot as easily backflow or retrograde back up needle track or through fine structures/cavities in the tissue. In several embodiments of the present invention, it is preferred that the injectate viscosity be greater than 4 centipoise and, more preferably, greater than 6 centipoise. However, the optimal viscosity will typically depend upon patient interface 400 (typically a needle or a catheter system). In that regard, patient interface 400 is most likely to be the fluid path component with the minimum inner diameter. Given the flow characteristics of patient interface 400 and other system consideration, on skilled in the art can readily determine an optimal viscosity for a given application.

The viscosity of the injectate can be increased in several ways. One way of increasing viscosity is to increase the fraction of cells in the mixture. Increasing cell concentration has the additional benefit of require a smaller injection volume to deliver a desired number of cell. Thus, less pressure is built up in the tissue, and there will be less of a chance of fluid backflow or retrograde flow. Because of the increased number of cells per volume, the flow rate can also be reduced, thereby helping to maintain the same shear strain in the fluid. The cells can be concentrated by settling or centrifuging to create a concentrated fraction. Alternatively, the cells can be collected on a filter and back washed or suctioned into the delivery system.

Alternatively, the viscosity of the carrier liquid can be increased with the addition of, for example, non-essential or "excipient" cells (for example red blood cells) or other particles, such as collagen particles, for example spheres, in the range of tens of nanometers to tens of microns in diameter.

In the strategies discussed herein, it is desirable to maintain the proper osmotic pressure so that the cells are not adversely affected by swelling or shriveling. This can be measured and corrected by adding water or a salt solution as appropriate. It is also necessary to maintain the proper pH which can be done through various organic or inorganic buffers.

The viscosity of the injectate can also be increased by increasing the viscosity of the molecular part of the fluid, for example, by increasing the fraction of albumin in the liquid. This result can be accomplished by simply adding albumin to the fluid. Alternatively, the cells can be concentrated and separated from much of the liquid as discussed above, and a new liquid having a sufficiently increased viscosity added. The addition of dilute collagen molecules is another alternative. Both collagen and albumin have the advantage of occurring naturally in the body, and both are readily removed or decomposed. Other naturally occurring large molecules can be used as clear to those skilled in the art. Synthetic molecules can also be used. For example X-ray contrast is a large molecule, is water soluble, and has a high viscosity at physiological osmolality. Among X-ray contrasts, the greatest viscosity comes from those with dimmeric molecules, for example Visipaque (iodixanol) manufactured by Amersham Health, a division of General Electric Medical Systems. The 270 mgI/ml concentration has a viscosity of 6.3 centipoise at 37 centigrade, 12.7 centipoise at 20 centigrade and a physiological osmolality. The 320 mgI/ml concentration has a viscosity of 26.6 centipoise at 20 centigrade, also at a physiological osmolality. Thus, a reasonable amount of Visipaque will sufficiently increase the injectate viscosity. Addition of an imaging contract can also assist in a marking, tracking or mapping function in conjunction with imaging device or system 500. Other suitable synthetic materials include synthetic peptide hydrogels use to form the Puramatrix tissue scaffolding, made by 3DM Inc. of Cambridge, Mass. In sufficiently low concentrations, the long chain molecules increase viscosity of the injectate, but do not form a solid gel. Synthetic infusion products such as Hemohes, Gelofusine, and Venofundin manufactured by B Braun could be used. A particularly useful material is carboxymethylcellulose (CMC), an example of which is Aqualon manufactured by Hercules, Inc. of Wilmington Del. A 2% solution has a viscosity of 60-80 centipoise. CMC is used as a viscous carrier or excipient in Sculpta, an injectable treatment for lipoatrophy, available from Aventis Pharmaceuticals, Bridgewater, N.J. Additionally, molecules or droplets of inert synthetic large molecules such as perfluorocarbons or perfluoropolyethers (see, for example, Published PCT International Application No. WO002005072780A2, the disclosure of which is incorporate herein by reference) can be used. It is preferable to use molecules that are sufficiently large that viscosity is increased quickly.

The viscosity of the injectate can optionally be increased to the point that it can be described as a gel or a paste. In the case of a gel or paste, the cells move very little with respect to each other. The cells can be considered to be trapped in the gel. When the gel is injected, there is very little backflow or retrograde of injectate back through the needle tract or through the tissue. The cells would initially stay where they were deposited. If the gel is made primarily of collagen, synthetic peptide hydrogels, or alginate, and the volume deposited is small enough that oxygen and nutrients can diffuse to the cells (which depends upon the density and type of cells), the cells will eventually be freed by the body's decomposition or degradation of the gel. The cells are then able to migrate, divide and/or perform the function(s) needed to achieve the treatment.

Because of the high viscosity of a gel or paste, the injections are either relatively slow, or a lubricating fluid, for example water, can be used between the gel and the walls of the fluid path to reduce the pressure and shear stress on the cells. Gels containing water tend naturally to form a water layer near the fluid path wall. Alternately, water can be injected from one of multiple containers or syringes 52 and 54 etc. concentrically around the gel as a lubricant. In the case of a gel, it is important that, as discussed above, transitions in inner diameter of fluid path elements be as gradual as possible.

The cells can, for example, be mixed with a precursor or pregel material before gelling occurs. Alternatively, an open gel can be created and then used as a filter to collect the cells. The cells would be embedded into the gel. Previous work on tissue scaffolds can be applied in this way to cell injections.

An example of such a matrix is the Puramatrix scaffold made by 3DM Inc. of Cambridge, Mass.

As the viscosity is increased still further, a rod or other element of "solid" cell-containing material is "injected" or deposited. The solid injectate can be created or formed as a rod outside of the injection device, and then loaded into the injection device as, for example, lead is loaded into a mechanical pencil. Alternatively, the injection device can be loaded with fluid/liquid injectate that solidifies in the injection device. Components that form a gel can also be separately introduced into the injection device, where they are mixed, and the gel forms. An example of such a material is alginate, which forms a gel in the presence of calcium ions. A material of this type is made by Neural Intervention Technologies, Inc of Ann Arbor, Mich. The alginate and the cells can, for example, be mixed. When calcium chloride is added, the cells are trapped in the alginate matrix as it forms. This solid can then be injected and the cells and will not leak back the needle track or elsewhere.

Alternately, a solid, cell-filled matrix can be created by growing cells into and through the matrix. Patient interface 400 in the form of a needle can be filled with the matrix by simply inserting the needle into the matrix and cutting a core. This coring/loading can be done by hand but is more repeatable if done using a mechanized fixture suitable to ensure that the needle cuts different sections each time. When the needle is placed into the proper position in the patient's tissue, the solid core is displaced from the needle by, for example, pushing from behind with liquid or with a solid stylet.

As mentioned above, one of the benefits of injecting a high-viscosity material or a solid is that it does not leak back the needle track, leak out of the tissue and into surrounding tissue/organs or spread throughout the tissue. However, those attributes limit the cell location to a small area within the tissue. In some uses, such as cell implantation in the scalp or into the brain for Parkinson's disease, this limitation is not a problem. In some other applications, such as cell therapy for the heart, current theory of operation dictates that the cells be applied over a range of tissue area. Thus, to spread the cells over a range of tissue, it is desirable that the viscous fluid or solid be injected as the needle is being pulled back as described above. The cavity created by the needle is filled, or optionally overfilled with injectate, rather than the return of the displaced tissue. If the needle is inserted at a shallow angle with respect to the tissue surface, this approach allows a large area to be treated even with a very viscous material. This concept can be used with multiple needle embodiments as described above. The coordination of the injection and needle withdraw is preferably accomplished, at least in part, using control system 200.

Alternatively, solid injectates can be pre-manufactured into cylinders that are inserted into multiple implantation needles as lead is placed into mechanical pencils.

Figure 13R:
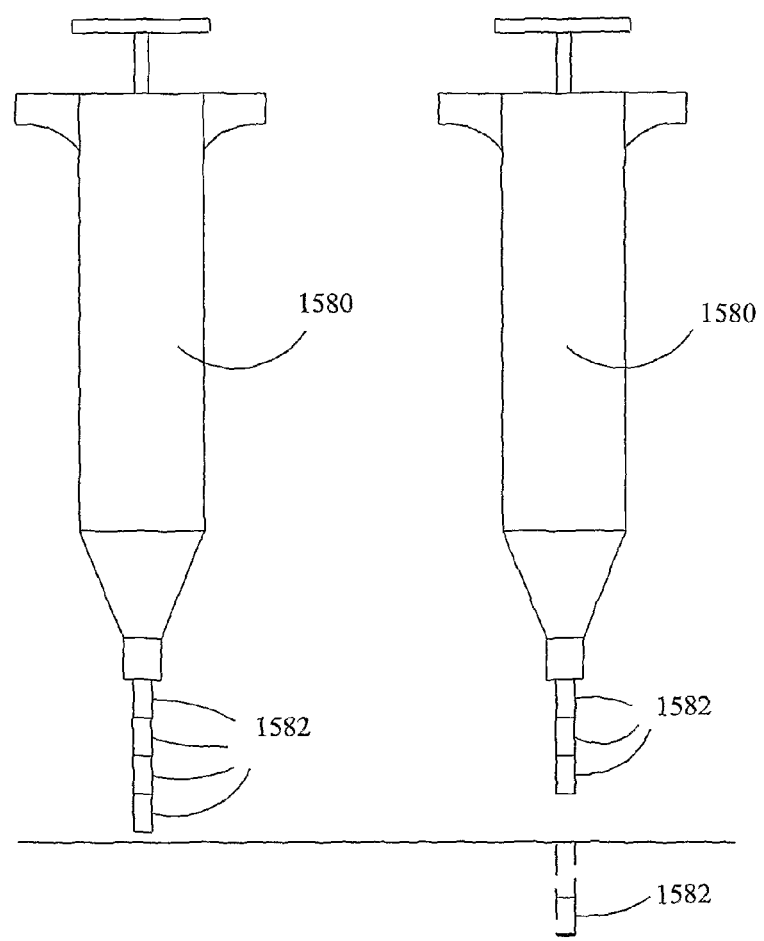

In still a further embodiment, solid rods containing cells can be formed to themselves pierce and embed within tissue such as heart tissue without the assistance of a needle or catheter. Multiple piercing or penetrating rods or other solid injection elements can, for example, be applied generally simultaneously or in a single application as an array with an applicator. FIG. 13R illustrates an example of an applicator 1580 including breakaway sections 1582 of solid injectate that are sequentially embedded, fully or partially, in the tissue (see the right side of FIG. 13R). The breakaway material can serve any number of additional functions, including, but not limited to, acting as a buffer that protects the primary therapeutic material from damage, a mechanism to push the primary therapeutic to further depth in the tissue, a cap for the therapy site, or as a color, radiological or other marker to allow the user to keep track of the injection visually or with a secondary sensing or imaging device.

If the needle holds more solid injectate than is delivered in a single injection, it is desirable to stop the delivery before or as the needle leaves the tissue. This is best done if control system 200 operates the injectate delivery and the depth stop. In this case the depth stop can be settable by control system 200. The user can, for example, set the initial depth and the volume to be delivered. The needle is then inserted until the depth stop contacts the tissue. The injector is then activated. As the injection occurs, the depth stop is moved so that the needle is controllably extracted as the injectate is delivered, while the user simply maintains contact between the depth stop and the tissue. User interface 700 can indicate when the injection is complete and the user can move to the next site. Rotary depth stops as, for example, illustrated in FIGS. 9B and 9E can, for example, be motorize with stepper motor. Linear depth stops as, for example, illustrated in FIGS. 9A and 9C can be motorized with a motor and a rack and pinion or a lead screw mechanism. Such drive mechanism can readily be controlled by control system 200 using control algorithm procedures as known in the art.

D. Generalized Cell Delivery Flow Modes

The discussion of the multiple and various flow modes and embodiments of this invention can, for example, be described generally with reference to FIGS. 14A through 14F. In FIG. 14*a*, three fluid path elements are shown diagrammatically as concentric cylinders A, B, and C, in this figure. The distal ends marked respectively with Ad, Bd, and Cd are the ends closest to the patient. The effectors are the distal ends of the fluid path elements that interact with the patient and the means for holding or position the effector. A fluid path is determined by one or more of the fluid path elements. In FIG. 14A, fluid path 1 is inside fluid path element A. Fluid path 2 is inside fluid path element B and outside of fluid path element A. Fluid path 3 is inside fluid path element C and outside of fluid path element B. Fluid paths 1 and 2 communicate where fluid path element A ends, and fluid paths 2 and 3 communicate where element B ends. This communication may be at or in the patient, or at some point before reaching the patient.

A fluid path can be made up of one or more physical fluid path elements, which may be made of any of the many materials know to those skilled in the medical device arts that can contain the fluid within them, either flowing or static, without contaminating the fluid. For example, they can be a single rigid fluid path element, such as a metal needle. They can be flexible, such as plastic tubing or catheters. Some elements can be rigid and others can be flexible. Or, a single fluid path can be made up of multiple fluid path elements, such as a flexible fluid path element, piece of tubing, connected to a rigid fluid path element, such as a needle.

The fluid path elements illustrated in FIGS. 14A to 14A are downstream of the powered pump and the manifold or their equivalents, if they are used in the system. By fluid path element is meant any element that touches the fluid, including the pumps and manifolds not shown in FIGS. 14A to 14F. The effectors of FIG. 4 that contact the fluid are included as fluid path elements.

The simplest fluid path is shown in FIG. 14B. It has one fluid path element A and one fluid path 1. In this invention, there are a number of fluids that can and will be transmitted via this fluid path. In the manual practice discussed in the background, the fluid path element A is a needle that is connected to a syringe for injection of a fluid with cells or drugs. In the prior art manual methodologies, the pump is the syringe and the operator's hand, the control system is his or her brain, the fluid being injected is the therapeutic fluid containing cells, and there is no manifold. The pump directly injects in to the fluid path 1.

In several embodiments, the present invention replaces the hand with one or more mechanically or electrically powered pumps or controlled injectors. If multiple injectors and/or a multi-container injector are used with a manifold or valve arrangement (see, for example, FIG. 3), then several fluids can be injected either sequentially or serially. As an example, fluids used include the therapeutic injectate, and could for example include one or more of saline or a similar physiological fluid for priming the fluid path elements or flushing the therapeutic injectate, a viscosity modifying agent, a lubrication agent, a tissue cracking or opening agent, a site marking agent, and a sealing or gluing agent to seal the site or fill the needle or catheter track. The detailed uses of such fluids are discussed in various parts of this description.

One embodiment with two fluids includes the therapeutic fluid and saline. The fluid path 1 is first filled with saline to remove all air from the path. Then, depending upon the volume contained in the fluid path as compared to the volume of the therapeutic fluid to be injected, the purging fluid can be left in the fluid path while the effector, needle in this case, is placed in the target tissue. The purge fluid in the fluid path is simply injected into the tissue before the injection of the therapeutic fluid. And, optionally, the injection of the therapeutic fluid can be followed by an injection of a flush fluid, for example saline, to drive more of the therapeutic fluid out of the fluid path elements and into the tissue.

In FIG. 14C, there are two fluid path elements, A & B. Similarly, there are two fluid path elements shown in FIG. 14D. An arrangement similar to this was disclosed in Published U.S. Patent Application No. 2004/0254525 A1, the disclosure of which is incorporated herein by reference. In that application, it was used to surround the injection of a drug that harmed vessel walls with a second fluid that did not harm the walls. In the current invention, injecting the therapeutic injectate through fluid path 1 and a fluid such as saline with a relatively lower viscosity through fluid path 2 will help protect the cells in the therapeutic injectate from the high shear stress as they travel through fluid path 2 to the patient. Using readily available computational fluid dynamic (CFD) modeling, for example Fluent and other software packages available from Fluent, Inc. of Lebanon, N.H., it will be possible to select the appropriate flow rates and velocities to maintain the desired flow and safe shear stress levels. In this case, it is likely that the distance of travel outside of fluid element A, the physical distance from Ad to Bd, will be relatively long.

A second application of the fluid paths of FIGS. 14C and 14D involves non-simultaneous delivery of fluids. The initial fluid through fluid path 2 could be relatively high pressure and velocity to "crack" or open a space in the tissue. After that fluid dissipates into the tissue, or after it is sucked back out through fluid path 2, then the therapeutic injectate can be delivered through fluid path 1. Alternatively, the second fluid is delivered through fluid path 2 after the therapeutic to flush or drive the therapeutic fluid into the tissue. A third application, show in FIG. 14D, has the vector distance Ad to Bd be very short or in fact negative. (A negative Ad to BD vector distance means that the fluid path element A actually sticks out past fluid path element B.) In this application of the embodiment, the injectate flows toward the patient in fluid path 1, and some of the injectate is drawn back in away from the patient through fluid path 2. The laws of fluid mechanics cause particles or objects in a developed fluid flow of sufficient velocity to concentrate in the center of the flow away from the walls. This happens in normal blood flow in the arteries. In physiological systems, some blood vessel branches use a "cushion" of tissue to take blood from the cell rich center flow. (*Physiology and Biophysics of the Circulation,* 2$^{nd}$ Edition 1972, Alan C Burton, LC#70-182003, chapter 5) In the opposite way, fluid path 2 is removing some of the fluid with less or no cells, so that the total fluid volume injected into the tissue is reduced for a given number of cells being delivered to the tissue. This reduces or eliminates the tissue swelling needlessly increased by fluid that is of no therapeutic value. Alternatively, fluid path 2 could withdraw fluid just long enough to remove the purging fluid from the system, but not withdraw fluid when the therapeutic fluid arrives. Fluid path 2 could incorporate the filter discussed in conjunction with FIG. 10A to ensure that cells are not needlessly removed and wasted.

Alternatively, fluid path 1 could be used for delivery of the therapeutic fluid and fluid path 2 is used to delivery a site marking fluid or a needle or catheter track filling. This is most likely done with an embodiment where fluid path element A extends past the end of fluid path element B so that fluid path 1 is not occluded by the track filling fluid. In addition, fluid path 2 could transport a fluid that reacts with the fluid in fluid path 1, for example, calcium ions that will cause the alginate in fluid path 1 to gel.

One of the challenges with cell delivery is that the cells tend to settle, stick, or clump to themselves or on the insides of the fluid path elements. One approach to over come this is to start the flow with a higher or more rapid velocity than is used for the majority of the injection. A second approach is that of FIG. 14*e*. The injectate is pulled back fluid path 1 while a purging or physiological solution is injected at the same flow rate down fluid path 2. This reverse flow in fluid path 1 will help loosen any clumping or adhesions, without pulling any fluid out of the patient. Then, when the injection starts to flow in the forward direction in fluid path 1, there is suction out fluid path 2 until it removes a volume approximately equals the volume that had been previously injected down fluid path 2. Similarly, this helps ensure that little or none of the purge fluid is delivered to the tissue. Then the injection can proceed according to the preferred delivery scheme.

FIG. 14F shows the fluid path elements of FIG. 14A, with an exemplary fluid flow indicated. Fluid path 1 carries the therapeutic injectate, fluid path 2 is delivered simultaneously with a lower viscosity "lubricating" fluid. The two fluids flow together to the end Bd of fluid path element B. At end Bd, the lubricating fluid is removed by suction on fluid path 3 so that a more concentrated cell carrying fluid is delivered to the tissue. From this example, it is apparent that all of the functions described above with respect to two fluid paths can be realized with the 3 fluid paths of FIGS. 14A and 14F.

In some embodiments, a solid needle, commonly called a stylet is inside the hollow fluid path element when it is inserted into the tissue. This is often done so that a core of tissue does not fill the hollow fluid path and to minimize the damage to the tissue. However, when the solid stylet is withdrawn, it created a suction on the tissue at the tip, and/or the hollow fluid path is filled with air. It is generally desirable that this air not be injected into the patient, especially when the delivery is through catheters in the blood vessels. A multiple fluid path embodiment of the present invention can be used eliminate this problem. When fluid path element A is originally a solid stylet, fluid path 2 can be used to slightly pressurize the space around element A, so that as it is moved, fluid flows to fill the space. This requires a seal at the proximal end of fluid path element B. Such seals, often made of an elastomeric material, are well know in the medical arts, especially in regards to catheters in interventional and special procedures labs. Hemostasis valves and needleless ports are examples of similar devices.

It is preferred that the injection of marking or track filling fluid is automatically coordinated with the withdrawal of the effector. The position of the effector can be tracked with various methods known in the art. Similarly, the injection of the therapeutic fluid can be synchronized with the motion of the effector, so that the track left by the effector is filled with therapeutic fluid. The marking could occur simultaneously with the indication to the user that the injection is over and that the needle can be removed, as was discussed above.

Several representative stylized fluid path elements of the present invention have, for example, generally been discussed and shown to incorporate, for example, concentric cylinders. In many cases this optimizes the uniformity of flow and helps preserve laminar flow. Eccentric cylinders can generally be easier to manufacture, especially if they touch and have a wall in common, and they may have some benefits in use. In addition to not demanding concentricity, most of the concepts of this invention can also be accomplished with parallel or adjacent fluid path elements, or in fact totally separate fluid path elements that only meet or connect at the patient. In the connection, they may then have or not have concentricity, dependent upon the need to be separate or mixed and upon the details of the fluids. The assembly of structures in such embodiments use techniques well know in the medical device and disposables art. Gluing can be used to assemble separate molded and/or machined parts. Insert molding can be used advantageously in some instances to capture metal or plastic elements in other plastic elements. Co-extrusion can create fluid path elements of significant length. Assembly with elastomeric seals is applicable to some embodiments such as those of FIGS. 12C and 12D.

In addition, the drawings of FIGS. 14A to 14F are for clarity of understanding and are not to scale in length, width or proportions. The fluid path elements may change diameter, cross section, shape, or size or taper over their length. Example geometries are discussed in relation to the examples applications. Generally for clarity and consistency, the therapeutic fluid is discussed as being delivered through fluid path 1, however, generally the fluids can be transmitted through any of the fluid paths provided that the fluid path elements are compatible with the fluids and the shear stresses are sufficiently low. The walls of fluid path elements are shown as lines. As discussed elsewhere, turbulence is generally damaging to cells.

The necessary rounding or tapering of any edges depends upon the thickness, roughness, and fluid flow parameters to be used in a particular case The generation of turbulence can be modeled and avoided using computational fluid dynamics packages as described elsewhere. In some embodiments and applications the effector itself does not need to penetrate the tissue but is inserted through a needle, through a previously made track, or over a guidewire. In others, where it needs to be strong and sharp enough to penetrate the tissue, there will be competing design needs on fluid path element wall thickness and edge geometry. It is anticipated that because the therapeutic fluid is flowing into the tissue at that point and entering an uncontrolled geometry, the desire for laminar flow can be relaxed and that the sharp edges will most likely be beveled in any event, which will minimize any step transitions and their subsequent generation of eddies.

Pump/Injector System and Container

In several embodiments of the present invention, pump/injector system 100 is designed to mechanically deliver fluid to tissue and, particularly, the myocardium. As discussed above, among the potentially beneficial fluids that can be delivered, autologous bone marrow-derived progenitor cells offer promise in the treatment of diseases of the heart tissue such as occurs in congestive heart failure and dopamine producing cells offer promise in treating, for example, Parkinson's disease. In light of these and other applications, in several embodiments of the present invention, pump/injector system 100 was designed with special attention to, for example, the handing and delivery of such cells. Features preferably present in several embodiments of a pump or injector for delivery of such cells include: 1) consistent, repeatable dosage size, 2) a 15-30 ml total volume, packaged in a disposable container, and/or 3) a specified volume to be mechanically injected on demand in a defined period of time, for example, one second or less. Thus, in several embodiments of the present invention, pump/injector system 100 provides consistent and accurate delivery of a specified volume of fluid into, for example, the myocardium of the heart or the brain, ensuring that the total volume is accurately distributed across the total number of injections and delivered at an appropriate rate.

In an embodiment illustrated in FIG. 15A, a disposable container or syringe 50" can be snapped securely and reliably into place with pump/injector system 100" in a simple, two-step operation. The easy and secure mounting of disposable container or syringe 50" reduces operator effort and time while also reducing the risk of error. The simple operative attachment enables syringe plunger 56" to be pushed forward for injections and withdrawn for removal and disposal (if necessary) with little user effort. As illustrated in FIG. 15A, injector 100" includes a seating or cradle section 105" for receiving syringe 100". A rearward section of syringe plunger 56" includes an attachment flange 58", which cooperates with a retaining seating 112" on a forward end of injector drive member 110". Flange 58" and/or seating 112" can, for example, be formed from one or more resilient materials (for example, polymeric materials as known in the polymer arts) so that a snap fit is formed to securely retain syringe 50" within seating 105" and within operative connection with injector 100". To attach syringe 50" to injector 100", syringe 50" is angled with respect to injector 100" as illustrated in the upper left portion of FIG. 15A. In this angled orientation, flange 58" is first placed in connection with seating 112" and then syringe is moved into alignment with seating 105" as illustrated in the upper right portion of FIG. 15A.

As illustrated, for example, in FIG. 15B, mechanical drive, drive member or piston 110" pushes the disposable syringe's plunger 56" forward with, for example, a screw drive. Injector drive mechanisms are, for example, described in U.S. Pat. Nos. 4,677,980, 5,383,858, 6,585,700, Published PCT International Patent Application No. WO 02/04049 and U.S. patent application Ser. No. 10/921,083, filed Aug. 18, 2994, the disclosures of which are incorporate herein by reference. The screw drive can, for example, be powered by a highly accurate stepper motor 120" and a small, powerful battery 122". This reliable method of driving a small pump maintains accuracy and power in a suitably small package.

As illustrated, for example, in FIG. 15C, a custom assembly 1600 including screw-drive components 1610 and portions of an electromagnetic motor 1620 can be inserted into a handle/housing 1630 containing additional circuits and motor components as known in the art, thus completing the motor assembly necessary for driving an injection. This significantly smaller approach to a mechanical drive assembly provides an injector suitable for even the smallest fluid injection volumes.

FIG. 15D illustrates use of an embodiment of a pump/injector system 1700 of the present invention for the use of injection of, for example, SPHERAMINE into the brain of a patient. In this embodiment, the injector system includes a syringe pump 1710 to deliver the SPHERAMINE from a syringe 1720 to the patient. As further described in connection with FIG. 16C below, syringe pump 1710 can be enclosed in a sterile bag or other containment system or barrier. In the illustrated embodiment, syringe 1720 is placed in fluid connection with a needle 1730 localized by a stereotactic frame or similar localization device 1740 via a length of flexible tubing 1750. As known in the art, needle 1730 can be provided with a removable stylet to prevent coring upon advancement within tissue. Further, needle 1730 can pass through a cannula in operative connection with stereotactic frame 1740. As compared to current manual techniques, connection of syringe pump system 1710 to needle 1730 via flexible tubing 1750 isolates needle 1730 and stereotactic frame 1740 from force, torque, or vibration.

As compared to current manual injection of SPHERAMINE, pump driven system 1700 of the present invention can also provide the benefits of flow, volume and pressure control and auto loading. Pump system 1710 is also capable of reversing before injecting, delivering the dose in pulses or conducting a two-phase or multi-phase injection.

In several embodiments, the injectate of interest (for example, SPHERAMINE) can be present only within needle 1730 and a flushing fluid is used to inject the SPHERAMINE into the brain of the patient. Such embodiment can, for example, limit shear experienced by the injectate.

FIG. 15E illustrates another embodiment of an injection system 1800 of the present invention suitable, for example, to inject cells (for example, SPHERAMINE). In this embodiment, a syringe pump or other injector 1810 in operative connection with a syringe 1820 including a fluid therein is used to mechanically or hydraulically drive a syringe 1830 (via tubing or conduit 1824) that delivers SPHERAMINE to the patient via a needle 1840 in operative connection with a stereotactic frame 1850. Once again, syringe pump 1810 and/or other components of system 1800 can be enclosed in a sterile barrier. By using syringe pump 1810 or other drive mechanism to drive syringe 1830 containing, for example, SPHERAMINE, as opposed to delivering the SPHERAMINE directly as illustrated in FIG. 15D, the fluid path length for the SPHERAMINE is reduced.

In several embodiments, the pump/injector systems of the present invention can be programmed to deliver a calculated volume, which equates to a predetermined amount of viable cells based on an algorithm such as a statistical algorithm. For a desired amount of stem cells the algorithm determines the required volume for a given time in the life cycle and processing time of the drug.

For example, it is known that FDG decays with a half-life of 110 minutes from the time it is fabricated. It is also known that living stem cells have a nominal life under the conditions they are subjected to during delivery, and experience a settling or packing as a result of time and syringe/vial orientation Given this information, the injector calculates from the time the cells were cultured to the present time to determine the percentage of live (viable) cells remaining in the syringe/container. If there is any significant settling that occurs over time, the injector can calculate the amount of settling and deliver a flow profile that, for example, includes less volume in early injections and more volume in later injections, or vice versa to provide a consistent amount of viable cells from the first to the last injection for a given container. The algorithm can calculate the volume required for each injection to deliver the predetermined amount of viable (viable cell count) cells for each injection. Other factors such as a slide cell count or temperature of the culture can also be considered in the algorithm. If cell measurements are taken periodically during a delivery session, this can be used to update the algorithm.

Further, if stem cells are known to require a high flow rate to break them loose from, for example, the needle, tubing, or syringe, the flow can be tailored to deliver a high flow at the beginning of the injection to break the cells free and taper off to give a steady delivery of cells over time.

User Interface System

The surgical field is often a crowded, stimulus-filled environment. The user of the devices and systems of the present invention is often wearing layers of surgical gloves, a gown, mask and face shield. User interface system 700 (see FIG. 4) of fluid delivery system 5 preferably provides easy, adequate and appropriate feedback and input control to the user during operation.

The feedback or information provided to the user can include, but is not limited to: total volume injected; volume remaining to be delivered; injection dosage volume; status of an injection in progress; map of injection area (for example, a 3-D computer generated map, position of injections made, position of injections to be made, cell viability, number of cells injected, number of cells reaming, and flow rate. The controls provided to the user can include, but are not limited to: dosage volume; injection start/stop; injection position, and flow rate. The controls afforded the user further preferably provide the user ready access to, and accurate control of, a repeatable, accurate and consistent dose size, without the inherent inaccuracies of a manually controlled injection.

In one embodiment as illustrated in FIG. 16A, a switch assembly 1850 is operatively connected in the vicinity of patient interface 400 (for example, to a depth stop mechanism 1900—either permanently or temporarily). Depth stop 1900 can, for example, include an abutment surface 1910 that abuts tissue and thereby limits the depth to which needle 400 penetrates tissue. The position of abutment face 1910 relative to the distal end of needle 400, and thus the penetration depth, can, for example, be adjusted via threading 1920 or other adjusting mechanism. Switch assembly 1850 can be used to trigger discrete injections. A button mechanism 1860 or other interface can, for example, provide tactile feedback to the user. Also, a small LED 1870 connected to the switch circuitry can be used to visually signal the start and stop of each injection.

In the embodiment of FIG. 16B, the system subassembly of pump/injector 100" and syringe 50", which is shown in operative connection with switch assembly 1850 and depth stop mechanism 1900, is attachable to and worn by the user. Part or all of control system 200 can also be contained within the injector housing. The user can, for example, operate the system by attaching the system subassembly to the forearm of the user, thereby freeing up both hands to manipulate the fingertip unit/switch assembly 1850 (see FIG. 16B through 16D) in the surgical field. With both hands free, the user has a greater degree of physical dexterity and an increased control of accuracy and precision during the procedure. Moreover, a user wearable injector system can free valuable space in the surgical field. FIG. 16C illustrates the use of a sterile barrier 1950 to enclose at least a portion of the fluid delivery system of the present invention. In the embodiment of FIG. 16D, barrier 1950 is, for example, a flexible barrier (for example, a flexible polymeric material) that is wearable by the user of the system subassembly of pump/injector 100" and syringe 50". The user can, for example, don the wearable system subassembly of pump/injector 100" and syringe 50" outside of the sterile field and then don sterile barrier 1950, covering the subassembly, to maintain sterility in the sterile field. Alternatively, the subassembly can be provided in sterile condition (for example, in sterile packaging). The pump/injector 100" and container 50" can be disposable after a single use. Pump/injector 100" can also be sterilizable to provide for multiple uses. Sterile barriers can also be used in connection with nonwearable embodiments of pump/injector 100" and other injectors of the present invention.

The system subassembly of pump/injector 100 and syringe 50 and other system components can, for example, be made to be MR compatible for use in an MR environment as described, example, in U.S. Pat. No. 5,494,035, Published PCT International Patent Application Nos. WO 02/082113 and WO 03/006101, and U.S. patent application Ser. No. 10/916,946, filed Aug. 12, 2004, the disclosures of which are incorporated herein by reference, as well as in other imaging system environments.

As illustrated in FIG. 16D, the system subassembly of pump/injector 100 and syringe 50 can be attached to the user with an attachment mechanism such as a simple adjustable armband or other strapping 1960. Strapping 1960 can, for example, include a hook-and-loop type fastener such as VELCRO® or other fastening mechanism as known in the fastening arts. Upon attachment of the subassembly to the forearm of the user, a set of controls located on device 100" preferably faces "upward" toward the user's eyes while in use. The proper orientation of displays and nomenclature facilitates use by both right- and left-handed users. With a clear view of the display on the forearm unit, the user has ready access to and knowledge of the variety of functional parameters of the device, reducing the possibility of error or miscalculation.

As illustrated in FIG. 16E, information displayed on one or more displays of the forearm unit can, for example, be clearly readable from up to 30" and provides continuous indication/feedback to the user of, for example: injections remaining; injections made; dose volume; volume remaining; volume injected; injection in progress; injection complete; device status, battery power injection etc.

Information/feedback to the user can alternatively or additionally be provided using a display mounted to remain in the user's field of vision. By placing pertinent information in the user's view at all times, the user may consult the information without taking the user's eyes off of the procedure at hand. In the embodiment of FIG. 16F, for example, a display 1970 in communicative connection with injector system 100" is mounted on a frame or support 1980 attached to a headband 1990 worn by the user.

In-Line Measurements/Sensor Feedback/System Control Architecture

A. Patient Physiological Parameters

In one embodiment of the present invention, patient interface 400 includes or has in operational connection therewith one or more physiological measurement devices, systems or function. For example, such devices can determine the location of damaged tissue, such as ischemic and infarcted areas of heart tissue.

Biosense-Webster, a J&J/Cordis subsidiary, has, for example, developed a system to create functional maps of cardiac electrical and mechanical activity using catheter-mounted electrodes. That NOGA catheter is used in the cath lab to determine the location of ischemic and infarcted areas of the endocardial wall. It is useful in assessment of treatment, since ischemia is caused by reduced oxygen delivery to cardiac muscle, and can be corrected by procedures that restore blood flow, while infarction is associated with unrecoverable dead tissue. Implantation of cells would follow different strategies based on the diagnosis of ischemia versus infarct.

In the NOGA system, the location of the contacting electrodes is tracked in real-time by a standard electromagnetic tracking system. Data is used by a computer to create maps of the cardiac activity. Data can be sampled from inside the heart (see following) or from the outside using catheters or sensing needles.

U.S. Pat. No. 6,892,091, the disclosure of which is incorporated herein by reference, discloses a catheter capable of mapping the electrical and mechanical activity of the heart by sampling the voltage and mechanical strain at unique points on the endocardium. A three-dimensional color-map of the activity is created by associating data with a location of the sampled tissue determined by electromagnetic tracking of the catheter tip.

Another way of monitoring ischemia or hypoxia in cardiac tissue is through the use of catheter-mounted or needle-mounted oxygen probes. These devices are electrochemical devices mounted in or upon invasive devices that make contact with tissue. These devices are capable of responding to the partial pressure of oxygen present in and around perfused tissues. Several commercial devices are available from Oxford-Optronix of the Oxford, United Kingdom In several embodiments of the present invention a therapeutic device is coupled with a diagnostic device to inject therapeutic fluids, cells, cell carriers (including, for example, beads), for example into sites of damaged heart tissue. As illustrated, for example, in FIG. 3, system 5 can, for example, include: (1) patient interface 400 (e.g. catheter or needle) to inject therapeutic fluids, emulsions, suspensions, gels, solids etc. into tissue as described above; (2) one or more sensors, measurement devices or monitors 600 (for example, mounted in or upon the patient interface 400 or otherwise placed in operative connection with the patient) to measure one or more biophysical properties of the patient and/or the patient tissue; (3) one or more imaging systems 500 to display regions of the patient (for example, ischemia or infarction distinguishable from healthy tissue); and (4) a feedback system by which an operator can use imaging system 500 to guide patient interface 400 (for example, with sensor(s) as described above) to a region of damaged tissue (for example, ischemic tissue) to inject therapeutic fluids, cells, or cell carriers The sensing device(s) can, for example, make direct contact with the tissue to distinguish among well-perfused, or infarcted (dead) or ischemic (stunned) tissue, presuming that injection into ischemic tissue is more likely to restore function to the affected area. Based on the measurement, system 5, through control system 200, can allow or disallow the injection. Preferably, system 5 at least alerts or informs the operator of the tissue condition prior to delivery of a therapeutic fluid.

System 5 can also include a measuring or sensing device to detect the amount of blood flow or capillary perfusion in tissue. In one embodiment, the sensor makes direct contact with the tissue and responds rapidly to change in blood volume in a perfused tissue. One example of such a device is a thermistor, which is sensitive to rapid changes in blood volume as indicated by temperature change at the contact point. The thermistor changes its electrical conductivity in response to small temperature differences. Sensitivity of the measurement can be increased by using a pair of thermistors with one serving as a reference.

In another embodiment, the measuring or sensing device is a contacting or a non-contacting infrared light source and an infrared sensor arranged as a pair. This sensor pair responds to small changes in blood perfusion by sensing reflected and scattered light in tissue. Highly perfused tissues is easily distinguished from ischemic or infarcted tissues because of the optical properties of blood with respect to the scattering and absorption of infrared light. This principle is known in the art (see, for example, U.S. Pat. No. 6,122,536, the disclosure of which is incorporate herein by reference), but sensing systems that probe perfusion of tissue on percutaneous medical devices are unique.

To position the sensor residing near the distal tip of patient interface 400 (for example, a catheter, needle, or endoscope), an additional miniaturized device can be provided to determine the sensor location with respect to the tissue under treatment. The location of the sensor can then be superimposed upon the image of the tissue displayed for the operator by imaging system 500. A medical positioning system of this type is described, for example, in U.S. Pat. No. 5,526,812, the disclosure of which is incorporated herein by reference. That system uses an electromagnetic field and multiple antenna loops to sense the field and to triangulate sensor position for processing by a computer graphics system. As described above, the present invention can provide a map of, for example, blood perfusion in tissue in near real-time prior to the administration of therapy.

Physiological parameters such as respiration and/or heart function can also be measure to, for example, provide a positioning function, a gating function or an injection timing function. For example, FIG. 17A illustrates an embodiment of system of the present invention in which an electrocardiogram (EKG) can be used to measures heart movement and synchronize injection. In this system, control system 200 is in operative connection with the EKG monitor 602 (for example, part of monitor system 600), which measures the heart's activity. Control system 200 uses that information to control pump system 2000 and/or patient interface or needle 2010 to, for example, deliver fluid when the heart muscle is relaxed (during diastole), enabling greater fluid delivery and distribution. In the illustrated embodiment, needle 2010 is equipped with a depth control device 2012 a position sensing mechanism 2014 as described above.

B. Measurement of System Variables other than Patient Physiological Variables

System variables other than patient physiological variables can be measured and data provided to control system 200 and/or to the user to effect control of one or more aspects of system 5. In several embodiments, parameters or variables such as injectate fluid pressure, injectate flow, injectate temperature, injectate nutrient information, cell viability indicators (for example, Adenosine Triphosphate (ATP) levels), injectate density, and/or cell level counts are measured. In several embodiments of the present invention, "lab-on-a-chip" technology can be used to effect such measurements. Lab-on-a-chip technology allows, for example, physiochemical and biological process measurement, previously made with the user of relatively large devices—to be performed on a small plates with fluid channels, known to scientists as microfluidic capillaries. In that regard, lab-on-a-chip technology incorporates photolithographic processes developed in the microelectronics industry to create circuits of tiny chambers and channels in a quartz, silica, or glass chip. The small sample size makes such measurement devices a viable method for real-time fluid path chemical analysis. For example, in one embodiment, such a chip can include a fluid pressure sensor, a flow rate meter, an ATP chemical analysis microfluidic circuit and other sensors. A primary commercial source for lab-on-a-chip technology is ISSY-Integrated Sensing Systems, Inc. of Ypsilanti, Mich. (see, for example, http://www.mems-issys.com/index.html).

A pressure sensing microchip or other sensing device to track fluid delivery pressure can be important in maximizing cell viability through, for example, closed loop control (via control system 200) of flow to prevent damaging pressure/shear during the fluid delivery. Once again, excessive pressure and related high flow rates can lead to excessive shear and corresponding cell damage or destruction. The device can be small enough to install within the fluid path (that is, within the internal aspect of the disposable tube or connector). The device can provide "real time" fluid pressure readings, without relying on motor current or other secondary or indirect means or methods of measuring injectate pressure. A closed loop control algorithm can manage the delivery automatically to minimize cell damage. Feedback data and control data can be communicated in a wired or wireless manner between control system 200 and other system components.

Several alternative embodiments of pressure measurement devices can be used in connection with one or more components of the fluid path of the present invention. Moreover, many such devices can also be used in connection with manually powered syringes, wherein it can be especially important to measure injectate pressure as there is no other way to know the pressure (and related shear force) being generated in delivering cells with a manual system. FIG. 17B illustrate a device 2100 in which an indicator 2110 such as a pop-up indicator (for example, a pop-up needle) in fluid connection with a needle 2120 pops up once a certain threshold pressure is reached. Pressure measuring indicator 2110 can, for example, perform two different function. It can, for example, provide an indication to the operator that excessive pressure has been generated and that flow rate should be reduces. In can also inform the operator that a pressure is still in syringe 2130 and that the operator should wait until the pressure drops before removing needle 2120 to prevent injectate leakage from the tissue. In the illustrated embodiment, indicator 2110 includes an elastomeric seal member of plunger 2112 within a housing 2114 that is biased by a biasing member 2116 such as a spring having a known spring constant. Increasing pressure in system 2100 causes plunger 2112 to raise within housing. An indicating element such as a pin or needle 2118 is in operative connection with plunger 2112, and movement of indicating element provides an indication to the user of increasing system pressure. Needle 2118 can include gradations 2119 that can provide a measurement of system pressure.

A real-time flowmeter 2140 can, for example, provide the user an immediate indication of fluid movement. This is important information, for example, with a device that is controlled by the user through a remote actuator. Flowmeter 2140 can also integrate seamlessly with a pressure sensing device, such that they would communicate continuously to manage the optimal flow profile without cell damage. Once again, flowmeter 2140 can be small enough (as, for example, in the case of "lab-on-a-chip" technology) to be placed within the fluid path of the disposable fluid delivery set. For example, as discussed above, the device can provide an indication to control system 200 and to the user (both directly and via user interface 700) that excessive pressure is being generated and that injection fluid pressure/flow rate should be decreased. Moreover, the device can provide an indication that the pressure is still in the fluid delivery system/fluid path and that user interface 400 should remain within the tissue until such pressure drops to prevent backflow, retrograde or leaking of injection fluid after interface 400 is removed (as discussed above in connection with system capacitance).

FIG. 17C illustrates the use of a disposable pressure transducer, pressure sensor or pressure switch 2150 with an indicator 2152 to indicate a certain pressure level. Indicator 2152 can, for example, be and LED that is programmed to turn on at a predetermined or adjustable setting to indicate that pressure has increased above the setting and to turn off at a predetermined or adjustable setting to indicate pressure has decreased below the setting. Pressure sensor 2150 can provide pressure data to control system 200 and to the user via user interface 700. Pressure sensor 2150 can, for be equipped with connectors 2154 such as Luer fittings to be placed in line with the fluid delivery path.

FIG. 17D illustrates a pressure measuring device 2160 including floating balls 2162 (or other indicator elements) in a transparent flow path element or housing 2164 that compress and drop as pressure increases. In that regard, the specific gravity of balls 2162 can be just a bit less than the density of the injection fluid. Under no pressure, balls 2162 float. As the pressure increases, balls 2162 compress, increasing the density of balls 2162, and balls 2162 sink within flow path element 2164. Filter elements 2166 can be provide at the entrance and exit of flow path element 2164 to allow fluid to pass therethrough but to retain balls 2162 therein.

FIGS. 17E through 17H illustrates a syringe device 2170 including a spring-load (or otherwise biased) rubber cover 2174 in operative connection with a plunger extension 2172 (which is slidably disposed within the syringe barrel) to measure force/pressure within the syringe barrel mechanically. As plunger 2172 is advanced, spring 2176 (positioned between rubber cover 2174 and plunger extension 2172) compresses to provide a measure of the pressure developed. In addition to transmitting pressure data to other system components, an indicator such as a rod or pin 2178 on plunger extension 2172 that passes through an opening 2181 in a rearward extending member 2180 connected to cover 2174 can provide a direct indication of pressure. In the case that the system is not under pressure, spring 2176 pushed plunger extension 2172 rearward. Pin 2178 also moves rearward and can come to rest at a stop 2182 formed by extending member 1280 as illustrated in FIG. 17G. Under pressure, spring 2176 is compressed. Plunger extension 2172 and pin 2178 move forward as illustrated in FIG. 17H. The amount pin 2178 moves forward can provide an indication of system pressure. Gradations 2182 can be provided around the edge of opening 2181 to indicate force/pressure.

FIGS. 17I through K illustrate the use of elastic tubing 2190 in the fluid path that is, for example, colored on the outside (only). As pressure increases, tubing 2190 expands, making the color of tubing 2190 lighter. The greater the pressure, the more tubing 2190 expands, and the lighter the color of tubing 2190 becomes. Parallel lines 2192 can also be marked on elastic tubing 2190. As the pressure within tubing 2190 increases, the distance between lines 2192 becomes greater, thereby providing an indication of the pressure within tubing 2190. In the illustrated embodiment, tubing 2190 is attached at each end thereof to clear plastic restraining collars 1294 which can be connected to connectors 1296 such as Luer fittings. Elastic tubing 2190 can also be use to impart controlled capacitance into a system if desired.

FIGS. 17L through 17M illustrate the use of a graduated ring 2200 that encompasses an expandable tubing device 2206 as, for example, described in connection with FIGS. 17I through K. As the pressure increases in fluid path 2208, ring 2200 is expanded and a measurement of pressure is provided. In that regard, ring 2200 includes an indicator 2210 (for example, on one end thereof) which is visible through an opening 2220 formed in ring 2200. Gradations 2222 can be provided on ring 2200 adjacent opening 2220 to provide an indication of pressure in the system.

Measuring motor current with pump/injector system 100 or the use of strain gauges in operative connection with the plunger or drive member as known in the art can also be used to provide a pressure measurement. Likewise, a flow meter 2240 with a known internal diameter can provide a measurement of pressure as illustrated in FIG. 17N. As mentioned above, one or more pressure transducers 2250 can be used and, as with other pressure measurement device, pressure data fed back to control system 200 as illustrated in FIG. 17O. Pressure measurement in injection systems and pressure control and/or limitation are, for example, discussed in U.S. Pat. Nos. 5,808,203, 6,673,033, 6,520,930 and 6,488,661, the disclosure of which is incorporated herein by reference.

If the fluid path configuration is known and the flow parameters thereof characterized (for example, a maximum shear rate is know for the fluid path, below which minimal cell damage occurs), an maximum allowable pressure can be calculated. The flow parameters of a particular fluid path element and/or the entire fluid flow path are readily characterized theoretically of via experimental data as known in the fluid dynamics arts. For example, the characterization of fluid pressure at various points in a fluid path is discussed in Published PCT International Patent Application No. WO 2006/058280, published Jun. 1, 2006, the disclosure of which is incorporated herein by reference. Disposable fluid path element can, for example, be coded with one or more indicators 2260 (using, for example, RFID, bar codes, labels etc.) and data input into or read by, for example, one or more sensors 2270 in communicative connection with control system 200 so that flow restrictions/flow profiles are known. A maximum or threshold pressure (to reduce shearing of cells) can be calculated and set as a limit. Also, as described above, container 2262 (also a fluid path element) can include one or more indicators 2264 to provide information regarding the nature of the agents therein (for example, cells) and the flow characteristics of the vessel. Indicators 2264 can be read by one or more sensors 2274 in communication with control system 200.

Pressure measurements and corresponding changes in system pressure/flow rate can be use to achieve objectives other than minimization of cell damage and maximization of fluid retention as discussed above. For example, flow can be changed (for example, reversed via plunger pull back) to break up cell clumps. The movement of the plunger can be tracked to ensure accurate fluid delivery. Moreover, a sequence of fluids can be injected, for example, at increasing pressure, to drive cells deeper into tissue as illustrated in system 2280 of FIG. 17P. In this embodiment, a first container 2282 including cells is in fluid connection with a first needle lumen 2284 and a second container 2286 including, for example, saline is in fluid connection with a second needle lumen 2288. A membrane filter 2290 or other control device as illustrated in FIG. 17Q can be placed in fluid connection with patient interface 400 that will allow fluid to pass only upon buildup of a certain pressure. One or more ultrasonic flow transducers 2300 (for example, using the coraolis effect) can be used to measure flow and assist in break up of clumps as illustrated in FIG. 17R.

ATP (Adenosine Triphosphate) is present in all cells. It is formed when energy is released from food molecules during cell respiration. As a nucleotide it performs many functions and is recognized as the "energy currency" of the cell. When a cell is damaged, ATP is released. Damage to a cell can be the result of mechanical forces, such as high pressure, vacuum, or shear forces as described above. Although much has yet to be learned, successful cell therapy is believed to be dependent on delivering the maximum numbers of cell to the affected organ or tissue. Counts can be in the millions of cells, with each injection potentially measured in the tens or hundreds of thousands. Cells are delivered to the affected organ or tissue through patient interface 400, with control and accuracy of the delivery being provided by control system 200 in operative connection with pump/injector system 100. For such embodiments, the ability to measure ATP during a cell delivery can be useful to measure cell damage caused by the handling or injection environment. As a result, cell viability can be tracked (that is, as measured ATP levels increase, the number of viable cells decrease). Sub-miniature chemical sensors or other sensors installed in the cell delivery disposable set (typically including, container 50, fluid path conduit or tubing 310 and patient interface 400) and represented by or included in in-line measuring units 72 and 74 can monitor ATP levels during delivery and communicate them to control system 200 and/or user interface 700. If ATP levels increase during injection, appropriate injection parameters may be adjusted, such as flowrate, to reduce the shear potential or fluid pressure.

FIG. 17S illustrates an embodiment of a system 2400 including a density measuring device 2410 based, for example, on the Coriolis effect in operative connection container 50, fluid path conduit 310 or patient interface 400. In the illustrated embodiment density measuring device 2410 is in fluid connection with container 50 via an intervening valve 2420. Density measuring device 2410 measures density of typically non-homogeneous injection fluid passing device 2410. The measure can, for example, be integrated over time to enable delivery a uniform mass of material. This uniform mass can provide an estimation of a cell count. In that regard, an algorithm can be executed by, for example, control system 200 to subtract the contribution of the carrier fluid by measuring the volume delivered (injection flow rate). In that regard, the weight of the delivered carrier fluid volume can be subtracted from the total weight delivered, leaving the weight of the cells delivered.

Alternatively or additionally, sub-miniature sensors and monitoring devices or other sensors and monitoring devices can be placed within cell storage container 30, within a transportation container or fluid path, and/or within cell processing unit 40 (as, for example, represented by in-line measurement unit 70). Continuous monitoring of the cell material can provide valuable information to determine live cell count during storage or transportation.

Marking and Mapping During Delivery

In several embodiments of system 5 marking of delivered injectate and mapping of tissue regions is provided. During the injection procedure, one goal of marking is to enable the doctor or operator to determine what tissue has been treated, both to avoid double treatment and to ensure sufficient coverage of the area to be treated. Marking also helps provide uniformity of treatment over the tissue surface, with the option of quantifying the treatment in two or three dimensions. These results are especially useful in external heart treatments and dermatological treatments. The marking can be such that it is used long term to monitor tissue response or cell migration. An ancillary benefit is that some of the marking mechanism can optionally help keep the injectate in the tissue.

One set of marking embodiments marks the surface of the tissue being treated, to indicate the location of the needle puncture or an approximation to the spread of the injectate within the tissue as or after the injection occurs. These markings may be visible to the eye, (either unaided and aided) such as dyes applied by a "rubber stamp" type applicator of U.S. Pat. No. 5,997,509, the disclosure of which is incorporate herein by reference. U.S. Pat. No. 6,322,536, the disclosure of which is incorporate herein by reference, discloses sutures or other surface mechanical devices. Embodiments also include the deposition of powders or foams through, for example, a second delivery channel as described above. Biodegradable solid segments can also be beneficially used as markers, with the added benefit of sealing the wound. Adhesive dots of tissue scaffolding material are one option. Gels or solid barbed pins, optionally filling the needle tract to reduce back flow, are another option. The applicator or patient interface itself can create a mechanical mark. It can, for example, use vacuum to hold the tissue being injected, thereby raising a small bleb. The hole made during the injection can bleed, and the bleeding or clotting can act as a mark. Alternatively or additionally, the process of touching the tissue surface can roughen the surface, providing visual indication. Further, a small region of tissue can be cauterized, possibly cauterizing the injection site itself, providing both marking and sealing the tissue to reduce injectate leakage. Devices for augmenting the operators vision include endoscopes or thorascopes, microscopes, and cameras which can be sensitive to visible or non-visible electromagnetic radiation. Fluorescence can also be used beneficially, where the output of the marker is in the visible range as it is excited by a possibly more intense light at a higher invisible wavelength.

Another marking approach is to mark the injectate itself. This has the benefit of allowing 3D visualization of the injection if an imaging system of some type is used. An injectate rich in water can, for example, be differentiated from many tissues using MR imaging. Addition of imaging contrasts—for example, ultrasound, X-ray/CT, or MR contrast to the injectate—can improve visualization by the respective imaging modalities. A radioactive component or PET tracer could be added to the injectate or to cell surface for imaging via nuclear medicine. Published U.S. Patent Application No. 2003/219385A1 and Published PCT International Patent Application No. WO 2005/072780A2, the disclosures of which are incorporated herein by reference, disclose two methods for marking cells so that it is possible to monitor cell proliferation and/or migration after the delivery as well as the delivery process itself. Alternatively, the cells being marked can be non-active cells so that their only use is to transport the marker. The marker could be in separate particles that could be solid, liquid, for example in liposomes or solid shells, or gaseous particles such that they are visible under one or more medical imaging modalities.

The marking process can involve a reaction during the injection. For example, injecting an alginate and the calcium salt solution required for polymerize enables a liquid to be delivered and a solid to be formed in the tissue. An alternative is to have the reaction be between the marking device and the tissue. An example, is a marker that changes color or imager contrast properties upon exposure to air, water, or a specific pH, such as present in commonly available pH indicators. Alternatively, the injectate can cause a quick physiological response, similar to a mosquito bite, with the resulting bump indicating the injection site.

If a computer based system is used to visualize or augment the visualization, then one of several virtual marking systems can be used. One embodiment of such a device or system incorporates an electromagnetic field position measuring system. Commercial or research systems are available from a number of manufacturers (Endocardial Solutions (EnSite 3000), Biosense Webster/J&J (CARTO XP, NAVI-STAR catheter), Medtronic (LocaLisa), Boston Scientific (RPM Realtime Position Management System)). By measuring the 3D position of the injection effector when an injection is given, a 3D model can be built and displayed to the operator.

In another embodiment, a virtual marking system can be used if, for example, an endoscope or thorascope with a camera is used. Using scene recognition algorithms similar to those used to place the virtual first down lines on the football field, every time an injection occurs, the imaging system can mark or color that segment of tissue, providing a virtual ink mark on the surface.

As an alternative to tracking the actual injection sites, the marking system can lay down a grid or pattern that the user is to follow. In one embodiment this is a physical grid, such as might be applied with ink or a label. Alternatively, the markings can be "painted" or drawn in real time onto the tissue, for example with light or laser. The markings can be static, or dynamic, for example moving or changing as the user performs an injection to indicate where the next injection should take place. A similar guidance capability can be achieved virtually using a computer and an image display mentioned above.

The computer guidance systems described above can be connected to a robotic system (for example, including patient interface positioning system 460) to automate the delivery. Such automation may be of particularly value when a very large number of injections are required (as in certain dermal implanting procedure as discussed above).

For many advantages, the marking is considered only during the delivery process. However, there can be a benefit to verifying injectate delivery in the time frame of hours, days, weeks or months. The more permanent marking schemes described, such as solid particles or solid surface, can provide verification of delivery at any time. Biodegradable markers can be used to provide marking for a desired time, and then degrade to reduce or eliminate any deleterious biological effects.

For those markers that are not part of the injectate, there can be a second pump and fluid path to deliver the marker to the tissue surface or the tissue depth. The marker and therapeutic injectate can be delivered through the same needle, with the marker going before, simultaneously, or after the therapeutic injectate. An example of the later is a polymerizing marker that also acts as a plug to reduce leakage through the injection site. A fluid marker can be delivered through a second independent fluid path, either to the surface or into the tissue. For delivery into the tissue, delivery can, for example, be through a needle, a high pressure jet, a cutting edge, or a roughing surface A mechanical marker can, for example, be mounted on a depth stop as described above or mechanically associated with an injectate effector as described above.

Information Encoding

Maintaining traceability of cells and ensuring that they are delivered for their intended purpose is one of the challenges facing cell therapy providers. In several embodiment of the present invention, cell container 50, the injection fluid and/or the cells are encoded with information such as batch, date of manufacture, processing and/or harvest, and target patient. System 5 preferably include a sensor or reader that is capable of reading the encoded information. Encoding of syringes/ container and sensors used to read such information are, for example, discussed in U.S. Pat. Nos. 5,383,858, 6,652,489 and 6,958,053 and PCT Published International Patent Application Nos. WO 99/65548, WO 02/056934, and WO 02/081011, the disclosures of which are incorporate herein by reference. The injection fluid can, for example, be encoded by providing a detectable and distinguishable characteristic (for example, color). One or more physical and/or chemical identifying markers or tags can also be added physically or chemically attached to the injection fluid molecules or to the cells themselves.

In one embodiment, patient information can be entered into control system 200 before cell-containing container or cartridge 50 is inserted. Upon insertion of container 50, the control system 200 (including, for example, a sensor or reader on pump/injector system 100) "reads" the encoded label and verifies that the patient information on container 50 matches the input information.

The above methodology can, for example, be particularly helpful in procedures involving autologous stem cells or cells that have been removed from a patient, processed, and then implanted as an assurance that the patient's own cells and not another patients are being injected.

Encoding of cell container 50 can also include information about how the cells should be handled and maintained by system 5 such as mixing speed, temperature, and or maximum injection speed. Cell therapies requiring buffers and other solutions to be mixed with them can provide this information to the fluid handling system through encoding.

Another area in which encoding is useful is ensuring traceability of the therapy itself. Pharmaceutical companies preferably take steps to ensure that the therapy is used in the intended way and not misapplied. Verification of this use can be important. Encoded information can, for example, be returned to the manufacturer as verification of proper use.

Cell Processing and Maintenance

In several embodiments of the present invention, systems are provided in which, for example, fluids can be delivered to a container including cells therein (for example, for cell processing and/or cell maintenance) and waste can be removed. Moreover, in several such embodiments, cells can also be delivered from the same container. Such devices can, for example, be used in system 5 in connection with injector 100 (for example, as part of or the whole of container 50). Several such devices are also described in U.S. patent application Ser. No. 11/460,635, the disclosure of which is incorporated herein by reference.

For example, FIG. 18A illustrates a syringe 2500 including a syringe barrel having a plunger 2502 slidably movable therein to draw fluid into the syringe barrel. In this embodiment, a first port 2504 is provided (for example, on the side of the syringe barrel) through which a fluid such as buffer solution such as Hank's Balanced Saline Solution (HBSS), other solutions (including solutions including nutrients and other sustaining components) or gases can flow into syringe 2500. A second port 2506 is provided (for example, on the side of the barrel) through which waste can be removed from syringe 2500. A filter 2508 is placed in operative connection with second port 2506 so that cells and/or other materials to be injected are prevented from exiting syringe 2500 through second port 2506. Cells can be injected via an outlet port 2510 or syringe tip on the forward end of syringe 2500. Valves (not shown) as known in the art can be provided in connection with one or more of the ports of syringe 2500 to control flow.

FIG. 18B illustrates another embodiment of a syringe system of the present invention. In this embodiment, syringe 2520 includes a syringe barrel having a plunger 2522 slidably disposed therein. A generally conical shaped transition region 2524 on a forward end of the syringe barrel connects to a neck 2525 which includes an outlet port 2526 at the forward end thereof. A second port 2528 is provided (for example, on the side of the neck). Second port 2528 or side port can be formed integrally or monolithically with syringe 2520. Alternatively, a fluid path section including an injection outlet port and a second port or can be added via an attachment to a standard syringe in forming the system of FIG. 18B.

The syringe of FIG. 18B can, for example, make use of gravity to separate cells from liquid. When expelling waste via side port 2528 in syringe neck 2525, syringe 2520 can be oriented upward as shown in the bottom left of FIG. 18B. In this orientation, the cells settle to the rearward portion of the syringe barrel. The liquid is ejected from the top as plunger 2522 is slowly advance forward (toward syringe outlet port 2526). When processing or maintaining cells with, for example, buffer solution, syringe 2529 is oriented as shown on the bottom right of FIG. 18B. In this orientation, the cells settle to the forward portion of syringe 2520. Fluid can then be drawn into syringe 2520 by drawing plunger 2522 rearward (away from syringe outlet 2526). Drawing the liquid into syringe 2520 in this manner causes the liquid to flow through the cells. Appropriate valves as known in the art can be placed in fluid connection with syringe outlet port 2526 and second or side port 2528 to control flow therethrough. The syringe system of FIG. 18B isolates the cells within syringe 2520, reducing the possibility of contamination. Additionally, syringe 2520 can be a part of or can form the entirety of a delivery device as, for example, described above.

FIG. 18C through 18E illustrate an embodiment of a syringe 2550 of the present invention including a plunger 2552 having a volume or chamber 2554 formed therein or in fluid connection therewith. Plunger 2552 interfaces with the fluid within syringe barrel via a filter 2556, which can be considered as partially replacing the rubber cover commonly used on the forward end of conventional plungers. Holes, pores or other transport paths of filter 2556 are sized such that liquid may pass though, yet cells cannot. Plunger chamber 2556 has in fluid connection therewith an inlet 2558, including an inlet valve 2560, and an outlet 2562, including an outlet valve 2564 as illustrated in FIGS. 18C through 18E. Valves 2560 and 2564 can, for example, include one-way check valves.

In a representative example of use of syringe 2550 of FIGS. 18C through 18E, syringe outlet 2566 on the forward end thereof is first capped with a cap 2568 and plunger 2552 is drawn back, introducing fluid into the plunger chamber 2554 (via inlet 2558) and through filter 2556 to contact cells held within the syringe barrel forward of filter 2556 (see, FIG. 18C). In a second step illustrated in FIG. 18D, plunger 2552 is pushed forward, forcing waste to exit outlet valve 2564 in fluid connection with plunger chamber 2554. The above steps can be repeated to thoroughly wash or contact the cells fluid. In a subsequent step illustrated in FIG. 18E, cap 2568 is removed from syringe outlet 2566 and outlet 2562 in fluid connection with plunger chamber 2554 is plugged or capped with a plug 2568. Upon forward advancement of plunger 2552, the cells are expelled from syringe outlet 2566.

The syringe of FIGS. 18C through 18E (as well as those of FIGS. 18A and 18B) can include a sterile bag to contain the syringe. As with the syringes of FIGS. 18A and 18B, syringe 2550 of FIGS. 18C through 18E isolates the cells in the syringe, reducing the possibility of contamination. Also, syringe 2550 can form part of or the entirety of a cell delivery system.

FIG. 18G illustrates another embodiment of a device or system 2580 for use in connection with a cell therapy system to provide a closed system to introduce fluids to the cells, remove waste from the cells and to deliver the cells. Device 2580 can be used with any structure to be injected, including cell structures, that can be size excluded via, for example, a micropore filter.

Device 2580 includes a cell chamber or transport vial 2582 that includes a mechanism or fluid path to introduce or flush fluid through chamber 2582 while retaining the cells in chamber 2582. In the embodiment illustrated in FIG. 18F, cell chamber 2582 includes an inlet port 2584 through which, for example, a nutrient containing buffer can be introduced into cell chamber 2582. A one-way check valve 2586 can be placed in fluid connection with inlet port 2584. A septum 2588 can cover a first end of cell chamber 2582. A filter 2590 covers the second end of the cell chamber 2582. Cell chamber 2582 is insertable within a housing section 2592. An annular sealing member 2594 on an outer wall of cell chamber 2582 forms a seal with an inner wall of housing section 2592. A buffer flush solution such as HBSS can be introduced through inlet port 2584 of cell chamber 2582 to, for example, remove a hibernation, transport or processing buffer solution. Such hibernation, transport or processing solutions can, for example, includes elements beneficial to cells during hibernation, transport and/or processing, but which are not desirable for injection into a patient. Waste flows out of device 2580 via an effluent port 2594 of housing 2592. A one-way check valve 2596 can be placed in fluid connection with effluent port 2594. Device 2580 can also be used as the administration syringe for delivery of cells by, for example, connecting patient interface 400 (for example, a needle, which is not shown in FIG. 18F) into fluid connection with cell chamber 2582 (for example, through septum 2588, through filter 2590 or through another port). A needle can also be placed in fluid connection with effluent port 2594 of housing 2592. Filter 2590 can be moved to the back of chamber 2582 to facilitate use of device 2580 as a hand syringe by attaching a needle to the front of device 2580. Device 2580 is relatively simple to use regardless of the skill set of the operator.

FIGS. 18G and 18H illustrates other embodiments of devices including a cell chamber or transport vial that includes a mechanism or fluid path to introduce fluid into the chamber while retaining the cells in the chamber. These embodiments are somewhat similar in operation to those of FIGS. 18C through 18F. In the system 2600 illustrated in FIGS. 18G and 18H, a cell chamber 2602 includes at least one inlet port 2604 through which a fluid or fluids can be introduced into cell chamber 2602. A one-way check valve 2606 can be placed in fluid connection with inlet port 2604. Cell chamber 2602 also includes at least one effluent port 2608. A one way check valve 2610 can be placed in fluid connection with effluent port 2608. As compared to the embodiment of FIG. 18F, by moving the flow into and out of cell chamber 2602 (via inlet port 2604 and effluent port 2610 during, for example, repeated reciprocation of plunger cell chamber 2602 relative to housing 2614) to the same side of a filter 2612 (with the cells isolated on the other side of filter 2612) packing of cells on filter 2612 is prevented. In that regard, filter 2612 is washed of cells each time fluid is introduced. A sealing member 2603 can be placed in connection with an outer wall of cell chamber 2602 to form a seal with an inner wall of housing 2614.

In the embodiments of FIGS. 18G and 18H, patient interface 400 is attachable to, for example, a connector 2616 (for example, a luer type connector or other connector as described herein) on the end of housing 2614 (for example, a graduated cylindrical housing) without the requirement of puncturing a septum.

In FIG. 18H, plunger/cell chamber 2602 is positioned within housing 2614. A cap 2618 is provided for use in connection with connector 2616. Further, cap 2620 is provided for use in connection with effluent port 2608 during an injection using device 2600.

With cap 2618 in closing connection with connector 2616 and cap 2620 not in connection with effluent port 2610, rearward movement of plunger/cell chamber 2602 relative to housing 2614 (that is, movement of plunger to the right in the orientation of FIG. 18H), results in drawing fluid through inlet port into device 2600. Forward movement of plunger/cell chamber 2602 relative to housing 2614 result in effluent exiting effluent port 2610. Repeated reciprocation of plunger/cell chamber 2602 result is fluid treatment (for example, buffer replacement) of the material (for example, cells) within device 2600. To inject using device 2600, cap 2620 is place in closing connection with effluent port 2610 and cap 2618 is removed form connection with connector 2616. Patient interface 400 can, for example, be placed in fluid connection with connector 2616.

Device 2600 can be used to process any type of solution have solids or other size-excludable agents suspended therein. Filter 2612 is used to separate such solids or other agents via size exclusion.

Moreover, as illustrated in the embodiment of FIG. 18I, a plunger 2650 can be used in connection with a conventional cryovial or other container 2660 to effect fluid treatment (for example, washing and/or buffer replacement) within a standard or convention cryovial or other container 2660. In general, plunger 2650 includes a filter 2654 on the distal end thereof to prevent cells (and/or other material in vial 2660) from entering either of two fluid pathways within plunger 2650. Fluid, which can pass through filter 2654, can enter vial 2660 through the first pathway and can exit vial 2660 through the second pathway formed through plunger 2650. One way check valves as described above can be used in connection with the first and second fluid pathways. A vial cap 2662 is first removed from vial 2660 (via, for example, threading 2664) as known in the art. Plunger 2650 is then placed within vial 2660.

In the embodiment illustrated on the left side of FIG. 18I, the first fluid pathway (which can, for example, be in fluid connection with a buffer solution) is a conduit 2656. A first check valve 2657 can be placed in fluid connection with conduit 2656 so that fluid can flow into vial 2660 through conduit 2656 but cannot exit via conduit 2656. The volume around conduit 2656 within plunger 2650 provides a second fluid flow pathway 2658 for effluent fluid to exit through plunger 2650 to waste. A second check valve (not shown) can be placed in fluid connection with second fluid flow pathway 2658. A sealing member 2659 (for example, an elastomeric, O-ring) is provided on plunger 2650 to form a seal with an inner wall of vial 2660. Upward (in the orientation of FIG. 18I) motion of plunger 2650 relative to vial 2660 results in drawing of fluid into the system. Downward motion of plunger 2650 results in forcing effluent out of the system.

In the embodiment of plunger 2650a on the right side of FIG. 18I, first fluid pathway 2656a and second fluid flow pathway 2658a are created by a divider 2653a in plunger 2650a. A first check valve 2657a is placed in fluid connection with first pathway 2656a and a second check valve 2657a' is placed in fluid connection with second pathway 2656a. Other like elements are numbered similarly to the numbering of corresponding elements of plunger 2650.

The foregoing description and accompanying drawings set forth the preferred embodiments of the invention at the present time. Various modifications, additions and alternative designs will, of course, become apparent to those skilled in the art in light of the foregoing teachings without departing from the scope of the invention. The scope of the invention is indicated by the following claims rather than by the foregoing description. All changes and variations that fall within the meaning and range of equivalency of the claims are to be embraced within their scope.

What is claimed is:

1. A nonimplantable system for delivering a fluid comprising cells to tissue of a patient, comprising:
   at least a first container for holding an injection fluid in which an agent is carried;
   a first powered drive in operative connection with the container, the first powered drive being operable to pressurize contents of the container;
   a control system in operative connection with the first powered drive and operative to control the first powered drive;
   a fluid path in fluid connection with the container, the fluid path including a patient interface adapted to deposit the cells within tissue of the patient;
   a sensor system; and
   a communication system in connection with at least the control system and the sensor system, the communication system being adapted to provide information to the control system, the control system being adapted to transmit a control signal to at least the first powered drive based at least in part on information provided to the control system, wherein the sensor system provides a measurement indicative of at least shear forces on the cells.

2. The nonimplantable system of claim 1 wherein the sensor system comprises at least one tissue sensor system to measure a property of the tissue at a delivery site and at least one fluid sensor system to measure a property of the fluid to be delivered.

3. The nonimplantable system of claim 1 wherein the sensor system comprises at least one cell health sensor system to measure the health of the cells.

4. A nonimplantable system for delivering a fluid including cells to tissue of a patient, comprising:
   at least a first container for holding an injection fluid in which the cells are carried;
   a first powered drive in operative connection with the container, the first powered drive being operable to pressurize contents of the container;
   a control system in operative connection with the first powered drive and operative to control the first powered drive;
   a fluid path in fluid connection with the container, the fluid path including a patient interface adapted to deposit the cells within tissue of the patient;
   a sensor system comprising at least one cell sensor system to measure one or more properties indicative of the health of the cells and shear forces on the cells; and
   a communication system in connection with at least the control system and the sensor system, the sensor system being adapted to provide information to the control system, the control system being adapted to transmit a control signal to the first powered drive based at least in part on information provided to the control system.

5. The nonimplantable system of claim 4 wherein the cell health sensor system measures at least one of presence of at least one nutrients, atmosphere, temperature, pressure, cell integrity, cell death, cell count, chemical labeling, conductivity, optical fluorescence, optical scattering, at least one cell biomarkers, DNA content, optical density, UV spectroscopy, IR spectroscopy, at least one metabolic variable, at least one cell culture biomarker, at least one genetic identification, cell apoptosis, or cell senescence.

6. The nonimplantable system of claim 4 wherein the control system is adapted to transmit a control signal to the first powered drive based at least in part on the measure of health of the cells from the cell health sensor system.

7. The nonimplantable system of claim 4 wherein the cells are stem cells.

8. The nonimplantable system of claim 4 wherein the system further comprises a cell maintenance system being adapted to affect at least one property of at least one of the injection fluid or the cells.

9. The nonimplantable system of claim 8 wherein the sensor system including at least one sensor in operative connection with the maintenance system to measure the value of the at least one property of the fluid or the cells.

10. The nonimplantable system of claim 9 wherein the controller system is adapted to transmit a control signal based at least in part on the measured value of the measured property.

11. The nonimplantable system of claim 8 wherein the cell maintenance system is in operative connection with the container.

12. The nonimplantable system of claim 8 wherein the cell maintenance system is in operative connection with the patient interface.

13. The nonimplantable system of claim 8 further comprising a cell processing system.

14. The nonimplantable system of claim 4 wherein the sensor system further comprises at least one patient sensor system adapted to measure at least one physiological property of the patient, the communication system being in connection with the patient sensor system to provide information of the measured physiological property of the patient to the controller system, the controller system being adapted to transmit a control signal based at least in part on the measured physiological property of the patient.

15. The nonimplantable system of claim 14 wherein the value of the physiological property of the patient is processed by the control system to transmit a signal to the first powered drive to time an injection.

16. The nonimplantable system of claim 15 wherein the physiological property of the patient is the position of a beating heart of the patient or a phase of a beating heart.

17. The nonimplantable system of claim 14 wherein the physiological property of the patient is processed by the controller to transmit a signal to the first powered drive to alter an injection protocol.

18. The nonimplantable system of claim 14 wherein the at least one property of the patient is related to mapping of a heart, characterization of tissue of a heart, characterization of a systolic or diastolic phase of a heart, a dynamic position of any portion of a beating heart, brain function, presence or absence of a neurotransmitter (for example, dopamine), EEG characterization, characterization of brain tissue (for example, determination of the presence of ischemic tissue associated with stroke), pancreatic function, presence or absence of hormone (for example, insulin) or islet cell function.

19. The nonimplantable system of claim 4 further comprising an imaging system adapted to image a region of the patient to which the cells are delivered.

20. The nonimplantable system of claim 19 wherein the communication system is in connection with the imaging system to provide information of a measured property from the imaging system to the control system, the control system being adapted to transmit a control signal based at least in part on the measured property from the imaging system.

21. The nonimplantable system of claim 4 wherein the at least one cell sensor system is adapted to measure cell viability.

22. The nonimplantable system of claim 4 wherein the at least one cell sensor system is adapted to measure at least one of cell count, cell viability, temperature, pH, concentration, pressure or flow rate.

23. A nonimplantable system for delivering a fluid including an agent to tissue of a patient, comprising:

at least a first container for holding an injection fluid in which the agent is carried;

a first powered drive in operative connection with the container, the first powered drive being operable to pressurize contents of the container;

a control system in operative connection with the first powered drive and operative to control the first powered drive;

a fluid path in fluid connection with the container, the fluid path including a patient interface adapted to deposit cells within tissue of the patient;

a sensor system comprising at least one tissue sensor system to measure a property of the tissue at a delivery site and at least one fluid sensor system to measure a property of the fluid to be delivered; and a communication system in connection with at least the control system and the sensor system, the sensor system being adapted to provide information to the control system, the control system being adapted to transmit a control signal to the first powered drive based at least in part on information provided to the control system, wherein the sensor system provides a measurement indicative of at least shear forces on the cells.

* * * * *

UNITED STATES PATENT AND TRADEMARK OFFICE
CERTIFICATE OF CORRECTION

PATENT NO.       : 8,182,444 B2                     Page 1 of 2
APPLICATION NO.  : 12/092448
DATED            : May 22, 2012
INVENTOR(S)      : Uber, III et al.

It is certified that error appears in the above-identified patent and that said Letters Patent is hereby corrected as shown below:

On the Title Page, in Field (57), under "ABSTRACT", delete "pregenitor" and insert -- progenitor --, therefor.

IN THE SPECIFICATION

In Column 5, Line 11, delete "pregenitor" and insert -- progenitor --, therefor.

In Column 8, Line 44, delete "havs" and insert -- have --, therefor.

In Column 10, Line 10, delete "invention-provides" and insert -- invention provides --, therefor.

In Column 20, Line 13, delete "delivery" and insert -- deliver --, therefor.

In Column 21, Line 41, delete "measure" and insert -- measured --, therefor.

In Column 21, Line 61, delete "an" and insert -- and --, therefor.

In Column 22, Lines 19-20, delete "semipermiable" and insert -- semipermeable --, therefor.

In Column 22, Line 57, delete "element" and insert -- elements --, therefor.

In Column 23, Line 12, delete "on" and insert -- one --, therefor.

IN THE CLAIMS

In Claim 4, Column 75, Lines 60-61, delete "indicative of the health" and insert -- indicative of health --, therefor.

Signed and Sealed this
Twenty-third Day of April, 2013

Teresa Stanek Rea
*Acting Director of the United States Patent and Trademark Office*

CERTIFICATE OF CORRECTION (continued)
U.S. Pat. No. 8,182,444 B2

IN THE CLAIMS

In Claim 5, Column 76, Lines 1-2, delete "wherein the cell health sensor system" and insert -- wherein the sensor system --, therefor.

In Claim 5, Column 76, Lines 2-9, delete "measures at least one of presence of at least one nutrients, atmosphere, temperature, pressure, cell integrity, cell death, cell count, chemical labeling, conductivity, optical fluorescence, optical scattering, at least one cell biomarkers, DNA content, optical density, UV spectroscopy, IR spectroscopy, at least one metabolic variable, at least one cell culture biomarker, at least one genetic identification, cell apoptosis, or cell senescence." and insert -- measures the presence of at least one of a nutrient, an atmosphere, a temperature, a pressure, a cell integrity, a cell death, a cell count, a chemical labeling, a conductivity, an optical fluorescence, an optical scattering, at least one cell biomarker, a DNA content, an optical density, an UV spectrum, an IR spectrum, at least one metabolic variable, at least one cell culture biomarker, at least one genetic identification, a cell apoptosis, or a cell senescence. --, therefor.

In Claim 6, Column 76, Lines 12-13, delete "measure of health of the cells from the cell health sensor system" and insert -- measure of the one or more properties indicative of health of the cells from the sensor system --, therefor.

In Claim 9, Column 76, Lines 23-24, delete "with the maintenance system to measure the value of the at least one property of the fluid or the cells." and insert -- with the cell maintenance system to measure the value of the at least one property of the injection fluid or the cells. --, therefor.

In Claim 10, Column 76, Lines 25-28, delete "wherein the controller system is adapted to transmit a control signal based at least in part on the measured value of the measured property." and insert -- wherein the control system is adapted to transmit a control signal based at least in part on the measured value of the at least one property. --, therefor.

In Claim 14, Column 76, Lines 42-43, delete "patient to the controller system, the controller system" and insert -- patient to the control system, the control system --, therefor.

In Claim 15, Column 76, Lines 46-47, delete "wherein the value" and insert -- wherein a value --, therefor.

In Claim 16, Column 76, Lines 50-52, delete "wherein the physiological property of the patient is the position of a beating heart" and insert -- wherein the at least one physiological property of the patient is a position of a beating heart --, therefor.

In Claim 17, Column 76, Lines 53-55, delete "wherein the physiological property of the patient is processed by the controller to transmit" and insert -- wherein the at least one physiological property of the patient is processed by the control system to transmit --, therefor.

In Claim 18, Column 76, Line 58, delete "one property" and insert -- one physiological property --, therefor.